(12) United States Patent
Merriman et al.

(10) Patent No.: US 11,724,244 B2
(45) Date of Patent: Aug. 15, 2023

(54) SEMICONDUCTOR CHIP DEVICES AND METHODS FOR POLYNUCLEOTIDE SYNTHESIS

(71) Applicant: Avery Digital Data, Inc., San Diego, CA (US)

(72) Inventors: Barry Merriman, La Jolla, CA (US); Ryan de Ridder, San Diego, CA (US); Matthew T. Holden, San Diego, CA (US); Tim Geiser, Petaluma, CA (US)

(73) Assignee: Avery Digital Data, Inc., San Diego, CA (US)

( * ) Notice: Subject to any disclaimer, the term of this patent is extended or adjusted under 35 U.S.C. 154(b) by 3 days.

(21) Appl. No.: 17/719,664

(22) Filed: Apr. 13, 2022

(65) Prior Publication Data
US 2022/0280906 A1   Sep. 8, 2022

Related U.S. Application Data

(63) Continuation of application No. PCT/US2022/018189, filed on Feb. 28, 2022.

(60) Provisional application No. 63/154,343, filed on Feb. 26, 2021.

(51) Int. Cl.
  *B01J 19/00* (2006.01)
  *C40B 40/06* (2006.01)

(52) U.S. Cl.
  CPC ........... *B01J 19/0046* (2013.01); *C40B 40/06* (2013.01); *B01J 2219/0059* (2013.01); *B01J 2219/00596* (2013.01); *B01J 2219/00653* (2013.01); *B01J 2219/00713* (2013.01); *B01J 2219/00722* (2013.01)

(58) Field of Classification Search
  None
  See application file for complete search history.

(56) References Cited

U.S. PATENT DOCUMENTS

| | | |
|---|---|---|
| 5,667,667 A | 9/1997 | Southern |
| 5,929,208 A | 7/1999 | Heller et al. |
| 6,017,696 A | 1/2000 | Heller |
| 6,093,302 A | 7/2000 | Montgomery |
| 6,251,595 B1 | 6/2001 | Gordon et al. |
| 6,867,048 B2 | 3/2005 | Kovacs |
| 7,075,187 B1 | 7/2006 | Maurer |
| 7,150,997 B2 | 12/2006 | Kovacs |
| 7,314,708 B1 | 1/2008 | Heller et al. |
| 7,541,314 B2 | 6/2009 | Suciu et al. |
| 7,718,579 B2 | 5/2010 | Maurer |
| 8,603,803 B2 | 12/2013 | Wang et al. |
| 8,614,086 B2 | 12/2013 | Holt et al. |
| 8,697,605 B2 | 4/2014 | Gao et al. |
| 9,023,601 B2 | 5/2015 | Oleinikov |
| 9,103,775 B2 * | 8/2015 | Bradley et al. ..... H01L 29/0673 |
| 9,267,213 B1 | 2/2016 | Maurer et al. |
| 9,394,167 B2 | 7/2016 | Maurer et al. |
| 10,195,580 B2 | 2/2019 | Hall et al. |
| 10,407,676 B2 | 9/2019 | Poehmerer et al. |
| 10,519,439 B2 | 12/2019 | Peterson et al. |
| 10,570,447 B2 | 2/2020 | Ronaghi et al. |
| 10,640,822 B2 | 5/2020 | Predki et al. |
| 10,704,088 B2 | 7/2020 | Su et al. |
| 10,745,814 B2 | 8/2020 | Kalhor et al. |
| 10,894,242 B2 | 1/2021 | Marsh et al. |
| 2003/0162214 A1 | 8/2003 | Heller et al. |
| 2004/0238369 A1 | 12/2004 | Southern et al. |
| 2005/0070009 A1 | 3/2005 | Klapproth et al. |
| 2006/0094024 A1 | 5/2006 | Pirrung et al. |
| 2006/0105355 A1 | 5/2006 | Maurer |
| 2008/0070803 A1 | 3/2008 | Egeland |
| 2019/0244109 A1 | 8/2019 | Bramlett et al. |
| 2019/0295644 A1 | 9/2019 | Arreghini et al. |
| 2019/0355964 A1 | 11/2019 | Vereecken et al. |
| 2019/0358604 A1 | 11/2019 | Nguyen et al. |
| 2020/0010827 A1 * | 1/2020 | Poehmerer et al. .... B03C 5/026 |
| 2020/0384434 A1 | 12/2020 | Nguyen et al. |

FOREIGN PATENT DOCUMENTS

| | | |
|---|---|---|
| WO | 2019145713 A1 | 8/2019 |
| WO | 2019222612 A1 | 11/2019 |
| WO | 2020020608 | 1/2020 |
| WO | 2020178603 A1 | 9/2020 |
| WO | 2020185896 A1 | 9/2020 |
| WO | 2020243072 A1 | 12/2020 |
| WO | 2020243075 A1 | 12/2020 |
| WO | 2020243076 A1 | 12/2020 |
| WO | 2020243077 A1 | 12/2020 |

* cited by examiner

*Primary Examiner* — Kaijiang Zhang
(74) *Attorney, Agent, or Firm* — Procopio, Cory, Hargreaves & Savitch LLP

(57) ABSTRACT

Systems and methods for polynucleotide synthesis utilize electrochemical deprotection and novel redox chemistries compatible with advanced CMOS nodes, for highly reliable and massively scalable parallel construction of polynucleotide segments having a desired sequence or sequences. Via use of these exemplary techniques, low-cost and large-scale polynucleotide synthesis is facilitated, for example for data storage and retrieval applications.

13 Claims, 141 Drawing Sheets

Chemical Structure of Nucleoside Phosphoramidites
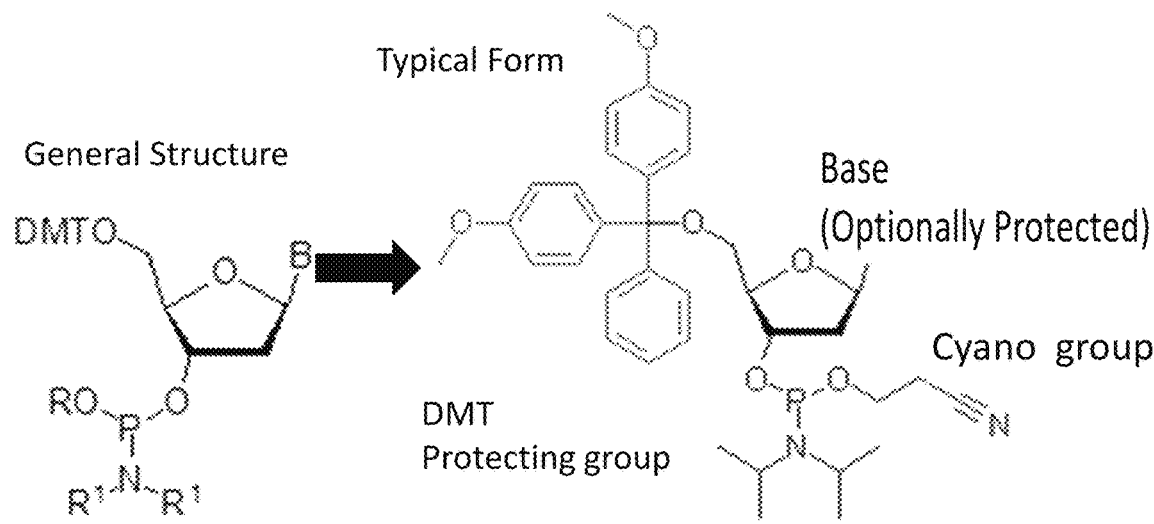
Bases (with Typical Protecting Groups)
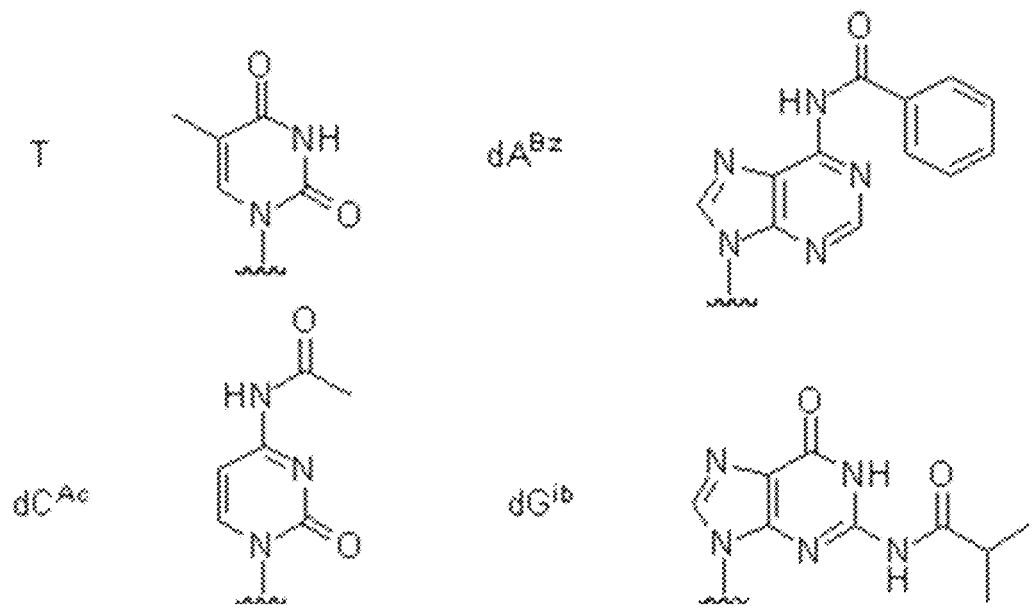
FIG. 2A

Voltage-directed synthesis chemistry on a scalable pixel array chip

Planar Geometry

Dithering Interdigitated Planar Electrodes
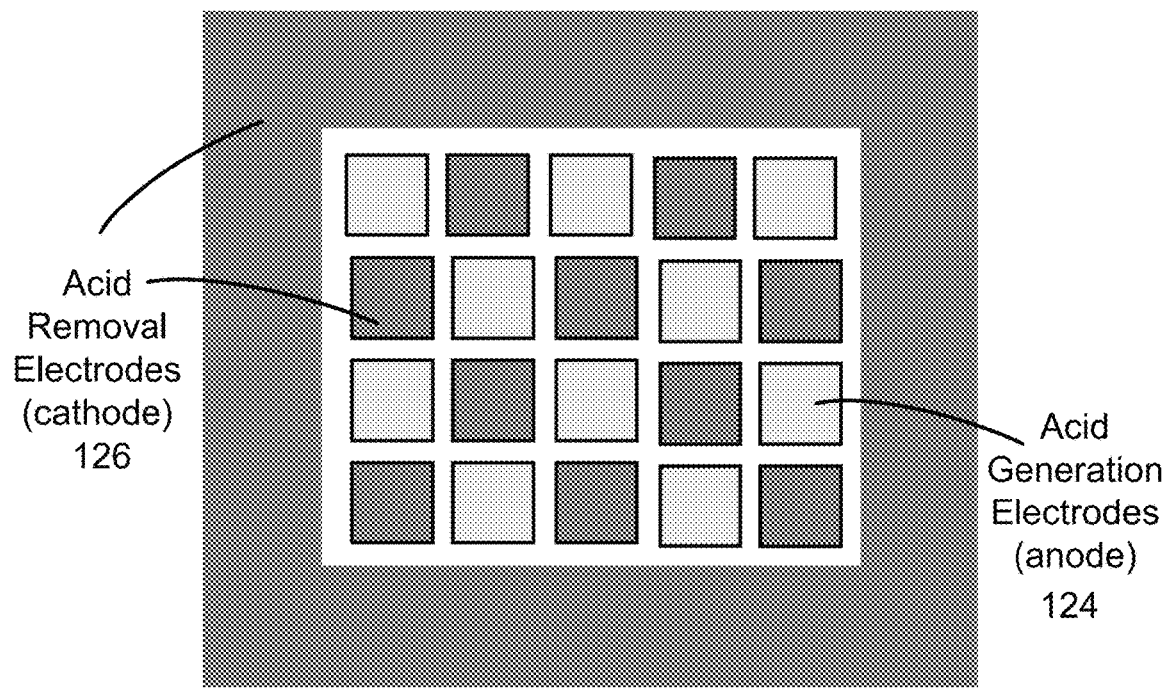
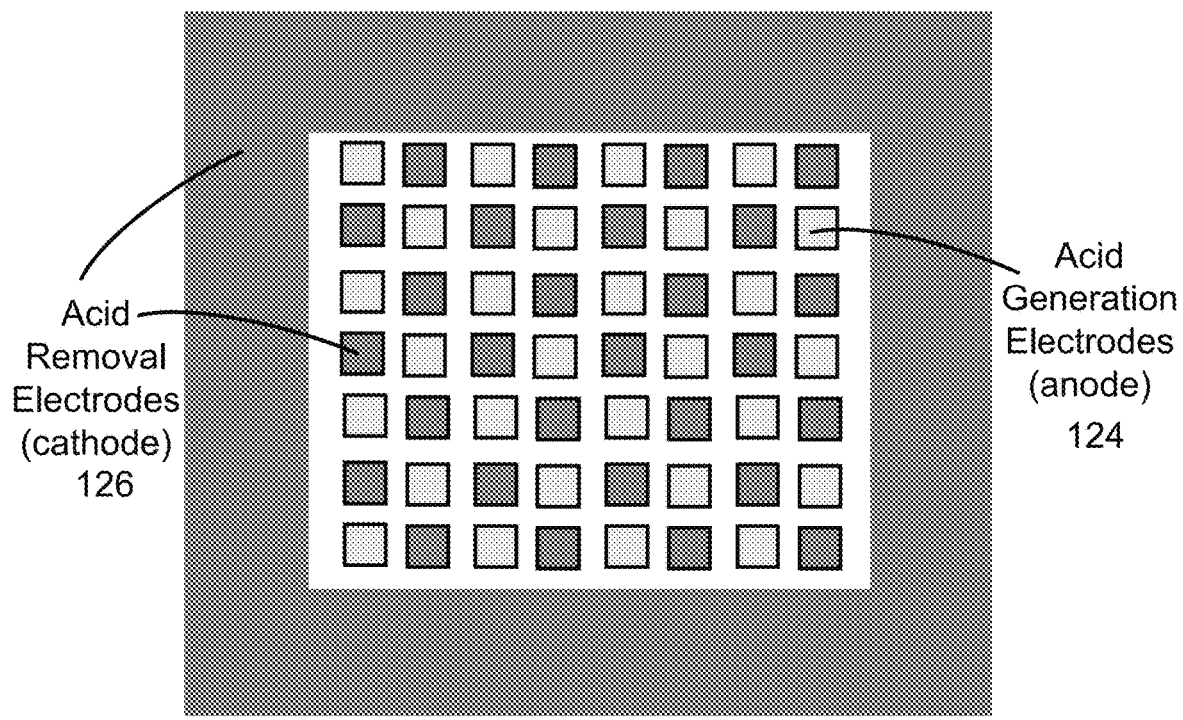
FIG. 19B

Acid-Confining Electrode Geometries
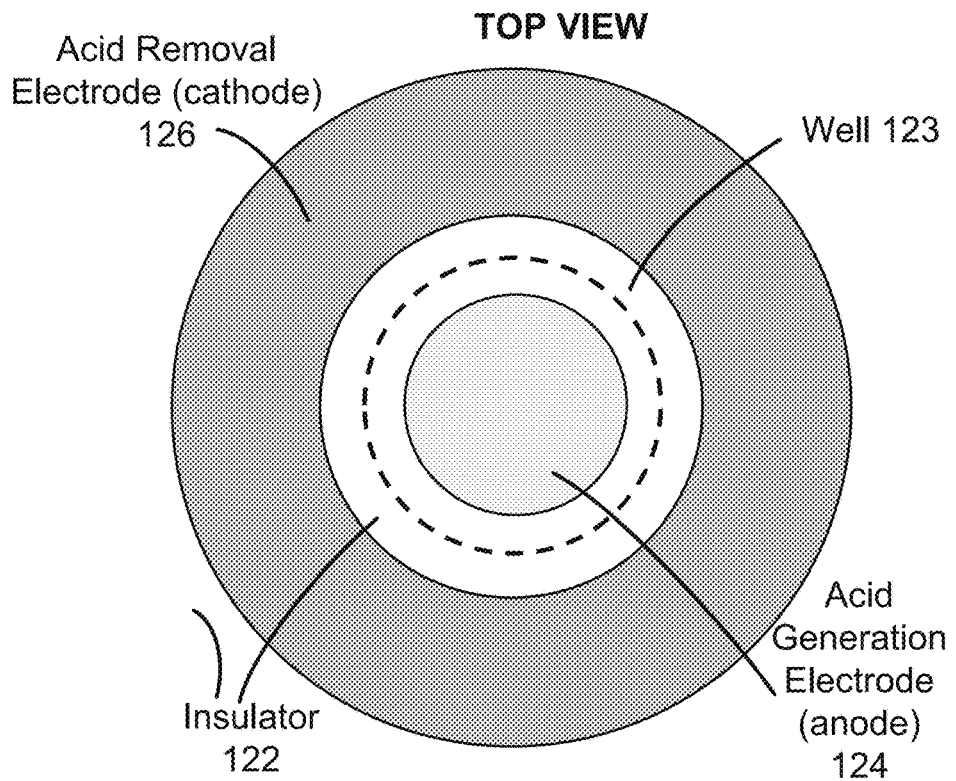
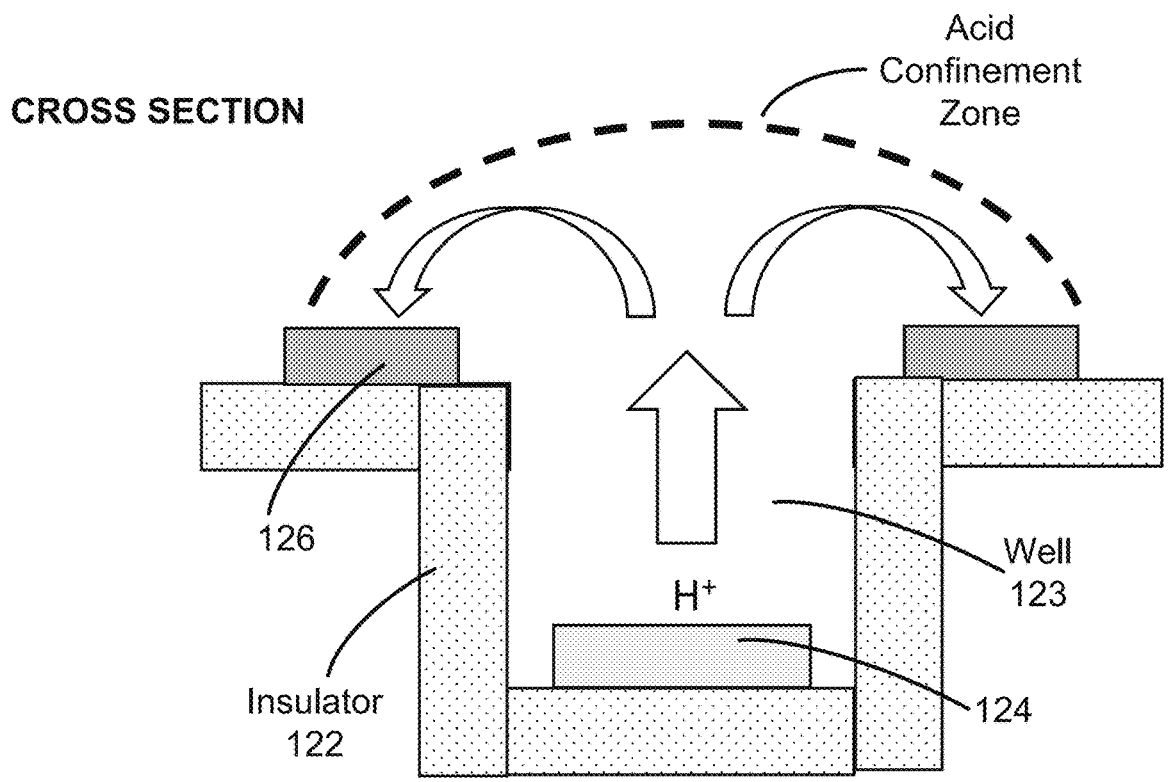
FIG. 20

Acid-Confining Electrode Geometries (CROSS SECTIONS)
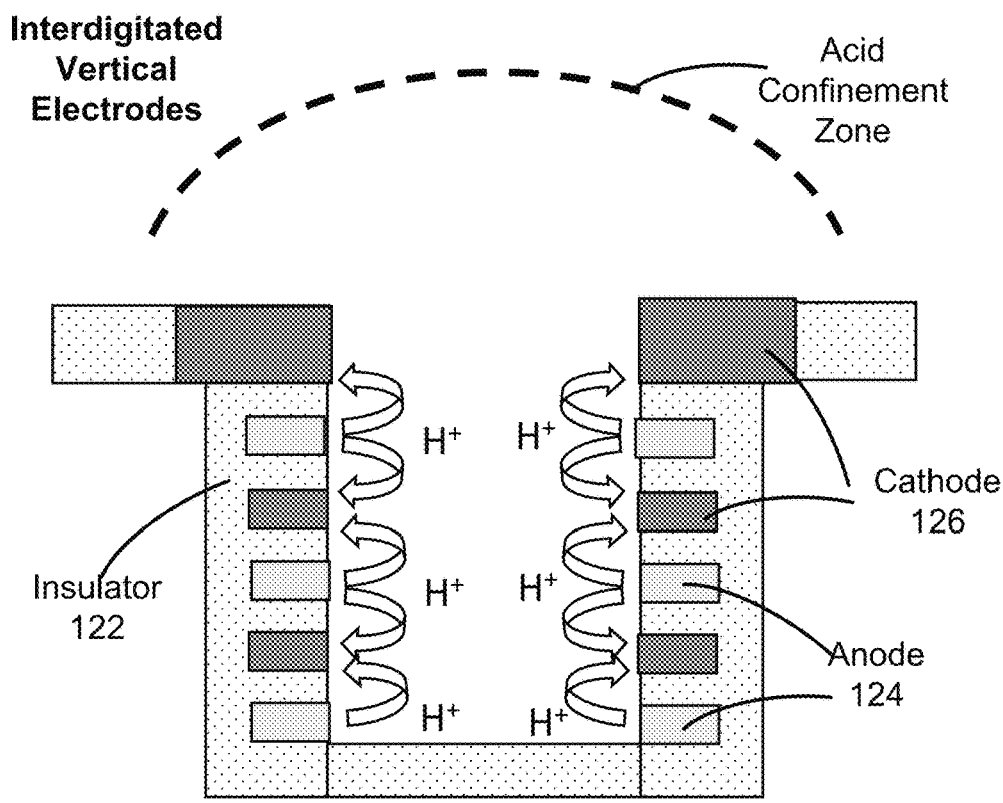
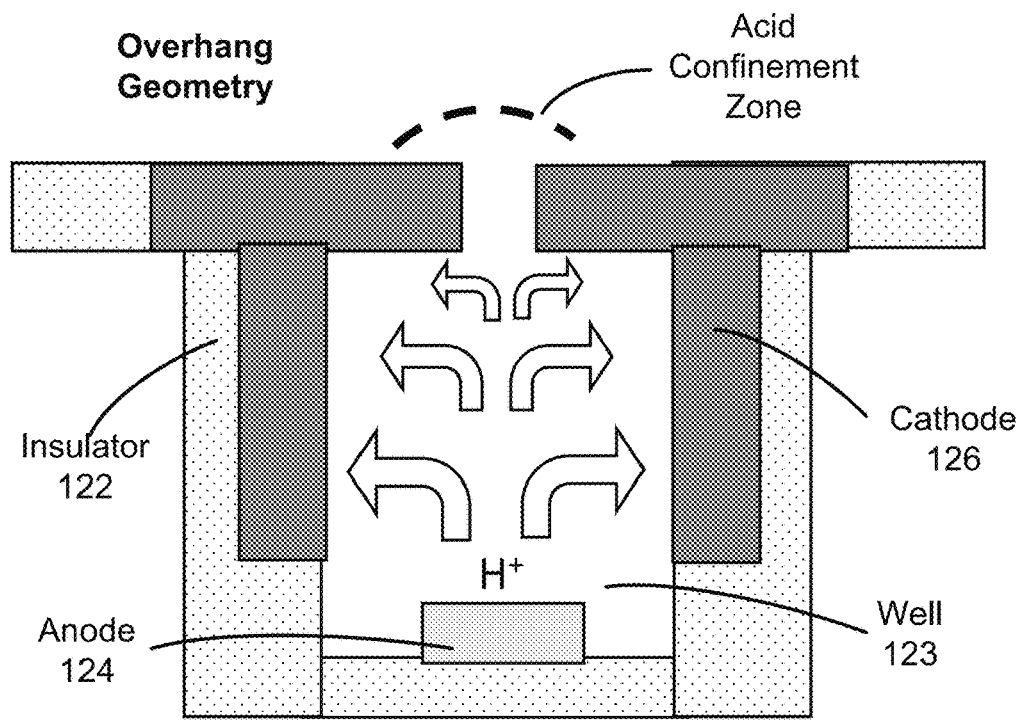
FIG. 22

Acid-Confining Electrode Geometries
With surface area enhancing features (CROSS SECTIONS)
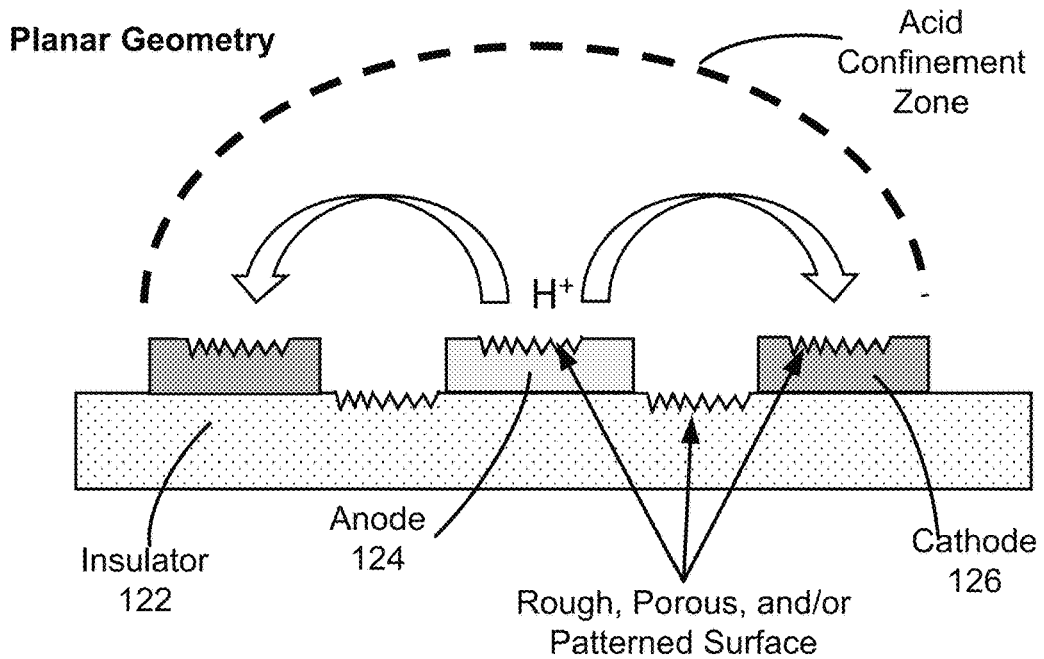
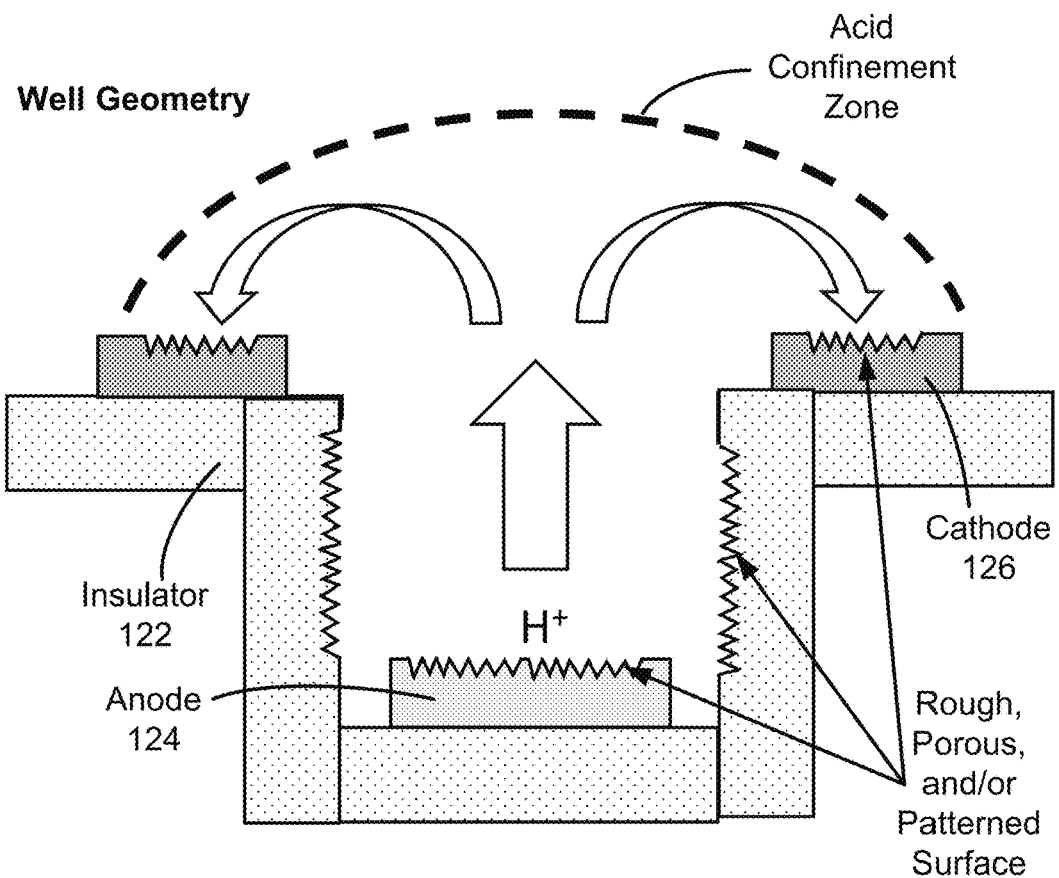
FIG. 23

Acid-Confining Electrode Geometries
With surface area enhancing features (CROSS SECTIONS)
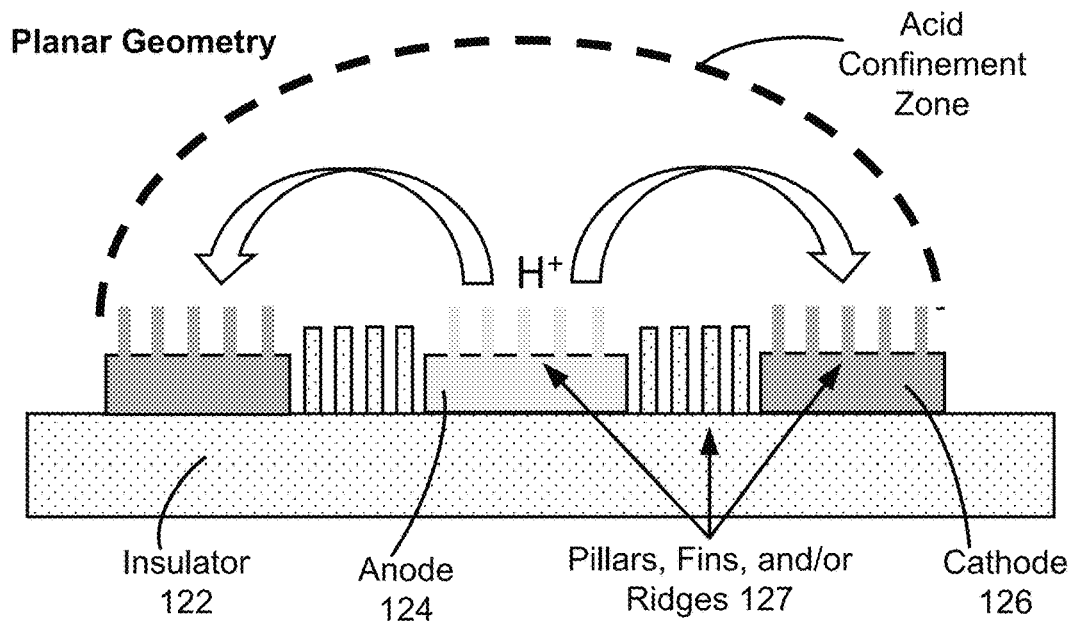
Planar Geometry
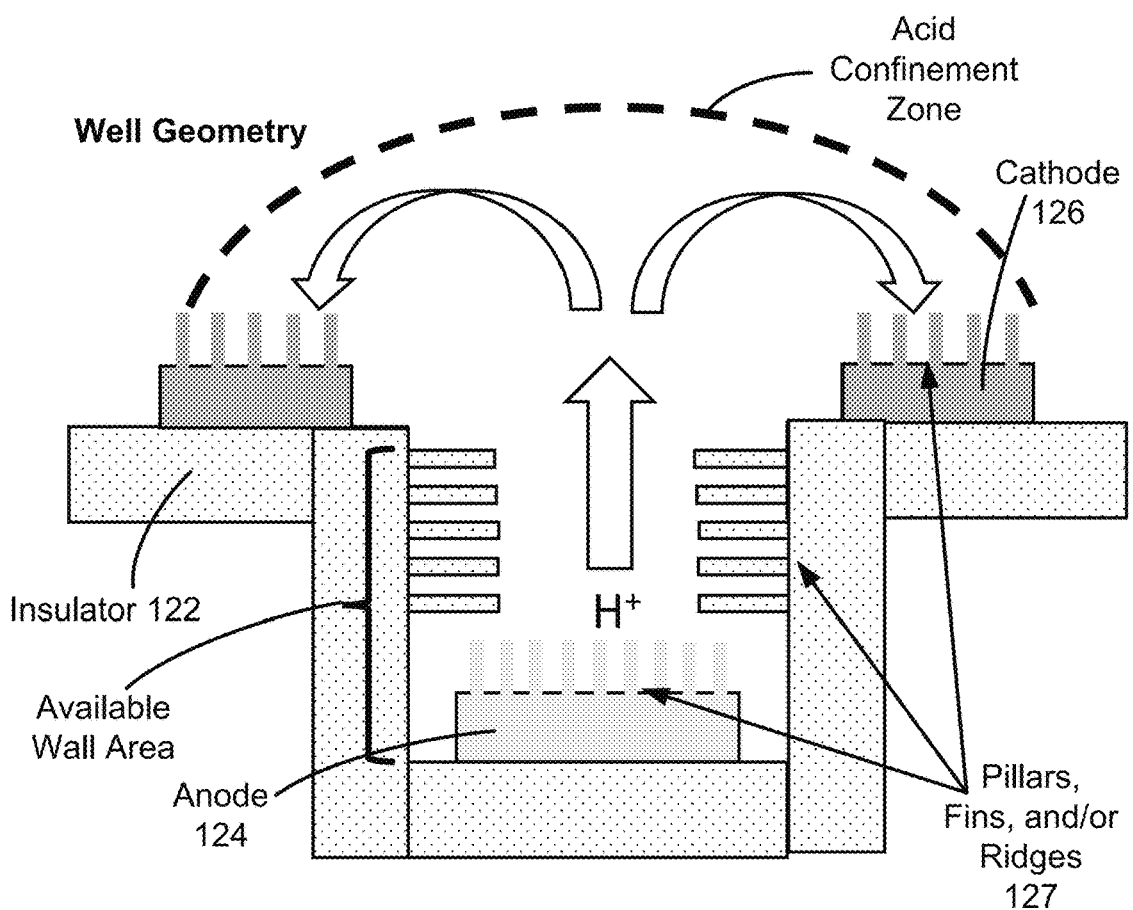
Well Geometry
FIG. 24A

Synthesis Zones Defined in 3D Material Matrices (CROSS SECTIONS)
Planar Geometry
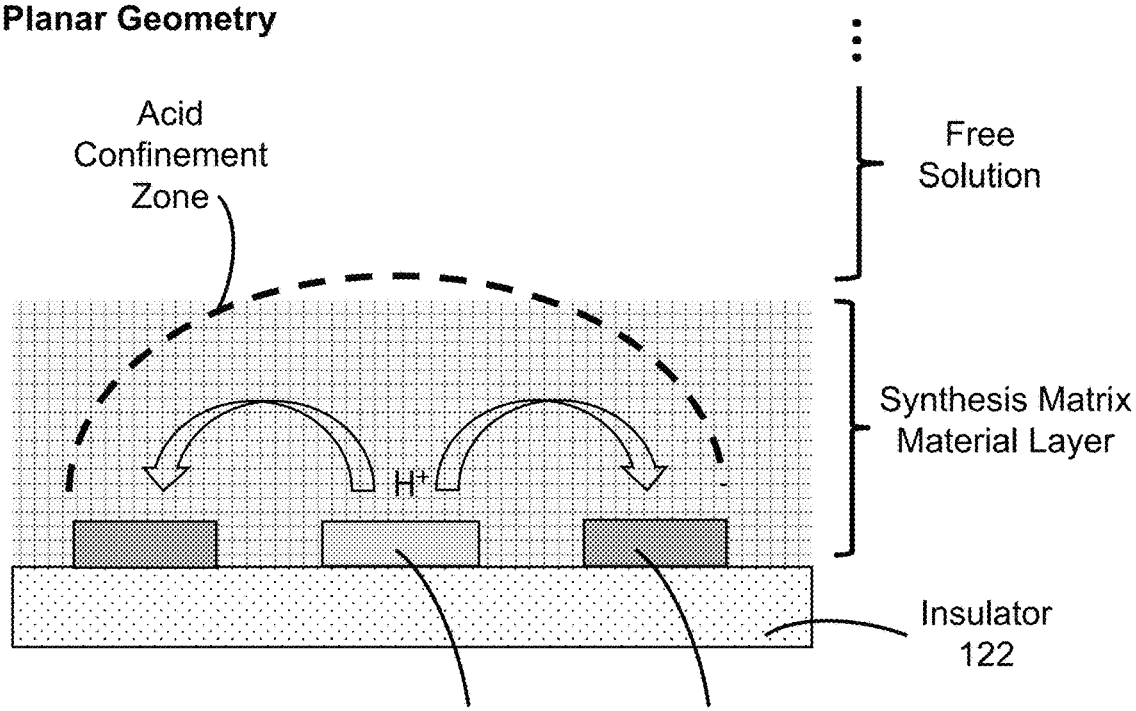
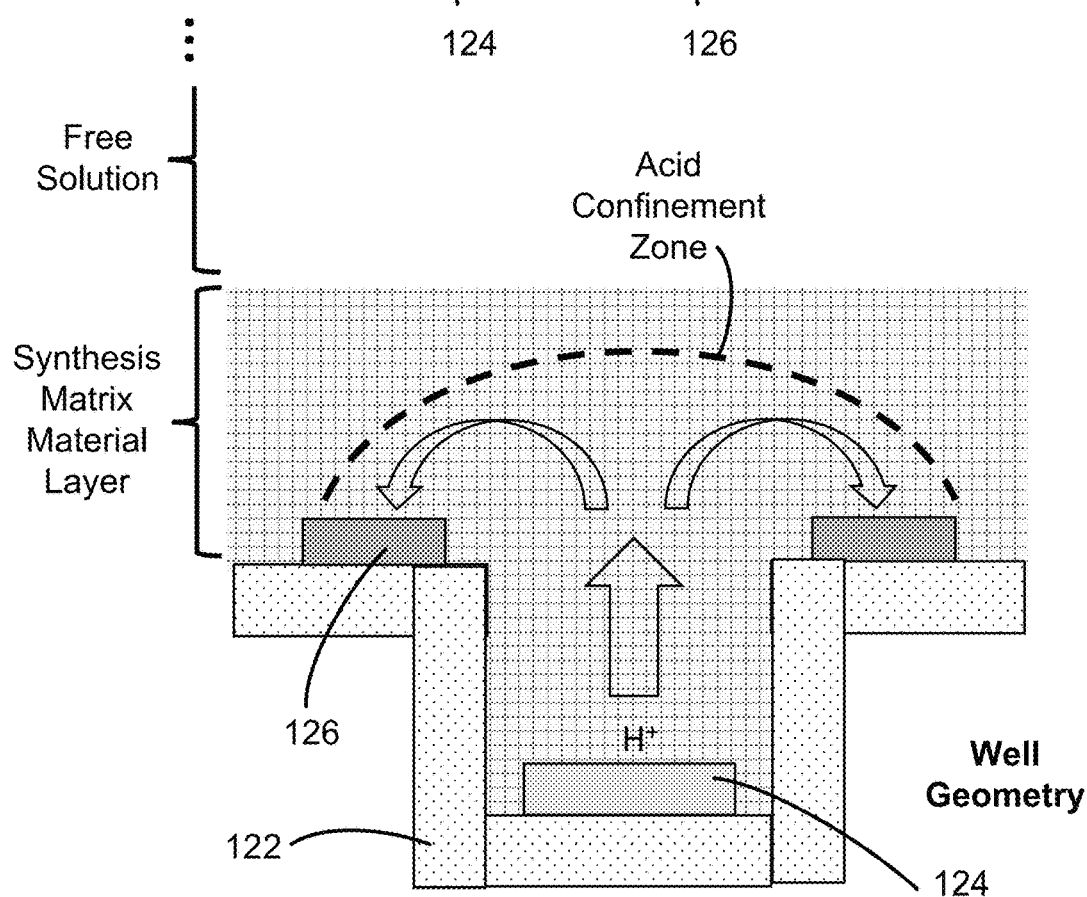
Well Geometry
FIG. 25

Acid High-Confinement Electrode Geometries (CROSS SECTIONS)
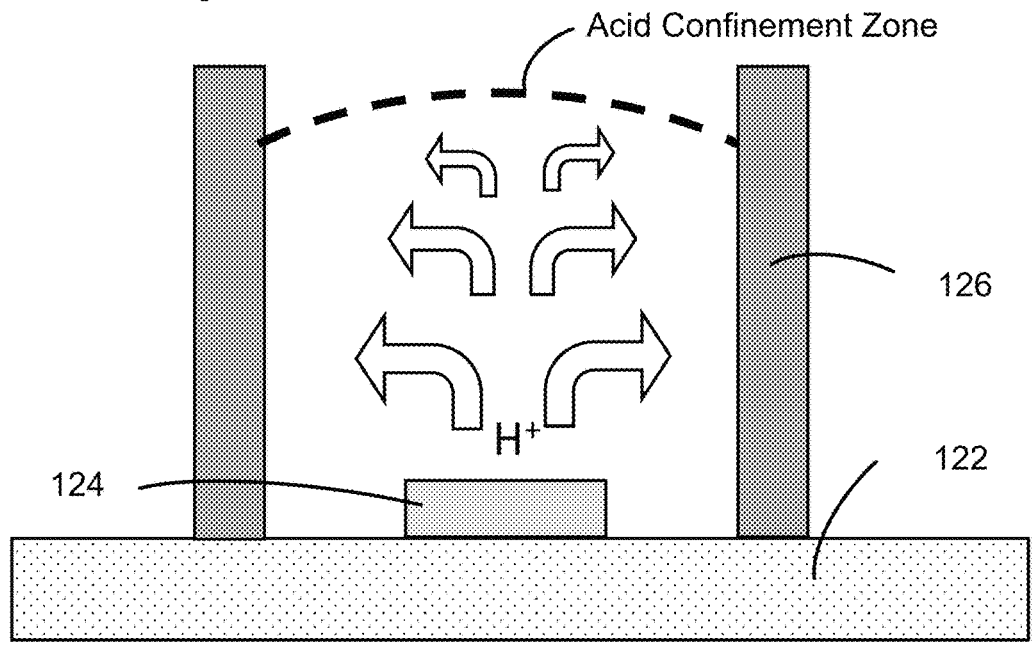
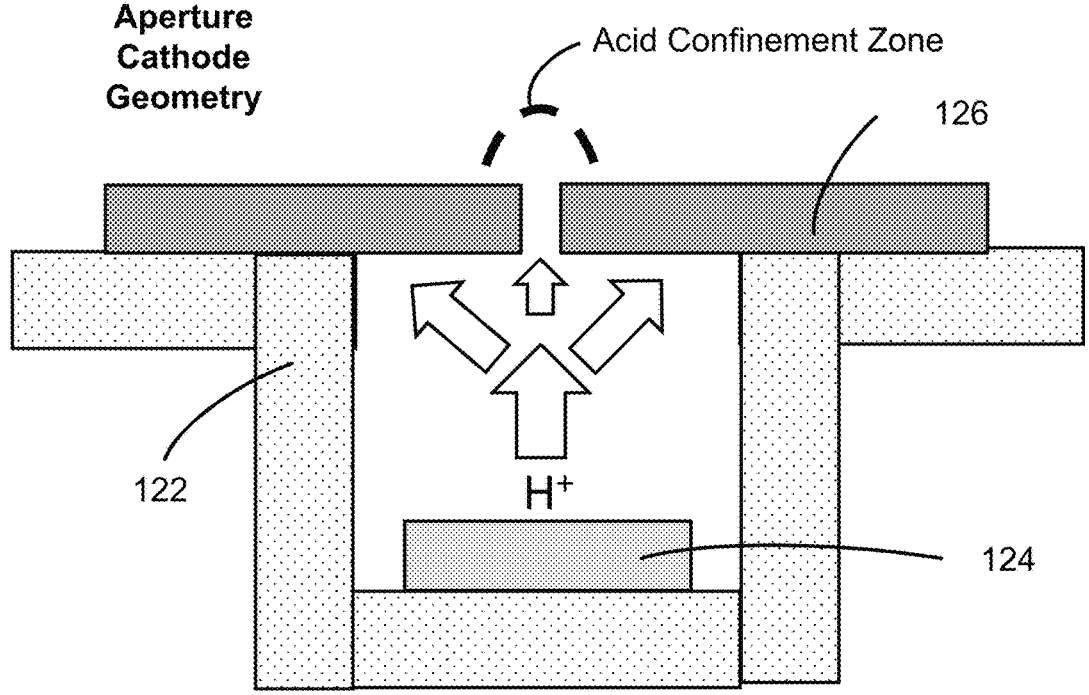
FIG. 26A

Acid High-Confinement Electrode Geometries (CROSS SECTIONS)
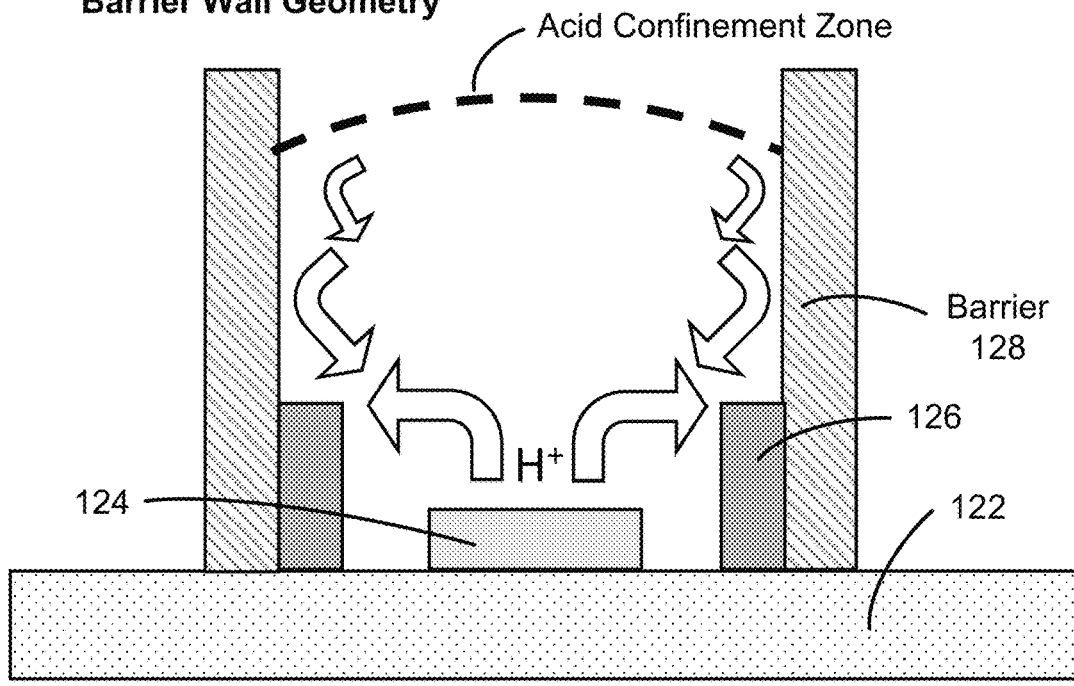
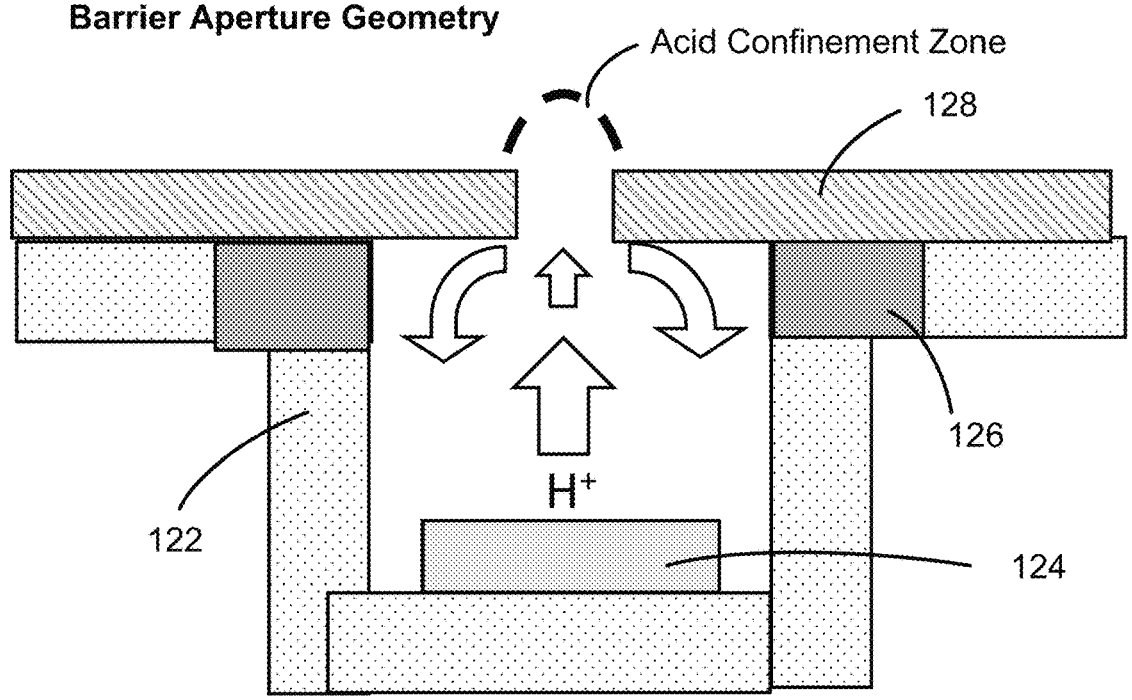
FIG. 26B

Acid Confining Electrode Geometries (CROSS SECTIONS)
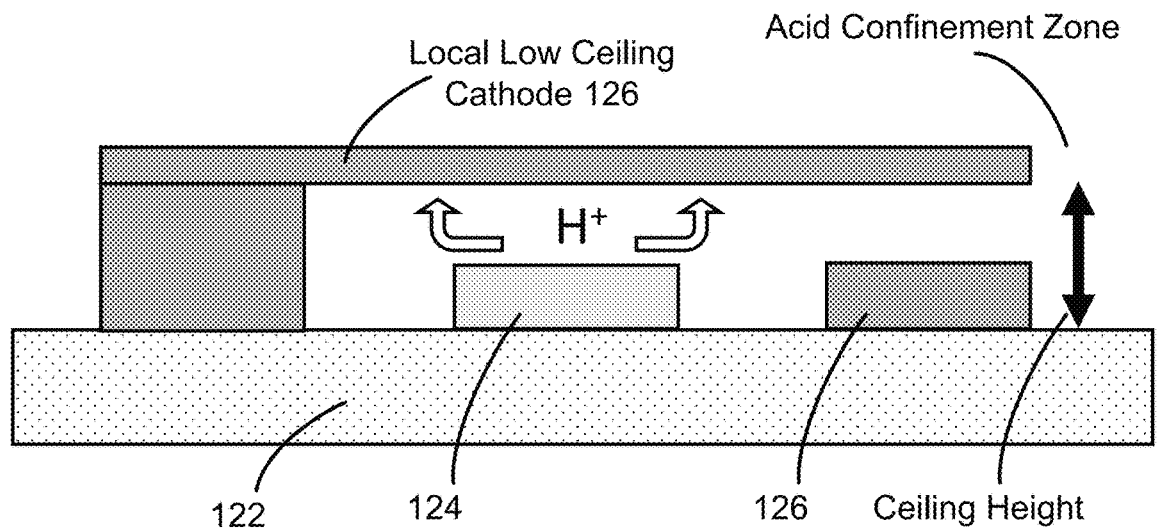
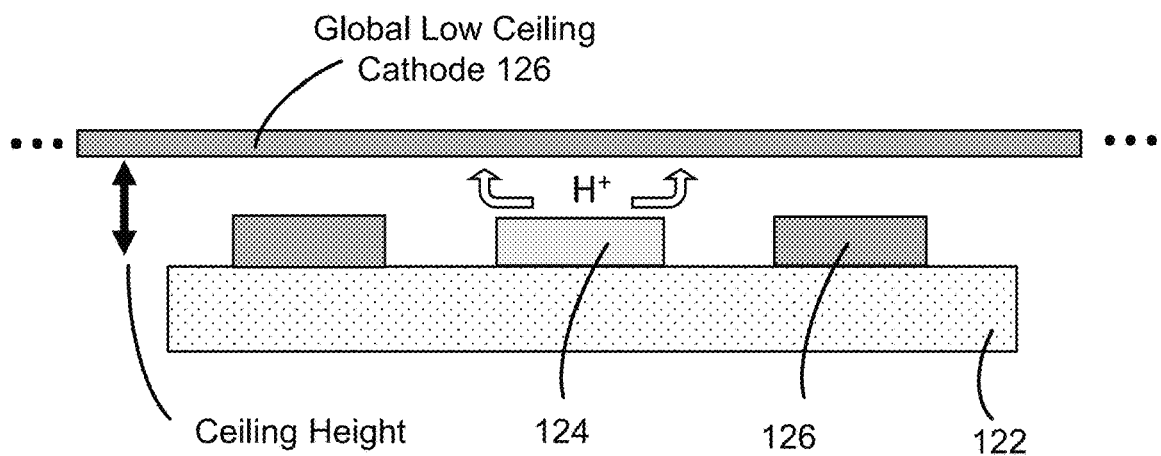
FIG. 27A

Acid Confining Electrode Geometries (CROSS SECTIONS)
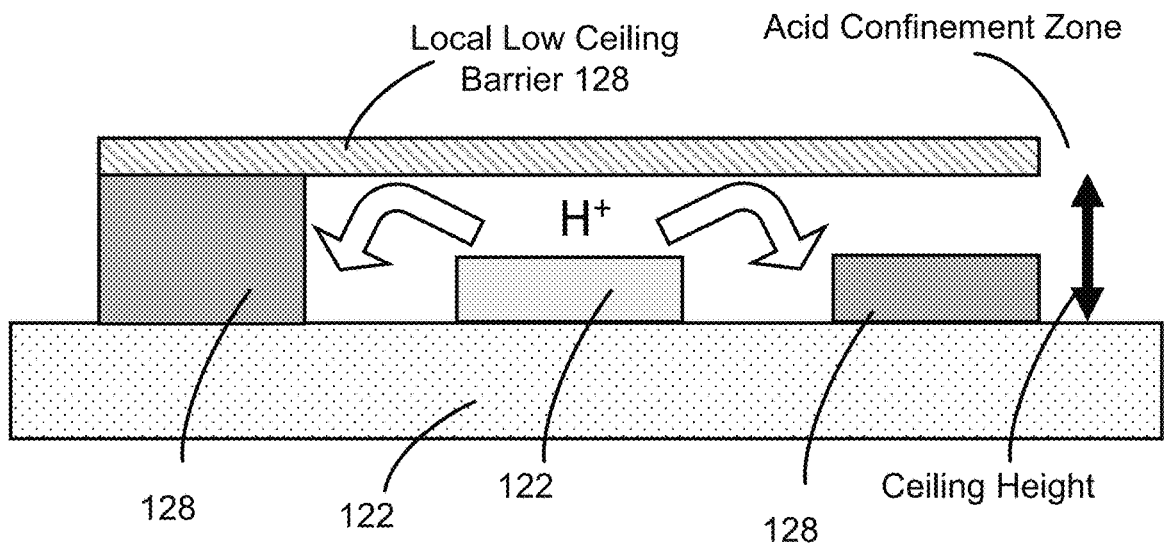
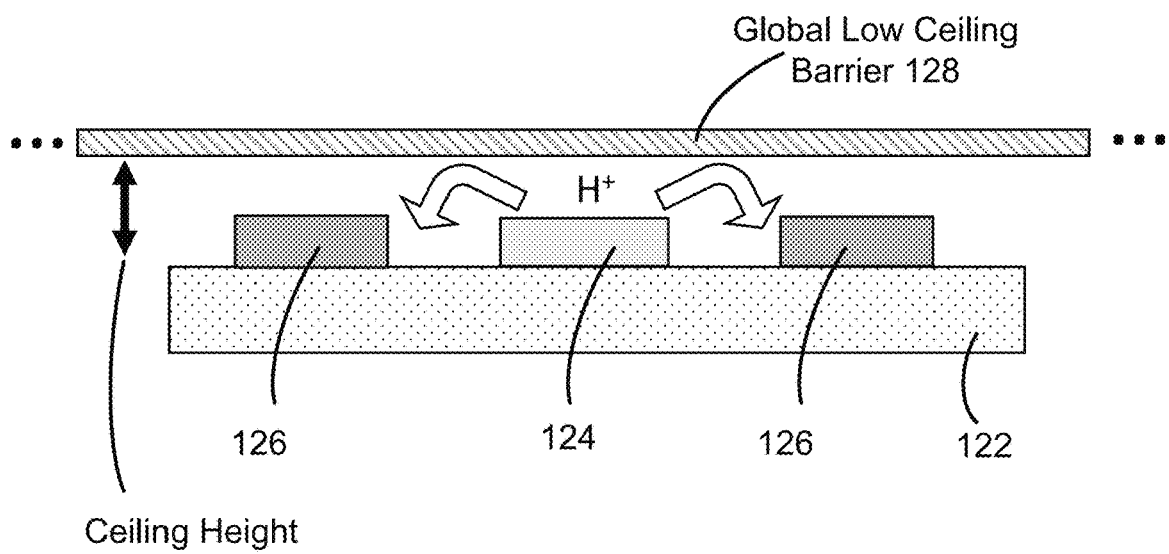
FIG. 27B

Solid State Buffer Acid Confinement (CROSS SECTIONS)
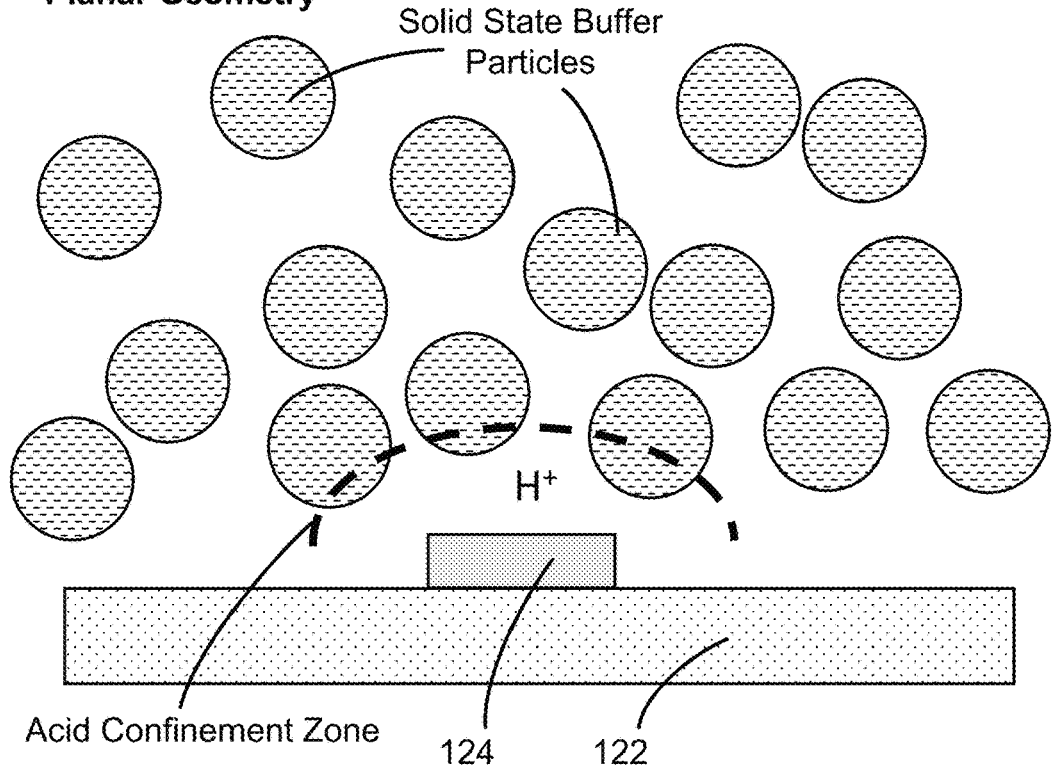
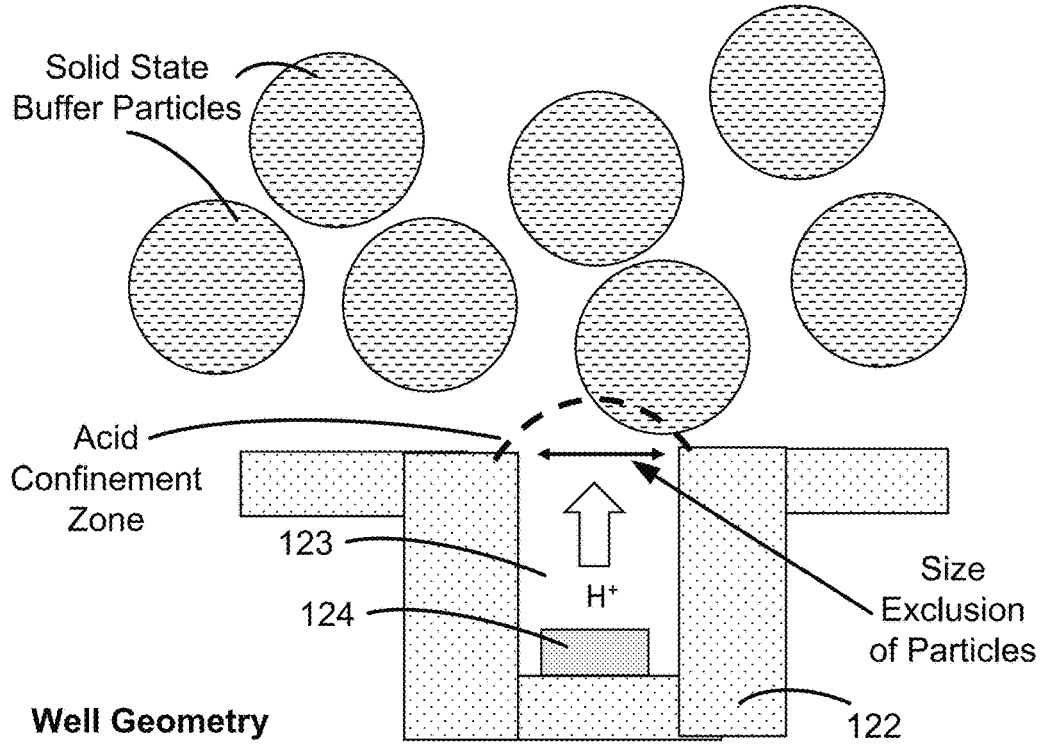
FIG. 29A

Solid State Buffer Acid Confinement (CROSS SECTIONS)
Well Geometry
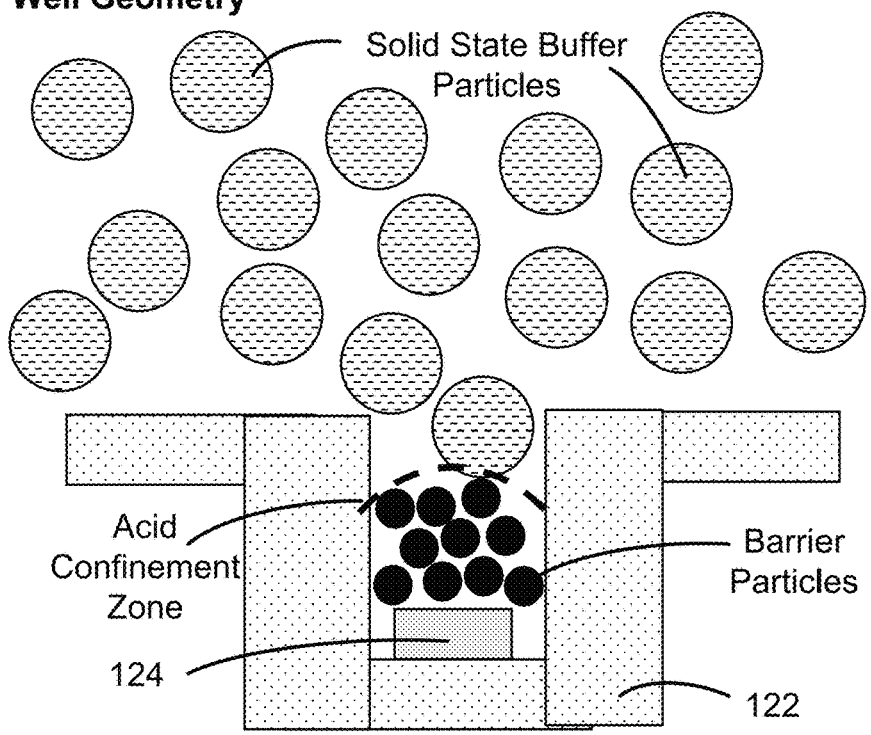
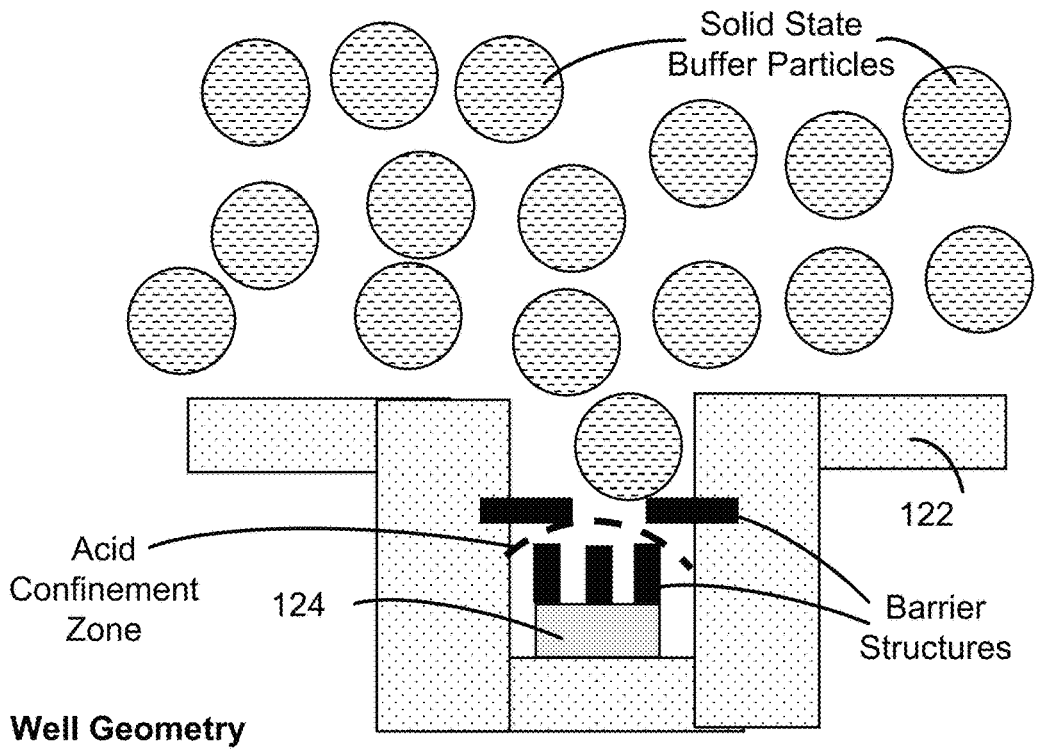
Well Geometry
FIG. 29C

Solid State Buffer Acid Confinement (CROSS SECTIONS)
Planar Geometry
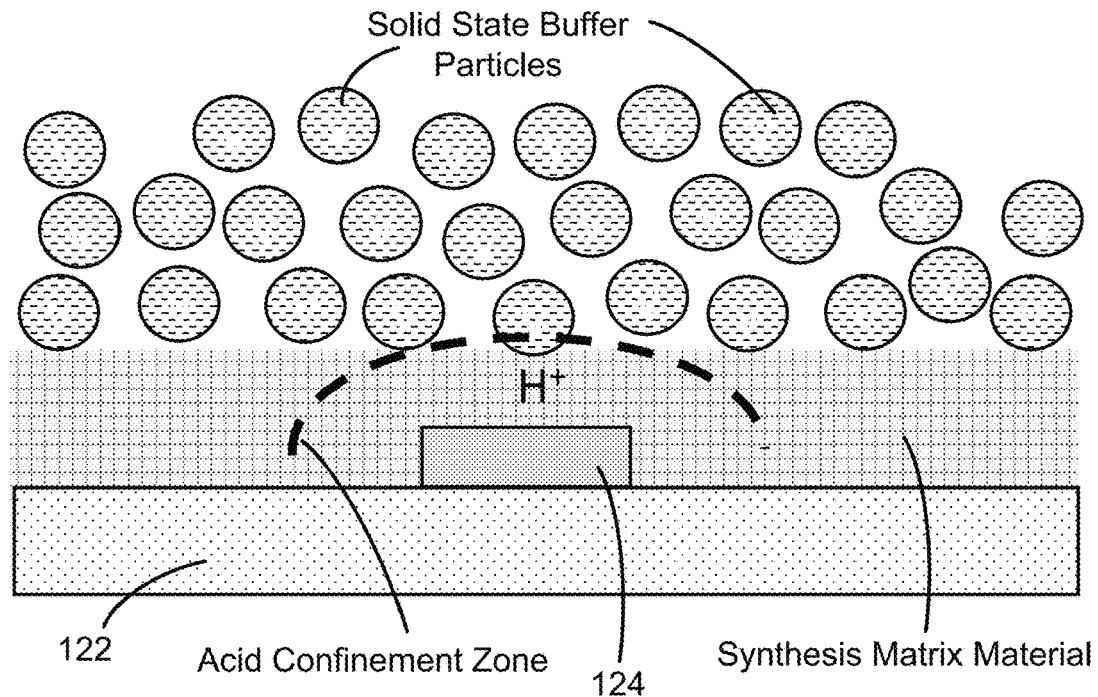
Well Geometry
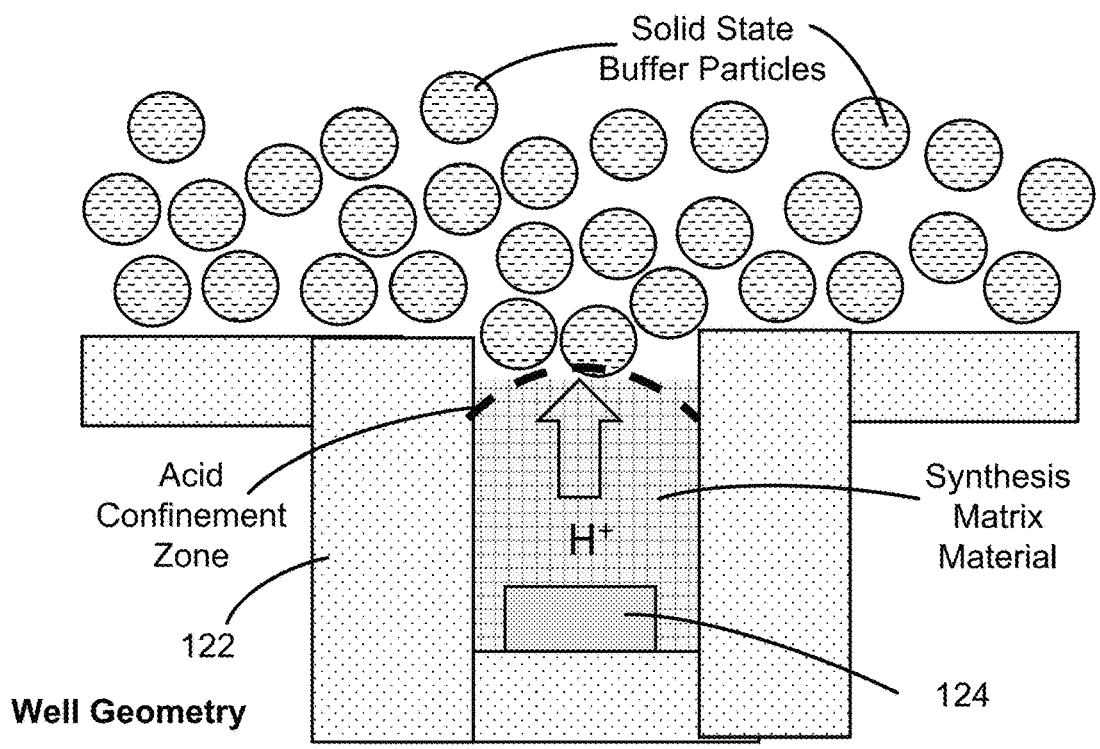
FIG. 29D

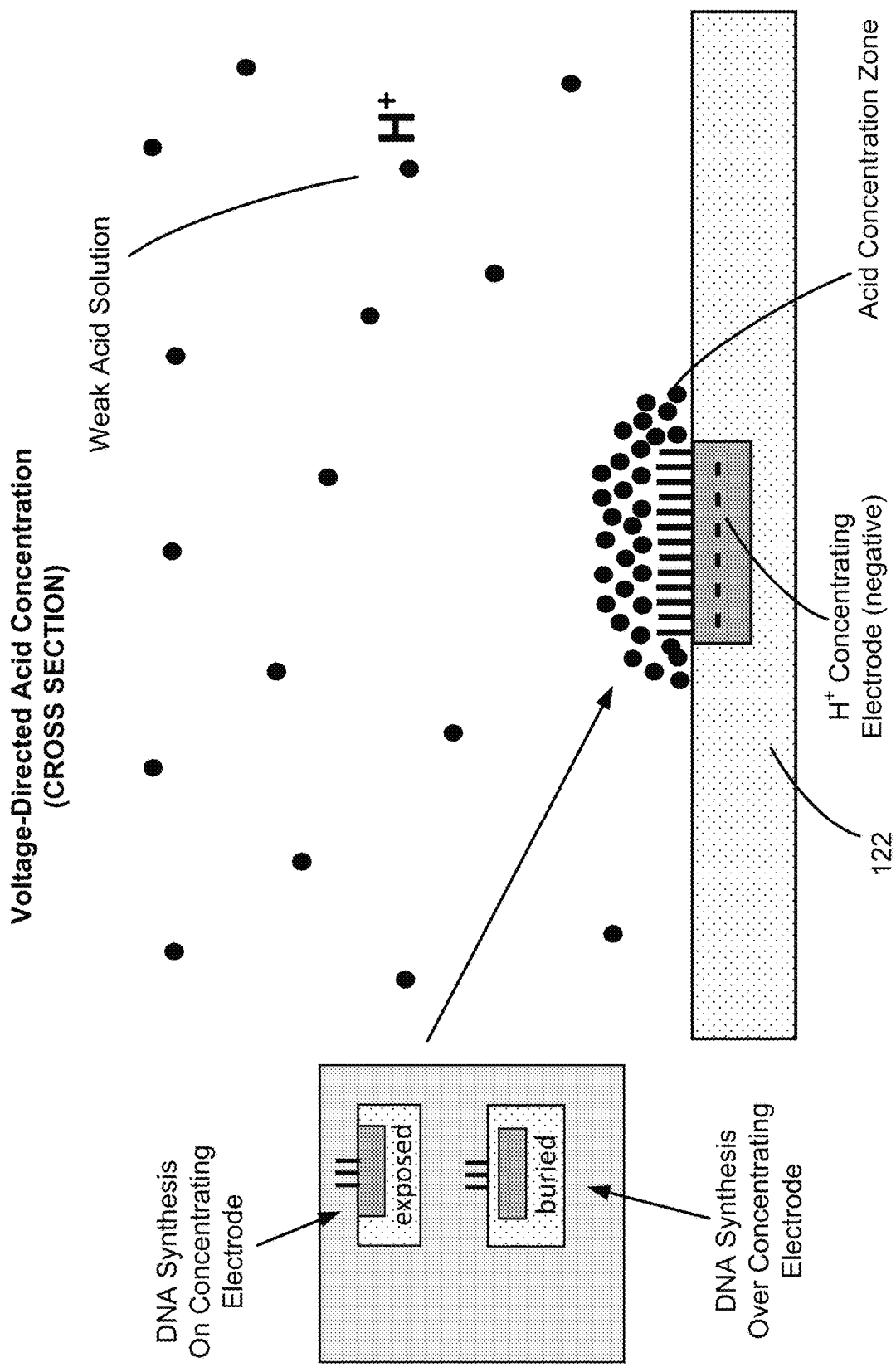

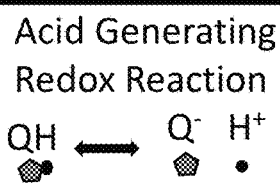
Quinone Redox Electrochemistry
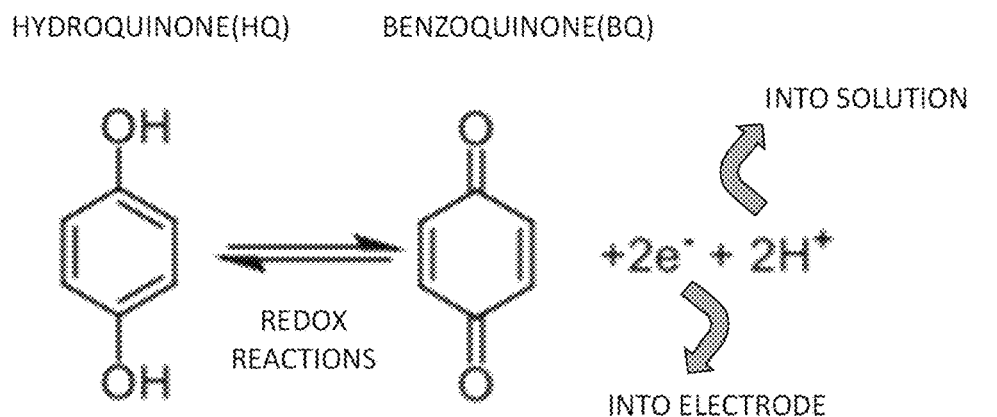
FIG. 33
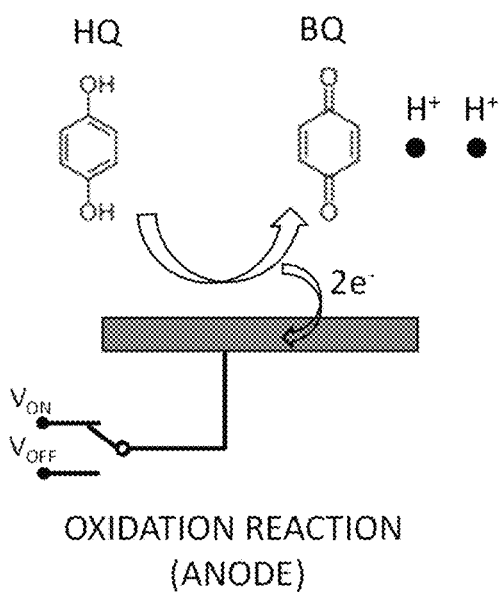
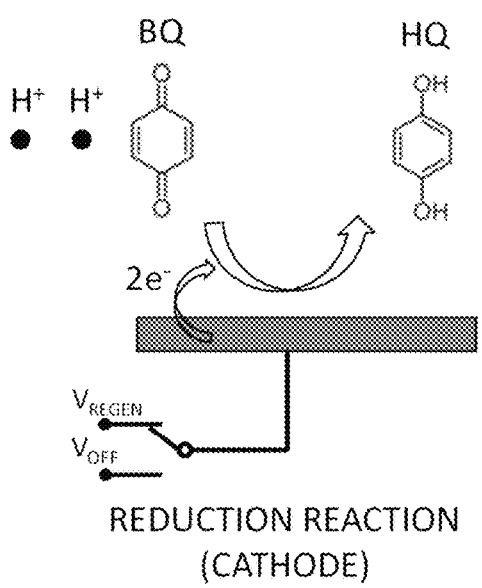
FIG. 34A

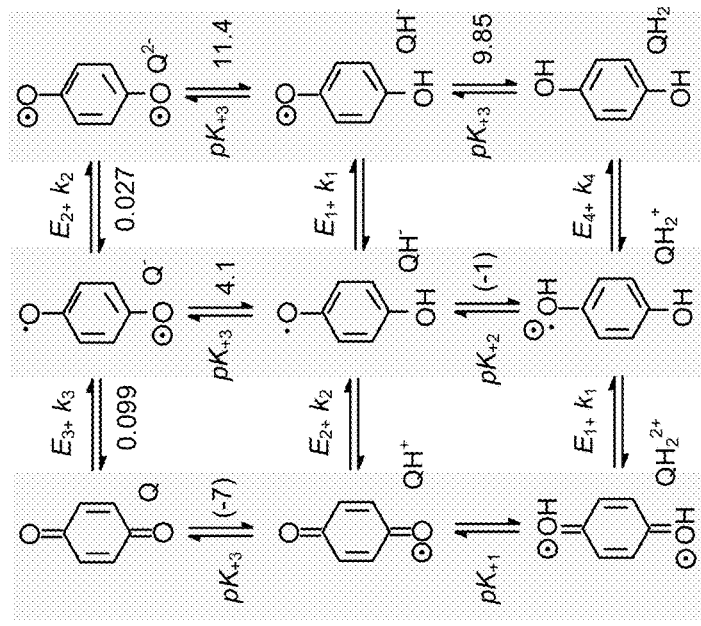
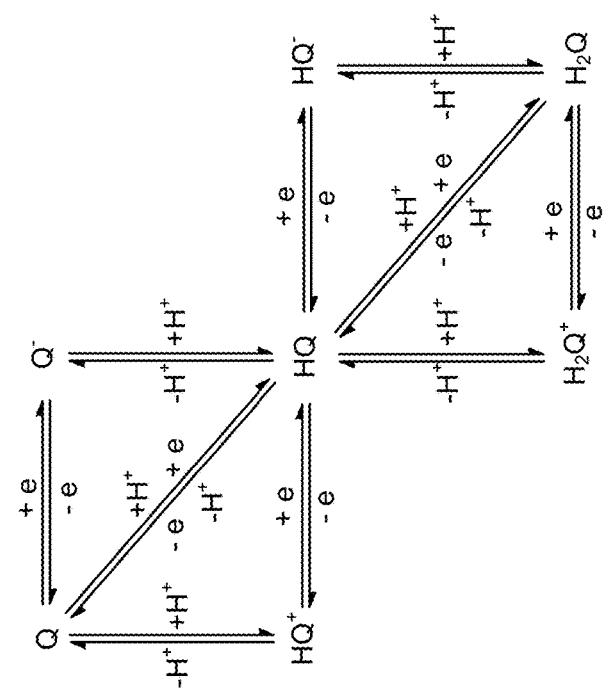
FIG. 34C

Various Quinone Redox Pairs
A 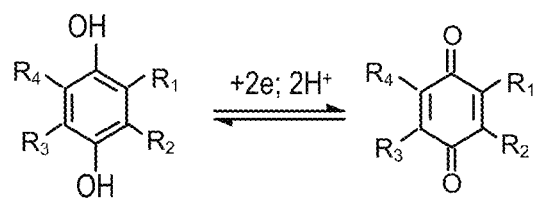
B 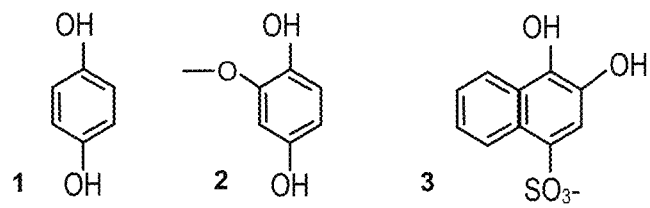
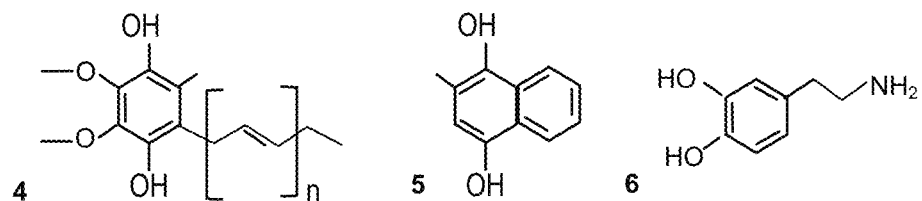
C 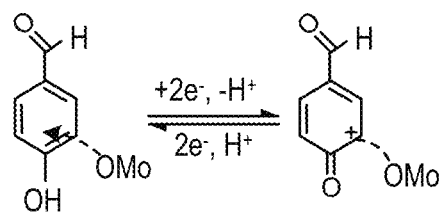
FIG. 36B

Various Carbonyl Redox Pairs
Anolyte
BP
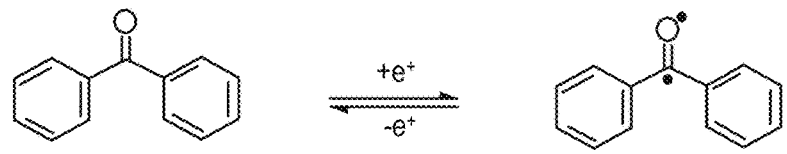
44DMBP
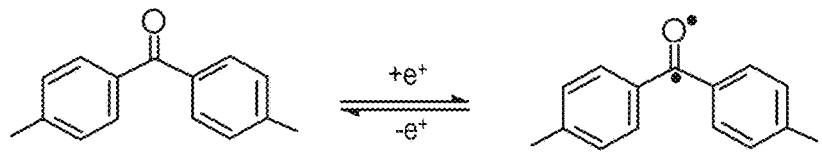
44DMOBP
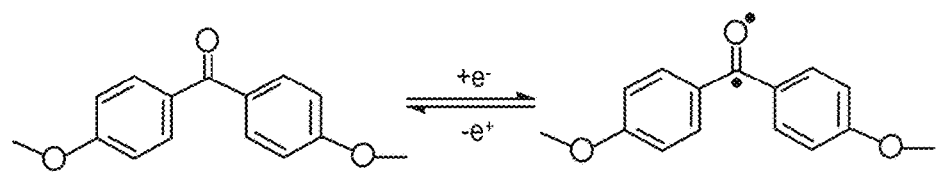
4NBP
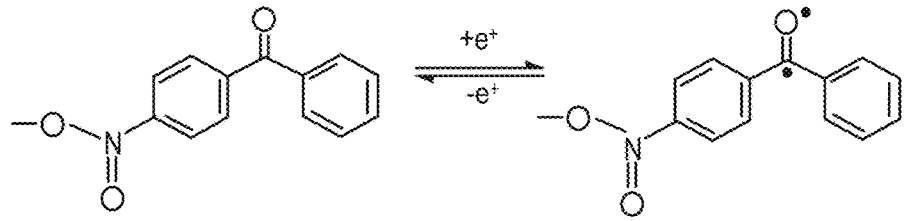
Catholyte
DBB
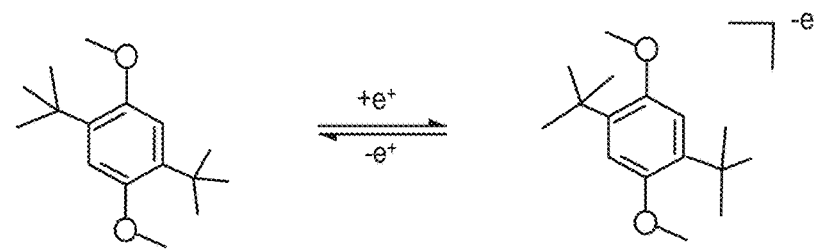
FIG. 38B

CV curves of (i) 0.01 M BP/0.01 M DBB, (ii) 0.01 M 44MBP/0.01 M DBB, (iii) 0.01 M 44MOBP/0.01 M DBB, and (iv) 0.01 M NBP/0.01 M DBB in 0.1 M TEAPF$_6$/MeCN at the scan rate of 0.5 V s$^{-1}$. Arrows mark the scan directions.

Chip from CMOS Foundry

Al Etch

Pixel Array 110 Top View

Close Up

Control System Architecture at Pixel Level

For Silanized Glass Synthesis

|  | Step | Command | Time | Reagent |
|---|---|---|---|---|
| Coupling | 1 | Pulse | 0.3 s | 250 mM DCI in acetonitrile |
|  | 2 | Wait | 0.1 s |  |
|  | 3 | Pulse | 0.3 s | 25 mM DMT-dT in acetonitrile |
|  | 4 | Wait | 0.1 s |  |
|  | 5 | Goto Step 1 (9x) |  |  |
|  | 6 | Pulse | 0.3 s | 250 mM DCI in acetonitrile |
|  | 7 | Wait | 0.1 s |  |
|  | 8 | Pulse | 0.3 s | 25 mM DMT-dT in acetonitrile |
|  | 9 | Wait | 0.1 s |  |
|  | 10 | Wait | 10 s |  |
|  | 11 | Goto Step 6 (11x) |  |  |
| Washing | 12 | Pulse | 5 s | Acetonitrile |
|  | 13 | Wait | 10 s |  |
|  | 14 | Goto Step 12 (2x) |  |  |
|  | 15 | Pulse | 5 s | Argon |
|  | 16 | Wait | 10 s |  |
| Oxidation | 17 | Pulse | 5 s | Oxidizer |
|  | 18 | Pulse | 0.3 s | Oxidizer |
|  | 19 | Wait | 10 s |  |
|  | 20 | Goto Step 18 (5x) |  |  |
| Washing | 21 | Pulse | 5 s | Acetonitrile |
|  | 22 | Wait | 10 s |  |
|  | 23 | Goto Step 21 (2x) |  |  |
|  | 24 | Pulse | 5 s | Argon |
|  | 25 | Wait | 10 s |  |
| Deblocking | 26 | Pulse | 5 s | 3% DCA/toluene |
|  | 27 | Pulse | 0.3 s | 3% DCA/toluene |
|  | 28 | Wait 20 s |  |  |
|  | 29 | Goto Step 27 (8x) |  |  |
| Washing | 30 | Pulse | 5 s | Acetonitrile |
|  | 31 | Wait | 10 s |  |
|  | 32 | Goto Step 30 (2x) |  |  |
|  | 33 | Pulse | 5 s | Argon |
|  | 34 | Wait | 10 s |  |

FIG. 81

For Electrochemical Deprotection

| | Step | Command | Time | Reagent |
|---|---|---|---|---|
| Coupling | 1 | Pulse | 0.3 s | 250 mM DCI in acetonitrile |
| | 2 | Wait | 0.1 s | |
| | 3 | Pulse | 0.3 s | 25 mM DMT-dT in acetonitrile |
| | 4 | Wait | 0.1 s | |
| | 5 | Goto Step 1 (9x) | | |
| | 6 | Pulse | 0.3 s | 250 mM DCI in acetonitrile |
| | 7 | Wait | 0.1 s | |
| | 8 | Pulse | 0.3 s | 25 mM DMT-dT in acetonitrile |
| | 9 | Wait | 0.1 s | |
| | 10 | Wait | 10 s | |
| | 11 | Goto Step 6 (11x) | | |
| Washing | 12 | Pulse | 5 s | Acetonitrile |
| | 13 | Wait | 30 s | |
| | 14 | Goto Step 12 (2x) | | |
| | 15 | Pulse | 5 s | Argon |
| | 16 | Wait | 10 s | |
| Oxidation | 17 | Pulse | 5 s | Oxidizer |
| | 18 | Pulse | 0.3 s | Oxidizer |
| | 19 | Wait | 10 s | |
| | 20 | Goto Step 18 (5x) | | |
| Washing | 21 | Pulse | 5 s | Acetonitrile |
| | 22 | Wait | 30 s | |
| | 23 | Goto Step 21 (2x) | | |
| | 24 | Pulse | 5 s | Argon |
| | 25 | Wait | 10 s | |
| Deblocking | 26 | Pulse | 5 s | 10 mM HQ/BQ in acetonitrile, 100 mM TBAP |
| | 27 | Apply 2 V | | 10 mM HQ/BQ in acetonitrile, 100 mM TBAP |
| | 28 | Wait | 900 s | |
| Washing | 29 | Pulse | 5 s | Acetonitrile |
| | 30 | Wait | 30 s | |
| | 31 | Goto Step 29 (2x) | | |
| | 32 | Pulse | 5 s | Argon |
| | 33 | Wait | 10 s | |

FIG. 83

For Producing a 15-mer

| | Step | Command | Time | Reagent |
|---|---|---|---|---|
| Coupling | 1 | Pulse | 0.3 s | 250 mM DCI in acetonitrile |
| | 2 | Wait | 0.1 s | |
| | 3 | Pulse | 0.3 s | 25 mM DMT-dT in acetonitrile |
| | 4 | Wait | 0.1 s | |
| | 5 | Goto Step 1 (9x) | | |
| | 6 | Pulse | 0.3 s | 250 mM DCI in acetonitrile |
| | 7 | Wait | 0.1 s | |
| | 8 | Pulse | 0.3 s | 25 mM DMT-dT in acetonitrile |
| | 9 | Wait | 0.1 s | |
| | 10 | Wait | 10 s | |
| | 11 | Goto Step 6 (11x) | | |
| Washing | 12 | Pulse | 5 s | Acetonitrile |
| | 13 | Wait | 10 s | |
| | 14 | Goto Step 12 (2x) | | |
| | 15 | Pulse | 5 s | Argon |
| | 16 | Wait | 10 s | |
| Oxidation | 17 | Pulse | 5 s | Oxidizer |
| | 18 | Pulse | 0.3 s | Oxidizer |
| | 19 | Wait | 10 s | |
| | 20 | Goto Step 18 (5x) | | |
| Washing | 21 | Pulse | 5 s | Acetonitrile |
| | 22 | Wait | 10 s | |
| | 23 | Goto Step 21 (2x) | | |
| | 24 | Pulse | 5 s | Argon |
| | 25 | Wait | 10 s | |
| Deblocking | 26 | Pulse | 5 s | 40 mM HQ/BQ in acetonitrile, 100 mM TBAP |
| | 27 | Wait | 30 s | |
| | 28 | Apply 1.85 V | | 40 mM HQ/BQ in acetonitrile, 100 mM TBAP |
| | 29 | Wait | 360 s | |
| | 30 | Set V to 0 | | |
| Washing | 31 | Pulse | 5 s | Acetonitrile |
| | 32 | Wait | 30 s | |
| | 33 | Goto Step 31 (2x) | | |
| | 34 | Pulse | 5 s | Argon |
| | 35 | Wait | 10 s | |

FIG. 87

Bank 1

Bank 3

SEMICONDUCTOR CHIP DEVICES AND METHODS FOR POLYNUCLEOTIDE SYNTHESIS

CROSS-REFERENCE TO RELATED APPLICATIONS

This application is a continuation of PCT Application Serial No. PCT/US2022/018189 filed on Feb. 28, 2022 and entitled "Semiconductor Chip Devices and Methods for Polynucleotide Synthesis." PCT/US2022/018189 claims priority to and benefit of U.S. Provisional Patent Application No. 63/154,343 filed on Feb. 26, 2021 and entitled "Semiconductor Chip Devices for DNA Synthesis and DNA Digital Data Storage Systems." The disclosure of each the foregoing applications is incorporated herein by reference in its entirety, including but not limited to those portions that specifically appear hereinafter, but except for any subject matter disclaimers or disavowals, and except to the extent that the incorporated material is inconsistent with the express disclosure herein, in which case the language in this disclosure shall control.

TECHNICAL FIELD

This disclosure is in the field of semiconductor chip devices, and in particular in the field of Complementary Metal Oxide Semiconductor (CMOS) chip devices. This disclosure is also in the field of polynucleotide synthesis chemistry. This disclosure is also in the area of digital data storage. In particular, this disclosure describes CMOS chip devices for the synthesis of polynucleotides such as deoxyribonucleic acid (DNA), and methods for using these, such as to store digital data.

SUMMARY

Systems and methods for polynucleotide synthesis are disclosed. In an exemplary embodiment, a polynucleotide synthesis system comprises a first substrate having a solution applied thereto; a first electrode coupled to the first substrate and operable as an anode to drive electrochemical acid generation in the solution; and a polynucleotide synthesis region functionalized to anchor and support polynucleotide synthesis through the addition of phosphoramidites.

The polynucleotide synthesis system may further comprise control circuitry operable to controllably apply and remove a first potential at the first electrode. The polynucleotide synthesis system may further comprise a second electrode coupled to the first substrate and operable as a cathode to absorb acid from the solution. The polynucleotide synthesis region may be located between the first electrode and the second electrode. The first electrode and second electrode may be planar, and the second electrode may surround the first electrode when viewed perpendicular to the first substrate. The first electrode and the second electrode may be interdigitated. The polynucleotide synthesis system may further comprise a plurality of first electrodes configured as an array. The second electrode may surround each of the plurality of first electrodes in the array such that the second electrode separates each first electrode in the plurality of first electrodes from all other first electrodes in the plurality of first electrodes. The solution may comprise a reversible redox pair comprising hydroquinone and tetrachloro-1,4-benzoquinone. The solution may comprise a reversible redox pair configured with a redox potential lower than 1.2 volts. The polynucleotide synthesis system may further comprise a second substrate advanceable toward and retractable from the first substrate, the second substrate comprising a protrusion extending from the second substrate, the polynucleotide synthesis region being located on the protrusion, and the first substrate comprising a well corresponding to the protrusion such that, when the second substrate is advanced toward the first substrate, at least a portion of the protrusion at least partially enters the well. The first substrate may comprise a well, and the first electrode may be disposed at a bottom of the well. The second electrode may be disposed at least one of (i) on a side of the well, (ii) on a rim of the well, or (iii) at least partially overhanging a rim of the well. At least a portion of the second electrode may extend over the first electrode with a gap therebetween occupied by the solution, forming a ceiling over the first electrode. At least a portion of the second electrode may extend from the first substrate to a height greater than a height of the first electrode to form a wall to at least partially contain acid generated at the first electrode. The substrate and the first electrode may comprise portions of a complementary metal oxide semiconductor (CMOS) chip fabricated on a node of 65 nm or below. The solution may comprise a plurality of solid state buffer particles.

In another exemplary embodiment, a polynucleotide synthesis system, comprises a first substrate having a solution applied thereto; an electrode coupled to the first substrate; and a polynucleotide synthesis region functionalized to anchor and support polynucleotide synthesis through the addition of phosphoramidites. The electrode is operable to drive acid concentration or acid shielding in the solution around the polynucleotide synthesis region.

In another exemplary embodiment, a method for synthesizing polynucleotides on a complementary metal oxide semiconductor (CMOS) chip comprises identifying a target polynucleotide sequence to be synthesized; providing, on or adjacent to a first electrode coupled to a substrate, a polynucleotide synthesis region functionalized to anchor and support polynucleotide synthesis through addition of phosphoramidites; applying a solution for electrochemical deprotection of polynucleotides to the electrode; applying a voltage to the electrode to drive acid generation for deprotection; and providing a desired monomer in the solution, followed by a step of backbone oxidation.

The CMOS chip may comprise a plurality of first electrodes configured as an array of synthesis pixels, and the pitch of each synthesis pixel may be 30 microns or smaller. The target polynucleotide sequence may represent at least a portion of an error correcting encoding of a digital data set.

The contents of this section are intended as a simplified introduction to the disclosure and are not intended to limit the scope of any claim. The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain exemplary principles of the disclosure.

FIGS. 2A and 2B illustrate the phosphoramidite method for the chemical synthesis of DNA;

FIG. 19B illustrates interdigitated electrode geometries for acid confinement, in the form of dithering of anode and cathode elements, in accordance with various exemplary embodiments;

FIG. 20 illustrates use of well-based electrode geometries for acid confinement, in accordance with various exemplary embodiments;

FIG. 22 illustrates use of interdigitated electrode geometries in well-based acid confinement, in accordance with various exemplary embodiments;

FIG. 23 illustrates use of rough surfaces to increase the area surface available on electrodes or in synthesis areas, without increasing overall 2D footprint, in accordance with various exemplary embodiments;

FIG. 24A illustrates use of perpendicular structures to increase the surface area available on electrodes or in synthesis areas, without increasing overall 2D footprint, in accordance with various exemplary embodiments

FIG. 25 illustrates use of a 3D material matrix for synthesis, with acid confinement defining the synthesis zones in 3D, to increase the areal density of DNA synthesis, in accordance with various exemplary embodiments;

FIG. 26A illustrates exemplary high-confinement electrode geometries, in accordance with various exemplary embodiments;

FIG. 26B illustrates exemplary high-confinement geometries using barrier materials, in accordance with various exemplary embodiments;

FIG. 27A illustrates use of a low-ceiling electrode for acid confinement, in accordance with various exemplary embodiments;

FIG. 27B illustrates use of a low-ceiling barrier for acid confinement, in accordance with various exemplary embodiments;

FIG. 29A illustrates use of solid-phase buffer particles for acid confinement in both planar and well geometries, in accordance with various exemplary embodiments;

FIG. 29C illustrates the use of in-well barriers for the creation of buffer-inaccessible zones for DNA synthesis, when using solid-state buffer particles for acid confinement within wells, and with buffer particles smaller than the well diameter, in accordance with various exemplary embodiments;

FIG. 29D illustrates use of a synthesis matrix material with solid-state buffer particles to create a buffer free zone for synthesis, when using solid-state buffer particles for acid confinement, in accordance with various exemplary embodiments;

FIG. 30 illustrates using voltage to drive acid concentration near a synthesis site, in accordance with various exemplary embodiments;

FIG. 33 illustrates principles of quinone redox chemistry for electrochemical acid generation and acid removal, in accordance with various exemplary embodiments;

FIG. 34A illustrates how hydroquinone electrochemistry may be used to generate and absorb acid at electrodes, in accordance with various exemplary embodiments;

FIG. 34C illustrates detailed redox reaction mechanism of hydroquinone (HQ)—benzoquinone (BQ) electrochemical reactions, as they occur in aqueous and non-aqueous solvents, in accordance with various exemplary embodiments;

FIG. 36B illustrates various quinone redox pairs that may be used for electrochemical acid generation, in accordance with various exemplary embodiments;

FIGS. 38B and 38C illustrate representative carbonyl redox pairs that may be used for electrochemical acid generation, in accordance with various exemplary embodiments;

FIG. 81 illustrates a protocol for DNA synthesis on glass slides, in accordance with various exemplary embodiments;

FIG. 83 illustrates a protocol for electrochemical DNA synthesis on chip, in accordance with various exemplary embodiments;

FIG. 87 illustrates a protocol for electrochemical DNA synthesis on chip, for producing a 15-mer, in accordance with various exemplary embodiments;

FIG. 88 illustrates results demonstrating electrochemical DNA synthesis of a 15-mer at one isolated pixel on a CMOS chip device, in accordance with various exemplary embodiments;

FIG. 89 illustrates a scanning electron microscope (SEM) image of an array of synthesis pixels on a CMOS chip device, in accordance with various exemplary embodiments;

FIG. 90 illustrates a SEM image of an array of synthesis pixels on a CMOS chip device, in accordance with various exemplary embodiments;

FIG. 91A illustrates a SEM image of an array of synthesis pixels on a CMOS chip device, in accordance with various exemplary embodiments;

FIG. 91B illustrates a SEM image of a synthesis pixel of a CMOS chip device, in accordance with various exemplary embodiments;

FIG. 91C illustrates an optical microscope image of synthesis pixels of a CMOS chip device, in accordance with various exemplary embodiments;

FIG. 92 illustrates a schematic and optical microscope image of a 3×3 array of exemplary synthesis pixels, in accordance with various exemplary embodiments;

FIG. 93 illustrates operation of an exemplary CMOS synthesis chip to produce a 100-mer, in accordance with various exemplary embodiments;

Figure 94:
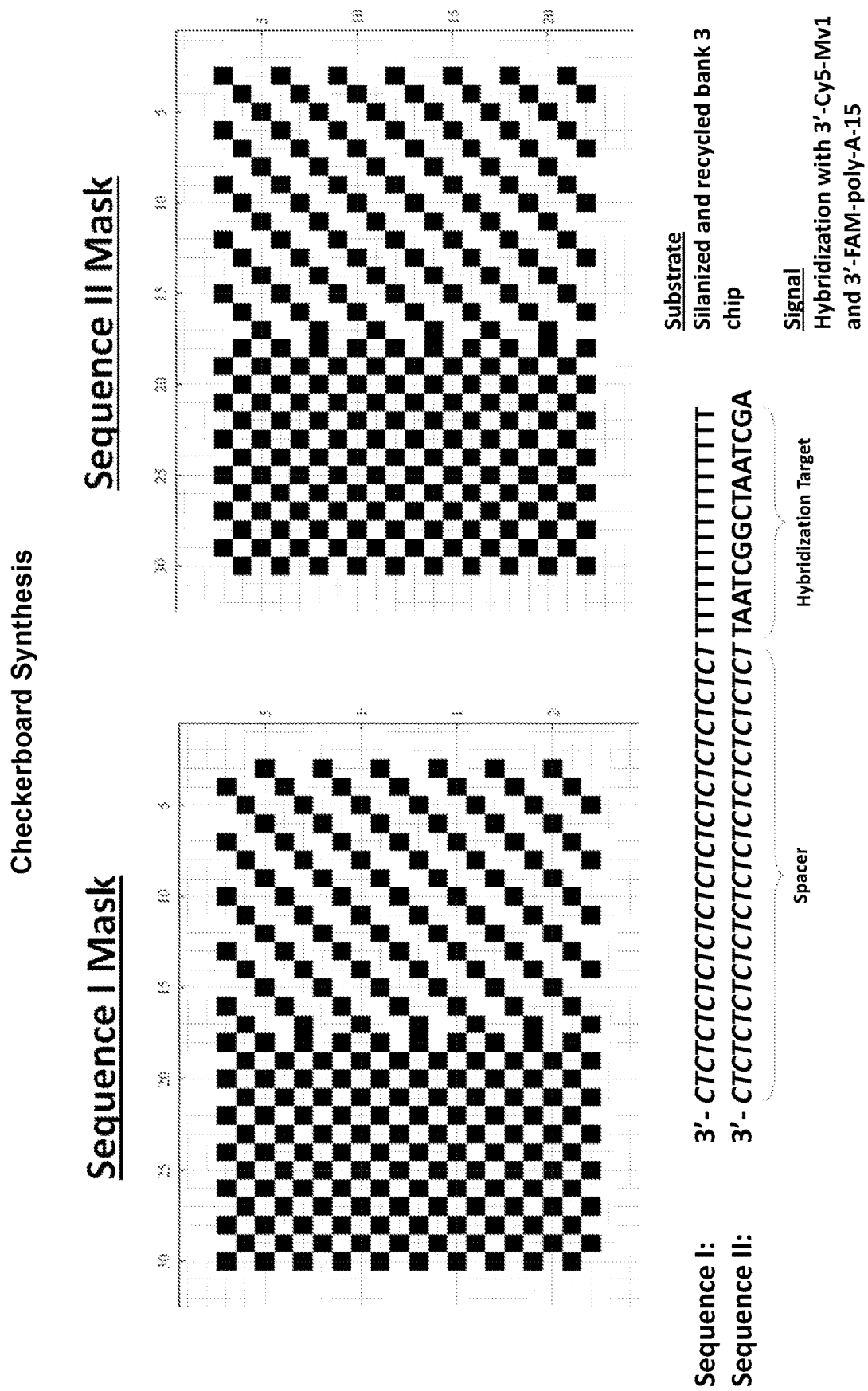
Figure 95:
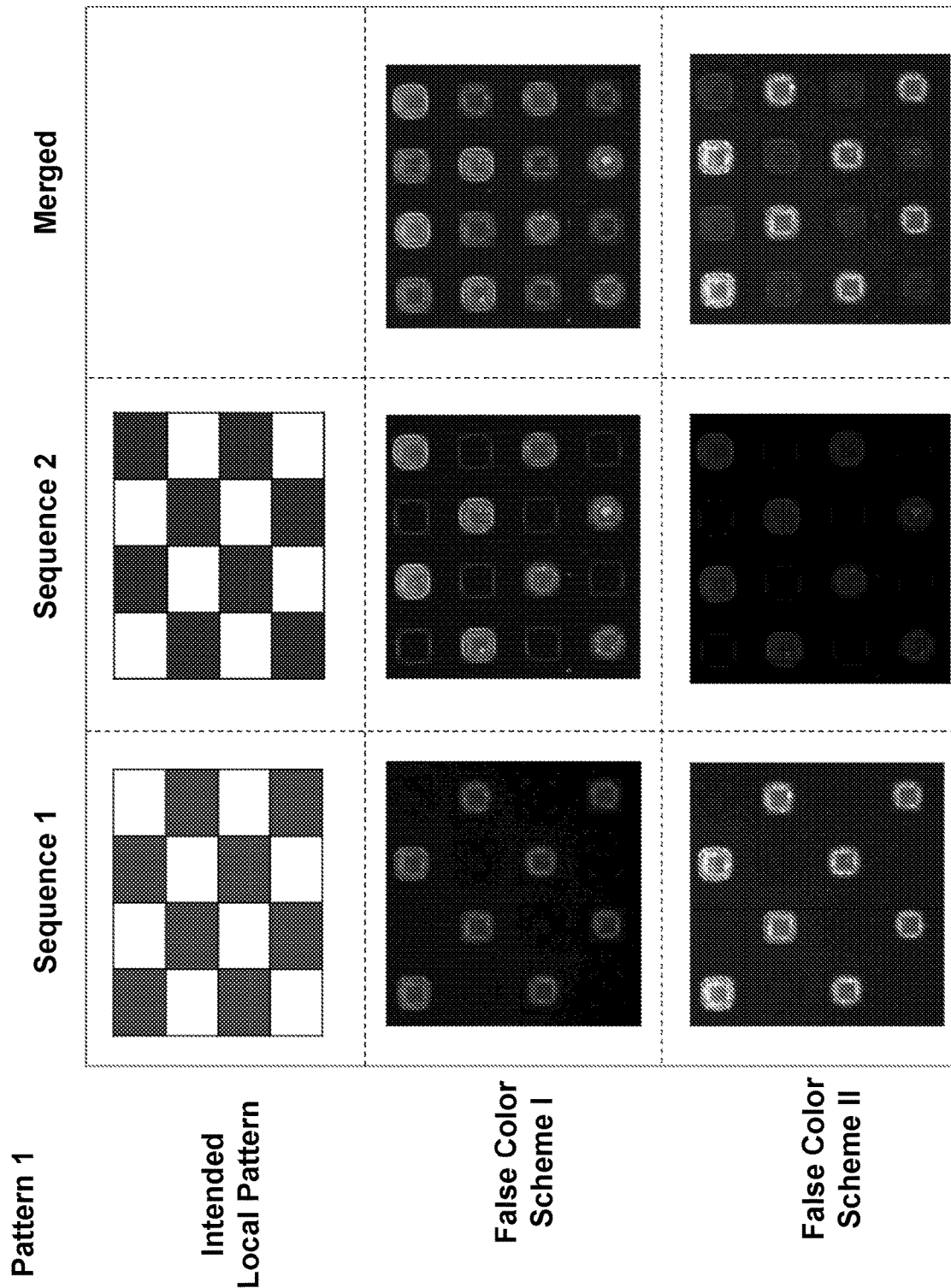
Figure 96:
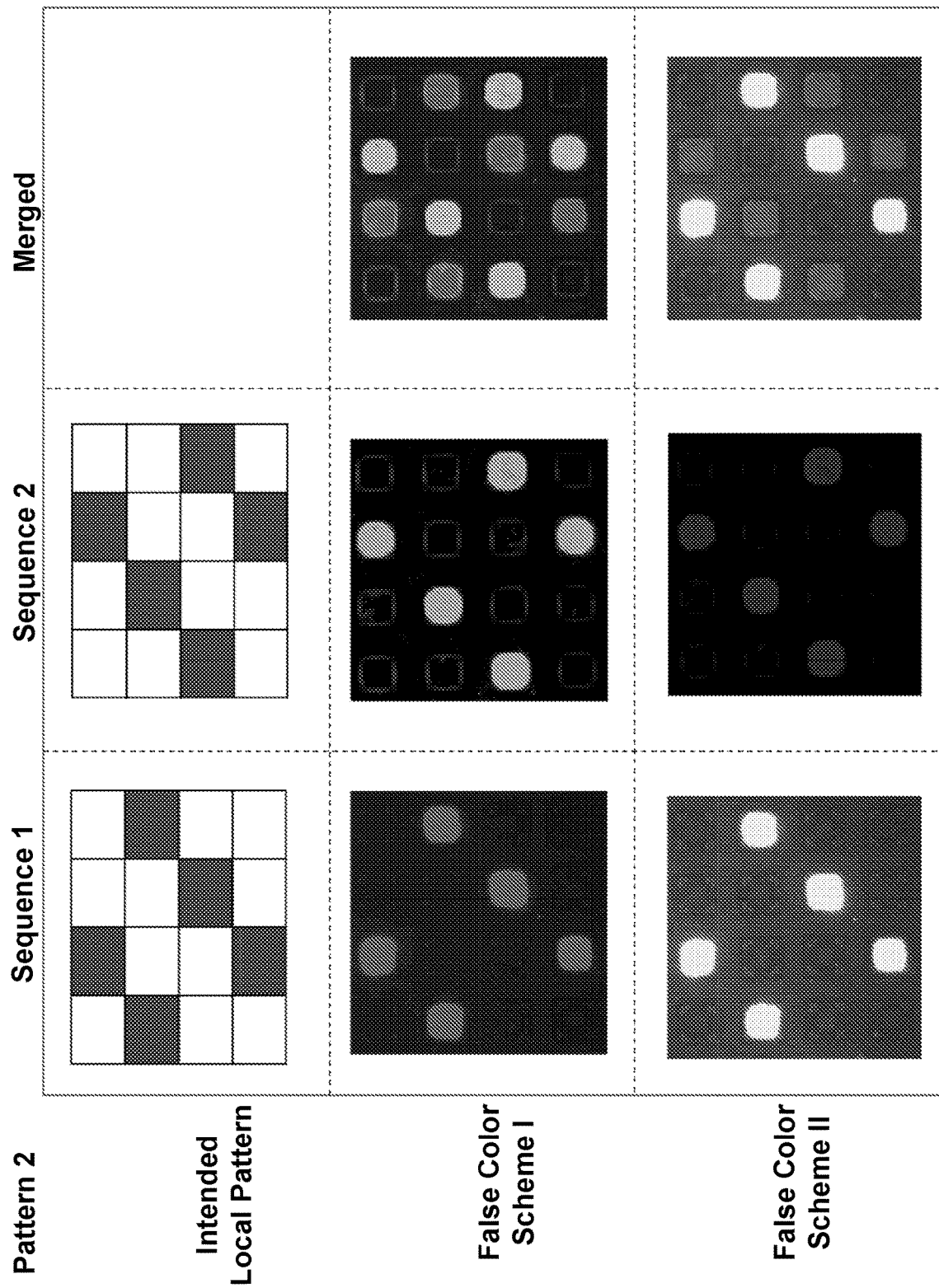
Figure 97A:
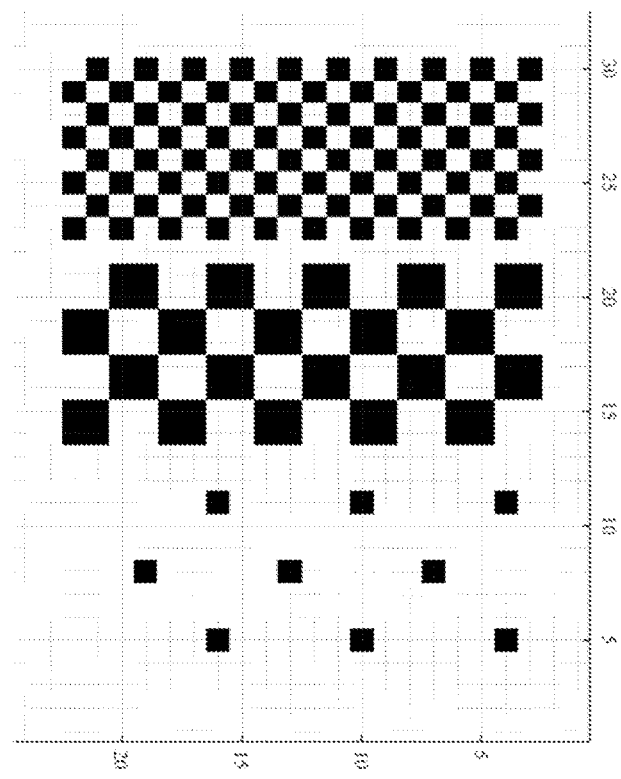
Figure 97B:
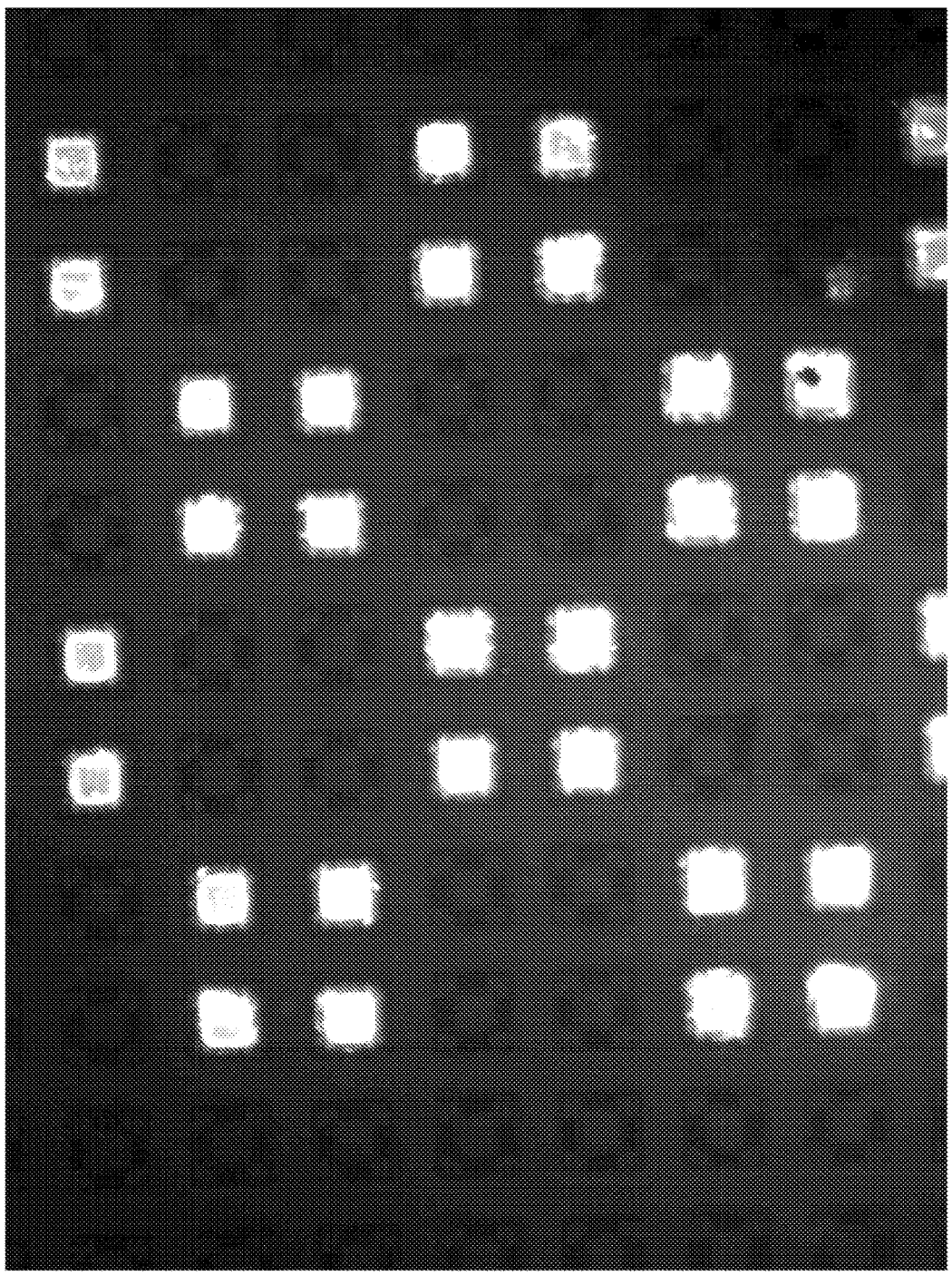
Figure 97C:
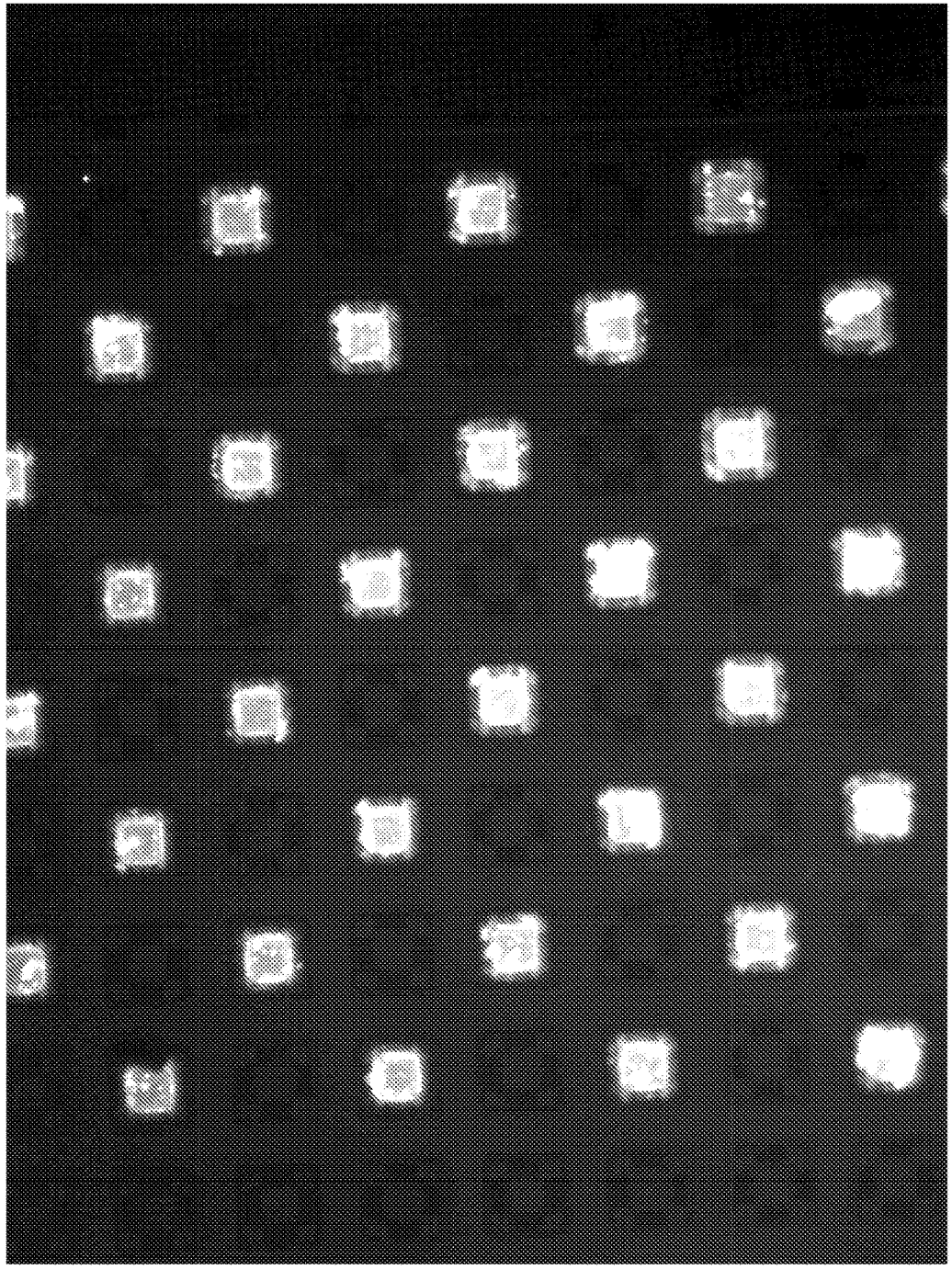
Figure 98:
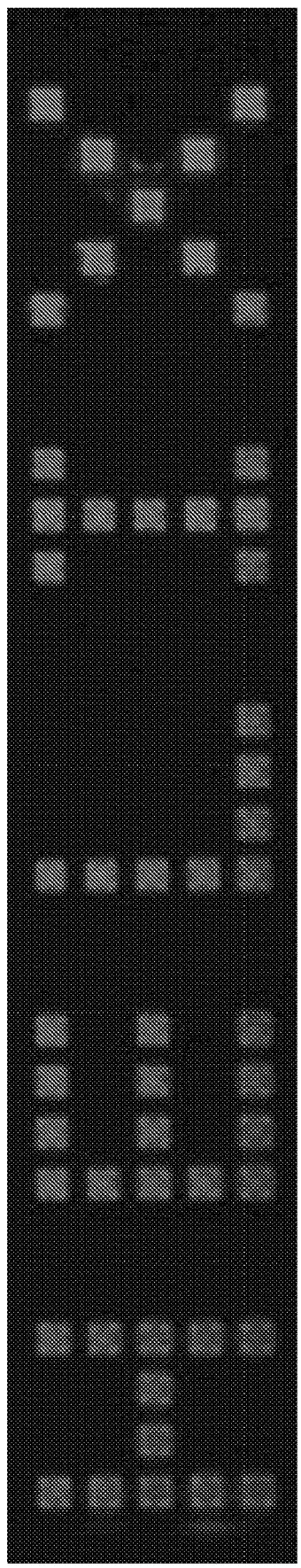

FIGS. 94, 95, and 96 illustrate DNA synthesis according to local masking patterns, in accordance with various exemplary embodiments;

FIGS. 97A, 97B, and 97C illustrate synthesis of a 60-mer homopolymer according to local masking patterns, in accordance with various exemplary embodiments; and FIG. 98 illustrates a fluorescent image of single sequence synthesis hybridization demonstrating implementation of varying patterns and pixel synthesis configurations, in accordance with various exemplary embodiments.

BACKGROUND

Chemical Synthesis of DNA: The seminal work of Oswald Avery in the late 1940's showed that DNA is the carrier of genetic information in biology. This set off tremendous interest in first knowing the chemical structure of DNA—resolved by James Watson and Francis Crick in 1953 as the double helix—and then in the ability to "read" the chemical sequence of DNA—resolved by Fred Sanger in 1978 with chain terminator sequencing—and finally in the ability to synthesize arbitrary DNA strands. This was resolved by Marvin Caruthers in 1981, with the phosphoramidite synthesis method, which has since then become the universal basis for commercial chemical synthesis of DNA.

Figure 1:
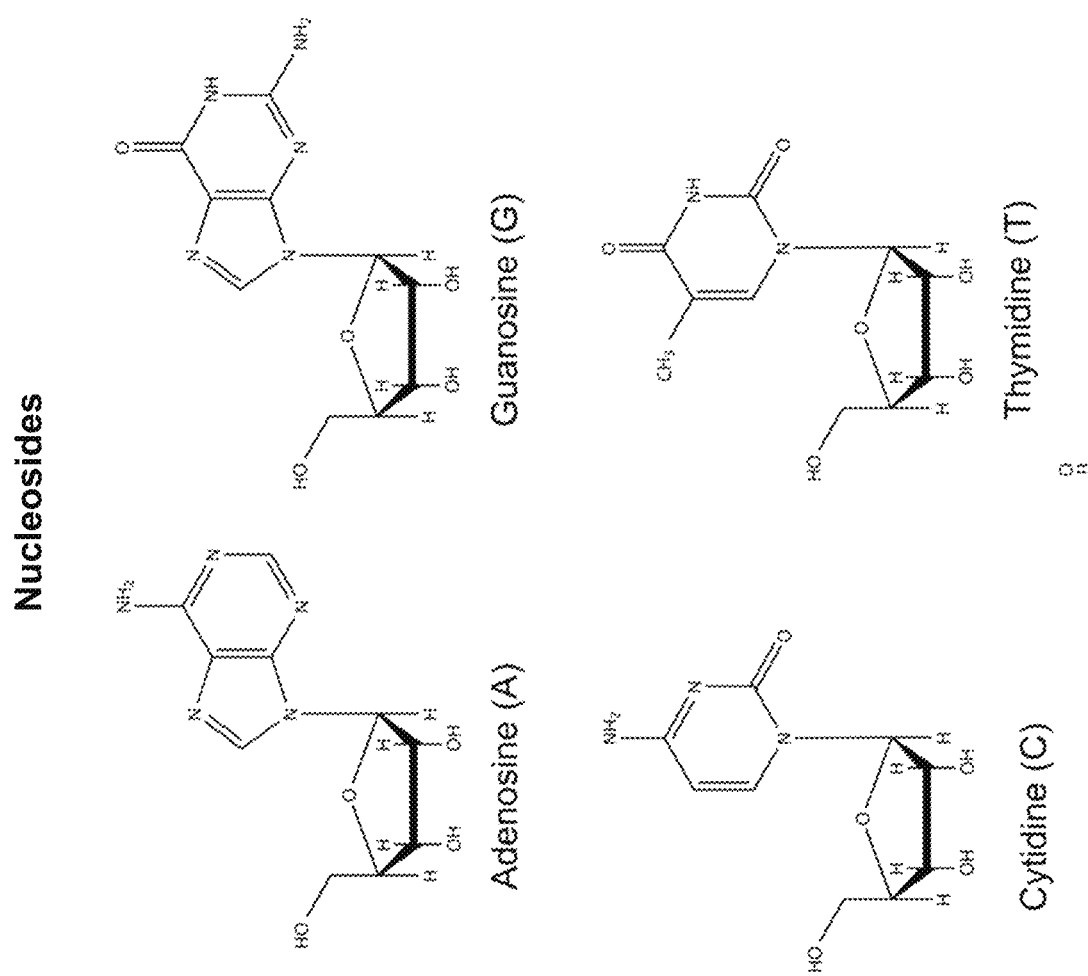
FIG. 1 illustrates the chemical structure of DNA.
Figure 2B:
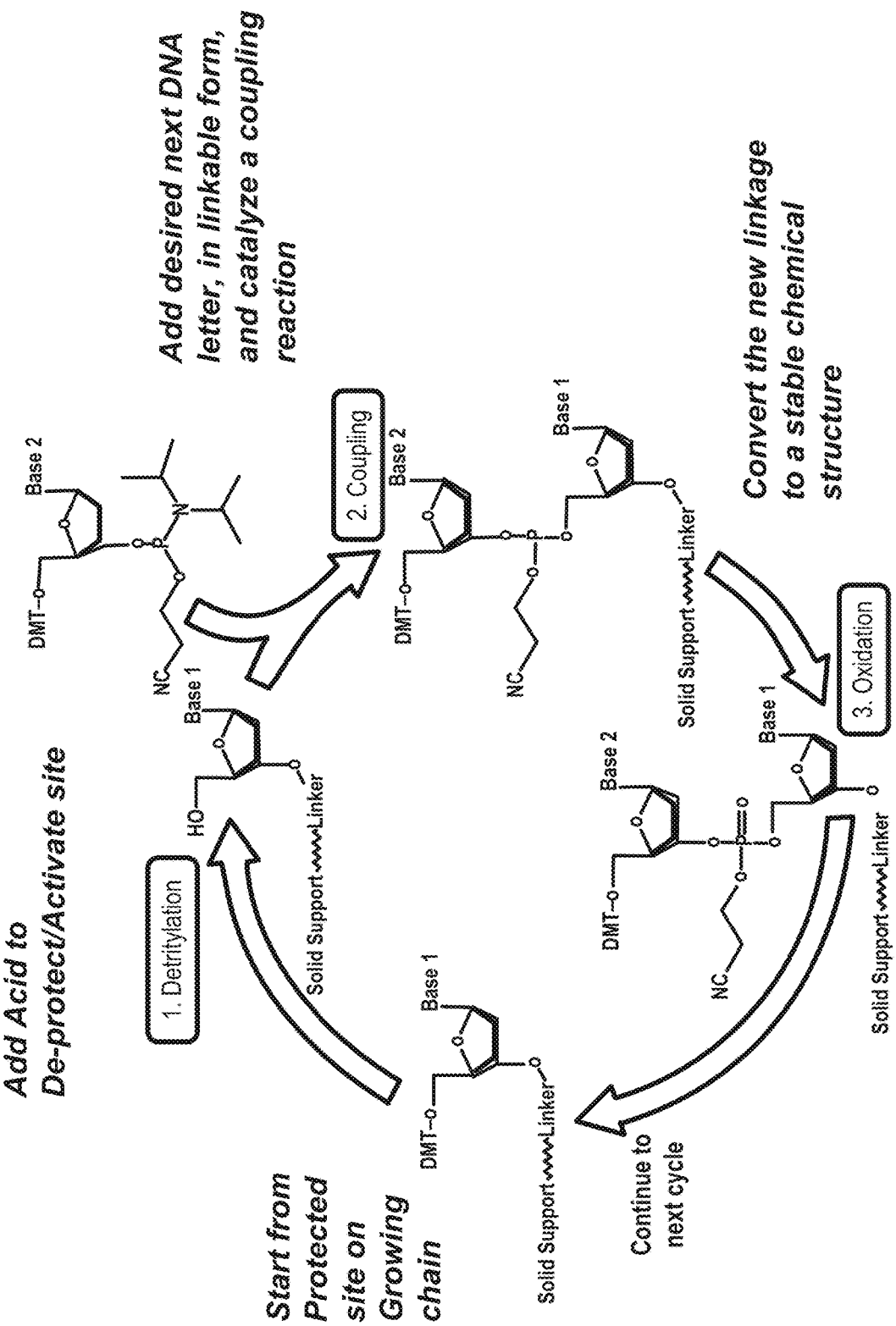
Figure 3:
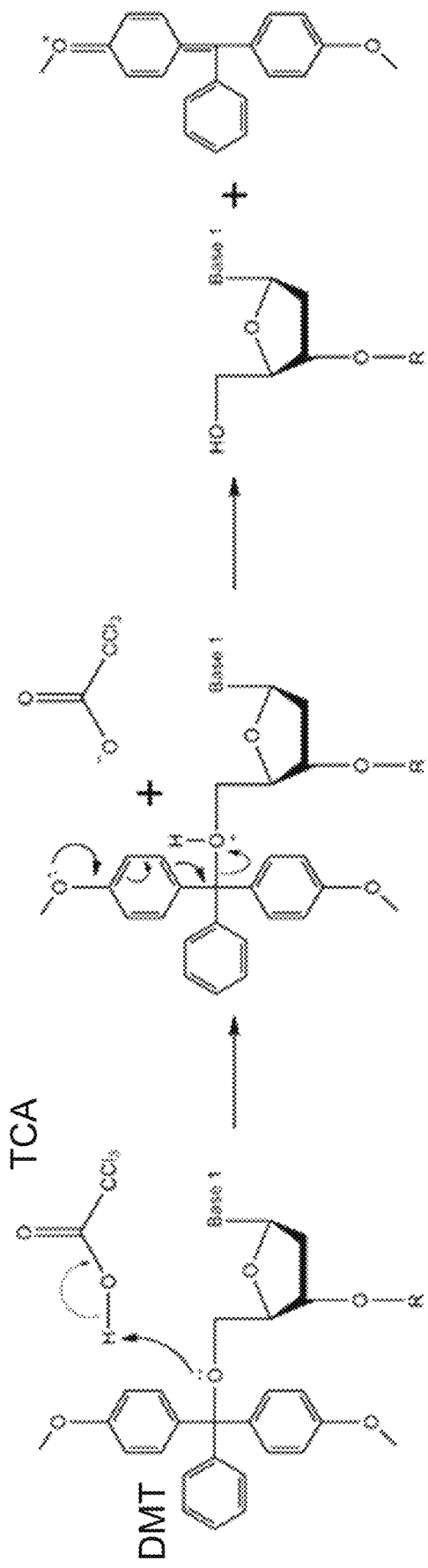
FIG. 3 illustrates the mechanism of a de-tritylation (deprotection) step in the phosphoramidite method.
Figure 4:
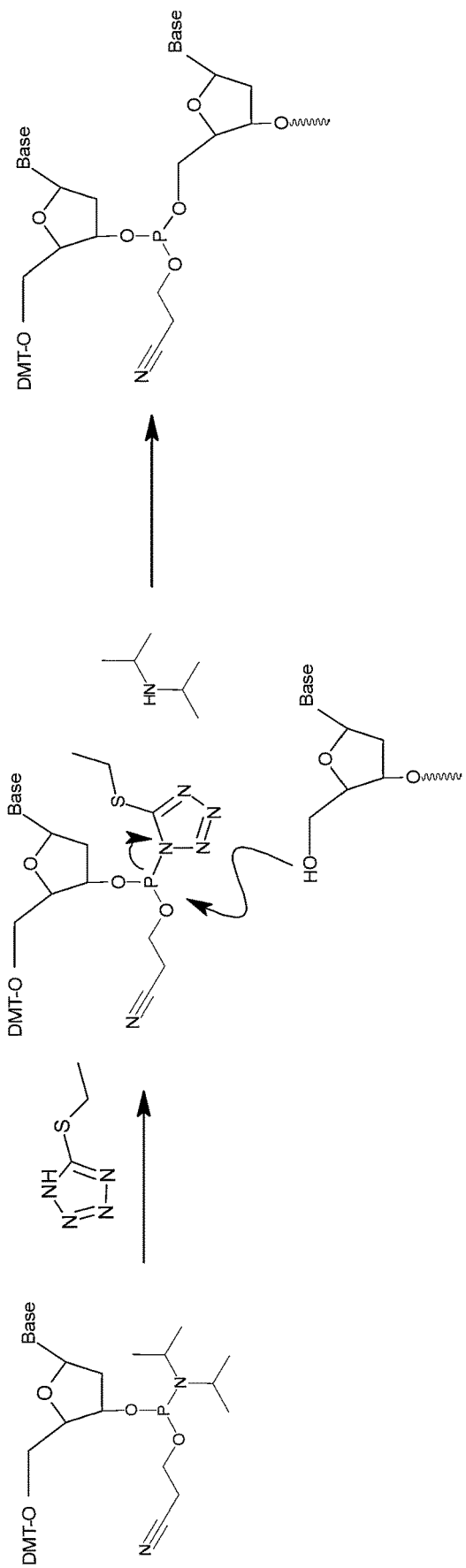
FIG. 4 illustrates the mechanism of a coupling step in the phosphoramidite method.
Figure 5:
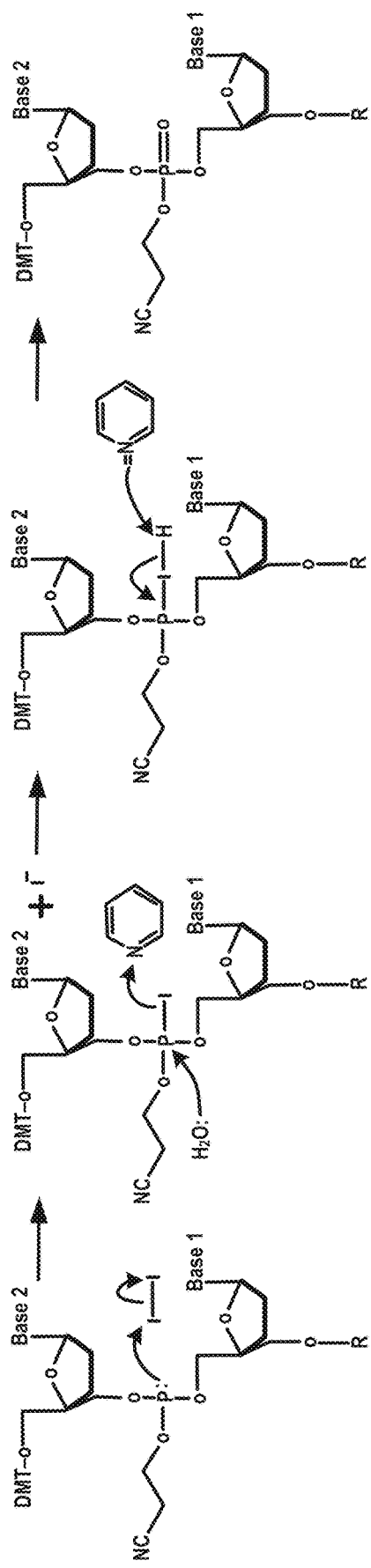
FIG. 5 illustrates the mechanism of an oxidation step in the phosphoramidite method.
Figure 6:
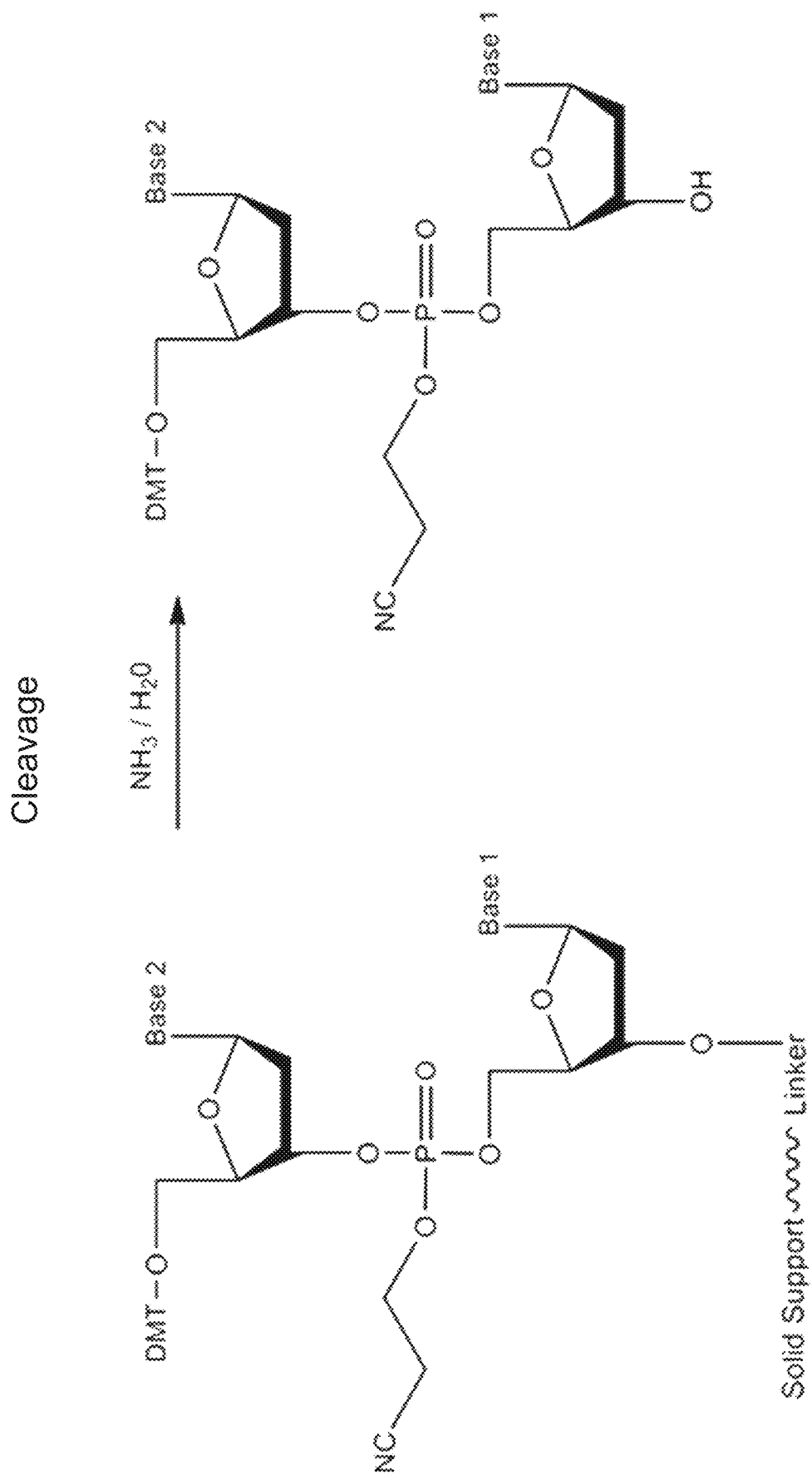
FIG. 6 illustrates the mechanism of a cleavage step in the phosphoramidite method.
Figure 7A:
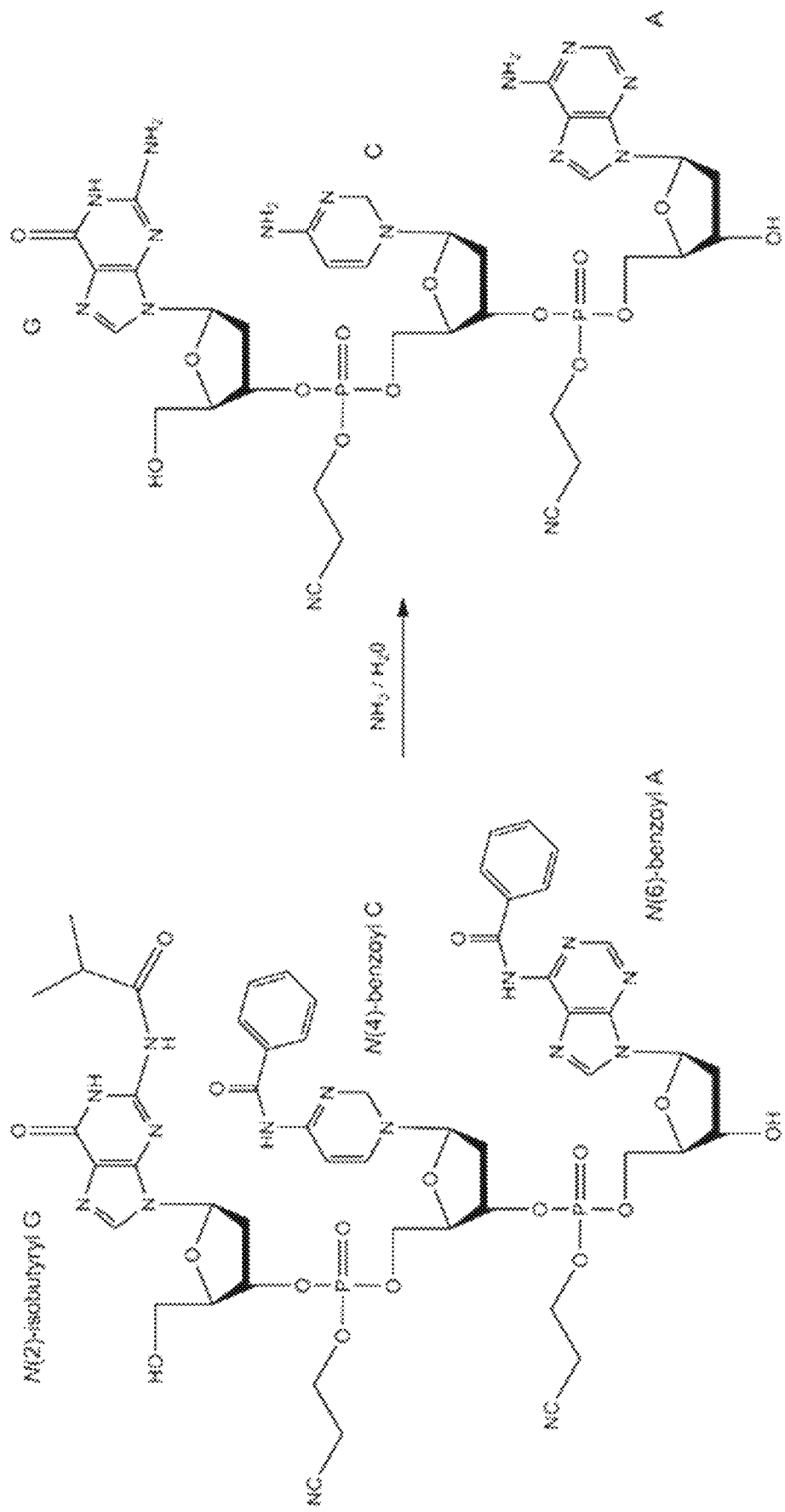
FIGS. 7A and 7B illustrate mechanisms of final removal of protecting groups and backbone conversion for the phosphoramidite method.
Figure 7B:
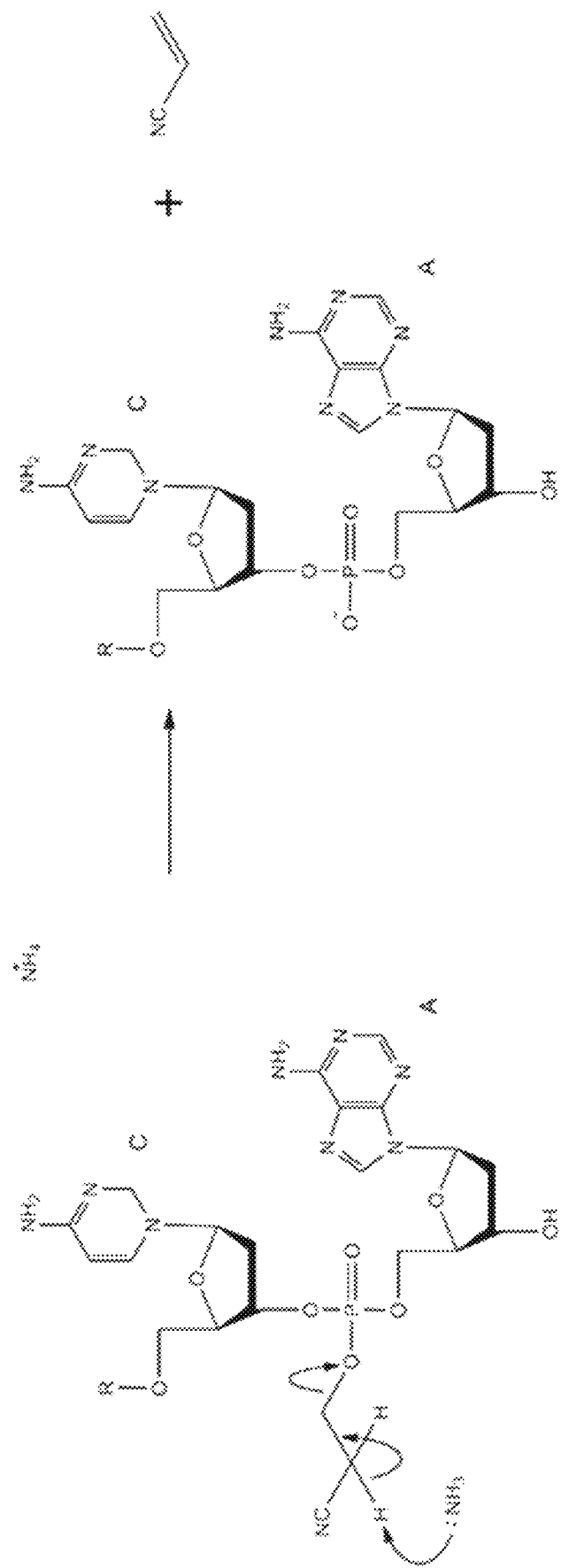

The phosphoramidite method is illustrated in FIGS. 2 through 8. FIG. 1 first shows the chemical structure of a DNA strand: at left is the chemical structure of the four common genetic letters, A, G, T, C, shown as nucleosides (nitrogenous base attached to a sugar ring, but no phosphate group); at right is shown the structure of a DNA strand, wherein the bases are linked together via phosphodiester bonds between adjacent sugar rings. FIG. 2 shows an overview of the phosphoramidite method of synthesis. In this method, suitably protected and linkable versions of nucleosides are joined together in a chain through a cycle of activation and coupling. At far left is shown the general form of such building blocks, a nucleoside phosphoramidite, with a general protecting group on the 5' hydroxy group, D, a possibly protected form of a base, B, and the phosphate with various protecting groups, R. At left is also shown a specific typical form of the nucleoside phosphoramidite as used in commercial chemical synthesis, in which DMT (4,4'-dimethoxytrityl), commonly referred to as "trityl", is the protecting group on the 5' hydroxy site of the nucleoside, the phosphate is protected as shown. The typical protected forms of the bases are shown below—T is typically unprotected, while other bases have protective groups as shown on their exposed primary amino groups, to protect them against the amino reactions during the coupling step of synthesis, that these groups are removed at the end of synthesis. At right is shown the synthesis cycle: note just a single molecule is indicated in the illustration, but it is understood that a number of identical molecules are proceeding through these reactions, with the goal being to produce a number of identical final strands. Typically, the synthesis starts from solid phase support, such as a glass surface, and the starting nucleotide has been attached to this via a cleavable linker. At this stage, or during the general cycle, the previous base is present as a nucleoside with the protecting trityl group (DMT) in place. Step 1 in the cycle is the removal of the trityl protecting group, "detritylation", to expose a reactive 5' OH group on the sugar ring. The detritylation Step 1 is performed by introduction of an acid in a suitable solvent, such as TCA (trichloroacetic acid) in the solvent dichloromethane. The detailed mechanism of that detritylation reaction is shown in FIG. 3. Step 2 is to introduce the next phosphoramidite, carrying the desired next base, which undergoes a coupling reaction shown. The details of this reaction are shown in FIG. 4. The incoming phosphoramidite is provided in the solvent acetonitrile, and its diisopropylamino group is activated (protonated) by mixing in the acidic catalyst, such as ETT (5-(ethylthio)-1H-tetrazole) as shown. The result is a phosphite triester linkage to the chain, and a free diisopropylamino group. Step 3 is oxidation of the phosphite group, to convert it to a stable phosphate form for the duration of the synthesis. The detailed mechanism is shown in FIG. 5, wherein oxidation of the phosphite triester is done by adding iodine and pyridine in water; the product is a phosphate triester that is the standard DNA backbone with a cyanoethyl protecting group remaining on the free oxygen. This cycle of detritylation, coupling, and oxidation continues, until the desired strand sequence of bases has been provided into the process. At the completion of the reaction cycles, the synthetic product is typically released from the support by a cleavage reaction, such as indicated in FIG. 6. As shown, this typically involves an ammonia treatment, to release the DNA strand with a free 3' OH end. These resulting products undergo final deprotection reactions to remove the protecting groups on the bases, and a conversion reaction to convert the DNA backbone to its standard phosphodiester form. These reactions are shown in FIG. 7: the upper figure shows the reaction that removes the protecting groups on the amines, by addition of aqueous ammonia, and the lower figure shows the conversion of the backbone to its standard form. The cyanoethyl groups are removed in concentrated aqueous ammonia via a process called β-elimination. The reaction is rapid, producing the desired DNA oligonucleotide with a native phosphodiester backbone and free acrylonitrile.

Figure 9:
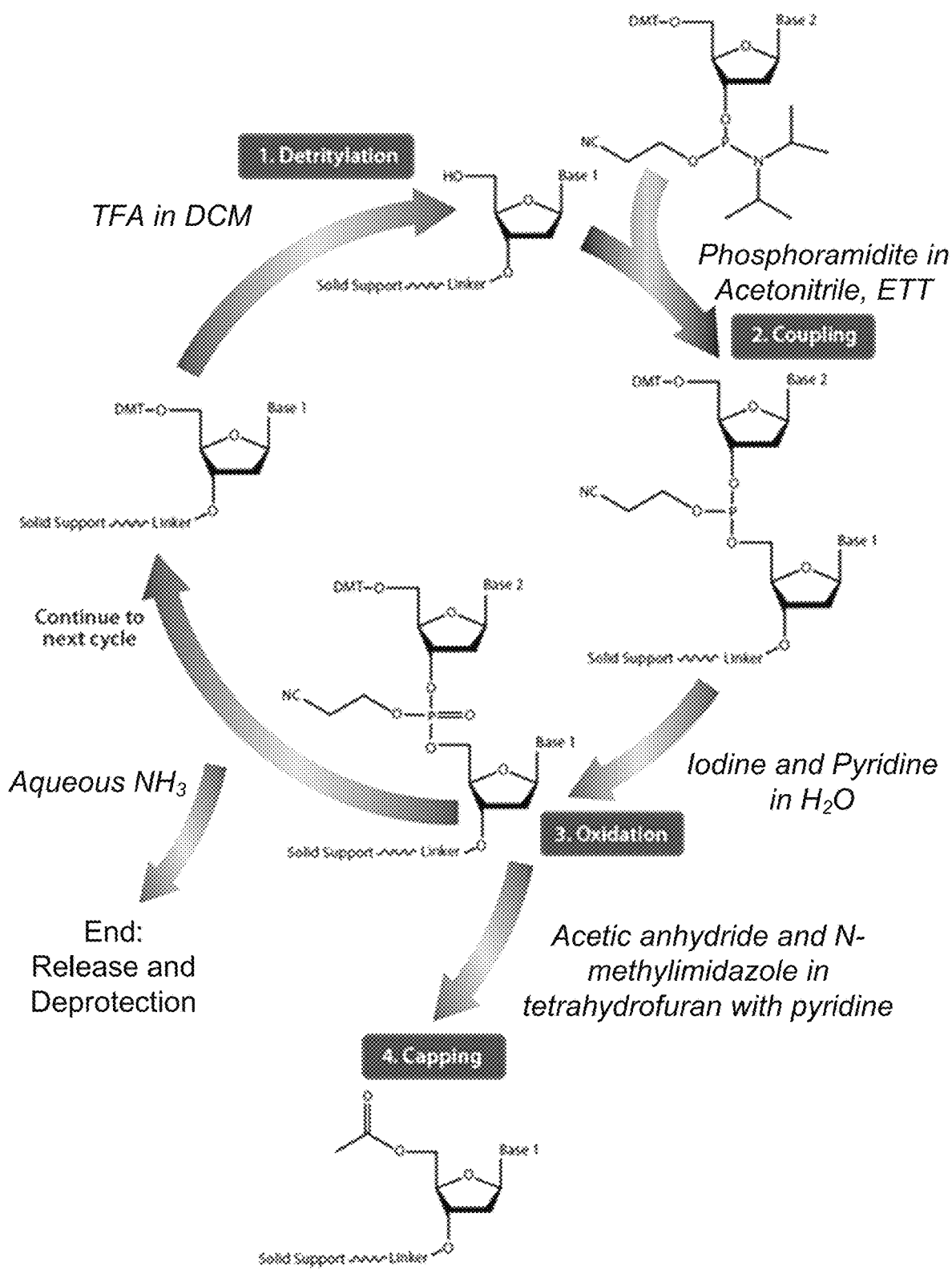
FIG. 9 illustrates details of the phosphoramidite method as it may be used in standard commercial DNA synthesis process.

Synthesis Systems: The phosphoramidite method as commonly carried out requires the strands to be synthesized on a solid support, and Controlled Pore Glass (CPG) beads are commonly use as the support, packed into a column, so as to provide a large glass surface area. The chemical reaction steps are then performed by pumping the various liquid phase reagents into the column, as needed. Typical commercial systems may work with multiple such columns, or with multi-well plates, so that simultaneous production of 16, 48, 96 or 384 different oligos is undertaken, and with suitable fluid control lines that allow for different phosphoramidite bases (A/C/G/T) to be delivered selectively to the different columns or wells, so as to support parallel synthesis of different sequences in different columns/wells. Thus, typical commercial systems have extensive fluid lines and valves, supporting the delivery of the key reagents, supplied in reservoirs, which are the 4 phosphoramidites (delivered selectively, via valves) and cycle reagents (delivered to all sites) such as the TCA, ETT and iodine solutions. FIG. 9 shows the synthesis cycle in detail, with the reagents that may be supplied by the fluidics in such a system.

Figure 8:
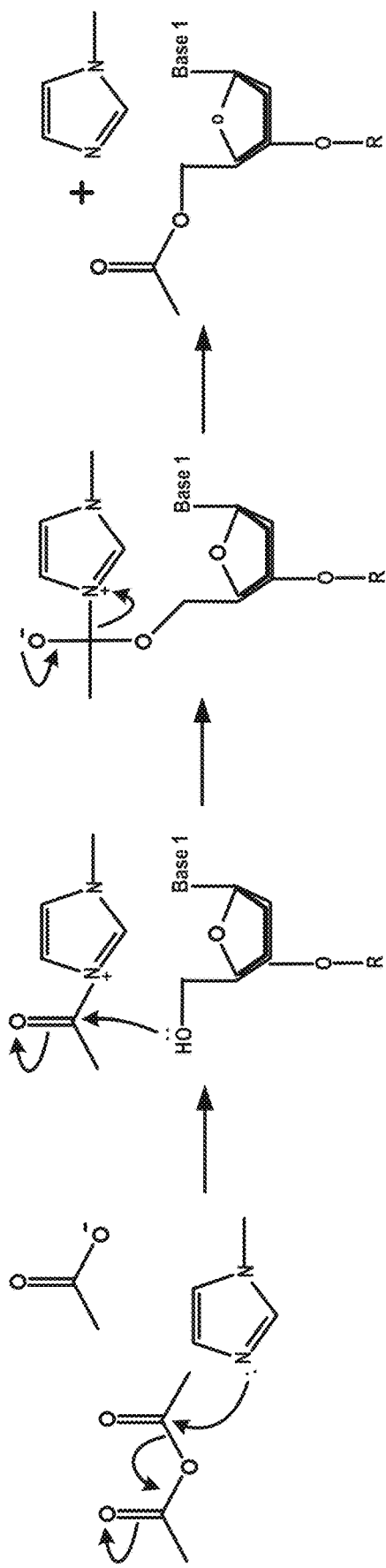
FIG. 8 illustrates the mechanisms of an optional capping step in the phosphoramidite method.

Limitations of Synthesis: Note that because these reactions will not all complete with perfect efficiency, a particular molecular strand will eventually not complete a desired reaction, and therefore out of the population of growing strands, only a fraction will be correctly synthesized to full length. The stepwise yield refers to the fraction that extend properly for base addition one cycle, and the cumulative or total synthetic yield is the fraction that ultimately achieve correct full-length sequences, which is the accumulation of the correct stepwise products. The stepwise yield is therefore key parameter of the synthesis process, which determines the yield for any target length. In present commercial synthesizes, the stepwise yield is typically higher than 99%, and up to the range of 99.5%-99.8%, and as a result, practical synthesis of oligos up to several hundred bases is possible by this method. For example, with a 99.5% stepwise yield, for a target length of 100 bases, 60.6% of strands will be full length, while for 200 bases, this drops to 36.7%. The synthesis of much longer oligos, such as 1000+ bases, is theoretically possible, but at achievable stepwise yields there would be a very low yield of desired product, which would then be difficult to separate from the very high background (90%+) of strands that have errors, such as missing bases. Therefore, this method is impractical as a means of synthesizing desired longer strands with high purity. The synthesis of DNA strands longer than several hundred bases—such as for genes, which are often 1000 bases or longer—typically relies on the phosphoramidite method to make shorter fragments, which are then highly purified for correct sequences, and ligated together by other means to form desired longer strands at high purity. One common additional step to the synthesis cycle of FIG. 2 is an addition of a Step 4, that facilities purification of full-length products, by capping un-reacted 5' OH groups on the growing strand. This will preferentially truncate such strands as soon as a synthesis error occurs, resulting in a length well below that of the intended product, making them easier to purify away. The mechanism of this optional capping step is illustrated in FIG. 8, wherein acetic anhydride and N-methylimidazole are reacted to form an intermediate in the solvent tetrahydrofuran (and also including a small amount of pyridine, to maintain basic pH so as to avoid de-tritylation during this capping step). The result is acetylated 5'-OH, which will not undergo further extension.

Digital Data Storage in DNA: The concept that DNA could be used to store general digital information was put forth in the scientific community in mid-1980s, not long after the development of efficient chemical synthesis of DNA, which thereby provided a means to "write" data into DNA as a storage medium. Since that time, various exemplar data storage projects were used to demonstrate this capability, such as storing notable books, music recordings or movies into DNA.

DNA is a compelling storage medium because, compared to standard media, it offers the potential for much greater data density and storage lifetimes, with much lower power consumption. DNA provides a way to store information at the single molecule level, thus it approaches the physical density limits. It is naturally stable for hundreds to thousands of years, and it does not require any power to maintain its stability during that time.

Common storage media used commercially for storing digital data include magnetic hard disk drives (HDD), semiconductor chip Random Access Memory (RAM), semiconductor chip Solid State Drives (SSD), optical disks (OD) such as Compact Discs (CD), Digital Video Discs (DVD), or Blu-Ray discs, and magnetic tape. RAM chips are used for the active storage of data, during computation, for periods up to hours or days. Magnetic HDD and SSD are typically used for mid-term storage, or storage on personal computers, or at data centers, for storage of days to a few years. For long term archival storage, for years, optical discs or magnetic tape are preferred for their overall lower cost of storage.

Magnetic tape is at present, by far the dominant medium and standard for long term archival storage of digital data. It was first introduced commercially by IBM in 1952, and it continues to provide for the lowest cost, long term, high density storage. However, archival tape must be re-recorded every 5-10 years to maintain the integrity of the magnetized tapes. At present, circa 2022, an effective cost of writing digital data to archival storage on magnetic tape is approximately $10 per terabyte (TB) ($10^{12}$ bytes), based on the cost of the tape medium and amortization of the writing head device, but not including the cost of re-recording for long term stability. Individual magnetic tape cartridges typically contain a tape which can hold up to 6 TB of data (uncompressed). Exabyte ($10^{18}$ byte) scale storage can be achieved by large scale deployment of thousands of tape drive heads, and automated robotic tape storage racks, into an automated system that manages hundreds of thousands of cartridges.

The fundamental physical unit of storage for a single bit on a current tape is a magnetized rectangular region in an iron oxide (ferrite) thin film, which currently in commercial tapes (circa 2022) has dimensions of approximately 50 nanometers (nm) wide by 1400 nm long. In the third dimension, this physical bit is approximately 4 microns (4000 nm) thick, including the ferrite film and the plastic tape support substrate. Thus, in magnetic tape storage, a single bit is stored in a physical volume of approximately 300,000,000 (3×10^9) cubic nm. In contrast, a single base of a DNA molecule occupies a volume of approximately 1 cubic nm, so there is the theoretical potential for an about 3-billion-fold ($3\times10^9$) density increase in DNA relative to tape.

The demand for a new storage medium, with much greater capacity than existing storage media, is driven by the exponential explosion of digital data, including email, photographs, video, smart phones, internet social media, and machine-generated digital data such as the output of sensors in wearable smart devices and smart vehicles. The cumulative total of global digital data in 2020 was estimated to be about 44 zettabytes (ZB) ($10^{21}$ bytes), and the rate of production is increasing at 60-80% annually. It is estimated by the World Economic Forum that by 2025, the global rate of digital data production will reach 0.46 ZB per day.

Existing storage technologies cannot scale to meet the demands from this growth of data production, and thus new forms of information storage media are needed, that can have much greater storage density than current means, particularly for archival storage. In particular, molecular information storage, in which single molecules are used to store information, would be ideal to meet this demand. The storage of data in DNA molecules offers one such solution, and moreover, as Oswald Avery first demonstrated, this is nature's information storage molecule, optimized over billions of years of evolution, and therefore it can be expected to be a nearly ideal solution. However, in order to address the practical demand for storage at the petabyte, exabyte, and zettabyte scales, the cost of synthesizing DNA needs to be reduced dramatically from that of current commercial synthesis as outlined above. In contrast to the current cost of $10 per TB for writing onto tape, current commercially available synthesis of DNA circa costs approximately $0.10 per base (i.e. 2 bits of information) for classical synthesis at minimal scale (e.g. ~1 nanomole of product) in well plate format, or $400,000,000,000 per TB (four hundred billion dollars), or, for a DNA microarray synthesis format, a 1 million spot 60-mer array (15 MB of DNA data) costs $860 (from Agilent), or about $57,000,000 per TB (fifty seven million dollars). Therefore, nearly a 10-million-fold reduction in synthesis cost is needed to compete economically with tape storage. It is notable that the lowest cost synthesis commercially available is for this microarray format, which performs parallel synthesis reactions on 1 million spots, using an ink jet printer micro-fluidic droplet system to deliver the liquid reagents required for the phosphoramidite method. For long term archival storage, approaching 100 years, or more, the cost of rewriting tape increases tape cost by an order of magnitude, but still a factor of one million reduction in cost of synthesizing DNA is required to achieve an economical alternative to magnetic tape.

While other factors might override these economics in favor of DNA for special use cases that have been proposed, such as ultra-long term passive storage (thousands of years), it is clear that major reductions in the cost of DNA synthesis are required even to store data in DNA at the gigabyte scale, much less the exabyte and zettabyte scales that are relevant to large data centers and future global data storage demands. Accordingly, improved systems and methods for polynucleotide synthesis, for example DNA synthesis, and applications thereof such as data storage, remain highly desirable.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, structural, chemical, electrical, and/or mechanical changes may be made without departing from the spirit and scope of the disclosure. Thus, the detailed description herein is presented for purposes of illustration and not of limitation.

For example, steps recited in any of the method or process descriptions may be executed in any suitable order and are not necessarily limited to the order presented. Furthermore, any reference to singular may include plural embodiments, and any reference to more than one component or step may include a singular embodiment or step. Also, any reference to attached, fixed, connected, or the like may include permanent, removable, temporary, partial, full, and/or any other possible attachment option. Additionally, any reference to without contact (or similar phrases) may also include reduced contact or minimal contact.

Principles of the present disclosure enable semiconductor chip devices that can use electronic control to drive the synthesis of independent polynucleotide sequences at an array of synthesis "pixels", and with an array architecture that is scalable to millions, tens of millions, hundreds of millions, or billions of pixels on a standard size chip. This has the advantage of providing for major reductions in the cost of synthesizing a diverse set of polynucleotide sequences, through massive parallelism and the miniaturization and low-cost mass manufacturing of such devices provided by the semiconductor chip industry. Moreover, it will be appreciated that while various of the exemplary embodiments discussed hereinbelow are presented in connection with utilization of a specific type of polynucleotide, namely DNA, principles of the present disclosure are compatible with, and exemplary systems and methods may utilize, other polynucleotides such as RNA, LNA, XNA, and so forth.

Principles of the present disclosure enable synthesis chemistries that can be used for chip-based polynucleotide synthesis, including suitable deprotection chemistries for use with standard phosphoramidite reagents.

Principles of the present disclosure enable designs for synthesis pixels that provide for electrical control of polynucleotide synthesis reactions, and which can be embodied on semiconductor chip devices. Exemplary embodiments disclose designs for synthesis pixels that provide means for localizing acids in the context of acid-based deprotection chemistries.

Principles of the present disclosure enable Complementary Metal Oxide Semiconductor (CMOS) chips for such polynucleotide synthesis chips. This has the advantage of CMOS chips enjoying the greatest existing manufacturing base among all types of semiconductor chips, and the greatest capacity for production and low-cost mass manufacturing, providing for both fundamental cost reductions and scale of device production desirable for polynucleotides to be used for large scale data storage, such as for exabyte and zettabyte scale storage and global demands. Exemplary embodiments herein disclose the composition and design of such chips, their manufacture, and methods of use for synthesizing polynucleotides.

Additionally, exemplary embodiments herein disclose suitable chemical synthesis methods using nucleoside phosphoramidites for synthesizing polynucleotides with exemplary chips. This provides the proven advantages of phosphoramidites for high-yield, robust, rapid polynucleotide synthesis, and the advantage of using commercially readily available and cost-effective phosphoramidite reagents, in the context of exemplary new chip devices.

In various exemplary embodiments, methods, systems, and business applications are provided for using exemplary polynucleotide synthesis chips, for example to store digital data into DNA. This provides the advantage of compact electronic systems, driven by CMOS chips and suitable for use at home, office, or in data centers, that provide for the economical and practical storage of digital data into DNA.

Figure 10:
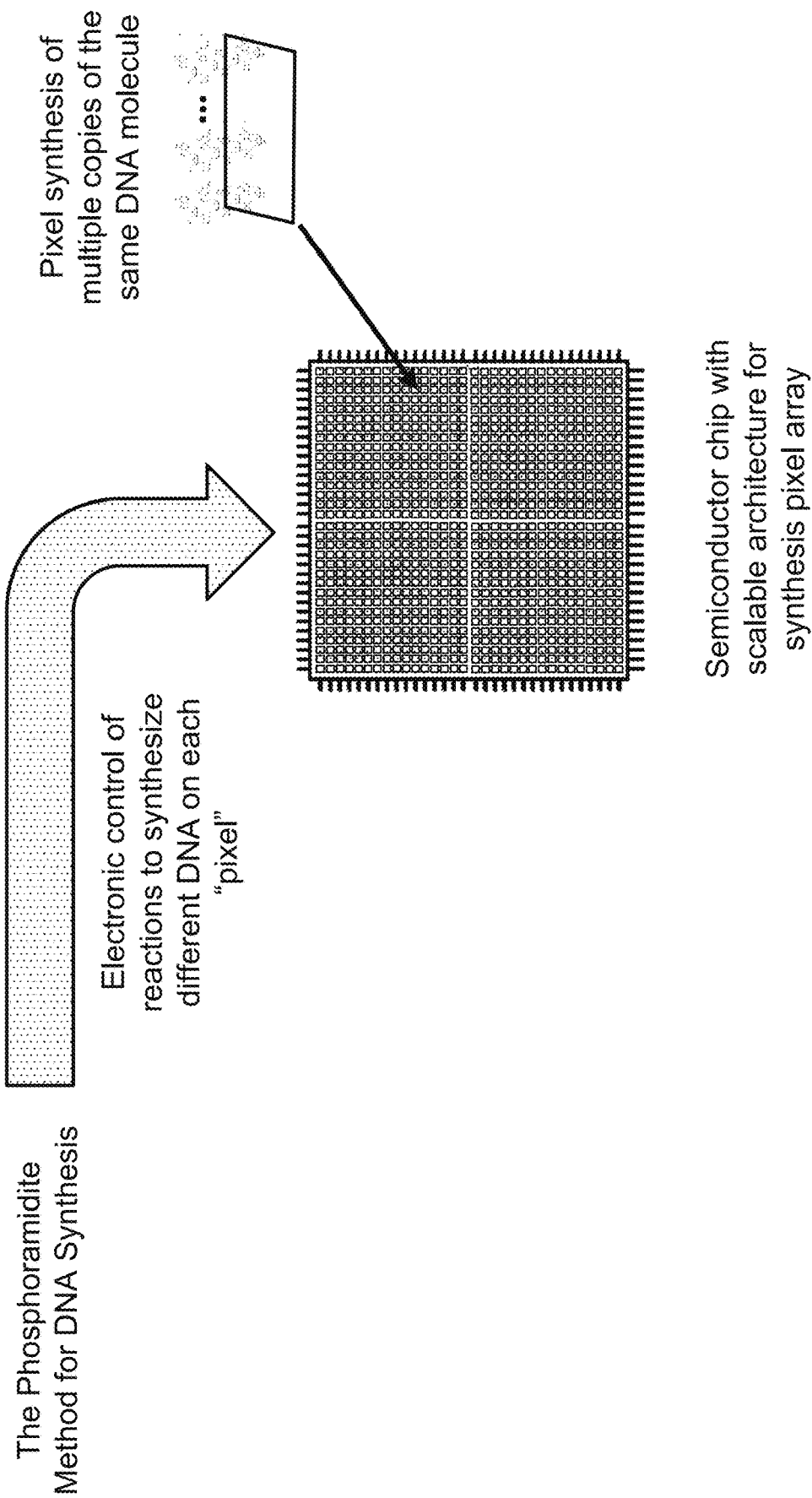
FIG. 10 illustrates a DNA synthesis chip and operation thereof, in accordance with various exemplary embodiments.
Figure 11:
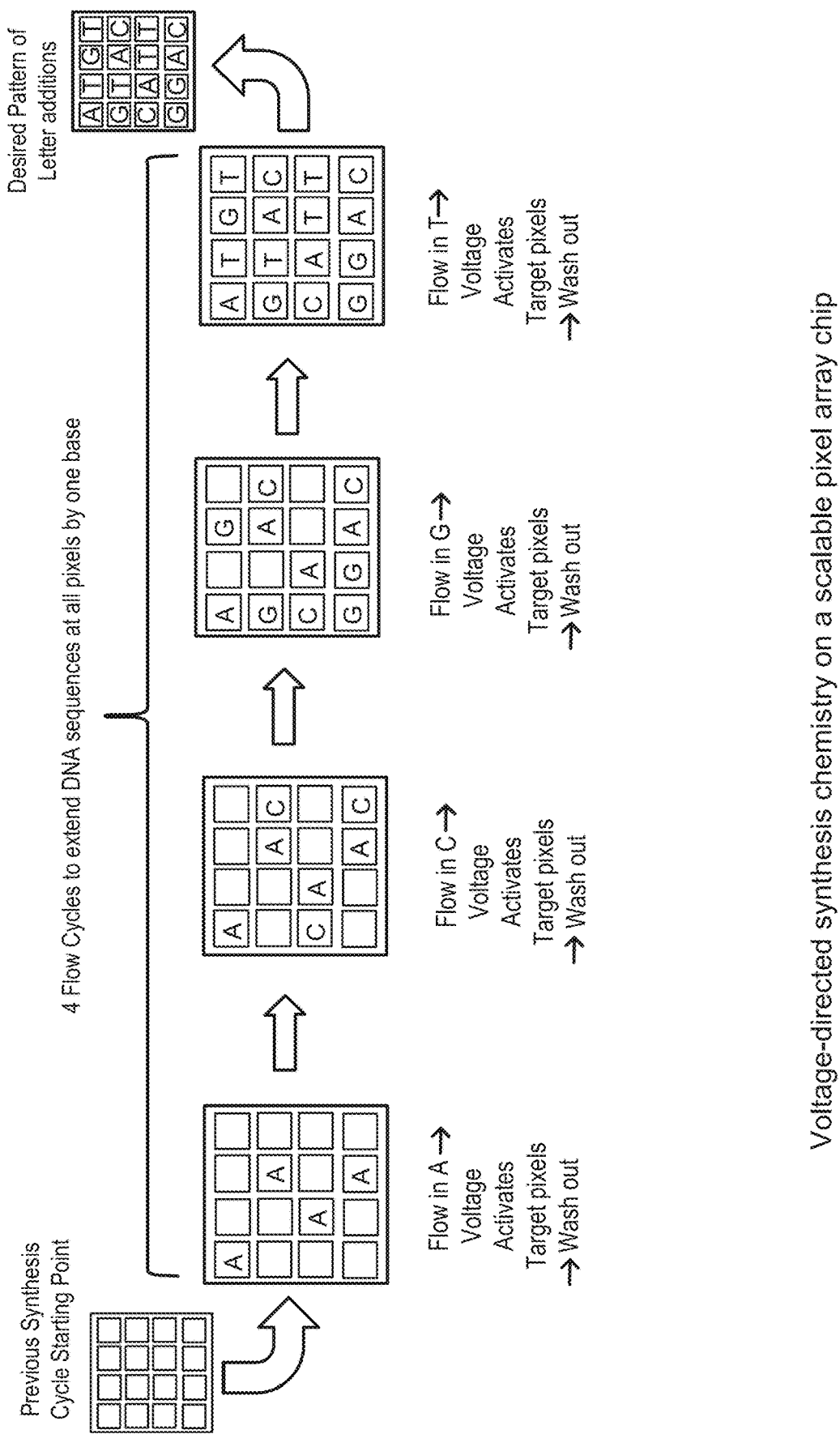
FIG. 11 illustrates principles for on-chip voltage-controlled DNA synthesis, in accordance with various exemplary embodiments.

In various exemplary embodiments, a general method for semiconductor chip-based polynucleotide synthesis (for example, DNA synthesis) is disclosed, as illustrated in FIGS. 10 and 11. As shown in FIG. 10, elements of the phosphoramidite method of synthesis are modified in novel and inventive ways, to provide for voltage-directed control of a coupling reaction. This voltage control is deployed on a semiconductor chip that provides an array of synthesis pixels, each of which allows for proper voltage control, to drive synthesis of a number of copies of the same polynucleotide sequence, at a suitable staging area of the pixel. Thus, each synthesis pixel provides for the independent synthesis of a different target polynucleotide sequence. This exemplary general method is further illustrated in FIG. 11, in which in each cycle, voltage control is used to activate a set of synthesis pixels that are to couple the A amidite, and then A amidite is provided and the coupling reaction proceeds, followed by using voltage control to activate a set of synthesis pixels that are to receive the C amidite, and then C amidite is provided and the coupling reaction proceeds, followed by using voltage control to activate a set of synthesis pixels that are to receive the G amidite, and then G amidite is provided and the coupling reaction proceeds, and then followed by using voltage control to activate a set of synthesis pixels that are to receive the T amidite, and then T amidite is provided and the coupling reaction proceeds. In general, the different amidites can be provided in any suitable order, and in exemplary embodiments, an order is repeated over and over for each 4-amidite cycle, such that for each cycle, every growing fragment across the entire array receives the next desired base, and this cycle is repeated to produce the desired target sequence of length N at each site, after N such cycles. In various exemplary embodiments, desired different length sequences can be produced at different sites, using the described voltage-directed selective activation.

In general, exemplary voltage control principles disclosed herein enable control of physical access of material transport of amidite to a synthesis region of a synthesis pixel, or can control activation of a coupling site on the growing strands in a synthesis region of a synthesis pixel, or both. These exemplary control methods may comprise electro-physical control, and/or electro-chemical control, of delivery of amidite to a desired location, and activation of certain molecules at the desired location.

Electro-Chemical Control of Activation of Coupling Sites

Figure 12A:
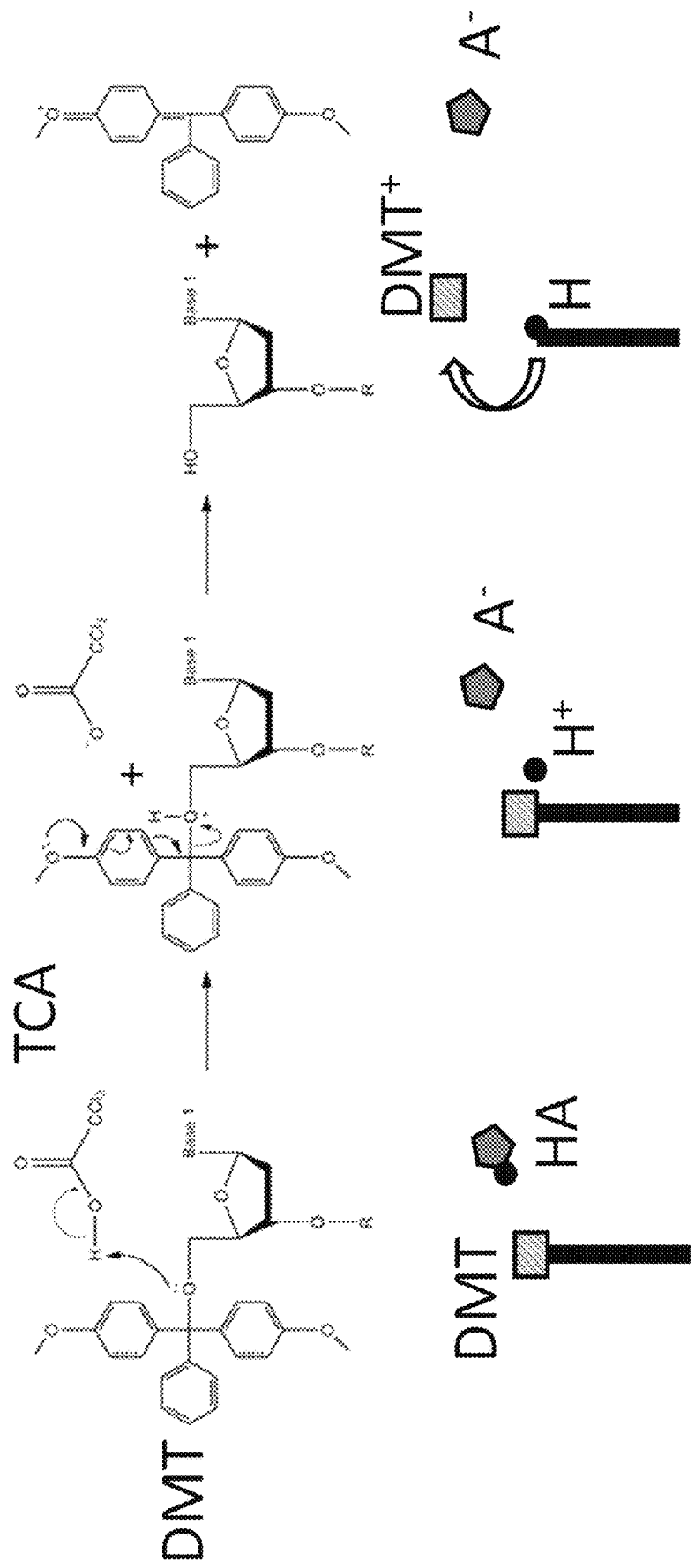
FIGS. 12A, 12B, and 12C illustrate principles of acid driven de-protection, in accordance with various exemplary embodiments.
Figure 12B:
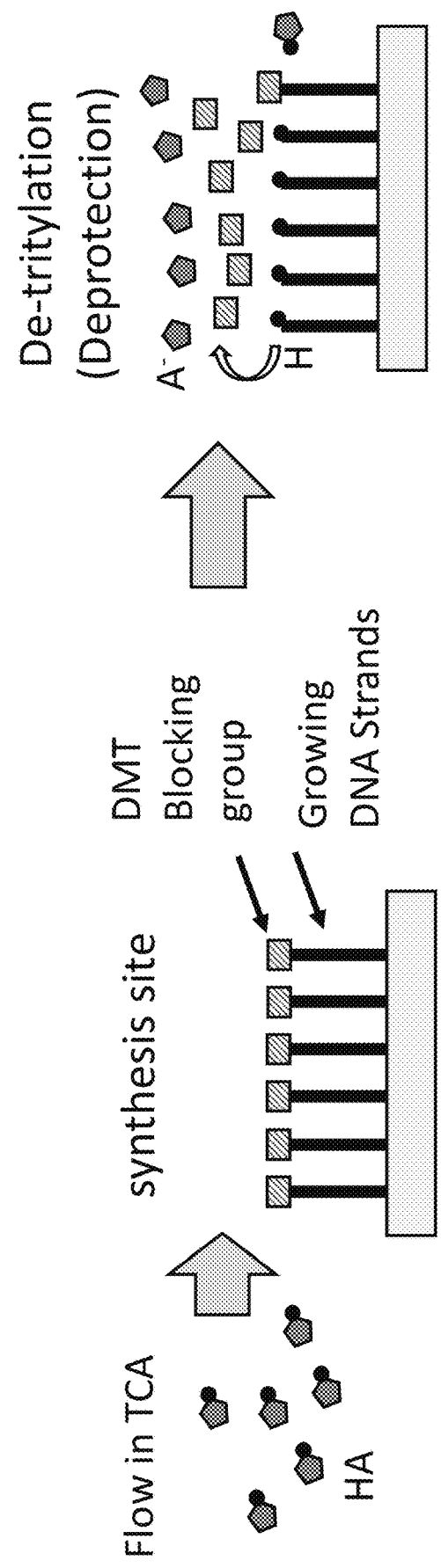
Figure 12C:
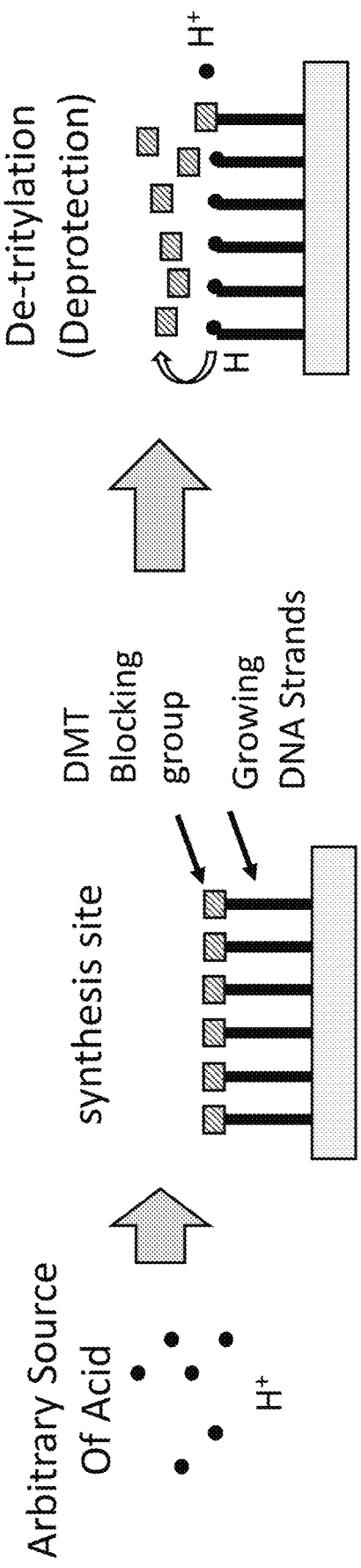

The phosphoramidite method of DNA synthesis, as illustrated in FIG. 2, contains a step in which the dimethoxytrityl (DMT) protecting group is removed via exposure to trichloroacetic acid (TCA) (shown in FIG. 3). In various exemplary embodiments, exposure to other acidic conditions may also be used to achieve acid-driven deprotection. In general, exposure to any acid, or directly to H+, as may be released from an acid, can achieve the same end of removing the DMT protecting group, or any similar protecting group that may similarly be removed via an acid. This is illustrated in FIG. 12, in which the upper panel shows the standard TCA-driven removal chemistry for DMT, along with a schematic illustration of a general acid-based chemistry where the acid, denoted by HA (which may be TCA or DCA (dichloroacetic acid)), can decompose in A− and H+, with the resulting H+ reacting to remove the DMT. The middle panel shows the logical and physical organization of the deprotection process in the phosphoramidite method of synthesis, in which the TCA is flowed into a reaction zone, in a suitable solvent, and a multiplicity of growing strands are attached to a solid-state substrate, with a terminal 5' DMT protecting group, and the resulting deprotection leaves the population of growing strands ready for coupling of the next phosphoramidite base to be introduced. The bottom panel illustrates the use of an arbitrary source of H+ to drive the deprotection process.

Figure 13:
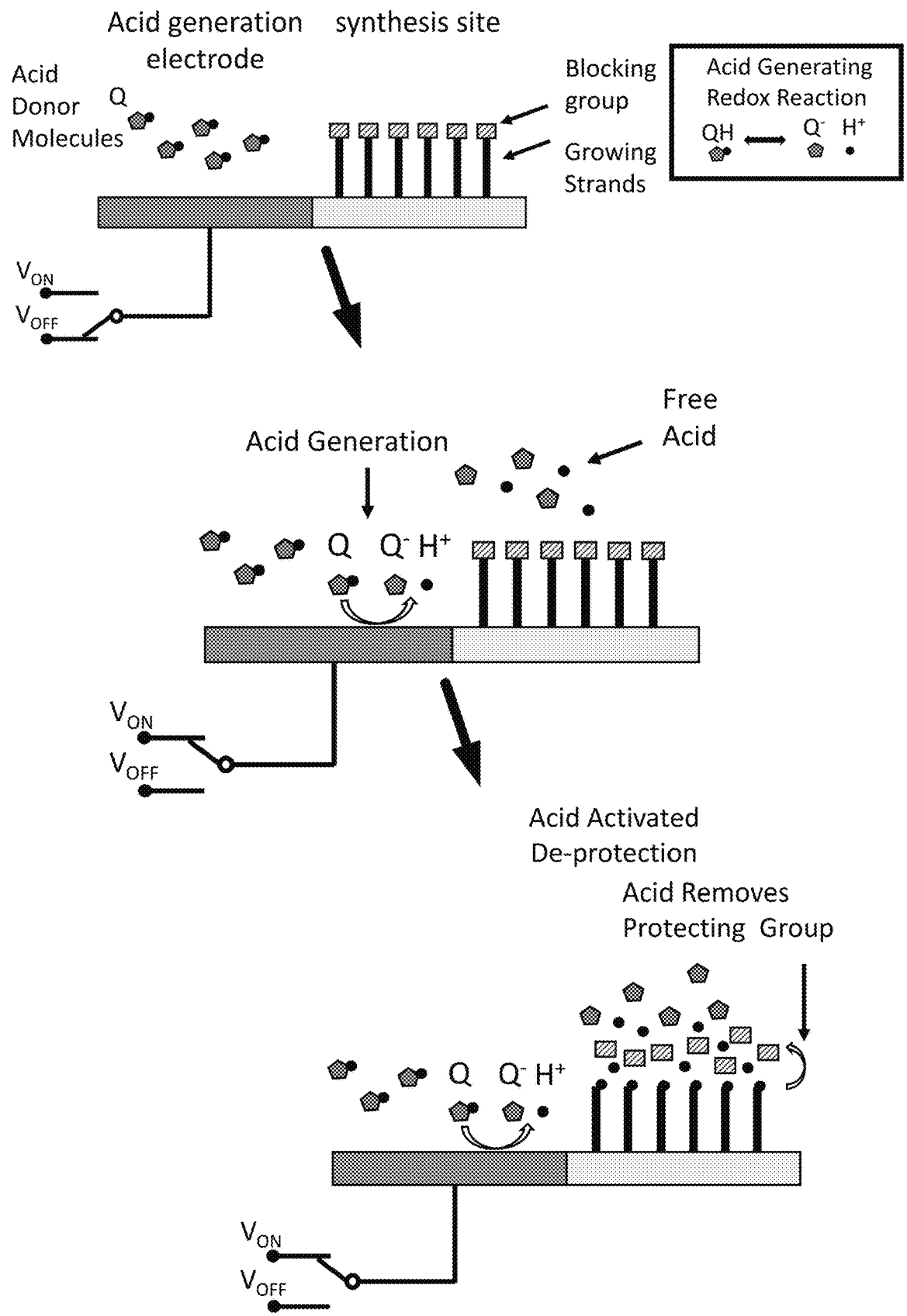
FIG. 13 illustrates electrochemical generation of acid for deprotection, in accordance with various exemplary embodiments.

In various exemplary embodiments, a source of H+ may be a redox reaction, performed on a molecule HA, at an electrode that is set to a particular voltage (relative to a reference electrode for the potential of the ambient solution), such as illustrated in FIG. 13. In these cases, the molecule HA undergoes electrochemical reaction, such that an H+ ion is released into solution. In particular, this may be a reduction reaction, such that H+ is released, and excess electrons are conducted into the electrode (anode). As shown in FIG. 13, an electrode generating the acid, and synthesis sites with protecting groups, are in close proximity, such that the H+ produced can react with the protecting groups to achieve deprotection in preparation for the next synthesis coupling reaction. FIG. 13 shows an exemplary embodiment wherein H+ itself is produced at the electrode. In other exemplary embodiments, an electrode may produce an acid molecule that comprises an H+, and this acid molecule transits to the protection site and donates the H+ for a deprotection reaction.

Figure 14:
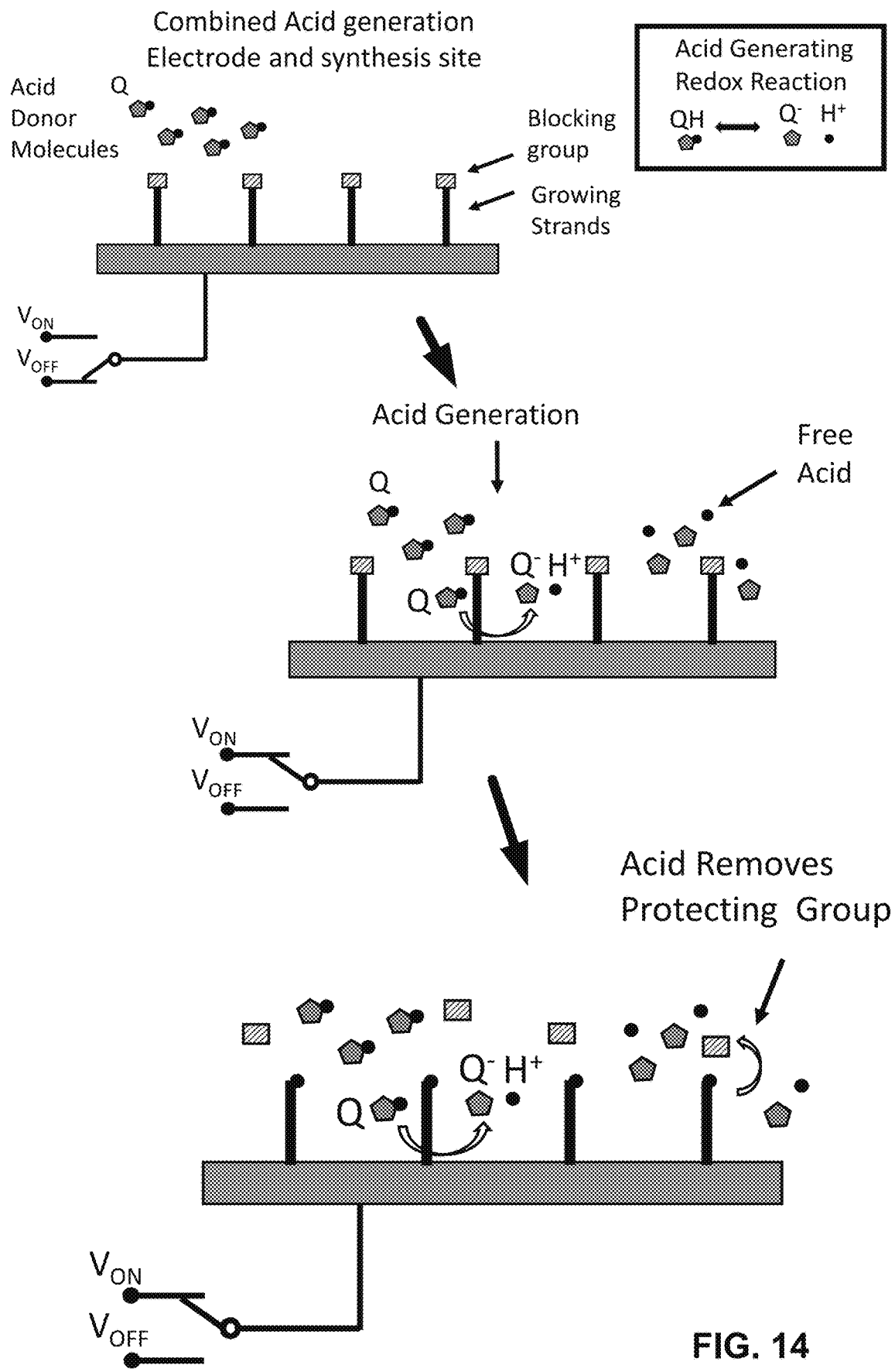
FIG. 14 illustrates DNA synthesis performed on an acid generating electrode, in accordance with various exemplary embodiments.

In certain exemplary embodiments, as shown in FIG. 14, the growing strands may be attached to an acid generating electrode, such that H+ produced at the electrode can immediately perform the de-protection reaction, without the need to transit greater distances. This provides for a high (and/or maximized) concentration of H+ for deprotection, because it is occurring within nanometers of the point of generation, and therefore the H+ is not diluted by spatial diffusion away from the deprotection sites being targeted. In this case, the strands may be attached via a suitable conjugation or linker, to an electrode surface, or in certain exemplary embodiments, to a chemical functionalization layer, such as silane, attached to the electrode. In exemplary embodiments of attaching the growing strands to the electrodes, the protection groups are positioned to be typically within 1 nm of the electrode surface. In various exemplary embodiments, the protection groups are positioned to be within about 10 nm, or about 20 nm, or about 50 nm, or about 100 nm of the electrode surface.

Figure 15:
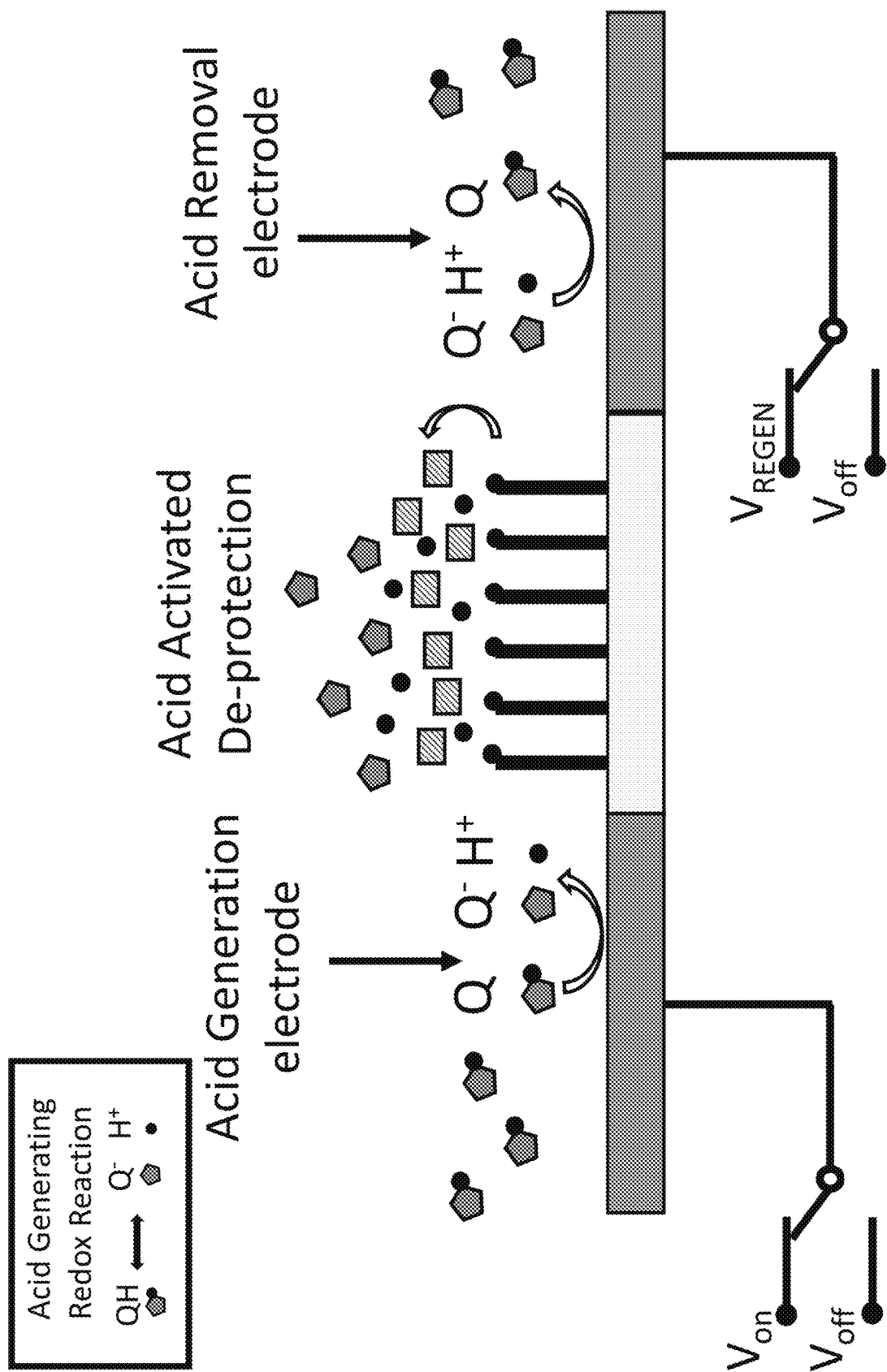
FIG. 15 illustrates using a second recombination electrode to actively remove acid generated by electrochemical means, in accordance with various exemplary embodiments.

In various exemplary embodiments, as illustrated in FIG. 15, an acid removal electrode may be utilized, at which the H+(or acid) that has been produced is (at least partially, and preferably completely) eliminated by an additional electrochemical reaction, which occurs when this electrode is set to a suitable voltage, $V_{REGEN}$. In exemplary embodiments, this acid removal activation comprises a reversal of the acid generation reaction, and in particular may be the complementary reaction of a redox pair of reactions. In exemplary embodiments in which an oxidation reaction is used to generate the H+ or acid, by pulling electrons into the acid generation electrode—in this case the anode—the acid removal reaction is the corresponding reduction reaction, and the acid removal electrode will in this case be the cathode, which will provide electrons to the reaction.

Acid Confinement Geometries

Figure 16:
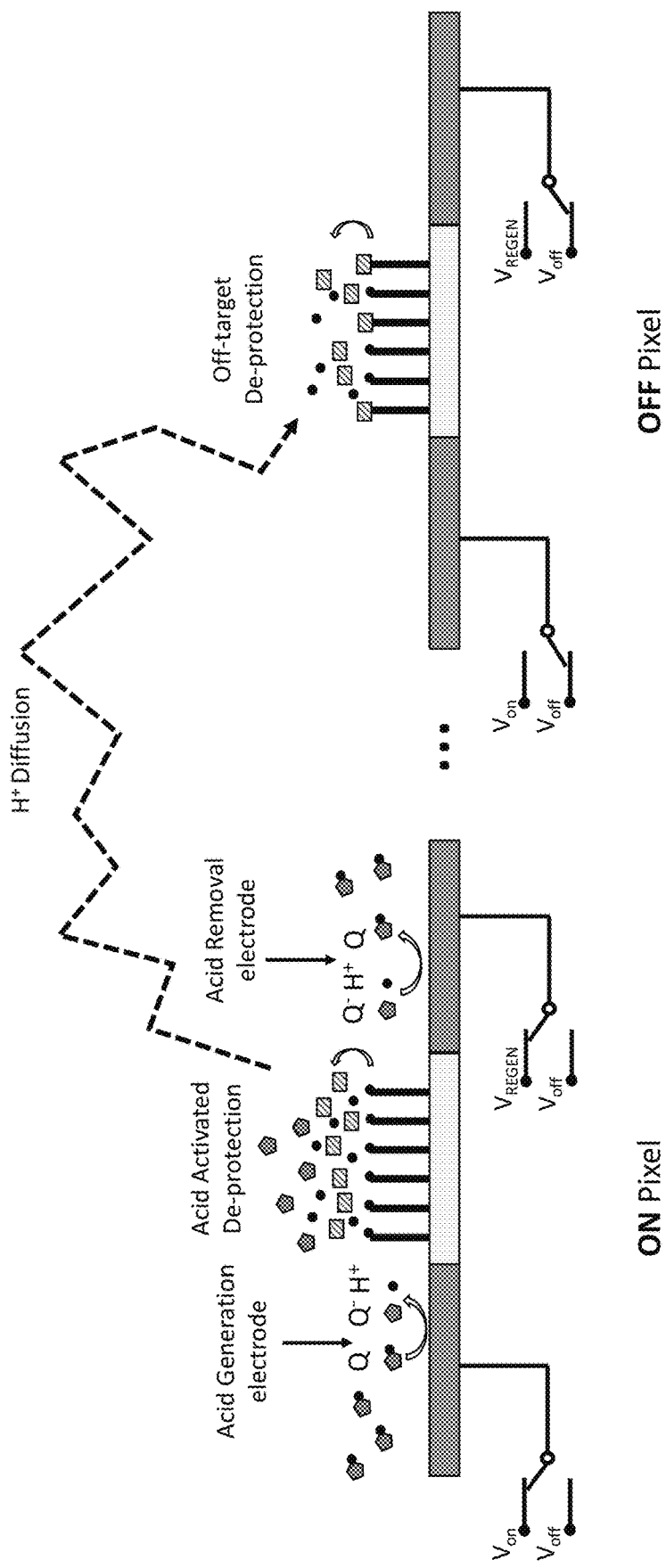
FIG. 16 illustrates unwanted acid deprotection due to diffusion of acid.

In various exemplary embodiments, an acid elimination electrode is used to localize acid near a synthesis zone where it is needed, and to thereby reduce the possibility of acid transiting to undesirable locations in an exemplary system—and in particular, to other synthesis regions where de-protection is not desired. In particular, this undesirable scenario is illustrated in FIG. 16. Illustrated is one synthesis region on the left, with proximate acid generation electrode, synthesis region undergoing the intended de-protection, and an acid removal electrode. Indicated by the zig-zag dashed line is the trajectory of a H+ that escapes from this region, and transits to a remote region where it induces deprotection, even though the local controlling electrodes there are turned off, and thus this is an unwanted or spurious de-protection reaction. The result of such unwanted diffusion of H+ in the context of a synthesis array chip as in FIG. 11 is a form of chemical "cross-talk" between pixels, in which desired deprotection at one pixel, via local electrochemical acid generation, may result in deprotection of one or more DNA strands at another pixel, via the unwanted leaking of H+ or acid to that site. This can result in synthesis errors, because the remote de-protected strands may undergo a spurious coupling reaction when the next base is introduced.

Figure 17:
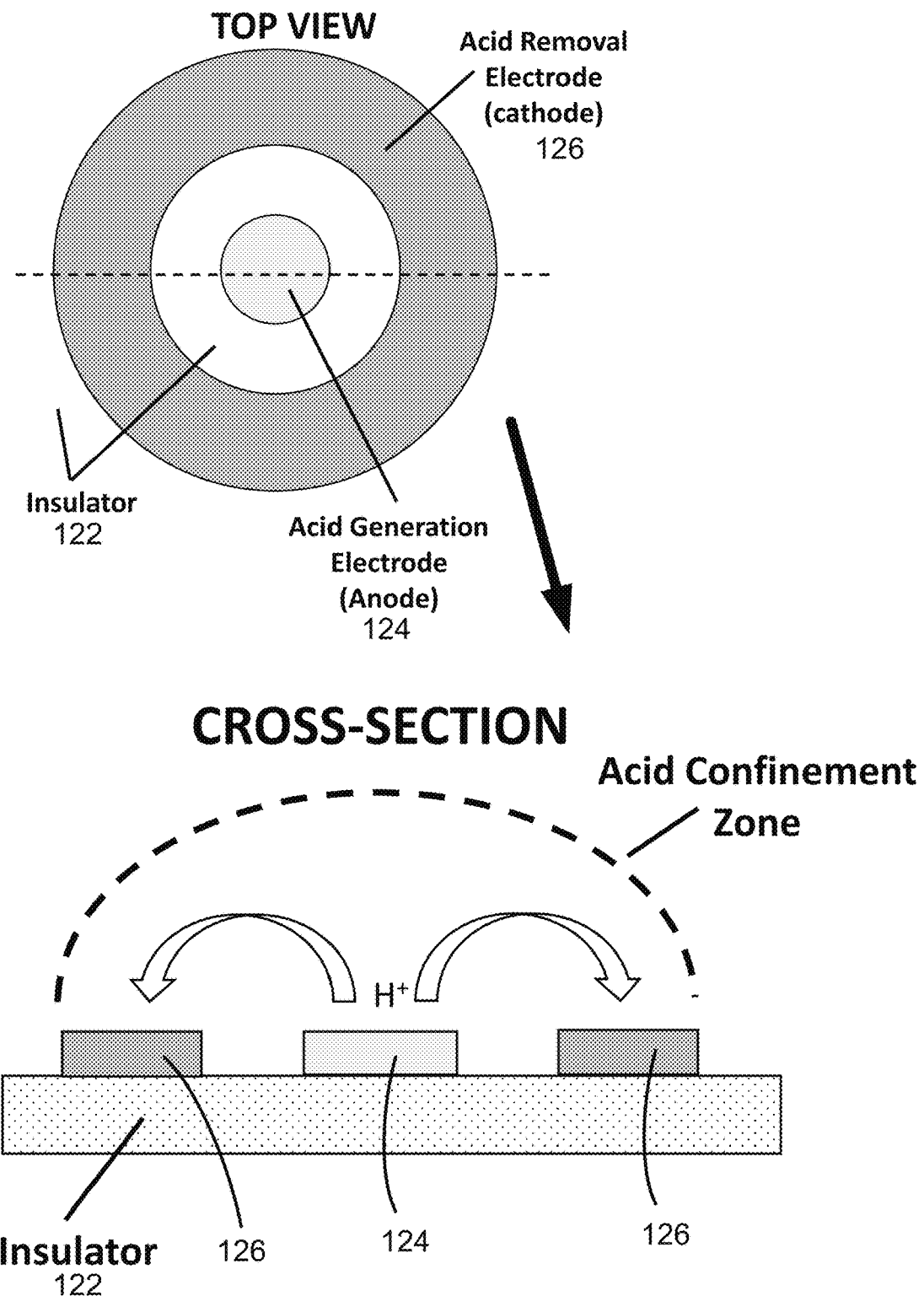
FIG. 17 illustrates acid confinement using an acid removal electrode, in accordance with various exemplary embodiments.

In exemplary embodiments for acid confinement, acid generating electrodes and acid absorbing electrodes are arranged in geometries that result in the local confinement of the H+ or acid generated, such that it is confined near the synthesis region where the deprotection reaction is intended. FIG. 17 illustrates an exemplary embodiment of such an acid confinement geometry, in which the electrodes are arranged on a planar substrate 122, and an acid generation electrode (anode) 124 is surrounded by an acid removal electrode 126, with a suitable insulating space between them. The upper portion of FIG. 17 illustrates a circular geometry for the shape of these electrodes, and the lower portion of FIG. 17 shows a corresponding cross-sectional view. The cross-section also illustrates where the H+ is created in the center, where it is removed along the outer ring, and the general shape of the confinement zone that results from this, as indicated by a dashed line that suggests the boundary of this zone, as defined by the mean concentration of H+ dropping below a suitable threshold value. Within the confinement zone, during active acid generation, there is a high concentration of H+, while outside of this zone, there is a much lower concentration, ideally to the point where unwanted levels of pixel-cross talk do not occur.

Figure 18:
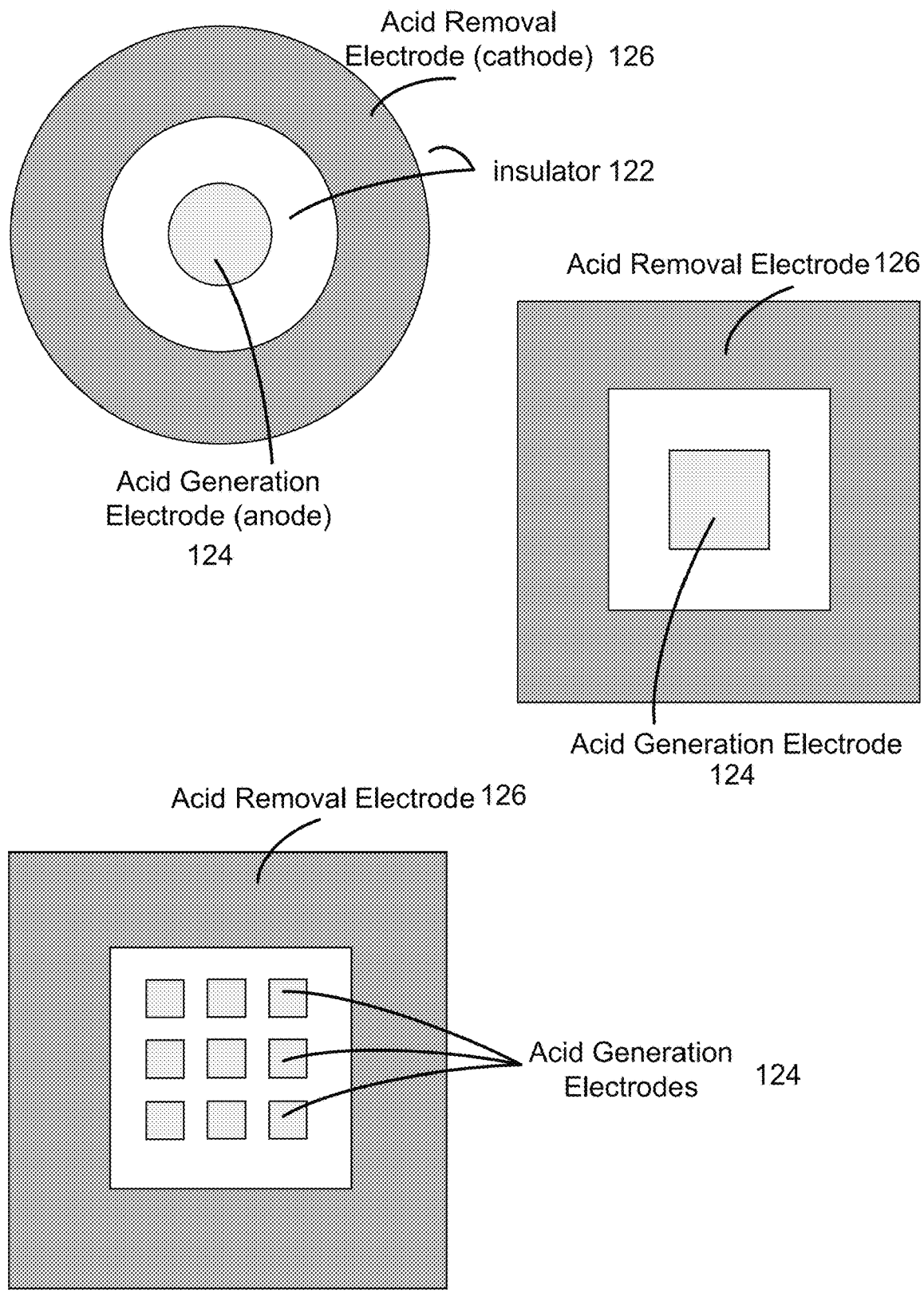
FIG. 18 illustrates exemplary acid confinement electrode geometries, in accordance with various exemplary embodiments.

FIG. 18 illustrates other exemplary embodiments for acid confinement for the planar electrode concept from FIG. 17. As indicated, such electrodes may be circular (top portion), square or rectangular (center portion), or other suitable shapes, and may further be divided on the surface (lower portion), where an acid generation anode 124 presented on the surface is shown divided into islands separated by space. This divided anode 124 geometry allows synthesis to occur in the lanes between electrodes, and in this way brings the deprotection sites closer to the acid generation sites. The anode 124 so depicted is electrically connected below the surface, so that the entire anode area exposed is at the same or very similar voltage. In various embodiments, other similar geometries may be contemplated, in which the electrodes are arranged to be planar, an acid absorbing electrode or electrodes 126 fully or partially surrounds an acid generating electrode or electrodes 124, and an acid generating electrode may be interlaced with lanes or regions where DNA synthesis occurs, in order to reduce the distance between each site where deprotection is desired, and the nearest acid generation site.

Figure 19A:
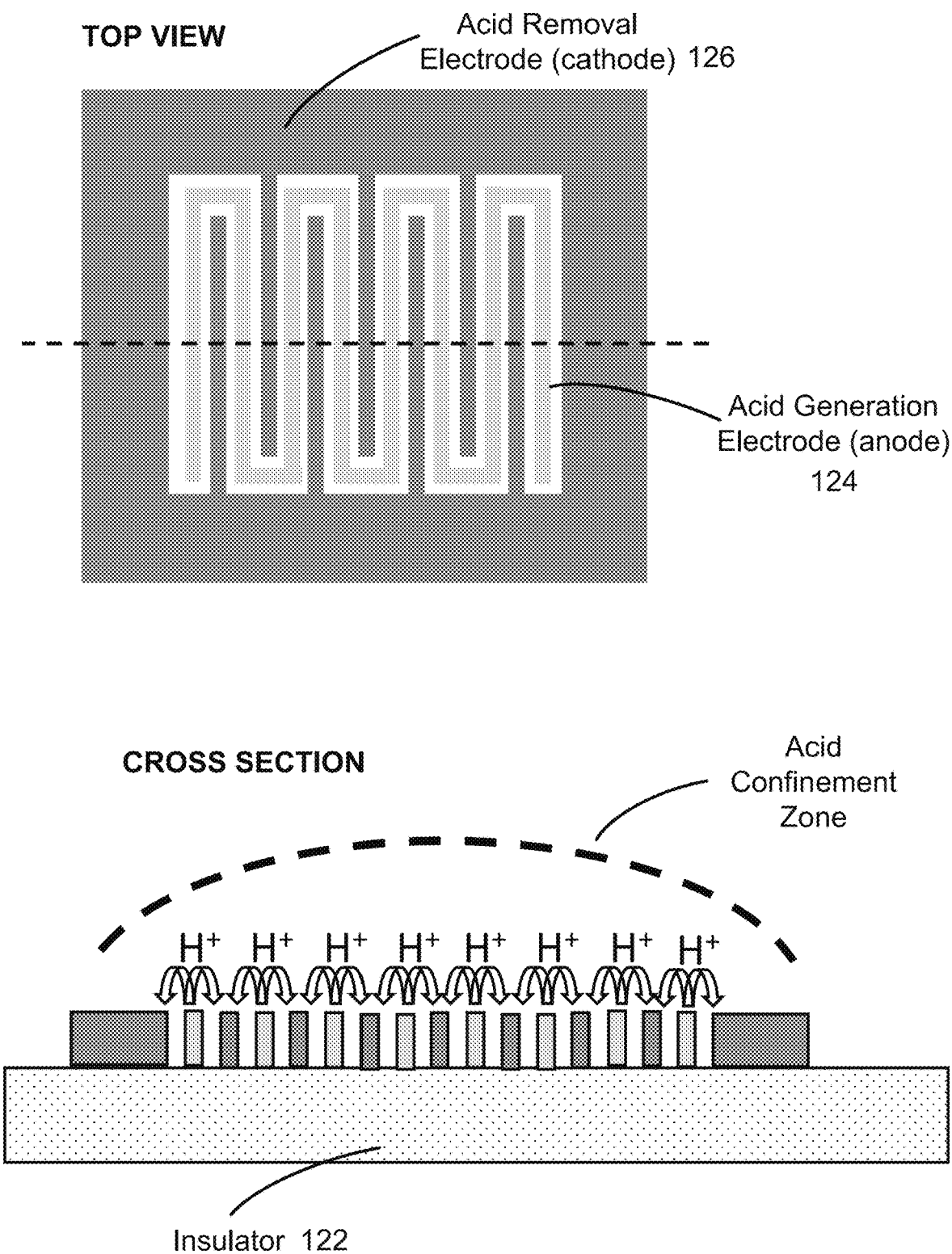
FIG. 19A illustrates interdigitated electrode geometries for acid confinement, in accordance with various exemplary embodiments.

FIG. 19A shows another exemplary embodiment for acid confinement, using the geometry of the planar electrodes, in which an acid generation electrode 124 and acid removal electrode 126 are interdigitated in the interior region, and with synthesis sites between such electrodes. As shown, this geometry has a benefit of reducing the distance from deprotection sites to H+ generation and enhancing H+ localization because the H+ does not have to travel far from a generation site on an anode 124 to a removal site on a cathode 126. In exemplary embodiments, a removal electrode 126 also surrounds an anode 124 region, in addition to interdigitation with it, as indicated, to further confine the H+ generated at an anode 124. It will be appreciated that there are many such interdigitating planar geometries, in which the surface exposed anode 124 and cathode 126 regions, and also the DNA synthesis regions, may be organized so that the length of the boundaries between them is much longer than the linear extent (diameter) of the pixel (or the square root of the total area of anode or cathode) region containing the electrodes. In exemplary embodiments, the surface exposed anode 124 does not need to be connected, nor does the surface exposed cathode 126 need to be connected, although they are to be connected below the surface, so that all parts of the anode are at the same or very similar anode potential, and the parts of the cathode all are at the same or very similar cathode potential. In exemplary embodiments, cathode(s) 126 and anode(s) 124 may be arranged in a "dithering" pattern, in the interior of the region, for example in the form of a dense pattern of small dots, of both anode and cathode type. Exemplary embodiments of such dithering interdigitating electrodes are shown in FIG. 19B. In some embodiments, dithering interdigitating electrodes may be configured in a checkerboard pattern. In other embodiments, dithering interdigitating electrodes may be configured in a pattern of concentric curve shapes alternating between anode and cathode, such as concentric rings, concentric rectangles, or concentric polygons. Moreover, the size and/or shape of the cathode 126 and anode 124 portions may be similar to one another, or may differ from one another. For example, in certain exemplary embodiments that provide a strong confinement of acid, the relative areas for a respective type of pattern are balanced such that the cathodes 126 provide capacity for removal of all acid generated at the anodes 124. In various exemplary embodiments, the regions of anode, cathode, and DNA synthesis are finely intermingled, so as to produce a short distance from any synthesis site to the nearest electrode site, and from any acid generation site to the nearest cathode site, and thereby produce strongly confined acid that has high concentration at the synthesis sites. In particular, many such geometries may implement interdigitation of electrodes, dithering patterns, pattern formation theory, and space filling curves. All such suitable geometries are considered to be within the scope of the present disclosure.

FIG. 20 illustrates an exemplary embodiment for acid confinement, wherein a well structure is used to enhance the confinement. Shown in top view, an acid generation anode 124 is in the center, and is surrounded by an acid removing cathode 126, as in FIG. 17. However, in this embodiment, the anode 124 and cathode 126 are not on a planar substrate. Instead, as shown in the cross section view, the anode 124 is recessed into a well 123 formed in substrate 122, so that H+ is generated deep within the well. The well serves to confine the acid laterally on the walls of the well. The acid is removed by cathode 126 around the mouth of the well. In this exemplary embodiment, DNA synthesis region(s) may be on the base and/or sides of well 123, which therefore serves to confine the acid near the synthesis sites, as the H+ transits from an anode at the base of the well, to the mouth of the well, as shown. In contrast to the plane geometry, where a dimension perpendicular to the synthesis region provides an unobstructed path for losing H+, in this exemplary embodiment the dimension perpendicular to the synthesis region is limited, and is only a path to additional synthesis sites, so thereby this geometry favors confinement.

Figure 21:
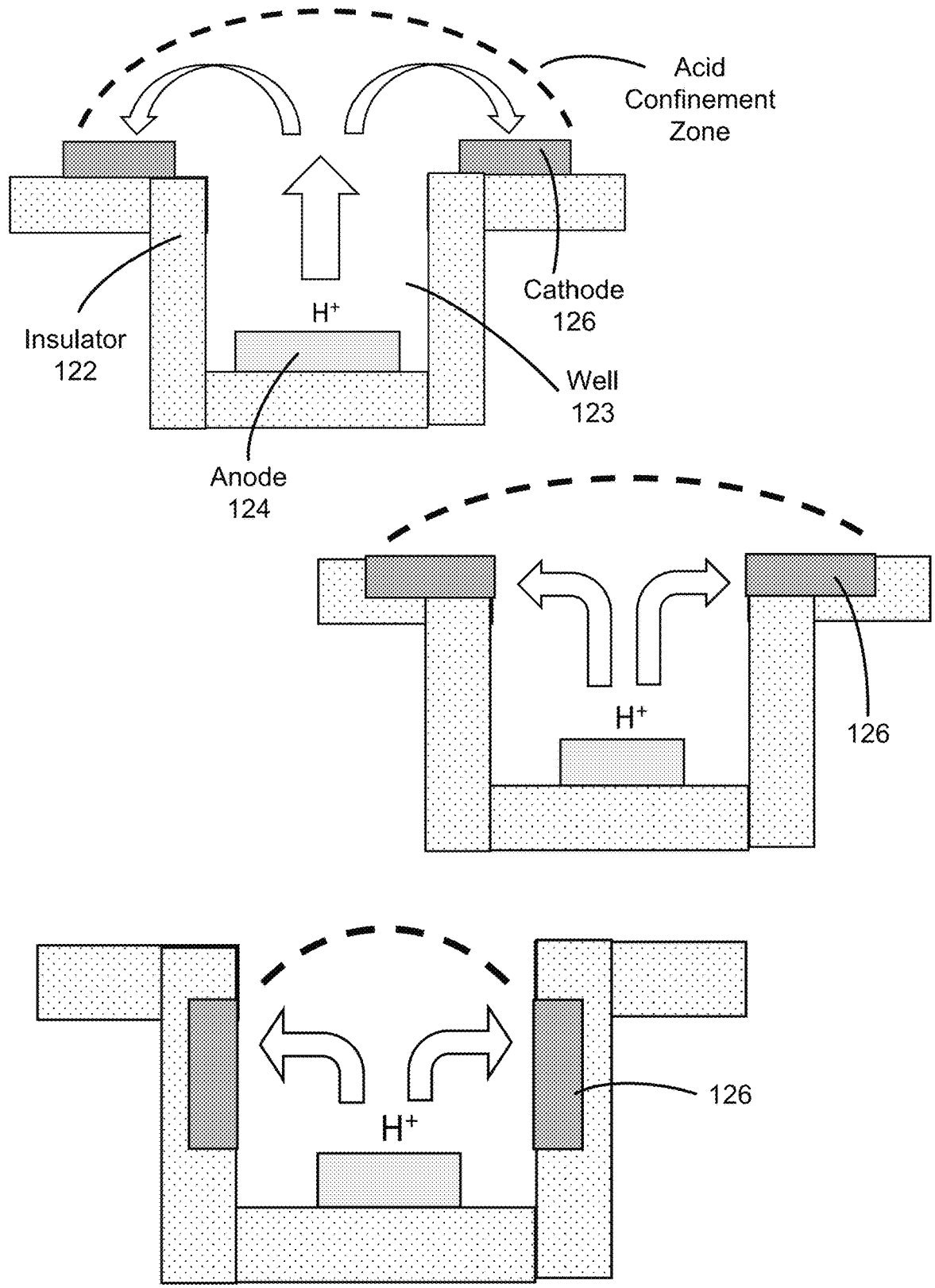
FIG. 21 illustrates exemplary well-based acid confinement electrode geometries, in accordance with various exemplary embodiments.

FIG. 21 illustrates other exemplary embodiments of well-based acid confinement geometry, showing in cross-section different geometries for location of acid removing electrodes 126. Such electrodes may be outside the mouth of the well 123, at the mouth of the well, and/or placed into the walls of the well below the mouth of the well. As indicated, these variations produce progressively greater confinement of the H+ in the well. FIG. 22 illustrates additional exemplary embodiments that further enhance acid confinement in well 123. Shown in cross-section is the use of interdigitated electrodes with a well-based geometry. This confines the acid near the walls and provides for each DNA strand to be near an H+ generation electrode 124, and each H+ generated to be near an acid removal electrode 126. The final cathode 126 at the mouth of the well is positioned to remove the remaining H+ as it exits the well 123 near the walls. It is understood, in this illustrated cross section, that all elements of anode 124 are connected, so they are at a common or very similar anode voltage, and all elements of the cathode 126 are connected, so that they are at a common or very similar cathode voltage. In exemplary embodiments, these electrodes are configured with cylindrical symmetry around the centerline of the well, so that all electrodes shown are rings or discs in three dimensions. In other exemplary embodiments, some or all of the electrodes may not have this symmetry, and may be electrodes that impinge on the well, without extending symmetrically all the way around the well (for example, extending only partially around, such as 30 degrees around, 45 degrees around, 90 degrees around, 180 degrees around, and/or the like). In FIG. 22 an exemplary embodiment is illustrated, in which the acid removing electrode(s) 126 at the mouth of the well 123 are configured with an overhang, such that the electrodes substantially narrow the exit opening of the well. The electrodes 126 may in addition extend into the well on the walls, as shown, for providing additional acid removing area within the well. As a result of the restricted opening, with acid removal capability, the acid confinement zone is highly restricted as indicated, with little acid escaping from the exit. By making this exit hole smaller, the probability that an H+ that is generated in the well 123 escapes can be reduced and/or minimized, for example to any suitable limit. It will be understood that the small exit hole also limits the transport of new reagents from above the well 123 into the well 123, as well as removal of the contents of the well 123, so the illustrated geometry may extend the time utilized to deliver reagents to the well 123, or remove used reagents from the well 123, and therefore may lead to longer duration for synthesis chemistry cycles. From the foregoing disclosures of well 123 geometries and their associated properties, many other geometries for the well 123, the associated electrodes, and/or synthesis regions may be utilized that would confer similar benefits and meet similar objectives, and all such suitable geometries are understood to be encompassed by this disclosure.

Reaction Area Enhancing Features

For the exemplary pixel array synthesis format shown in FIG. 11, each synthesis pixel has a relatively small and limited "area" footprint, as viewed from above. For many applications it is beneficial to have a high density of pixels, and therefore the area of each pixel may desirably be reduced and/or minimized. However, minimizing pixel area is in conflict with the synthesis process itself: the chemical processes of various exemplary embodiments that provide for the synthesis as disclosed are surface processes that each utilize respective dedicated surface area, and therefore limiting pixel area may limit these chemical processes, which directly impact both the quality and quantity of synthesis. Specifically, the acid generation and removal occur at the surface area of the electrodes, and so is surface area limited by this, and production and removal of acid limit the quality of synthesis; the synthesis process itself on a solid phase depends on the area available for the strand start sites, and thus this limits the quantity of synthesis.

Accordingly, principles of this disclosure contemplate approaches for increasing the area available for the electrode reactions and synthesis start sites, without increasing the pixel footprint area. This has the advantage of allowing for greater pixel density while still preserving quality and quantity of synthesis.

A class of exemplary embodiments for increasing the area available for these surface chemical processes is illustrated in FIG. 23. In these embodiments, the surface of the electrodes, or the synthesis support surface, may be a rough or porous surface. By having a rough or porous surface, the total available surface area for chemical reactions is increased, without increasing the area footprint from above. These surfaces may have a random roughness, for example created by the deposition or etching of materials, or a patterned roughness, for example created by a suitable controlled fabrication process such as ion-beam milling, contact lithography, or the like. These surfaces may also be rendered porous, i.e., infused with pores, cavities, holes or microwells, on a micro- or nano-scale. Many suitable approaches for making such rough, patterned, or porous surfaces may be utilized, as desired. By rendering the electrodes in such a manner, as indicated in FIG. 23 by the depicted zig-zag surface, the available surface area for the acid generation and acid removal electrochemical reactions may be greatly increased, for example, by 2 fold, 10 fold, 100 fold, or even more. Moreover, by rendering the DNA synthesis solid phase support in this manner, as also indicated in FIG. 23 by the zig-zag surface, the available area for start sites for the DNA synthesis may be increased by 2 fold, 10 fold, 100 fold, or even more.

Another class of exemplary embodiments for increasing available surface area is shown in FIG. 24A. In these embodiments, vertical surface structures, or structures generally perpendicular from the local surface, may be used to increase surface area of electrodes. The structures 127 indicated may be arrays or groups of posts, pillars, flanges, fins, or the like, all of which extend up from the surface to provide the side-wall area as additional useable surface area. It is possible for such sidewall area to increase the "footprint" area by an arbitrarily large amount, proportional to the height of the vertical structures. In particular, use of such vertical structures 127 on the electrodes can increase the area available for electrochemical processes on the electrode by 2 fold, 10 fold, 100 fold, or even more. Additionally, use of such vertical structures 127 on the solid-state support for the synthesis can increase the area available for starts sites by 2 fold, 10 fold, 100 fold, or even more.

FIG. 24A discloses the use of the well 123 depth to further provide the well wall area as useful area for electrodes or synthesis. The well 123 wall area can be increased arbitrarily by increasing the depth of the well 123 with no change to the footprint on the pixel, and so this provides a large source of additional area that may be used for anode, cathode, or synthesis solid phase support. This wall area can then further be combined with local perpendicular structures 127 as shown, to further expand the desired area. In exemplary embodiments, on the well 123 walls there may be multiple symmetrical flanges that provide substantial area. The well walls can provide 2 fold, 10 fold, 100 fold, or even more increase in area available for electrodes that reside in the walls (anode or cathode). Additionally, the well 123 walls can provide 2 fold, 10 fold, 100 fold, or even more increase in area available for the DNA synthesis with start sites on the walls. The addition of generally perpendicular area features 127 to the walls can further expand the area 2 fold, 10 fold, 100 fold, or even more for either electrodes or synthesis starts.

Figure 24B:
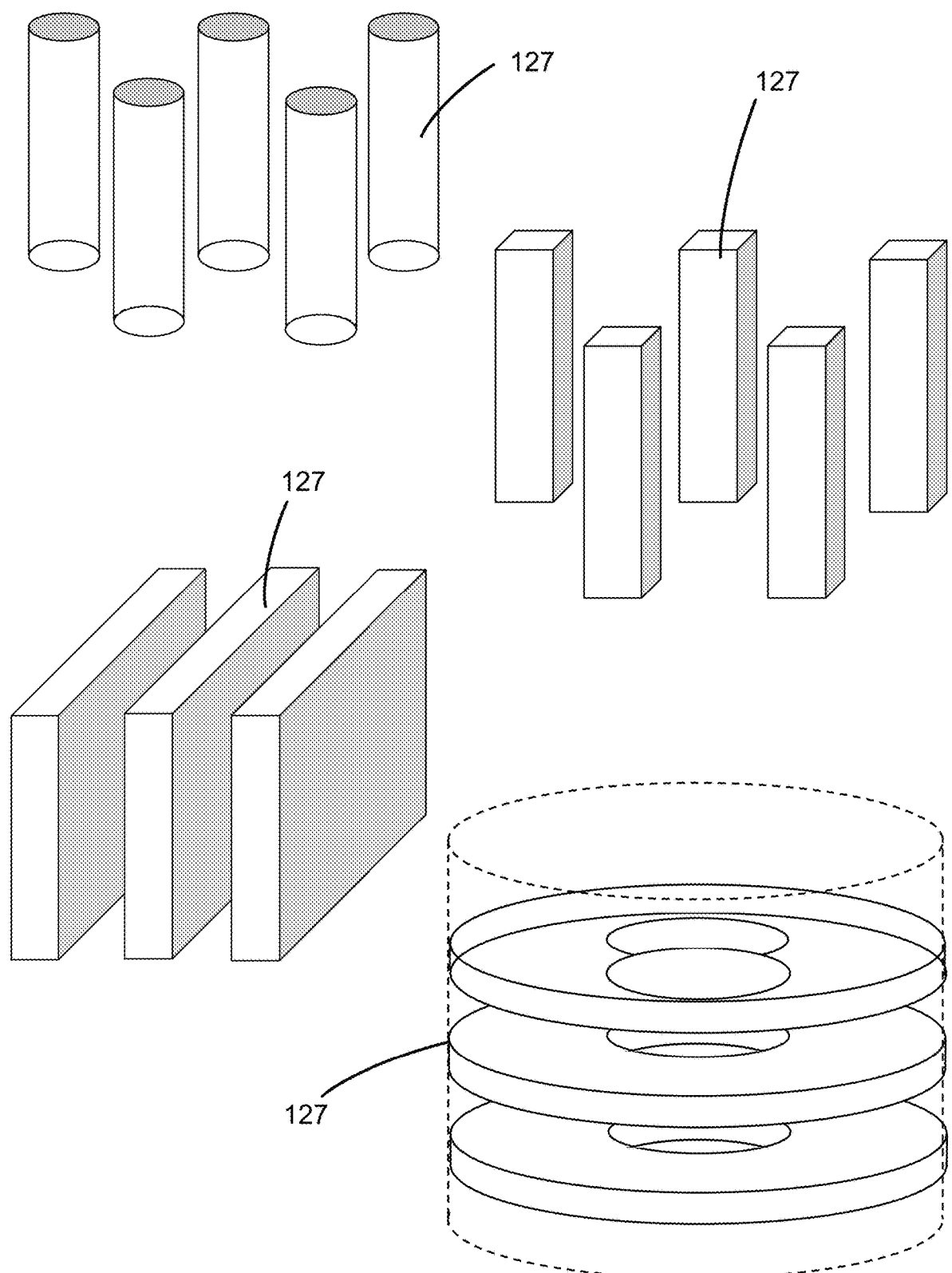
FIG. 24B illustrates exemplary perpendicular structures that can be used to increase available surface area, without increasing overall 2D footprint, in accordance with various exemplary embodiments.

FIG. 24B illustrates exemplary embodiments for generally perpendicular area-enhancing structures 127 indicated in FIG. 24A. Shown as exemplars are an array of circular pillars (upper left), an array of square pillars (upper right), a series of vertical plates or ridges or fins (lower right) and a series of circular flanges in a well (lower right). Such arrays can be extended to arbitrary large numbers to fill available areas with such vertical or perpendicular structures. Moreover, area-enhancing structures 127 may be combined and/or intermingled with one another and may not necessarily all be of a similar size, orientation, or geometry.

In various exemplary embodiments, DNA synthesis start sites are not solely confined to a solid support surface. Rather, they may be distributed throughout a 3D porous matrix, with sufficient porosity to allow liquid reagents and H+ to permeate the matrix and reach the target chemical reaction sites on the synthesis strands. Exemplary embodiments are illustrated in FIG. 25. The matrix material is indicated as the shaded and cross-hatched region. In exemplary embodiments, this exists as a thin film of material on top of the electrode structures disclosed (planar or well geometries, as shown in FIG. 25). In exemplary embodiments, this matrix material may be a polymer matrix, such as a silane matrix, or gel, such as a hydrogel, or a deposition of fine grains, particles or beads, which may be porous, or solid, and which may have interstitial spaces between them. This matrix allows the synthesis start sites to be distributed in 3D, and thus greatly increases the area density of start sites, for example by 2-fold, 10-fold, 100-fold, 1000-fold, or even more. The thickness of this matrix layer in exemplary embodiments may be up to 1 nm, up to 10 nm, up to 100 nm, up to 1000 nm, or greater than 1000 nm. The region of synthesis in this matrix is defined by the 3D acid confinement zone as indicated in FIG. 25, because the synthesis will occur wherever the acid is present in the matrix. The confinement zone may extend beyond the film, as indicated in FIG. 25 on the top, or the film may entirely encompass the confinement zone, as shown toward the bottom.

From the foregoing disclosures of area enhancement—which provide more sites for chemistry without increasing the pixel area footprint—it will be appreciated that many combinations and variations of these embodiments can be used to increase the available reaction surface area, and all such extensions, combination, and variations are considered within the scope of this disclosure.

FIGS. 26A, 26B, 27A, and 27B illustrate exemplary embodiments of electrode geometries that provide for high confinement of generated acid and/or H+. FIG. 26A illustrates use of "wall"-like electrodes, where the cathode 126 surrounding the anode 124 comprises generally vertical walls or similar structures, and such that height of these walls enhances the confinement of H+, to the point where the confinement zone may be contained within the walled volume, as illustrated. Such walls in exemplary embodiments are relatively tall and thin, with a height-to-thickness aspect ratio that may exceed 2, 5, 10, 20, or even more. The height of such walls may also equal or exceed the diameter of the pixel, and may be up to 1, 2, 5, 10, or even more times high than the diameter of the pixel. Correspondingly, the physical height of such walls, for various possible pixel sizes ranging from the nanometer to micron scales, may exceed 100 nm, 500 nm, 1 micron, 5 microns, or 10 microns. FIGS. 26A and 26B also illustrate use of "aperture"-like electrodes (or barriers) for the well geometry, where a cathode 126 surrounding a well 123 opening forms a cover with a relatively small aperture, to reduce the probability that an acid or H+ molecule exits the well before encountering the acid removing electrode 126. Because the aperture hole may be made arbitrarily small, such an aperture may reduce the cross-sectional area of the exit relative to the well 123 mouth area by up to a factor of 2, 5, 10, 100, 1000, 10,000, or even more.

FIG. 27A illustrates exemplary embodiments of electrode geometries that provide for high confinement of generated acid by means of introducing a "ceiling" acid absorbing electrode 126. To provide for high confinement of acid, this ceiling is relatively large in coverage over the anode 124, encompassing the anode area beneath its footprint, including a large margin around the anode footprint, and is also configured to be relatively low and close to the anode 124. By making this ceiling both "broader" over the anode 124, and "lower" and closer to the anode 124, the acid can be more highly confined near the anode 124 and synthesis region, without limit as the suitably broad ceiling approaches the anode 124. The confinement so achieved may vary depending on the extent that the ceiling areal footprint has a large margin around the cathode 126, and moreover on the extent of how low/close the ceiling is relative to the cathode 126. In exemplary embodiments, the height of the ceiling above the synthesis region is less than the distance to the nearest adjacent pixel, to effectively prevent cross talk. In various exemplary embodiments, the height is less than 100%, less than 50%, less than 20%, less than 10%, or even less than 1% of the distance to an adjacent pixel. The "low ceiling" cathode 126 in exemplary embodiments may be an extension of a local pixel cathode 126, as shown in the cross section on the top in FIG. 27A. In other exemplary embodiments, as shown in FIG. 27A bottom portion, the low ceiling cathode 126 is a global electrode that extends across a multiplicity of pixels, which may comprise some or all of the entire pixel array. In exemplary embodiments, the global low ceiling electrode 126 is mechanically movable up and down, or removable, so that as needed, it can be moved away vertically, to provide greater access to the synthesis area, or moved closer to the surface to provide more confinement, to facilitate additional or removal of reagents during synthesis steps, or to facilitate access to or removal of the DNA post-synthesis. In all such cases, the ceiling cathode 126 is desirably maintained at the same potential or very similar potential as the local cathodes 126.

FIGS. 26A and 27A show use of an acid removing electrode 126 itself to provide an extreme geometry with high confinement of acid. In other exemplary embodiments, the electrode is not used for this purpose, and instead a separate barrier material that is not a part of the cathode is used to provide high confinement, simply by acting as a barrier to reflect H+, or both reflect and absorb H+, so as to prevent it from leaving the desired acid zone. FIG. 26B shows such an exemplary embodiment, in which the walls or aperture are formed from a barrier material, that is not the acid removing electrode 126 itself. This material barrier 128 may just reflect, or passively absorb and reflect, the H+ or acid molecules, and provides for physical confinement, while the active acid removal occurs at the cathode electrode 126, which need not have a high confinement geometry in these embodiments. In exemplary embodiments, the barrier 128 material is a chemically inert and strong reflector of H+, such as an oxide or nitride material. In other exemplary embodiments, the barrier 128 is of a material that strongly passively absorbs H+, such as palladium or platinum, so that it may assist in the removal of H+(in the case of metal or conducting barriers 128, in exemplary embodiments such components are insulated from the cathode 126 and anode 124, and maintained at a distinct potential, and for absorbing H+, preferably a negative potential relative to the solution in order to attract the H+). In exemplary embodiments where the barrier 128 material is conductive and intended to reflect H+, it may be maintained at a potential that repels H+, i.e. a positive potential relative to the solution, to enhance the reflective capability, or to render a metal that might absorb H+, such as platinum or palladium, into a strong reflector. In exemplary embodiments, the barrier 128 material may also be selectively removable, preferably by solution phase chemical dissolution, so that at the end of synthesis, it may be selectively removed to facilitate the access to, or release of, the DNA that has been synthesized. In particular, this can provide access to the DNA in the case of the aperture barrier with a very narrow exit, which would otherwise strongly impede post-synthesis access to the DNA produced. In the case of the aperture geometry, in exemplary embodiments post-synthesis access to recover released DNA may also be achieved by biasing the solution outside the well 123 to a positive potential, which will strongly force the released DNA through the aperture. In exemplary embodiments this may be achieved conveniently by placing the anode 124 at a suitable negative potential relative to the external solution phase and the cathode 126. Similarly, FIG. 27B illustrates such an exemplary embodiment, in which the low ceiling is formed from a barrier 128 material, rather than the cathode 126. The same considerations apply as for the wall and aperture barrier geometries. In particular, the low ceiling may be a metal such as platinum or palladium which absorbs H+. Post-synthesis, the low ceiling barrier 128 may be either sacrificially removable, or, in the case of the global low ceiling barrier in FIG. 27B, it may be simply mechanically removed. As described, electrical forces may also be used to recover released DNA post-synthesis from such highly confined low ceiling geometries, for example by applying a positive potential to the solution outside the low ceiling region, relative to the potential inside where the DNA is located.

From the foregoing examples, it will be appreciated that many variations and combinations of such extreme confinement geometries are may be utilized, for example involving both the electrodes or barrier materials, as well as sacrificial barrier materials or the use of electrical bias to access DNA post-synthesis, and all such variations and combinations are considered to be within the scope of the present disclosure.

Exemplary embodiments described above demonstrate confinement of acid through the use of an acid removing electrode or cathode 126 (i.e., a solid electrode used to drivel electrochemical removal of acid or H+). Other exemplary embodiments utilize other approaches for confining the acid near the acid generating electrode 124, that do not rely on such an acid absorbing electrode 126. These approaches for acid confinement can, in general, be used instead of, or in conjunction with, such exemplary acid absorbing electrodes 126 as those disclosed above.

Figure 28:
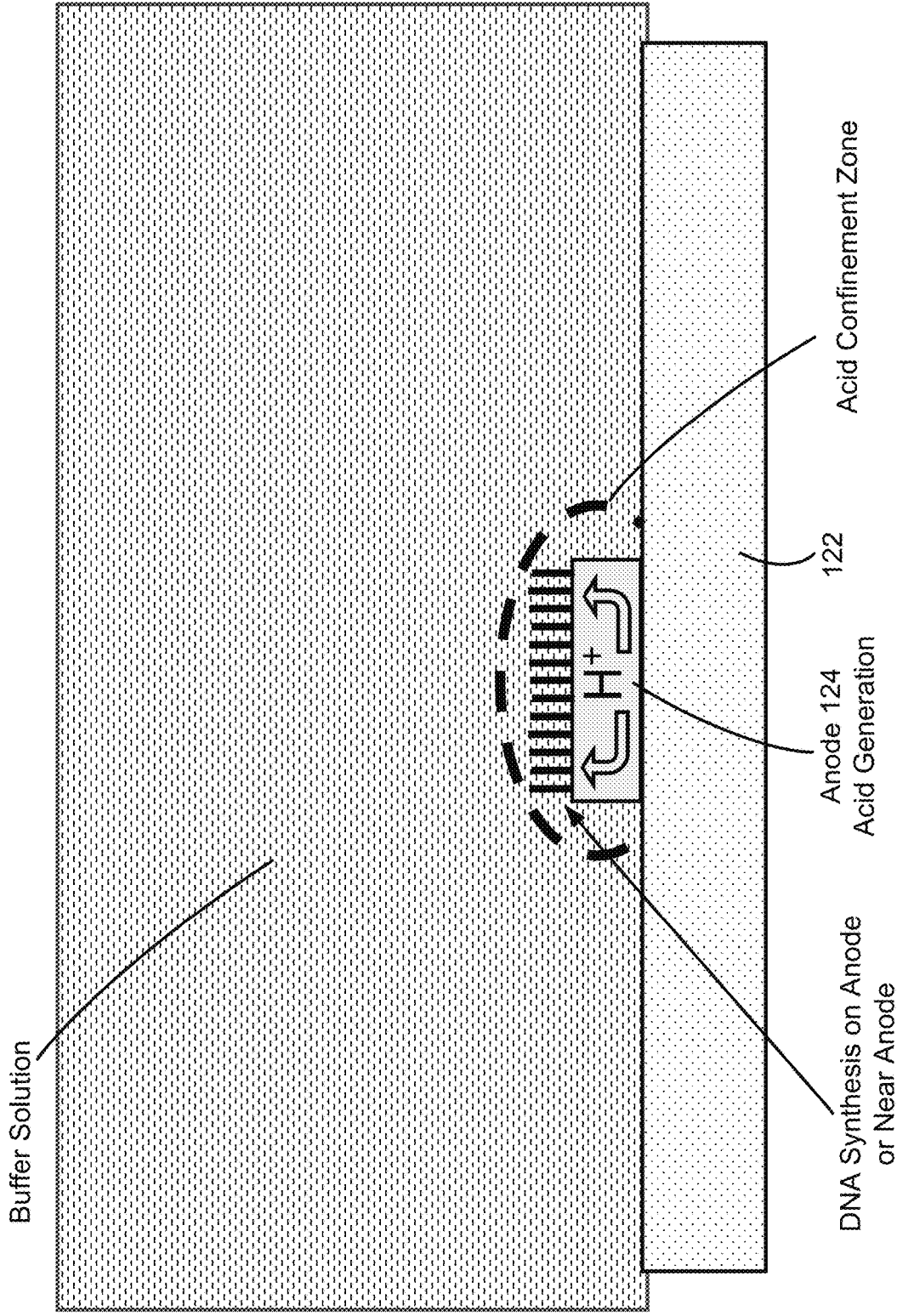
FIG. 28 illustrates use of a solution phase buffer for highly localized acid confinement, in accordance with various exemplary embodiments.

With reference now to FIG. 28, in accordance with various exemplary embodiments is illustrated acid confinement, in which a buffer solution in contact with the acid generating anode 124 is used to confine H+ generated. Buffers are a well-known and broad class of chemicals that have the capacity to neutralize an acid or absorb a free H+. A great many buffer chemicals, compositions and solutions are well known to those skilled in the art of chemistry and biochemistry, and many such, in solution phase in a suitable solvent, are suitable for this purpose, for example solutions including organic bases such as 2,6 lutidine, pyridine, N-methylimidazole, diisopropylethylamine, or related derivatives. As illustrated in FIG. 28, if the anode 124 is immersed in such a buffer, the H+ produced at the anode 124 will be rapidly removed from solution by the buffer, up to some limit of the rate of production, which depends on the buffering capacity of the solution. By controlling the chemical composition and concentration of the buffer, and the buffering capacity of the solution, the extent of the acid confinement zone can be adjusted and can in particular be made to be very near to the anode 124. In exemplary embodiments, this acid zone may extend as little as 1 nm, 10 nm, 100 nm, or 1000 nm from the anode 124. In exemplary embodiments using such a buffer solution, DNA synthesis takes place either on the anode 124, for example as illustrated in FIGS. 14 and 28, or very near the anode 124, such as in anode configurations illustrated in FIG. 18, or in FIGS. 19A and 19B, where anode area is distributed so as to be interspersed with synthesis areas. The anode 124 may be in planar and/or well configurations for use with such a buffer solution.

With reference now to FIGS. 29A, 29B, 29C, and 29D, illustrated are other exemplary embodiments where a buffer is used to confine acid, in which the buffer chemical or capacity is confined to a solid particle, and the solid particles are put into solution. In various such embodiments, the buffer chemical stays bound to the solid phase particle, so that it is not free to scavenge acid or H+ arbitrarily close to the anode 124, as it would be if it were in molecular form in solution. In these embodiments, the solid particles serve the purpose of creating steric hindrance of the buffer chemical reaching close to the anode 124, and therefore provides a means to extend the acid zone. In exemplary embodiments, the buffer particles have buffer molecules exposed on their surface. In other exemplary embodiments, the buffer particles may be porous and be infused with the buffer chemical, such that the H+ or acid has to permeate the porous particle to become neutralized. For example, such particles may be buffer resin particles, and resins impregnated with buffers are a format for working with buffers that is well known to those skilled in chemistry. For example, such particles may also be nano-particles that have buffer ligands on their surfaces. In other exemplary embodiments, the buffer particles made be made of materials that provide the capacity to absorb H+. In one exemplary embodiment, micro or nano-particles of hydrogen absorbing metals such as palladium or platinum, or magnesium, titanium, or particles rich in such metals, including alloys such as Pd—Rh alloys, or other suitable materials that absorb hydrogen or form hydrides in micro-particle or nano-particle format may be used as buffer particles. Many such suitable metals, alloys, compounds, or materials may be utilized, and use of all such suitable materials are considered to be within the scope of the present disclosure.

The buffer particles in these exemplary embodiments provide an approach to set a length scale for the acid confinement zone, where this confinement length scale is closely related to, and at least partially controlled by, the mean diameter of the particles, and the mean spacing between particles in the solution suspension of particles, and to the buffering capacity of each particle (e.g., how much H+ it can maximally absorb per unit of time, as a function of local H+ concentration). At high concentration of buffer particles, the diameter of the particles becomes a dominant factor, while at lower concentration the spacing between particles becomes a dominant factor in determining the extent of the acid zone.

Figure 29B:
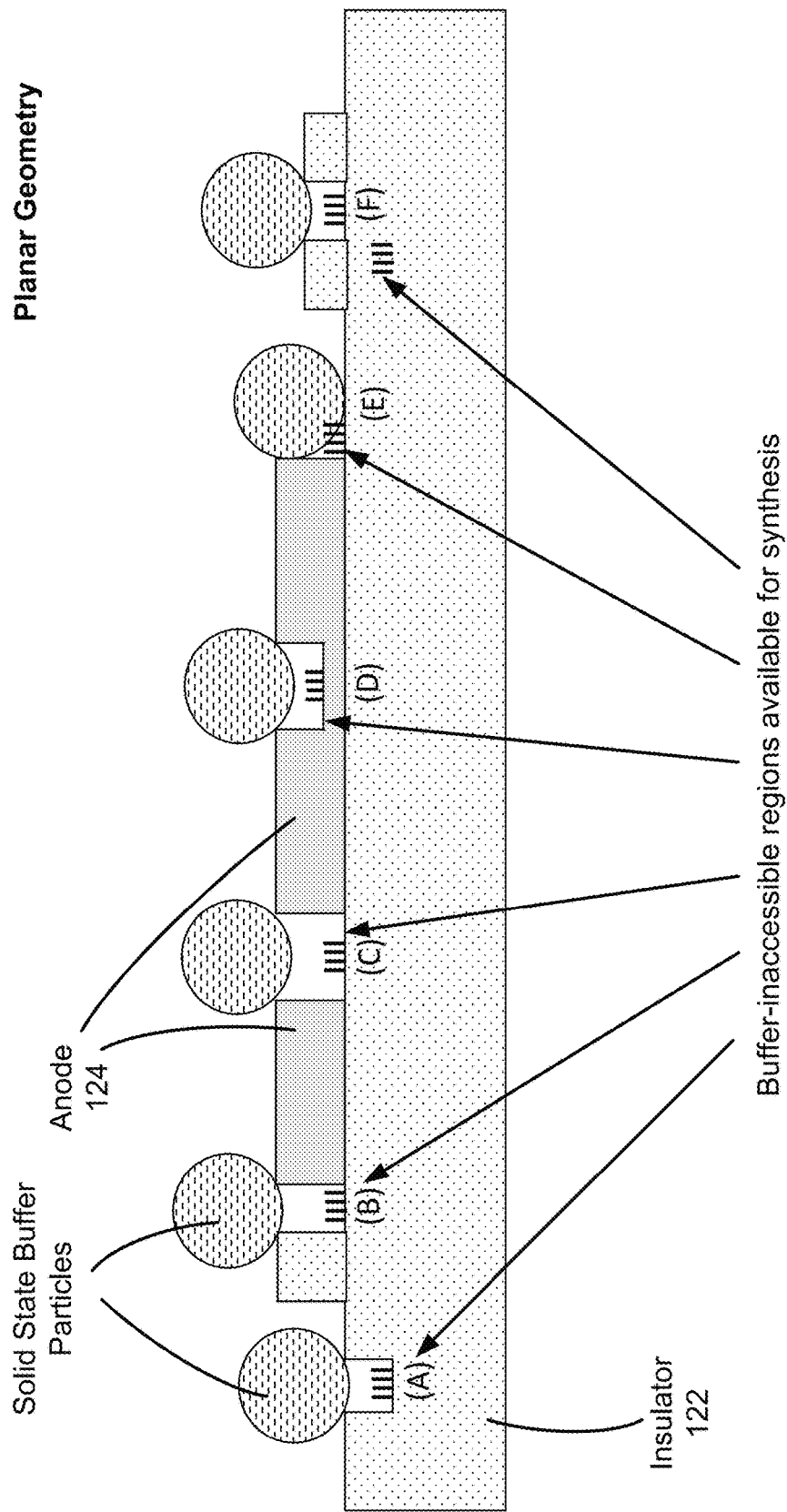
FIG. 29B illustrates the creation of buffer-inaccessible zones for DNA synthesis, when using solid-state buffer particles for acid confinement in a planar geometry, in accordance with various exemplary embodiments.

In various exemplary embodiments, for a given anode 124 and substrate 122 surface geometry, the steric hinderance effects of the buffer particles can provide for sheltered regions on or near the anode 124, which are accessible to H+ as needed to drive deprotection for synthesis, but inaccessible to the buffer confined to particles so that the buffer cannot inhibit deprotection in such zones. Preferred embodiments of such buffer particle-inaccessible synthesis regions are shown in FIG. 29B, where the depiction of growing strands indicates these inaccessible regions that could optionally be used as sites for synthesis. In FIG. 29B, there are shown exemplary embodiments of various types of local geometry features that create inaccessible regions for the buffer particles: a pit in the substrate 122 (location A), a crevice between a substrate projection and the anode 124 (location B), gaps between surface segments of the anode 124 (location C), a pit in the anode 124 creating an inaccessible region on anode 124 (location D), a corner between anode 124 and substrate 122 (location E), or closely spaced projections from the substrate 122 (location F). Beyond the disclosed embodiments, many variations and combinations of such geometric features can be used to create buffer-inaccessible zones for DNA synthesis, and all such variations and combinations are considered to be within the scope of the present disclosure. Moreover, the use of inaccessible zones with buffer particles allows for highly effective confinement of the acid, to prevent pixel crosstalk, without impairing the efficiency of the synthesis chemistry.

FIG. 29A at bottom illustrates exemplary embodiments where the solid-state buffer particles are combined with an anode well geometry, and where the buffer particle diameter exceeds the 123 mouth diameter, so that the buffer particles are prevented from entering the well 123. The result is that the entire interior of the well 123 is a buffer inaccessible zone. In these exemplary embodiments, the volume inside the well 123 can maintain a high acid concentration, while the external buffer particles eliminate the H+ as it exits the well 123. This provides for DNA synthesis zones inside the well 123, such as on the side walls or bottom. This exemplary use of solid-state particles thereby creates a strong and well-defined confinement zone in the well that greatly reduces the probability that an H+ produced in one well 123 could transit to a different well 123 in a different pixel to create crosstalk. Accordingly, in exemplary embodiments, the buffer particle diameter is greater than the well 123 diameter, for example, preferably greater than 1.1 times the well diameter, preferably greater than 1.5 times the well diameter, preferably greater than twice the well diameter, or preferably greater than ten times the well diameter, for example to minimize the extent that portions of such buffer particles can impinge upon the well entrance, and to reduce and/or minimize the likelihood that through variation in the particle diameter, some sub-population of such particles may be small enough to enter the well 123.

FIG. 29C illustrates exemplary embodiments where buffer particles that would fit in the anode well can be restricted by various forms of barrier structures in the well 123. In the upper portion of the figure is shown the use of barrier particles deposited in the well, forming a barrier in which reagents and acid can move through the interstitial spaces, but which the buffer particles are too large to penetrate. The result is that the confinement zone is precisely defined by the upper envelope boundary of the barrier particle layer. Such barrier particles may be an inert material that serves only as a physical barrier to the buffer particles, or may in exemplary embodiments also be used as solid support sites for DNA synthesis. In the lower portion of FIG. 29C is illustrated an exemplary embodiment in which barrier structures are present in the well 123, which may be solid projections from the sides or base of the well 123, that again block the smaller buffer particles from penetrating fully into the well, thereby creating a buffer inaccessible zone for synthesis. In exemplary embodiments, the barrier structures indicated may be composed of the wall insulator material extended from the wall, of the anode 124 material when connected to the anode 124, or of another material which may be inert, serving only as a physical barrier to the buffer particles. In exemplary embodiments, this barrier material may also provide surface sites for the DNA synthesis.

FIG. 29D illustrates exemplary embodiments where solid buffer particles are used to confine the acid, and where a layer of matrix material that supports DNA synthesis sites, as described for FIG. 25, is used to also physically block the buffer particles from impinging on the synthesis region, which itself extends into a 3D volume in the matrix. At top is shown the use of such a matrix layer with a planar geometry, and at bottom is shown the use of such a matrix layer with a well geometry. In both cases, the physical matrix material excludes the buffer particles, and thereby creates a buffer inaccessible zone in 3D where synthesis can occur unimpeded, while outside this layer a high concentration of small buffer particles can be used to strongly absorb the released H+, to prevent pixel crosstalk.

From the exemplary disclosures above, many suitable variations and combinations of approaches for using solid-state buffer particles for acid confinement may be understood, and all such variations and combinations are considered to be within the scope of this disclosure.

Figure 31:
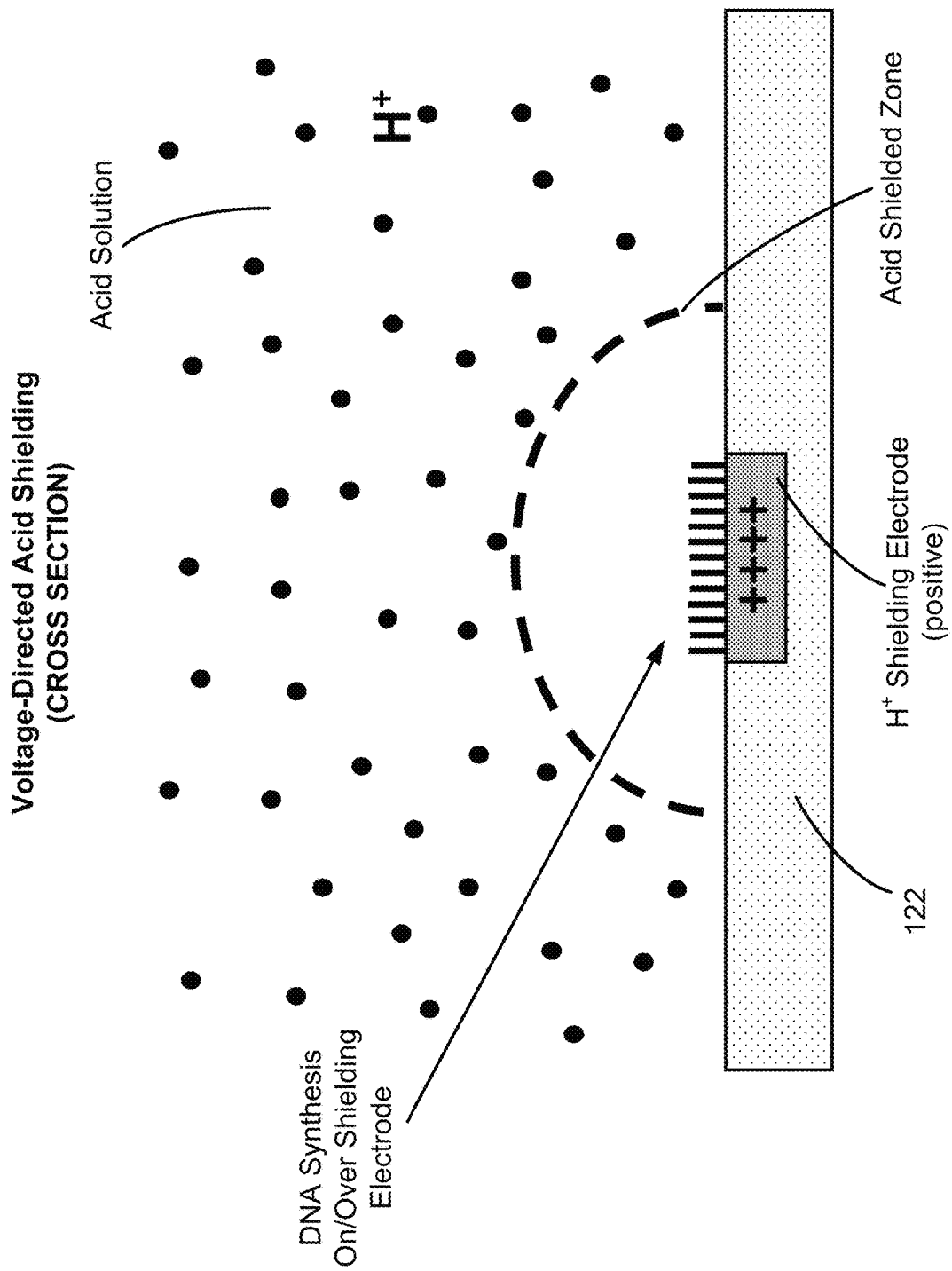
FIG. 31 illustrates using voltage to repel acid from a synthesis site, in accordance with various exemplary embodiments.
Figure 32A:
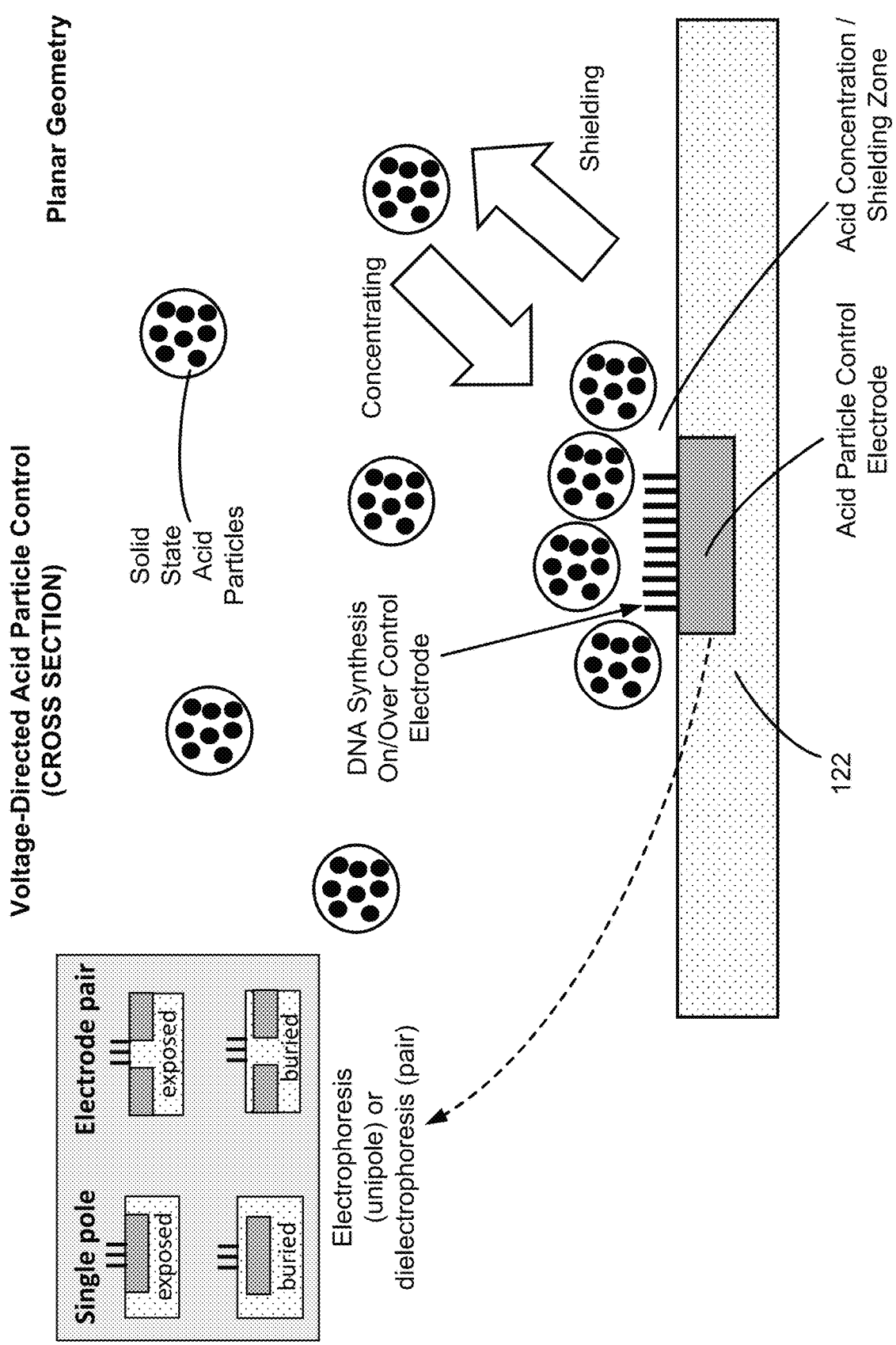
FIG. 32A illustrates using acid-bearing particles under voltage control to deliver acid for deprotection, in accordance with various exemplary embodiments.

FIGS. 31 and 32A illustrate a class of exemplary embodiments which do not utilize a cathode and anode as disclosed above—i.e., where acid can be concentrated for deprotection, or eliminated to avoid deprotection, without using an anode to generate acid or a cathode to remove acid by electrochemical approaches. Such "electrode-free" approaches for modulating H+ concentration can be used instead of, or in combination with, electrode-based acid generation and removal approaches including those disclosed previously above. As illustrated in FIG. 31, in various exemplary embodiments, there is a weak acid in solution, resulting in a low concentration of H+. By applying a negative voltage on a concentrating electrode, the H+ in solution is electrically attracted to this concentrating electrode, forming a local elevated concentration of H+, and a corresponding acid concentration zone. If this area is also the site for DNA synthesis, this can be used to attract the H+ needed to drive de-protection for synthesis. As shown in the close-up inset at left in FIG. 32A, in an exemplary embodiment the synthesis takes place directly on the concentrating electrode (presumed to have a suitable functionalization with start sites), or in another exemplary embodiment, the concentrating electrode is buried below the surface, and synthesis takes place on this surface, such as an oxide or nitride surface (suitably functionalized). As shown in FIG. 32A, the opposite electrical process may be used to shield such a synthesis region from H+, by applying a positive voltage to the shielding electrode, in order to repel the H+ locally. In exemplary embodiments, this is used to shield against an ambient solution acid concentration and/or used to disperse the high H+ concentration resulting from the concentration effect in FIG. 32A. Both these effects, H+ concentration and H+ shielding, may be used to perform the selective modulation of H+ concentration needed to drive independent synthesis processes at distinct pixels. The amount of shielding or concentration may vary, for example based at least in part on how far the electrical field emanating from the electrode can extend into solution without being screened away by ions in solution. This characteristic length is known as the Debye length, and it is a function of the ion concentration and temperature of the solution. The local H+ ions can be attracted from a zone extending a few Debye lengths, and they can be repelled from a similar sized zone. In exemplary embodiments, the Debye length may be more than 1 nm, more than 10 nm, more than 100 nm, or more than 1000 nm.

FIG. 32A illustrates an exemplary embodiment in which an acid is bound to solid particles, and electrical forces are used to attract the acid particles to the control electrode or repel such acid particles away. This provides per-pixel control usable for selective deprotection at desired pixels, while preventing acid driven de-protection at other pixels. This solid phase acid provides the advantage that such carrier particles can be manipulated (concentrated or expelled) by using electrical forces, specifically electrophoresis (forcing based on particle net charge, using a single pole electrode, which will attract the opposite charge or repel a like charge) or dielectrophoresis (forcing based on polarization of the particles, which utilizes an electrode pair for control, in order to apply an opposing voltage across these control electrodes, so that they attract dipoles). Because the electrophoretic and dielectrophoretic forces can be large on such particles, and such particles can therefore be readily moved to or away from an electrode, having an acid bound to such particles, such as TCA, provides a convenient approach for providing the acid utilized for deprotection at selected pixels, while preventing such acid from deprotecting at other pixels. In exemplary embodiments, acid bearing particles are present in solution at a nominal concentration, for example between about a 10 nano-Molar concentration and about a 0.1 pico-Molar concentration, and the control electrode (or control electrode pair for dielectrophoresis) is used to locally increase this concentration for deprotection or reduce the concentration or repel these particles to retain protection. The control electrode(s) may be exposed or buried as indicated in the inset in FIG. 32A, and for the uni-polar electrode, the synthesis in exemplary embodiments occurs on or above the electrode driving electrophoresis, while for the pair of electrodes driving dielectrophoresis, the site of greater concentration is between the electrode tips, and hence this is the preferred synthesis location, with electrodes that may be either buried or on the surface.

Print Head DNA Synthesis Configuration

In various exemplary embodiments disclosed above, such as illustrated for planar and well acid generation geometries (FIGS. 17 and 20), it is implied that the DNA synthesis region is on the surfaces indicated, near or on the electrodes, and generally coupled to the same solid support as the electrodes, as indicated explicitly in FIGS. 13, 14, and 15. In the context of an exemplary DNA synthesis chip, this implies that the synthesized DNA is in this manner coupled to the chip surface.

Figure 32B:
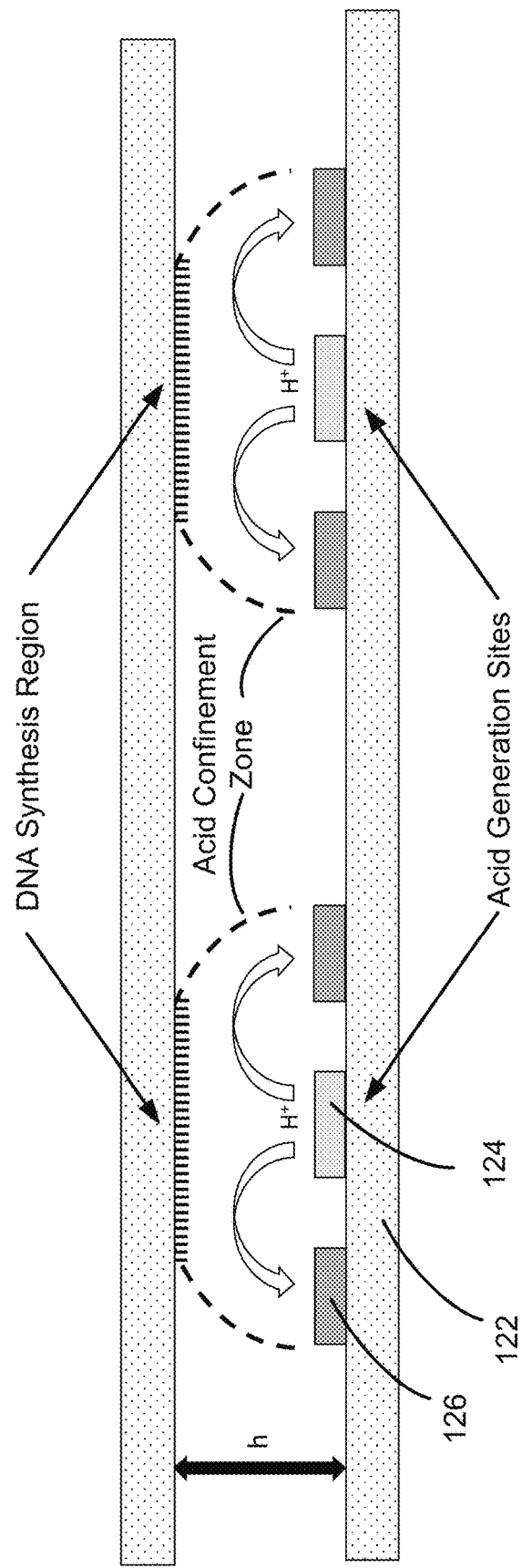
FIG. 32B illustrates a print head configuration for synthesis for a planar acid generation geometry, and an exemplary embodiment of a print head configuration for synthesis, in which synthesis occurs on an opposing surface, for a planar acid generation geometry, in accordance with various exemplary embodiments.

However, principles of the present disclosure contemplate that, in various exemplary embodiments, in contrast DNA synthesis can take place on a surface opposing the surface of the chip, so that the synthesized DNA is attached to this opposing surface, and no synthesis takes place on the actual chip surface. This geometry may be referred to as a "print head" configuration, and certain exemplary embodiments are illustrated in FIG. 32B. Illustrated therein are two adjacent acid generation sites, with the respective acid confinement zones in which the generated H+ is concentrated, which may be by any of the suitable approaches disclosed herein. As shown, there is an independent opposing surface, separated by a height h from the acid generation electrode substrate surface, that impinges on these acid generation zones, and in these regions is where the synthesis takes place, with the synthetic DNA fragments growing on the opposing surface as indicated. In various exemplary embodiments, the height h is comparable to or smaller than the diameter of the pixel, and in exemplary embodiments h may be less than 100 microns, less than 50 microns, less than 20 microns, less than 10 microns, less than 5 microns, less than 2 microns, less than 1 micron, or less than 0.5 microns. The opposing surface may be configured with regions functionalized for DNA synthesis. In certain exemplary embodiments, the entire surface may be so functionalized, in which case the extent of the acid zones determines the size of the regions where synthesis occurs. In other exemplary embodiments, the functionalized regions on the opposing surface are patterned and/or otherwise constrained in size, and may be aligned with the acid generation sites, so as to provide a limit on the diameter of the area where synthesis occurs, which in exemplary embodiments may be smaller than the area where the acid zones contact the opposing surface. These exemplary approaches provide for smaller synthesis spots.

Figure 32C:
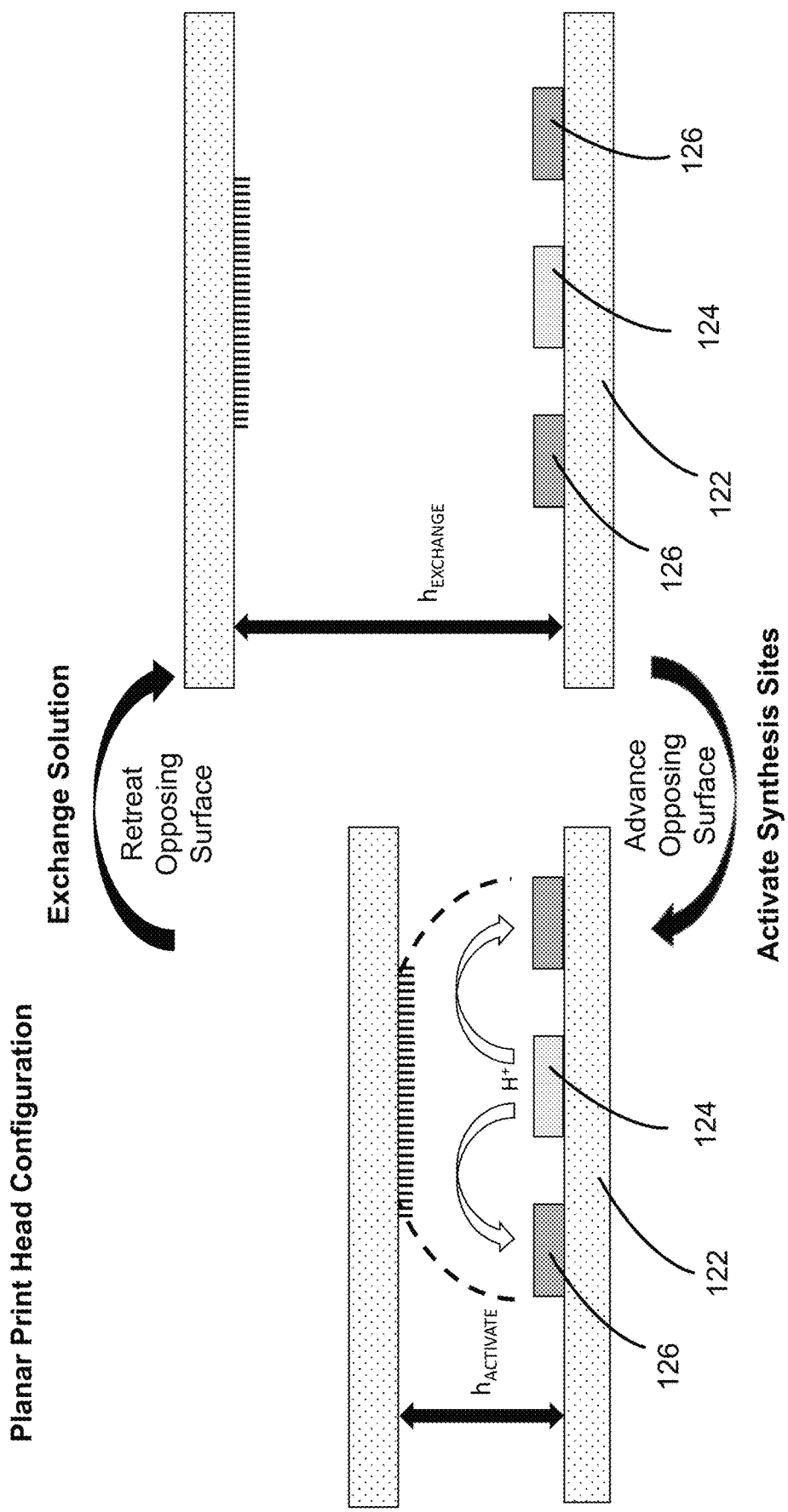
FIG. 32C illustrates moving an opposing surface in a print head configuration for synthesis for a planar acid generation geometry, to facilitate reagent exchange, in accordance with various exemplary embodiments.

When the off-set height of the opposing surface, h, is small, it restricts the ability to flow in liquid reagents or exchange the solution volume sandwiched between the opposing surface and the electrode surface, due to the large viscous drag that may result, particularly when h is less than 50 microns. In exemplary embodiments, this issue is resolved by providing for the opposing surface to be able to mechanically move up and down relative the electrode surface. Operation of such embodiments is illustrated in FIG. 32C. At left is shown the configuration with acid generation underway, and the opposing surface has advanced close to the electrodes for activation of synthesis, at a distance $h_{ACTIVATE}$. At right is shown the configuration where the opposing electrode has retreated to a greater distance, $h_{EXCHANGE}$, which is larger, and facilitates the exchange of reagents or solution in the volume between the upper and lower surfaces. In various exemplary embodiments, either one or both of the opposing surface or the electrode surface may be the one that physically moves, to change the relative separation, h. In exemplary embodiments, $h_{EXCHANGE}$ may be more than twice, more than 10 times, or more than 100 times, more than 1000 times larger than $h_{ACTIVATE}$. In various exemplary embodiments, $h_{EXCHANGE}$ may be at least 10 microns, or at least 20 microns, or at least 50 microns, or at least 100 microns, or at least 500 microns, or 1 mm, or even more. Moreover, in various exemplary embodiments, as indicated, the separation cycles through advances and retreats as desired for the acid-driven activations in the synthesis cycles.

Figure 32D:
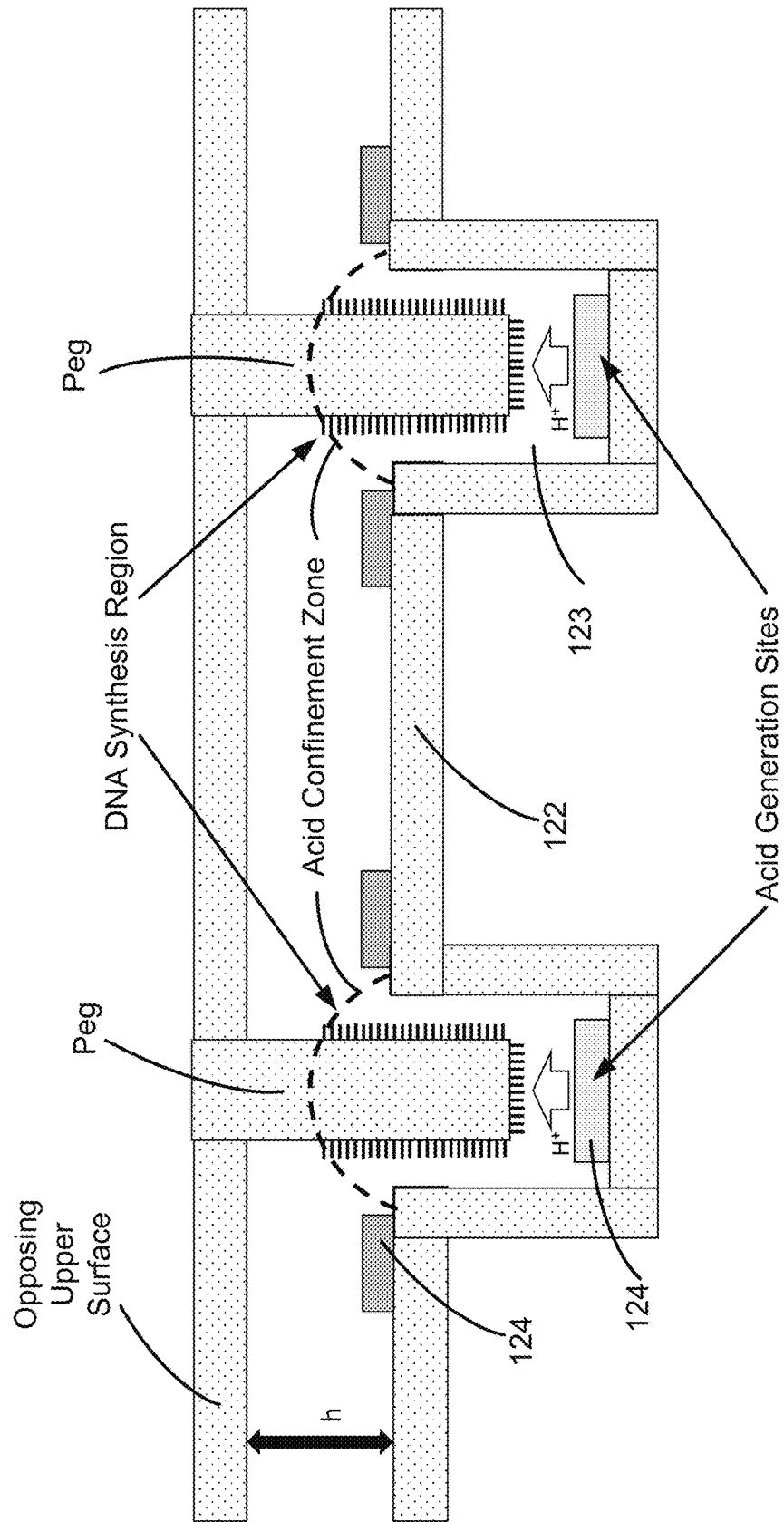
FIG. 32D illustrates an exemplary embodiment of a print head configuration for synthesis, in which synthesis occurs on an opposing surface, for a well acid generation geometry, in accordance with various exemplary embodiments.
Figure 32E:
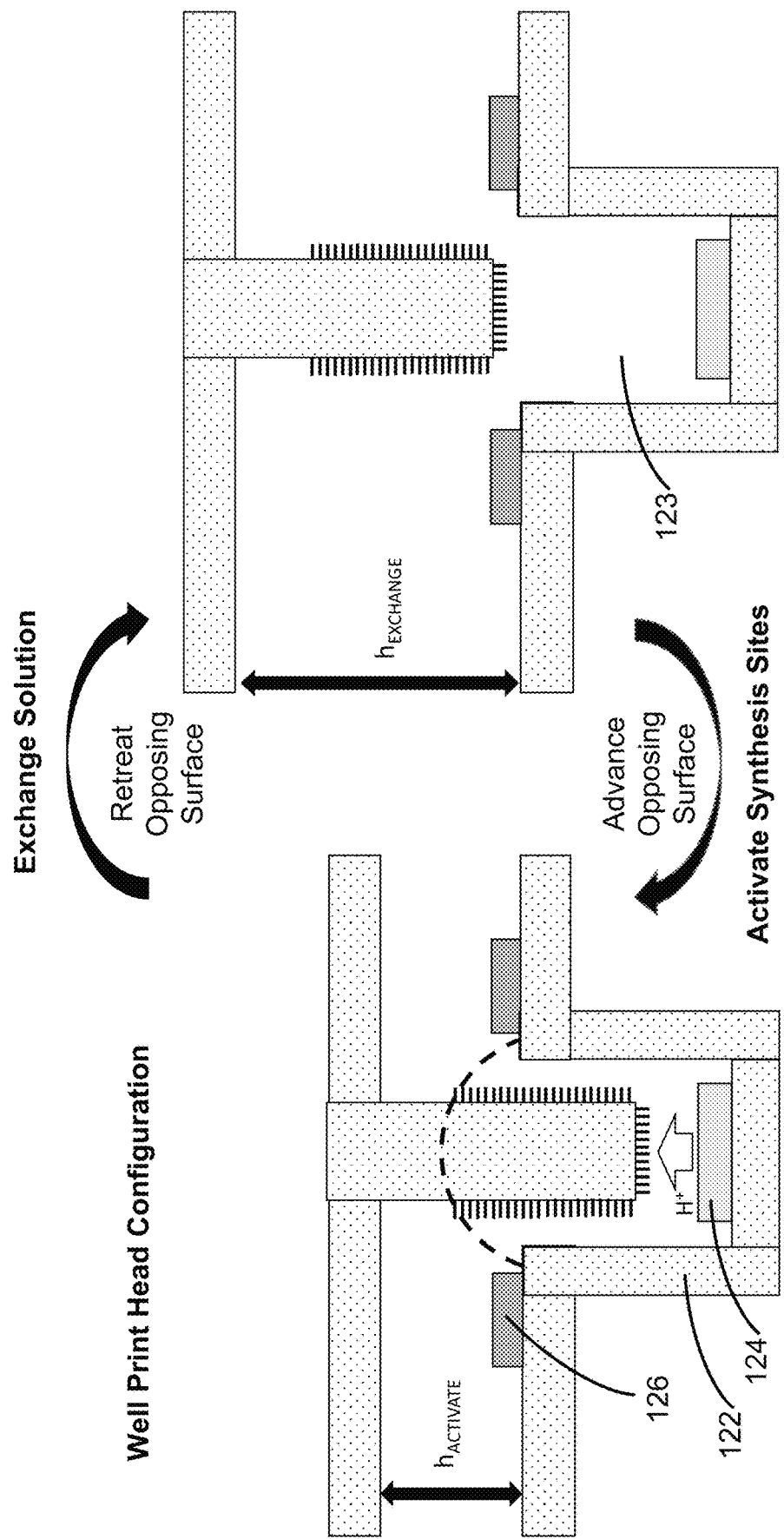
FIG. 32E illustrates moving an opposing surface in a print head configuration for synthesis for a well acid generation geometry, to facilitate reagent exchange, in accordance with various exemplary embodiments.
Figure 32F:
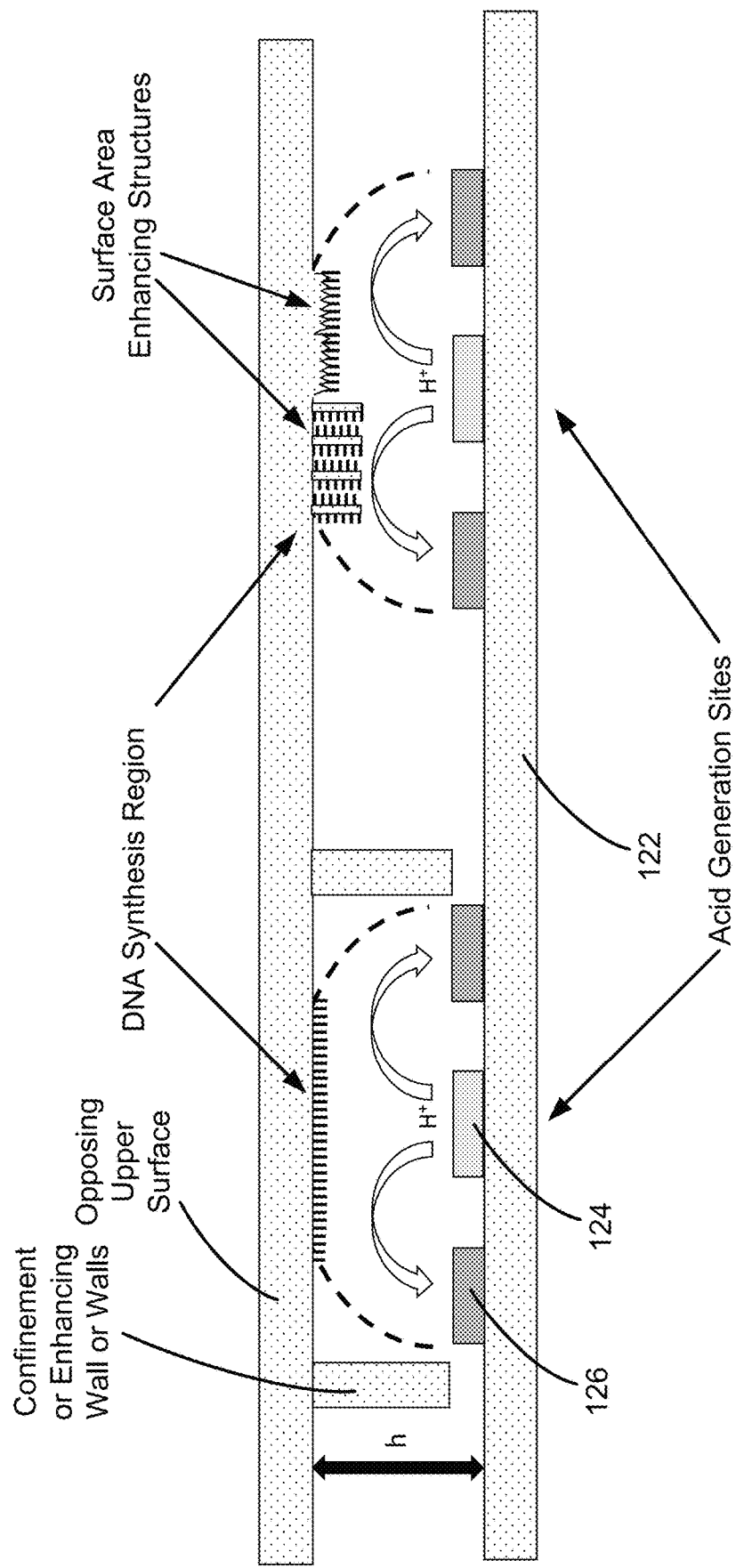
FIG. 32F illustrates use of confinement enhancing or area enhancing features on an opposing synthesis surface, in a print head configuration, in accordance with various exemplary embodiments.

Turning now to FIG. 32D, illustrated are other exemplary embodiments of a print head configuration, for cases where acid generation is done in a well geometry. In various such embodiments, as shown, the opposing surface is configured with pegs, protrusions, or the like that extend deeper into the acid zones of the acid generation sites. In exemplary embodiments, such pegs extend at least partially down into the wells. As indicated, DNA synthesis in exemplary embodiments may take place on both the end and the sides of the peg, thereby increasing synthesis area. Any of the approaches for enhancing confinement and increasing surface area, disclosed above for use for synthesis on the lower surface, may likewise be applied to synthesis on this opposing surface in the print head configuration. In certain exemplary embodiments illustrated in FIG. 32F, at left there is a well geometry or wall geometry provide on the opposing synthesis surface, to enhance H+ confinement near the synthesis site (to avoid cross talk or increase H+ concentration for greater activation). At right in FIG. 32F are illustrated exemplary embodiments wherein the opposing surface is provided with area-enhancing protrusions, such as the structures disclosed above in FIG. 24B, or is provided with a rough, porous, or patterned surface having increased surface area. Similar enhancements apply to the well geometry of FIG. 32E as well.

Figure 32G:
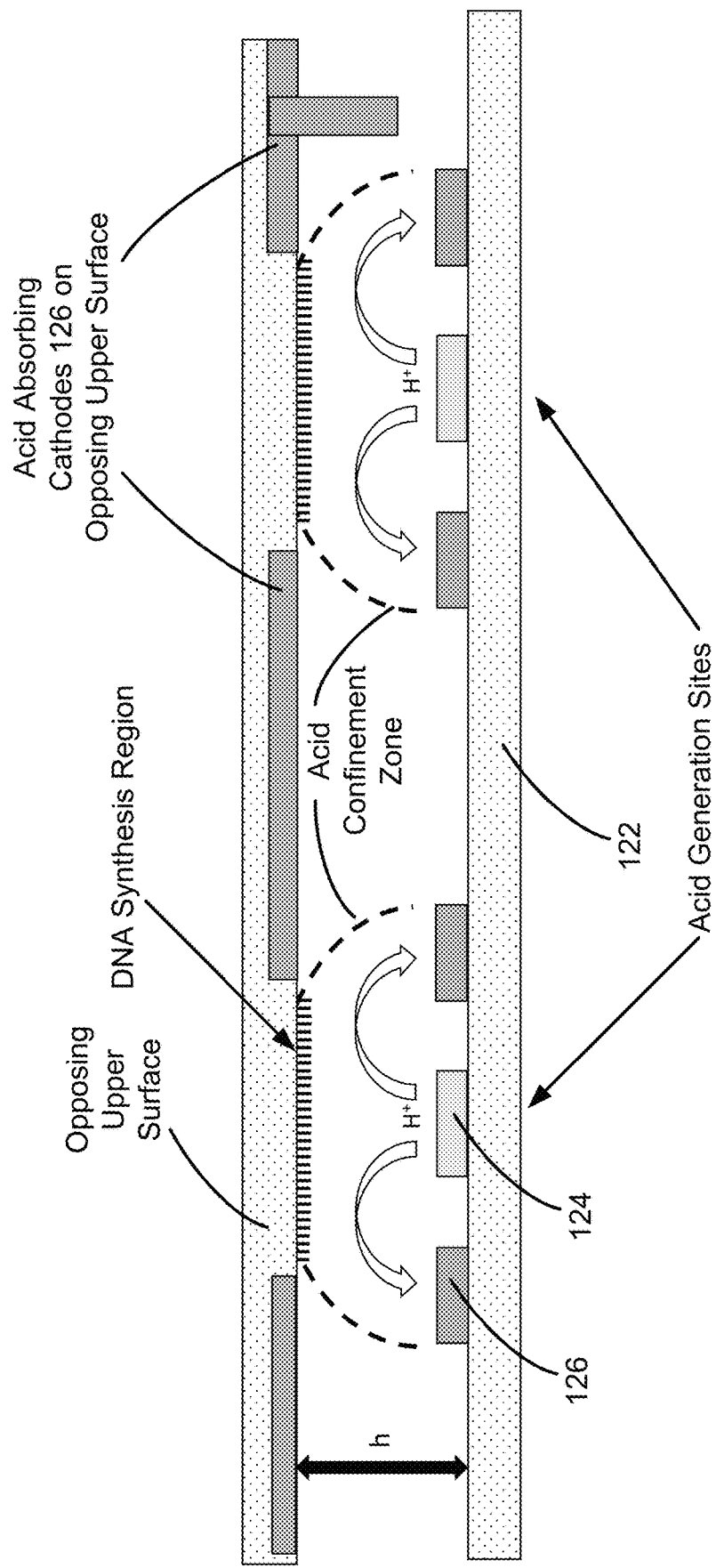
FIG. 32G illustrates use of confinement enhancing cathodes on an opposing synthesis surface, in a print head configuration, in accordance with various exemplary embodiments.

In various exemplary embodiments, the opposing surface contains acid absorbing cathode electrodes, such as illustrated in FIG. 32G. Such cathodes on the surface can further reduce crosstalk between the synthesis sites on the opposing surface, by removing H+ or acid. As shown, in exemplary embodiments such cathodes on the opposing surface may cover large areas and/or be connected in common across extended areas or the entire opposing surface. As shown at right in FIG. 32G, such cathodes may also be configured with confinement enhancing geometry, such as the wall geometry indicated. In exemplary embodiments, the opposing surface is provided with common passive cathode electrodes, and is not a CMOS chip or integrated circuit device. In other embodiments, the opposing surface comprises an integrated circuit device.

From the foregoing disclosures of print head configuration concepts, it will be appreciated that many suitable combinations or variations to enhance acid confinement or synthesis yield can be applied in this context, including disclosed approaches for increasing surface area or enhancing acid confinement through surface properties, barriers and barrier geometry, and cathodes and cathode geometry, and all such combinations and variations are considered to be within the scope of the present disclosure. It will also be appreciated that there are various suitable mechanisms and methods of performing precision relative motion of the opposing surface and chip surface as disclosed herein, for example as illustrated in FIGS. 32C and 32E, such as the use of mechanical motion controllers, stepper motors with optical encoders, piezoelectric motion control devices, or the like. Such suitable precision methods and all other suitable methods for achieving such motion are considered to be within the scope of the present disclosure.

Electrochemical Acid Generation and Removal

In various exemplary embodiments, as disclosed above, and generally illustrated in FIGS. 13 and 15, acid generation to drive the deprotection step of a synthesis cycle may be done by electrochemical approaches. In addition, as disclosed above and illustrated in FIGS. 15 and 16, removal or neutralization of acid so generated may also be done by electrochemical approaches, for example for the purpose of preventing undesirable acid-driven deprotection at pixel sites other than the intended pixels.

Accordingly, exemplary embodiments contemplate such electrochemical acid generation and removal, and related compositions and methods. In certain exemplary embodiments, redox (reduction-oxidation) reaction pairs which are reversible under different applied potentials and which produce in one direction free H+ or an acid can be used for this purpose, as generally illustrated in FIG. 15. Driving the forward reaction at an anode in a solution providing an abundance of the reactant provides the H+ or acid, while driving the reverse reaction at a cathode in a solution providing an abundance of the oxidized reactant removes the H+ or acid.

Figure 34B:
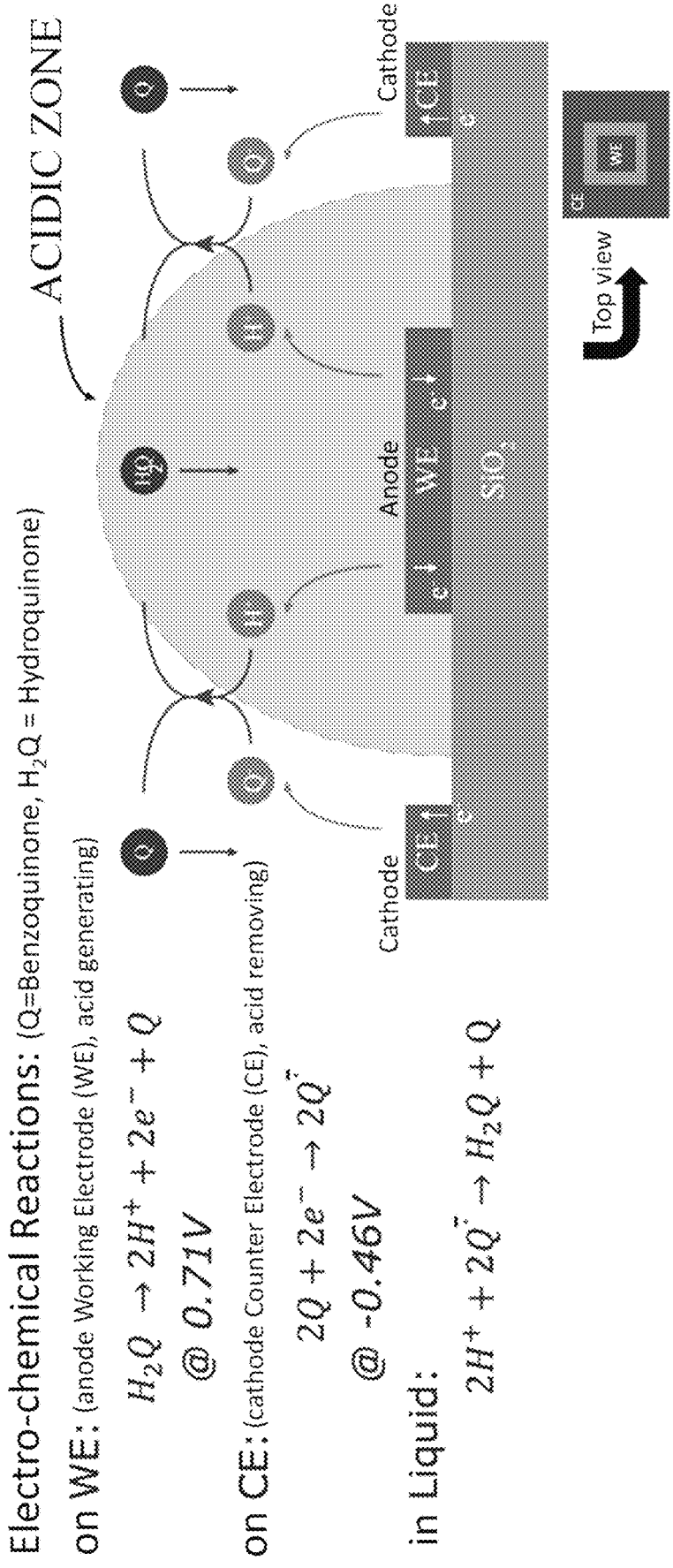
FIG. 34B illustrates spatial organization of hydroquinone-benzoquinone electrochemical reactions as driven by proximate anode and cathode electrodes at sufficient applied voltages, in accordance with various exemplary embodiments.

In various exemplary embodiments, quinone redox pairs can be used for such acid generation and removal reactions. An exemplary embodiment of such a quinone pair is shown in FIG. 33, which shows the redox reaction: the chemical hydroquinone (HQ) (left) is oxidized through the removal of two electrons at a certain applied potential to produce the chemical benzoquinone (BQ) (right) plus two H+ ions, and conversely, BQ can be reduced at an electrode at a certain potential that supplies two electrons, and so that it subsequently recombines with two free H+ to reform HQ. The HQ-BQ pair thus provides a system which in various exemplary embodiments may be used for H+ generation and H+ elimination at electrodes, as shown in FIG. 34A. In FIG. 34A, as seen at left at an anode electrode set to suitable potential VON relative to the ambient solution potential, the HQ is oxidized to release BQ and 2H+. This provides for electrochemical acid generation at a driving electrode (anode). As also shown at right in FIG. 34A, if the BQ is proximate to an electrode set to a suitable potential $V_{REGEN}$ it may be reduced by the addition of two electrons, such that in the presence of local H+ it will recombine with the H+ to form HQ. This provides for electrochemical H+ removal at a driving electrode (cathode). An exemplary embodiment of spatial organization of such acid generating and acid removing electrodes to make an H+ confinement zone is shown in cross section in FIG. 34B. There, in an exemplary embodiment in which the anode (or Working Electrode, WE) is a central electrode surrounded by an outer cathode (or Counter Electrode, CE) (as shown in the small inset bottom right), spatial organization of these processes is shown in cross section, and the corresponding reaction equations for processes occurring at the CE and WE and in solution are illustrated, along with representative potentials utilized to drive these reactions. As shown, with the anode at a potential of 0.71 volts relative to the ambient solution potential of an aqueous solvent solution (which may be set and controlled, for example, with a potentiostat), the hydroquinone (denoted $H_2Q$) is reduced, with electrons conducting into the anode, and the two H+ released in solution, and releasing Benzoquinone (denoted Q). At the cathode, at a potential of −0.46 volts relative to the aqueous solution, Benzoquinone in solution (denoted Q) is reduced to Q−, with an electron conducting from the cathode, and, in the presence of H+ in the proximate solution, recombines to HQ. This process can occur twice, re-generating the hydroquinone $H_2Q$. With the cathode surrounding the anode as indicated, production of H+ in the center and removal at the edges results in an acid zone, within which there is an elevated concentration of H+, and the neutralization by recombination with Q− from the perimeter results in a confinement of this acid zone as indicated.

Figure 34D:
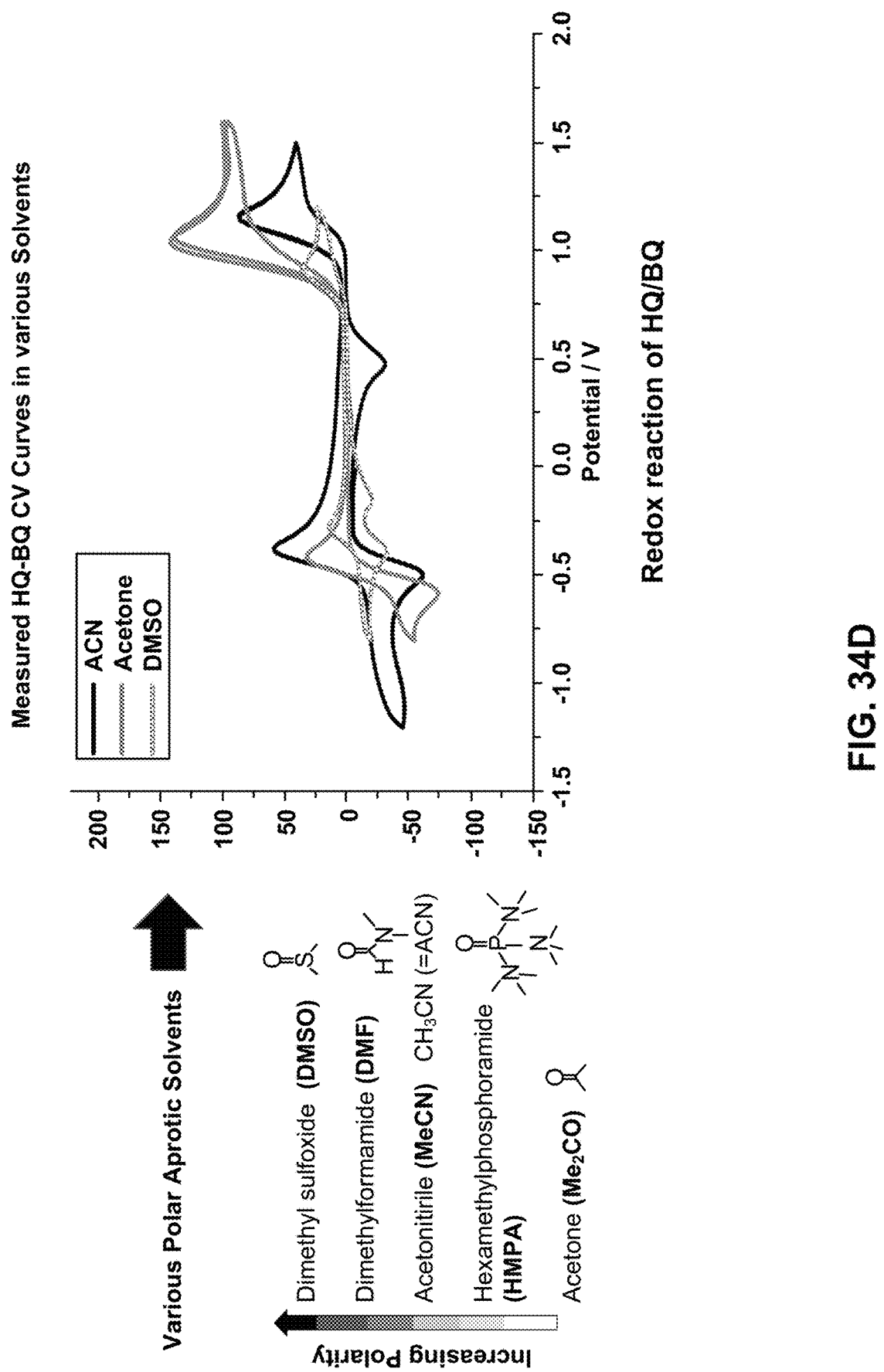
FIG. 34D illustrates various polar aprotic solvents, and the measurement cyclic voltammograms for the HQ-BQ redox pair in selected of these solvents, in accordance with various exemplary embodiments.

Preferred Solvents: Note that the exemplary HQ-BQ oxidation and reduction steps depicted in FIGS. 33, 34A, and 34B result in addition or removal of two electrons and two hydrogens, and thus in reality are complex multi-step processes in their precise reaction details; accordingly, only the net effect of the redox is indicated here for simplicity and relevance. In addition, the details of these aspects further depend on the solvent in which the HQ and BQ reside, and thus so do the details of FIG. 34C, which as described is relative to a suitable solvent. FIG. 34C illustrates such detailed intermediate steps for the HQ-BQ redox reaction, in aqueous solutions (left) and in non-aqueous solutions (right). A distinction therebetween is that in aqueous solvents, the $H_2O$ present can act as a proton donor, and so the "corner states" of the canonical square reaction diagram at right are not accessible. In certain exemplary embodiments, the solvent used is not able to donate protons, so as to not interfere with the desired intrinsic H+ generation chemistry of the quinones. In exemplary embodiments, the solvent is a polar aprotic solvent, which refers to a well-known and large family of solvents that are polar and do not have an acidic proton. FIG. 34D illustrates various polar aprotic solvents (left), of increasing polarity, and (right) the measured cyclic voltammograms of HQ-BQ in select of these solvents, which may be used in various exemplary embodiments. These considerations are illustrated for the HQ-BQ quinone redox pair, but similar considerations and exemplary embodiments apply to other quinone redox pairs, and in particular, various exemplary embodiments using such quinones may use a polar aprotic solvent.

Figure 35:
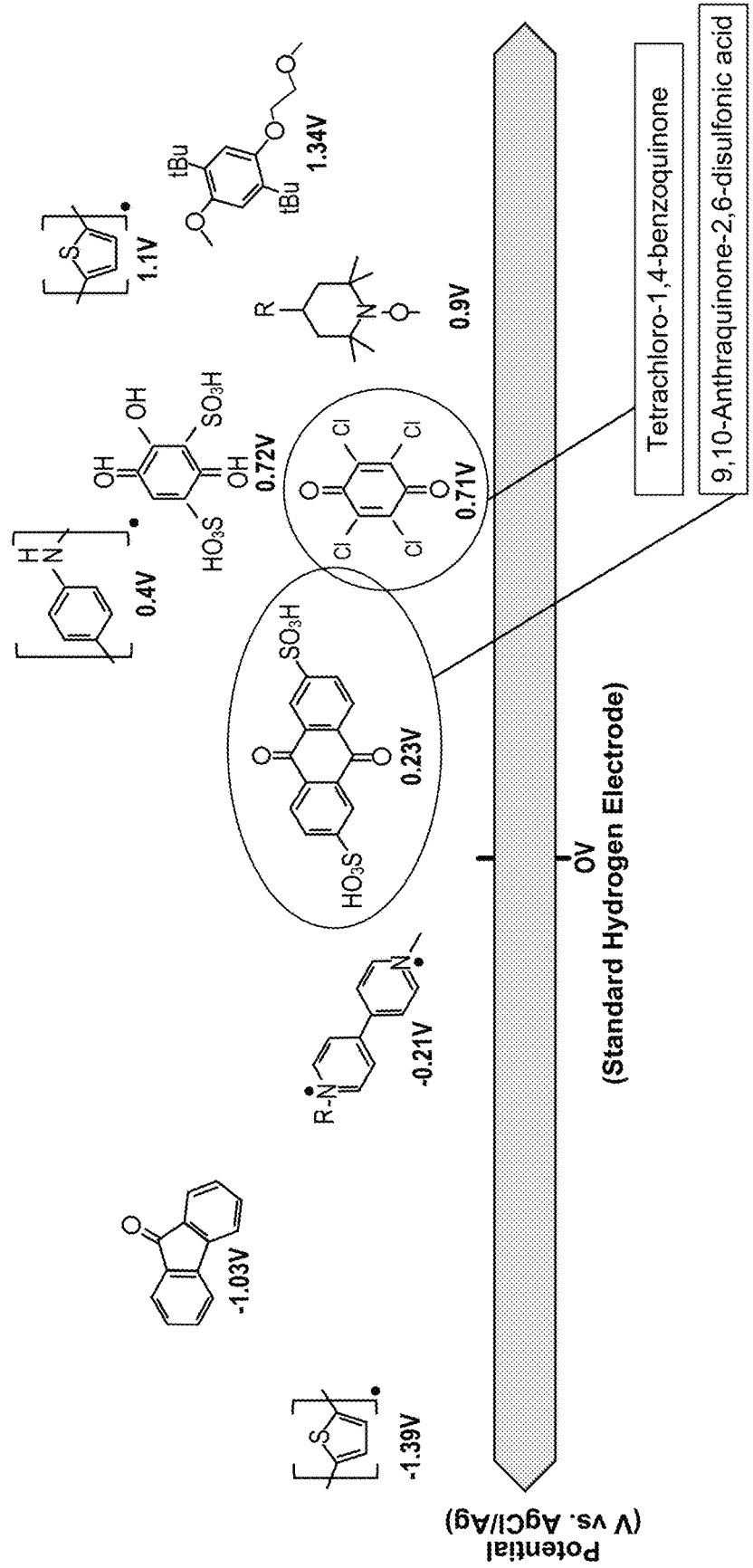
FIG. 35 illustrates various exemplary quinones that may be used for electrochemical acid generation, and their redox potentials, in accordance with various exemplary embodiments.
Figure 36A:
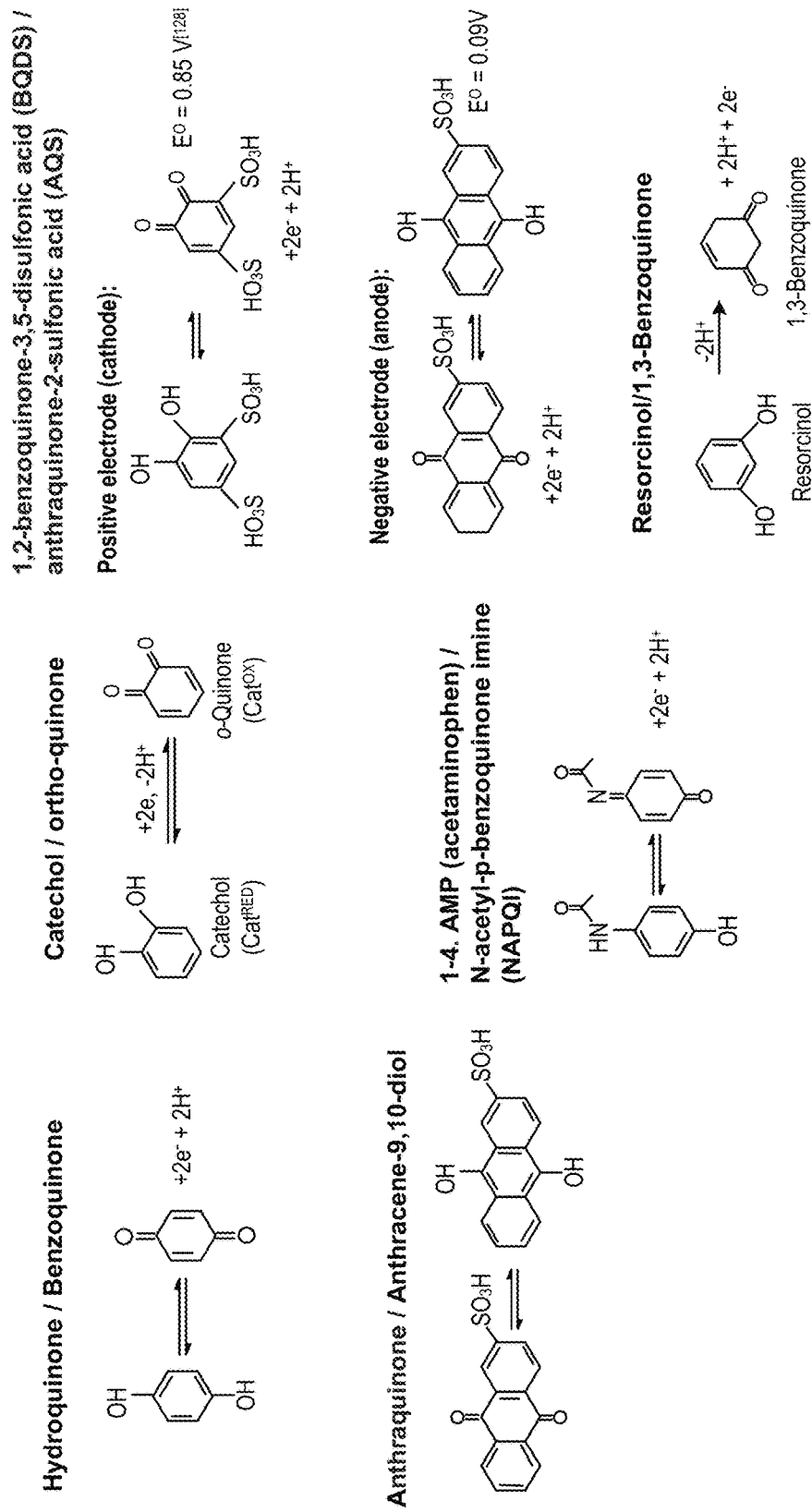
FIG. 36A illustrates various quinone redox pairs that may be used for electrochemical acid generation, in accordance with various exemplary embodiments.

More generally, quinones are a large, well-known, and well-defined class of chemical molecular structures that generally have a reduced form with a cyclic ring structure with two (or an even number of) OH groups, and an oxidized form in which two (or the corresponding even number of) electrons are removed in solution by anode electrode, and two (or the corresponding even number of) H+ ions are released into solution, leaving the O groups, and providing (here, desirably) H+ generation. The reverse reaction, performed at a cathode, reduces the oxidized form by addition of a pair (or the corresponding even number) of electrons, such that it recombines with a pair (or the corresponding even number) of H+ ions in solution, removing (again, as desired) H+ from solution. This reaction is reversible and can be cycled, under control of electrodes, such that a solution providing a reservoir of both the oxidized and reduced forms can be used to generate H+ at an anode and remove H+ near a cathode. FIG. 35 illustrates the redox potential of two quinones (circled), specifically Anthraquinone (0.23V) and Chloranil (0.72V), and also of various quinone-derivative molecules. Moreover, FIGS. 36A and 36B illustrate a number of suitable quinone redox pairs that may be utilized in various exemplary embodiments of the electrochemical H+ generation and removal.

Figure 37:
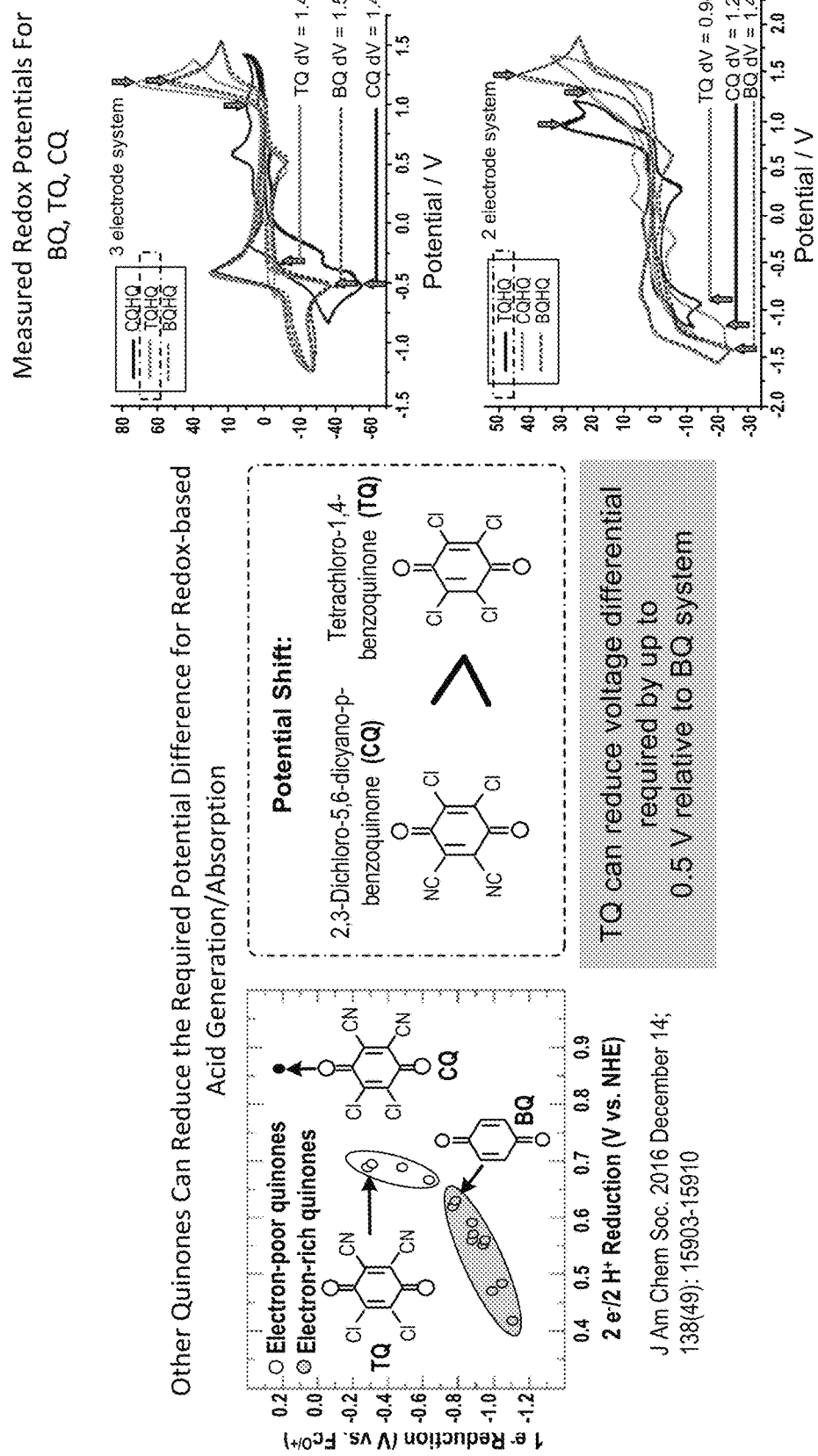
FIG. 37 illustrates selection of quinones such as tetrachloro-1,4-benzoquinone (TQ) that can operate at reduced potential differentials between anode and cathode relative to BQ, in accordance with various exemplary embodiments.

In exemplary embodiments, certain quinones are selected to reduce the voltage differential utilized to cycle between H+ generation and H+ removal, and an exemplary embodiment of such a lower voltage quinone is illustrated in FIG. 37. This is beneficial for an exemplary synthesis pixel array chip, and in particular for a CMOS chip, because CMOS technology nodes widely available for chip manufacturing typically place limits on the voltages that can be applied to the transistor circuits in such chips. For example, widely used CMOS nodes of 180 nm, 65 nm, and 45 nm limit such voltage differentials to 1.8V, 1.2V, and 0.9V respectively (and the 0.9V limit may extend down to finer CMOS nodes, such as to 28 nm, 20 nm, and below). Referring back to FIG. 37, at left is shown a plot of reduction voltages of a large representative set of quinones, with particular members (TQ, BQ, and CQ) highlighted. Electron poor and electron rich quinones tend to fall into different groups in this view, with the electron rich generally having lower reduction potential. At right for the highlighted quinones, TQ, BQ, and CQ are measured cyclic voltammograms in accordance with various exemplary embodiments, that provide a measurement of the voltage differential (horizontal lines) between the reduction potential (highlight arrows at left) and oxidation potential (highlight arrows at right). The upper plot illustrates work performed in a 3-electrode electrochemical cell (CE, WE, RE) and the bottom plot illustrates work performed in a 2-electrode cell (CE and WE). As can be seen, TQ can have up to 0.5V less voltage differential to drive the redox reactions, and thus TQ is desirably used for the quinone in various exemplary embodiments of the quinone electrochemical acid generation and acid removal pixel system disclosed herein.

Figure 38A:
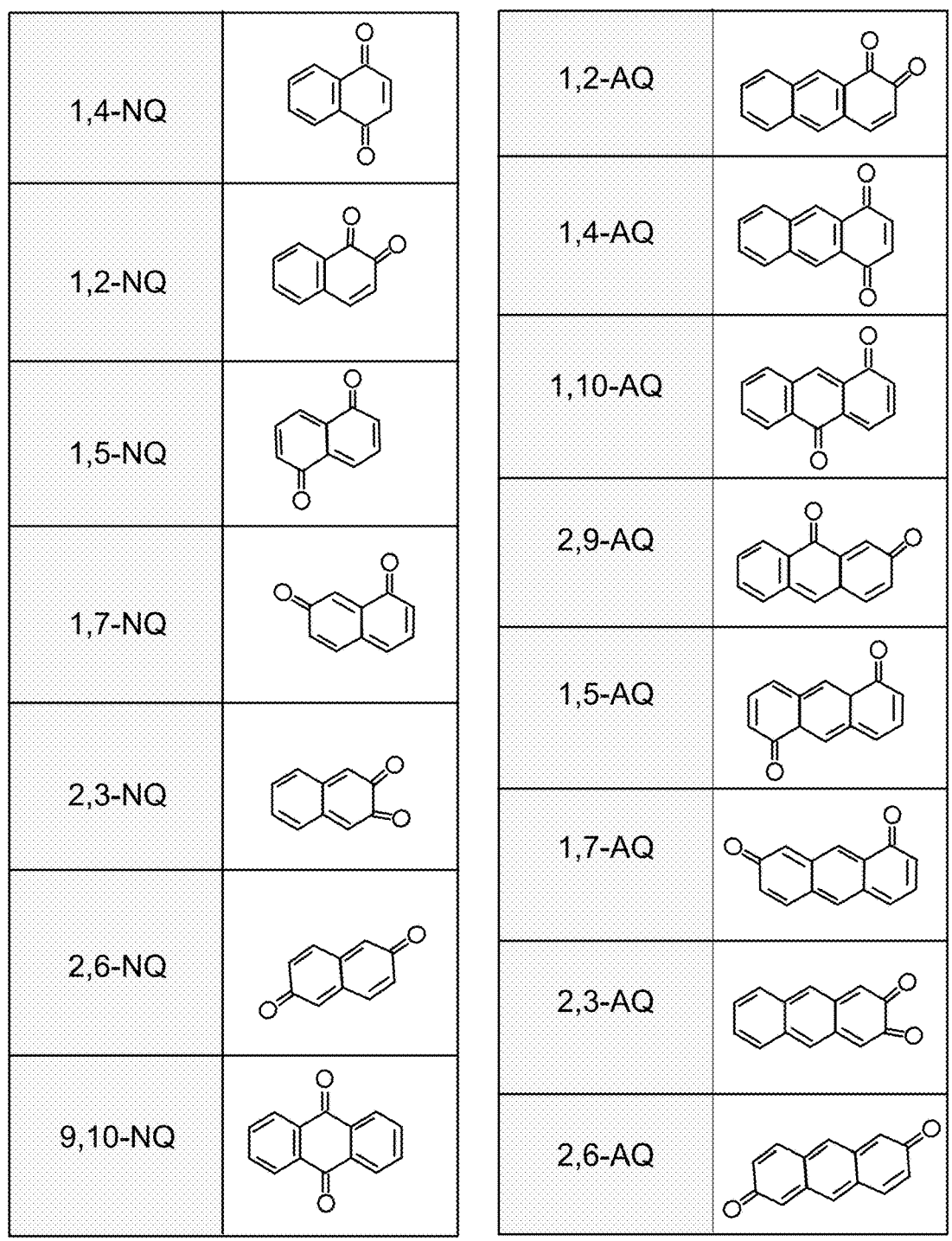
FIG. 38A illustrates additional representative quinones that may be used for electrochemical acid generation, in accordance with various exemplary embodiments.

FIG. 38A further illustrates other suitable quinones, from the much larger quinone family, that can be assessed in this manner, for use in certain exemplary embodiments of an acid generation and removal system, so as to reduce the voltage differential utilized in such a system, or to improve on other desirable performance properties.

Figure 38C:
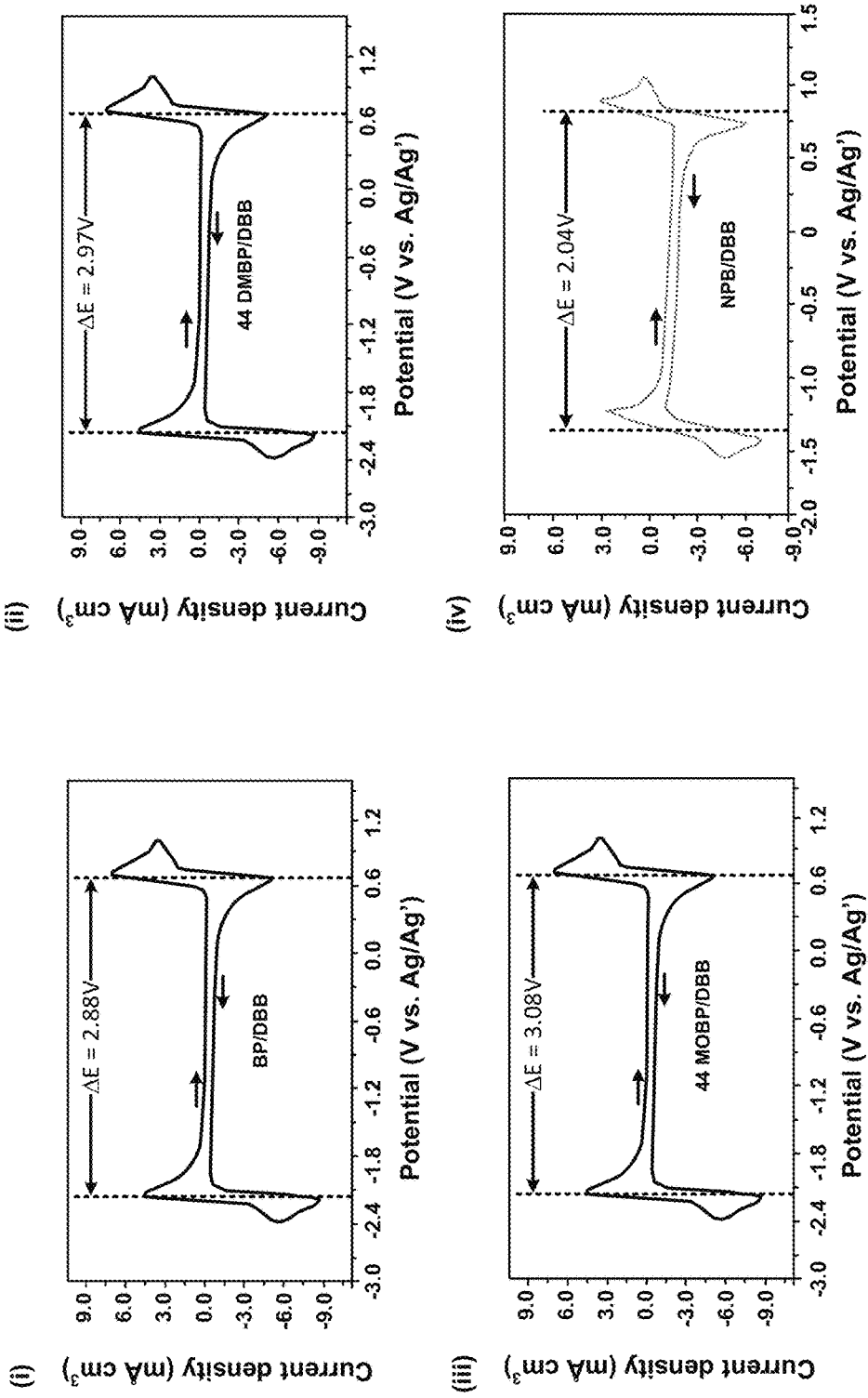

As disclosed above, in various exemplary embodiments redox pairs other than quinones may be utilized for electrochemical acid generation and removal. Carbonyls are another such large chemical family, defined as generally having at least one oxygen double bound to a carbon, which can support oxidation and reduction for the desired electrochemical acid generation and removal. FIG. 38B illustrates representative carbonyl redox pairs utilized in exemplary embodiments of an acid generation and removal system, to improve on desirable performance properties. FIG. 38C illustrates measured cyclic voltammograms for the indicated redox pairs, and corresponding differential voltages utilized, which vary from 2-3 volts.

Figure 39:
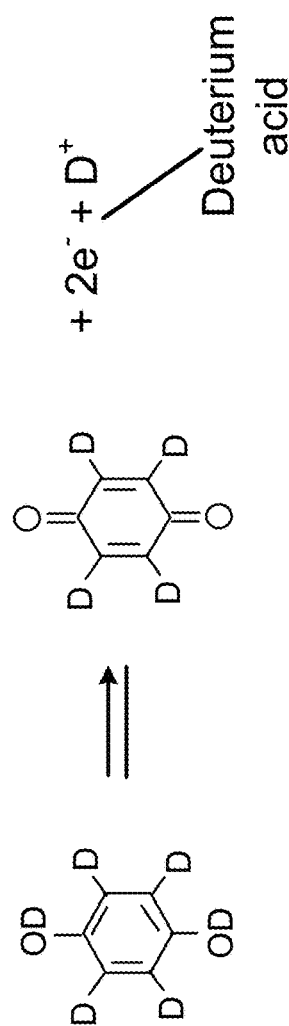
FIG. 39 illustrates deuterated quinones that may be used to electrochemically generate deuterated acid solution ($D^+$), for improved confinement of acid due to reduced molecular diffusion rate, in accordance with various exemplary embodiments.

As illustrated with returning reference to FIG. 16, unwanted diffusion of H+ created at one pixel anode, to a synthesis protection site at another pixel, can result in synthesis errors from this pixel-to-pixel chemical crosstalk. Accordingly, exemplary embodiments utilize approaches for reducing such H+ diffusion, beneficial to achieving acid confinement as described in FIG. 17. In various exemplary embodiments, use of the deuterated form of quinones, in which all removable hydrogens are replaced by deuteriums, D, (heavy hydrogen, having a proton and neutron), acid generation from such deuterated quinones results in the release of D+, and this reduces the diffusive transport of the acid, thereby helping to confine the acid generated at the anode. The deuterated forms of two representative quinones are shown in FIG. 39, deuterated hydroquinone, and deuterated benzoquinone, as well as the reversible redox reaction between them, releasing 2D+ instead of 2H+. Also shown in FIG. 39 are the relative diffusivities of D+ and H+ in water ($D^0$, the molecular diffusion coefficient, in units of $10^5$ cm$^2$/s) at lower left, showing that the diffusivity for D+ is 34% lower than for H+(6.2 vs 9.4). Because the rate of diffusive spreading of a species released at a point in solution scales like $\sqrt{D^0}$, this means the initial diffusive spreading of D+ will be less, by roughly $\sqrt{(6.2/9.4)}=0.81$, i.e. a 19% reduction in the rate of spreading versus H+ acid. Thus, in various exemplary embodiments of electrochemical acid confinement systems disclosed herein, the deuterated form of quinones is used, to further enhance acid confinement.

Electrode Materials: In certain exemplary embodiments, metal electrodes disclosed (anode, cathode) may comprise a chemically inert metal, such as gold or platinum, for example for advantages of durability and resistance to chemical attack in the diverse solutions used for DNA synthesis. In some exemplary embodiments, the metal electrodes are metals that absorb hydrogen, such as palladium and platinum, which may be especially advantageous for the H+ removing electrode. Moreover, in certain exemplary embodiments, the electrodes are metals that resist damage from hydrogen, such as resisting hydrogen embrittlement, such as iridium. In various exemplary embodiments, alloys of the above metals may also be used, to confer similar benefits. In exemplary embodiments, the electrode metals are CMOS-foundry compatible materials, to enable in-foundry fabrication, such as platinum or iridium. Moreover, in some exemplary embodiments metal electrodes operable as an anode may comprise a first metal, and other metal electrodes operable as a cathode may comprise a second metal different than the first metal.

Synthesis Chip Architecture

Disclosed above are electronic approaches for controlling the de-protection step within a DNA synthesis cycle, and components and methods for localizing this deprotection to DNA strands being synthesized in close proximity to electrodes which provide electronic control.

Figure 40:
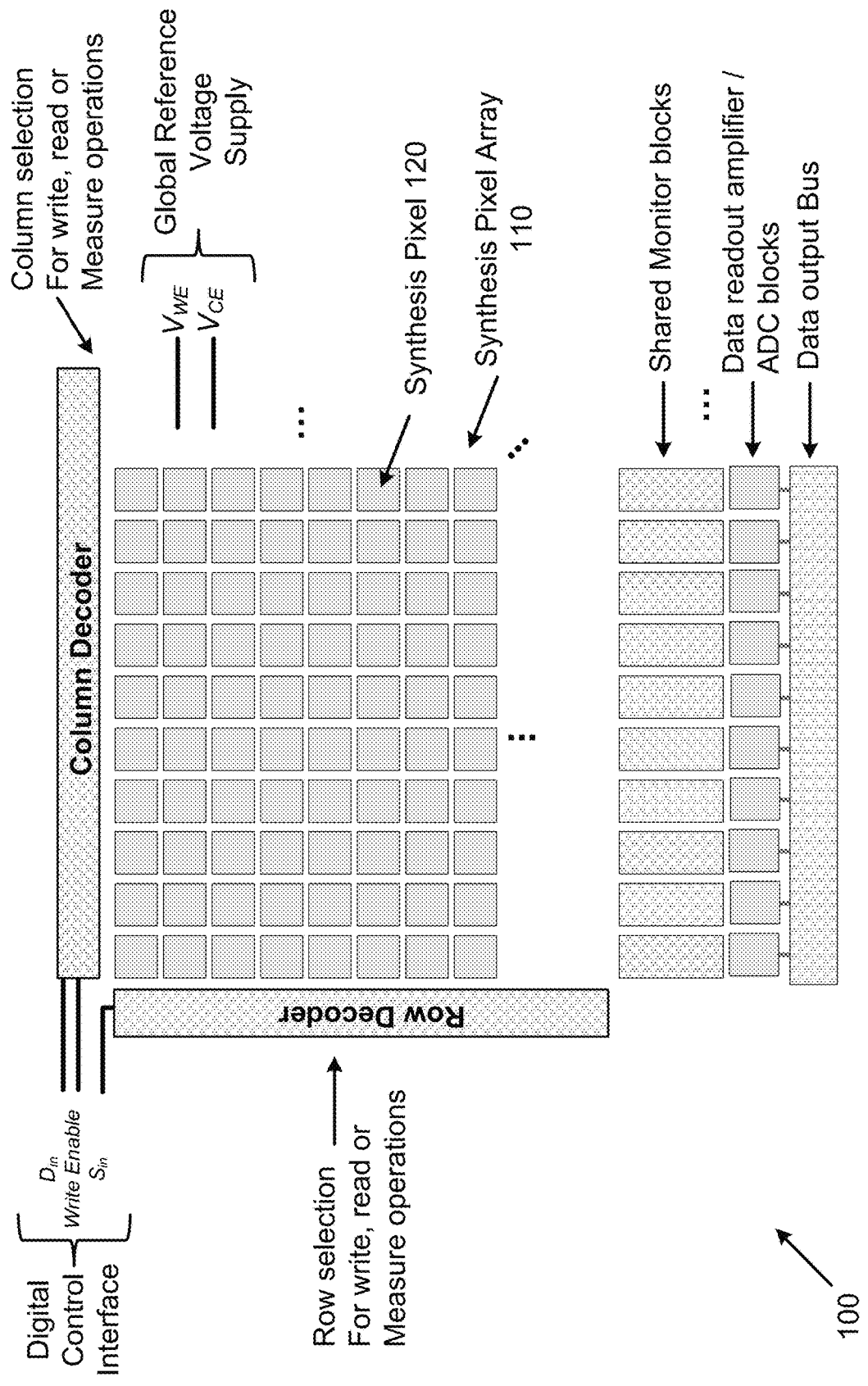
FIG. 40 illustrates an exemplary semiconductor chip architecture for on-chip DNA synthesis at pixel sites of a pixel array, in accordance with various exemplary embodiments.
Figure 41A:
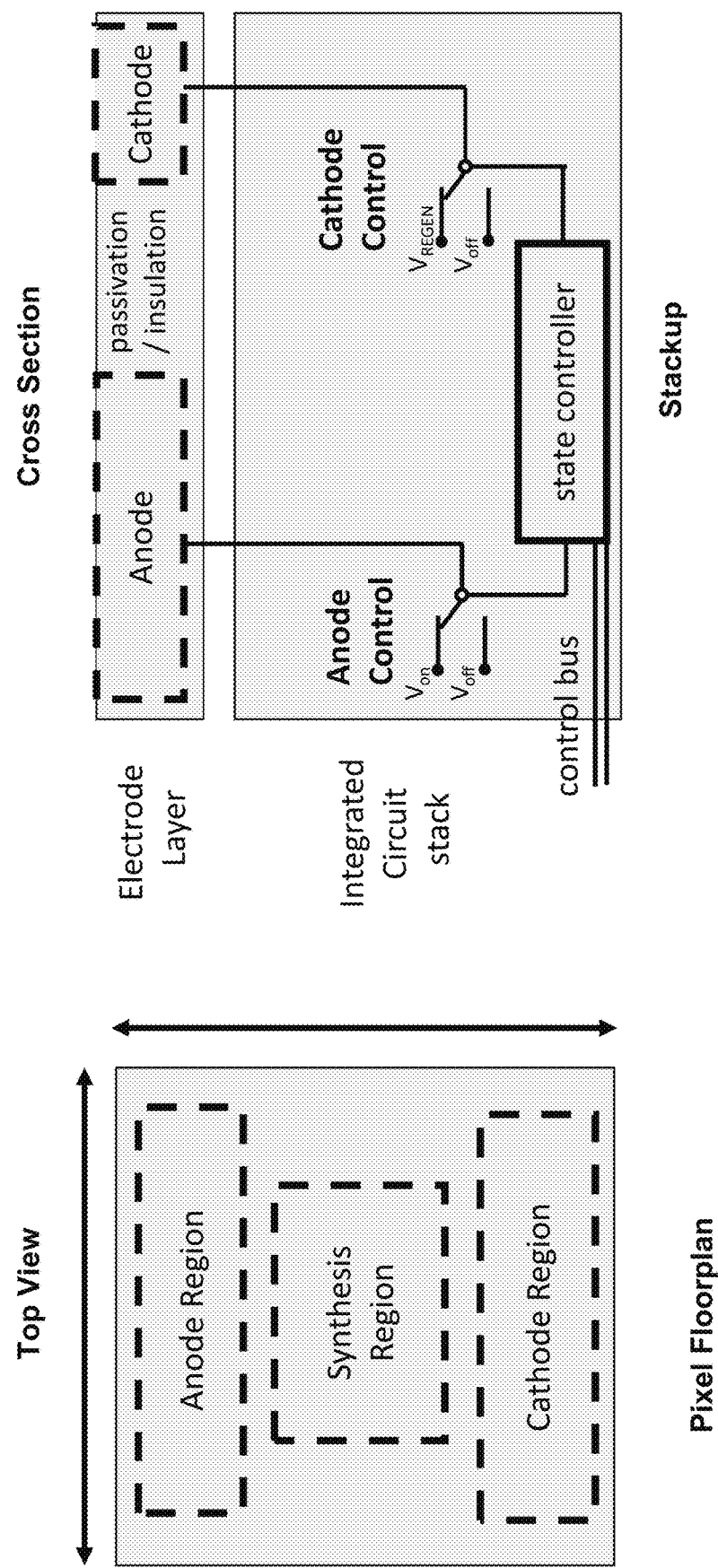
FIG. 41A illustrates high-level functional organization of pixels for an exemplary synthesis chip, with surface electrodes to drive electrochemical acid generation, and integrated circuits to control and monitor electrodes, in accordance with various exemplary embodiments.
Figure 41B:
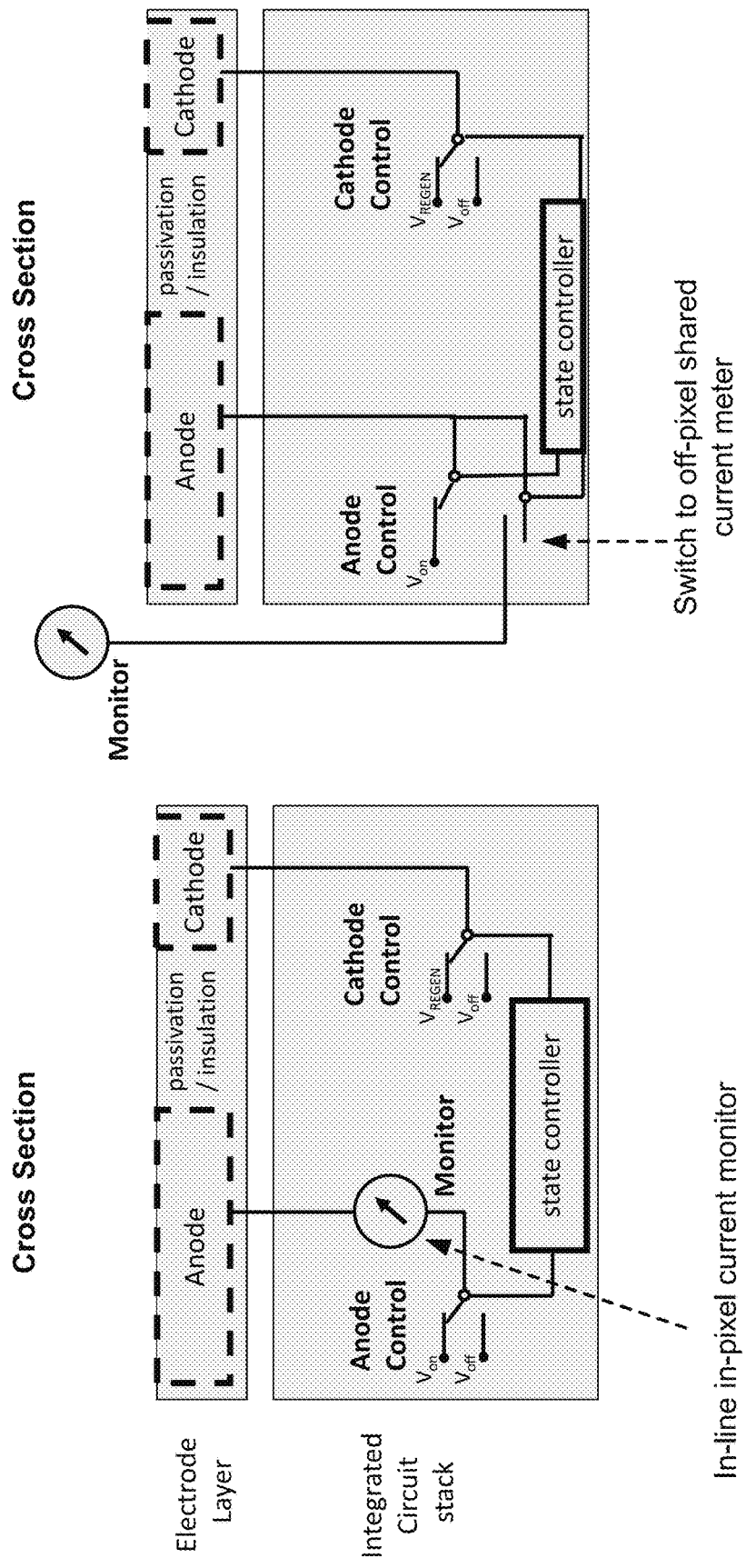
FIG. 41B illustrates high-level functional organization of pixels for an exemplary synthesis chip, with the addition of an anode current monitor, in accordance with various exemplary embodiments.
Figure 41C:
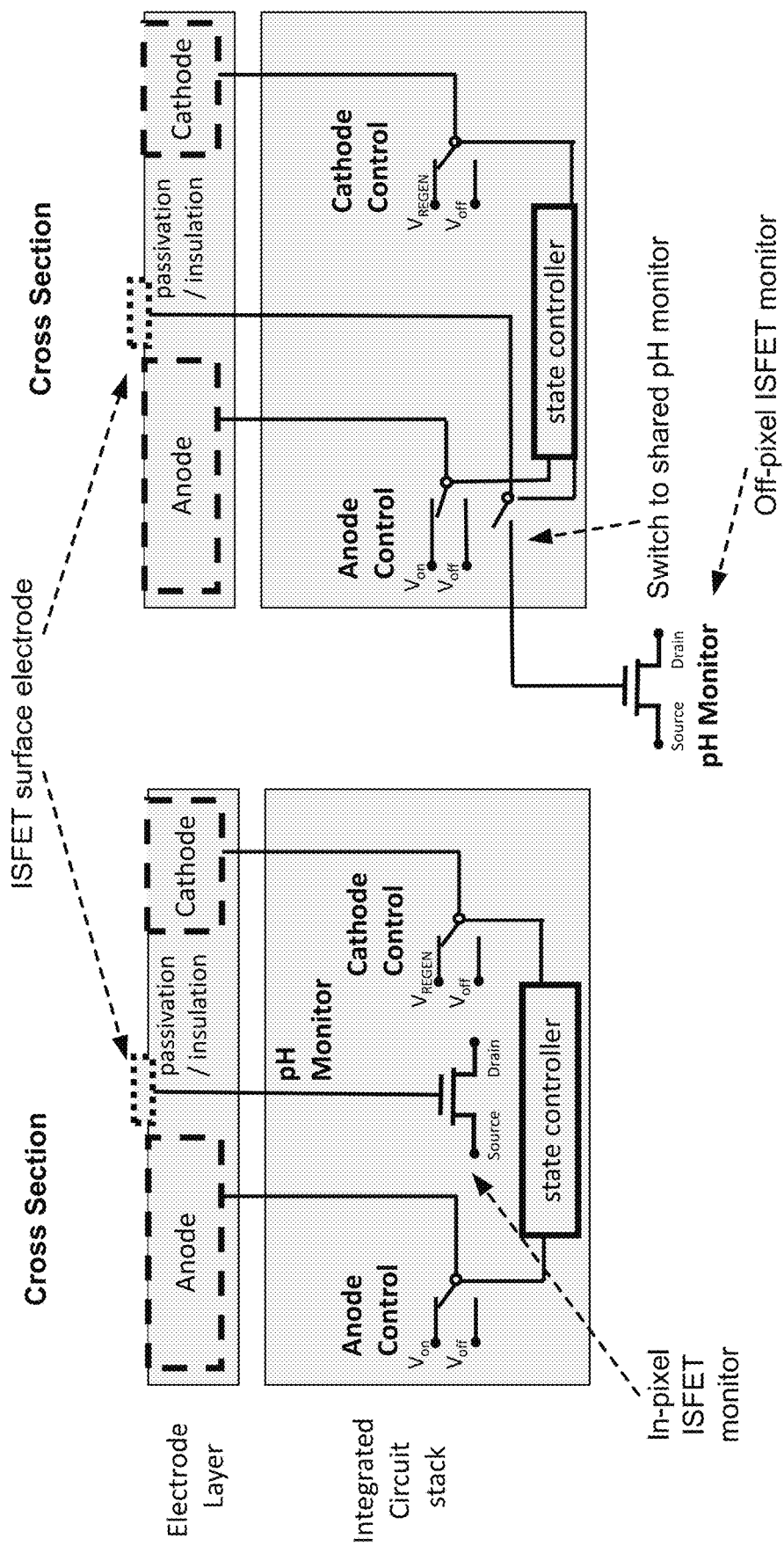
FIG. 41C illustrates high-level functional organization of pixels for an exemplary synthesis chip, with the addition of a pH monitor for a region above a pixel, in accordance with various exemplary embodiments.

In various exemplary embodiments, a multiplicity of such localized control electrodes, capable of performing the localized synthesis of independent DNA sequences, are deployed as an array of synthesis pixels on a semiconductor Integrated Circuit (IC) chip, including all the relevant control circuitry, both internal to such pixel circuits, as well as external as utilized to manage the array operation. An exemplary embodiment of a chip architecture is shown in FIG. 40, which shows a high-level circuit block diagram for an exemplary DNA synthesis chip 100, comprising a scalable pixel array 110. As illustrated, the array 110 of synthesis pixels 120 is, in exemplary embodiments, organized into a rectangular array, with row decoder and column decoder blocks providing the ability to set which pixels 120 are to be turned on or off for electronic acid generation, as well as the ability to select rows for readout of pixel data, and the ability to select pixels 120 or groups of pixels 120 to be connected to off-array monitor circuit(s). The row and column decoders are controlled by a digital interface, which may comprise row and column selection registers, and a write enable line, for writing selection ("on") state data to pixels 120. In exemplary embodiments, this may be performed by serially selecting each pixel 120 in the array 110, and setting an internal control state memory bit to an on or off state as desired for the pattern of deprotection utilized to couple the next applied amidite base at the appropriate synthesis pixels sites. In exemplary embodiments, the DNA synthesis chip is configured with global supply voltages $V_{WE}$ (WE=Working Electrode, for the role of the anode) and $V_{CE}$ (CE=Counter Electrode, for the role of the cathode), that are used to set electrode potentials within pixel 120s or on common shared or global counter electrodes. In certain exemplary embodiments, DNA synthesis chip 100 circuitry also comprises monitoring circuits, for making measurements, such as of current or impedance or voltage, on electrodes in pixels or in groups of pixels, such as for, in exemplary embodiments, monitoring anode current during acid generation, performing impedance spectroscopy on synthesis products or reaction intermediates, performing local pH measurements via ISFET sensors, or otherwise monitoring parameters related to quality of DNA synthesis, related reaction steps, or post-synthesis processing. In various exemplary embodiments, DNA synthesis chip 100 is configured with in-pixel monitor circuits (such as illustrated in FIGS. 41B and 41C), in some or all of the pixels 120, and suitable readout circuitry to transfer such measured signals off the array 110, digitize them via Analog to Digital Converters (ADCs), and transfer them off chip 100 for subsequent analysis, as indicated by the data readout banks and data output bus shown at the bottom in FIG. 40. In other exemplary embodiments, as illustrated in FIG. 40, DNA synthesis chip 100 is configured with shared monitoring circuitry, such that through suitable control architecture, individual pixels 120 or groups of pixels are switchable into the monitoring circuits to make measurements. The results of such measurements can again be digitized and moved off chip 100, as indicated by the readout circuit blocks shown. In certain exemplary embodiments, pixels 120 also have internal state memory bits, which can be set as noted to control their on/off behavior for acid generation. In various exemplary embodiments, these programmable status bits can also be read off DNA synthesis chip 100 using the indicated readout circuit blocks, in order to verify the status of pixels 120.

The architecture of exemplary DNA synthesis chips 100 as indicated in FIG. 40 can support pixel arrays 110 of any suitable number of pixels 120, such as up to 10 pixels, or up to $10^2$, or $10^3$, $10^4$, $10^5$, $10^6$, $10^7$, $10^8$, $10^9$, or $10^{10}$ pixels per chip, or even more. In certain exemplary embodiments, the pitch of such pixels 120 in the array 110 is less than 100 microns, less than 10 microns, less than 1 micron, less than 500 nm, less than 200 nm, or less than 100 nm.

In various exemplary embodiments, DNA synthesis chip 100 comprises a CMOS chip, which thereby provides for the ability to efficiently manufacture such chips in commercial foundries. In exemplary embodiments, CMOS nodes of 180 nm, 90 nm, 65 nm, 40 nm, 28 nm, 20 nm, 14 nm, 10 nm, 7 nm, or finer nodes may be used for the manufacturing of DNA synthesis chip 100. In various exemplary embodiments, DNA synthesis chip 100 may comprise a chip formed on a silicon substrate; in other exemplary embodiments, DNA synthesis chip 100 may comprise a chip formed on a substrate of gallium nitride (GaN) or other suitable semiconductor materials.

It will be appreciated that exemplary architecture for DNA synthesis chip 100, as illustrated in FIG. 40, may be implemented using various suitable circuit blocks, and the associated array control and monitoring and readout circuitry, and also many suitable approaches exist to lay out the circuit designs of such chips for fabrication, and many specific chip technology manufacturing methodologies exist in which to implement such exemplary DNA synthesis chips 100, and all such details and variations are considered to be within the scope of the present disclosure.

Pixel Architecture

In various exemplary embodiments, pixels 120 of the pixel array 110 on DNA synthesis chip 100 provide sites at which independent DNA sequences are synthesized. As such, these comprise the electrodes and control circuitry used for local acid generation and acid removal, optional measurement-related circuitry for process monitoring, and such pixels 120 also provide the region where the DNA synthesis strands reside. FIGS. 41A, 41B, and 41C illustrate elements of various exemplary embodiments of a synthesis pixel 120. At left in FIG. 41A is a schematic top view looking down on a synthesis pixel 120 from above, showing that this area comprises a region occupied by an acid generating electrode or anode, a region occupied by an acid removal electrode or cathode, and a region in which the growing DNA strands undergoing synthesis reside. As disclosed and described previously herein, there are many exemplary geometries for such anode, cathode, and synthesis regions, and the schematic views of FIGS. 41A, 41B, and 41C reflect this by showing these as having dashed boundaries, meant to suggest the various suitable possibilities for organization of these regions. At right in FIG. 41A is a schematic cross-sectional view of the synthesis pixel 120, cutting through the chip, which shows that in general the anode and cathode reside in upper layers of the chip, separated by insulating dielectric material, and with exposed surface with a passivation suitable for supporting the DNA synthesis start site region. At deeper layers in the chip are the control circuitry for the pixel, which comprises a switch for turning on and off the anode, and a switch for turning on and off the cathode, and a state controller that controls (or is responsive to control signals associated with) these actions. In exemplary embodiments, the state controller includes one or more memory bits, usable to set and retain the state, and which may be programmed through the control bus or lines. In such exemplary embodiments, the desired on and off states may be programmed into all synthesis pixels 120 in the array 110, and then once the desired states are loaded and retained in all synthesis pixels 120, through a sequential programming process, acid generation is activated by application of the global $V_{WE}$ supply voltage to the anodes in the on state, for the next deprotection step of the synthesis cycle. Subsequent to the deprotection process, global $V_{WE}$ supply voltage is removed. The acid removal cathode undergoes a similar activation pattern, being set to the global cathode supply voltage $V_{CE}$. In exemplary embodiments, the in-pixel cathode control switch may be omitted, and the cathodes may be maintained in an on-state for acid removal at all times, and with global application of the cathode supply voltage $V_{CE}$.

FIG. 41B illustrates exemplary embodiments of synthesis pixel 120 circuitry comprising additional monitoring circuitry. At left is shown an exemplary embodiment comprising an in-pixel current monitoring circuit, used to monitor anode current. This provides process monitoring information that the H+ generation reaction is occurring at the anode. The output of the in-pixel current monitor in this exemplary embodiment may be read out and transferred off chip 100 using the array readout architecture disclosed above and indicated in FIG. 40. At right in FIG. 41B is illustrated another exemplary embodiment wherein a current monitor circuit used to monitor the anode is on the chip but outside synthesis pixel 120, and a control switch internal to the pixel is used to switch the anode into the metering circuit for measurement as desired. In exemplary embodiments, this shared current monitor may be used to monitor individual synthesis pixel 120 anodes, or the combined anode current of groups of pixels, if such a group is simultaneously switched into the meter. As indicated in FIG. 40, in exemplary embodiments, a suitable current meter circuit resides outside the pixel array 110, such as in a bank of such monitors that may be aligned with columns of synthesis pixels 120, or otherwise suitably organized for convenient switching access by groups of synthesis pixels 120.

FIG. 41C illustrates exemplary embodiments of synthesis pixel circuitry 120 comprising additional monitoring circuitry. At left is shown an embodiment in which there is an in-pixel pH monitoring circuit, and which in exemplary embodiments is a ISFET circuit, as depicted, used to monitor the local pH changes due to H+ generation at the anode. This provides process monitoring information, that may be used to assess that the local concentration of H+ generated is reaching the level desired for efficient deprotection. The output of the in-pixel pH monitor in these embodiments may be read out and transferred off chip 100, for example using the array readout architecture disclosed above and indicated in FIG. 40. At right in FIG. 41C is shown another exemplary embodiment in which the pH monitor circuit used to monitor local pixel pH is on chip 100 but outside synthesis pixel 120, and a control switch internal to synthesis pixel 120 is used to switch the pixel into the monitoring circuit for measurement as desired. In exemplary embodiments, this shared pH monitor may be used to monitor individual pixel pH, or the combined average pH at groups of synthesis pixels 120, if such a group is simultaneously switched into the meter. As indicated in FIG. 40, in exemplary embodiments, such a pH meter circuit resides outside the pixel array 110, such as in a bank of such monitors that may be aligned with columns of synthesis pixels 120, or otherwise organized for convenient switching access by groups of synthesis pixels 120.

In exemplary embodiments, the cathode as indicated in FIGS. 41A, 41B, and 41C3, is always held at a fixed voltage, $V_{REGEN}$, during the synthesis process, while the anode voltage is switched between different levels to control the acid generation.

Figure 42:
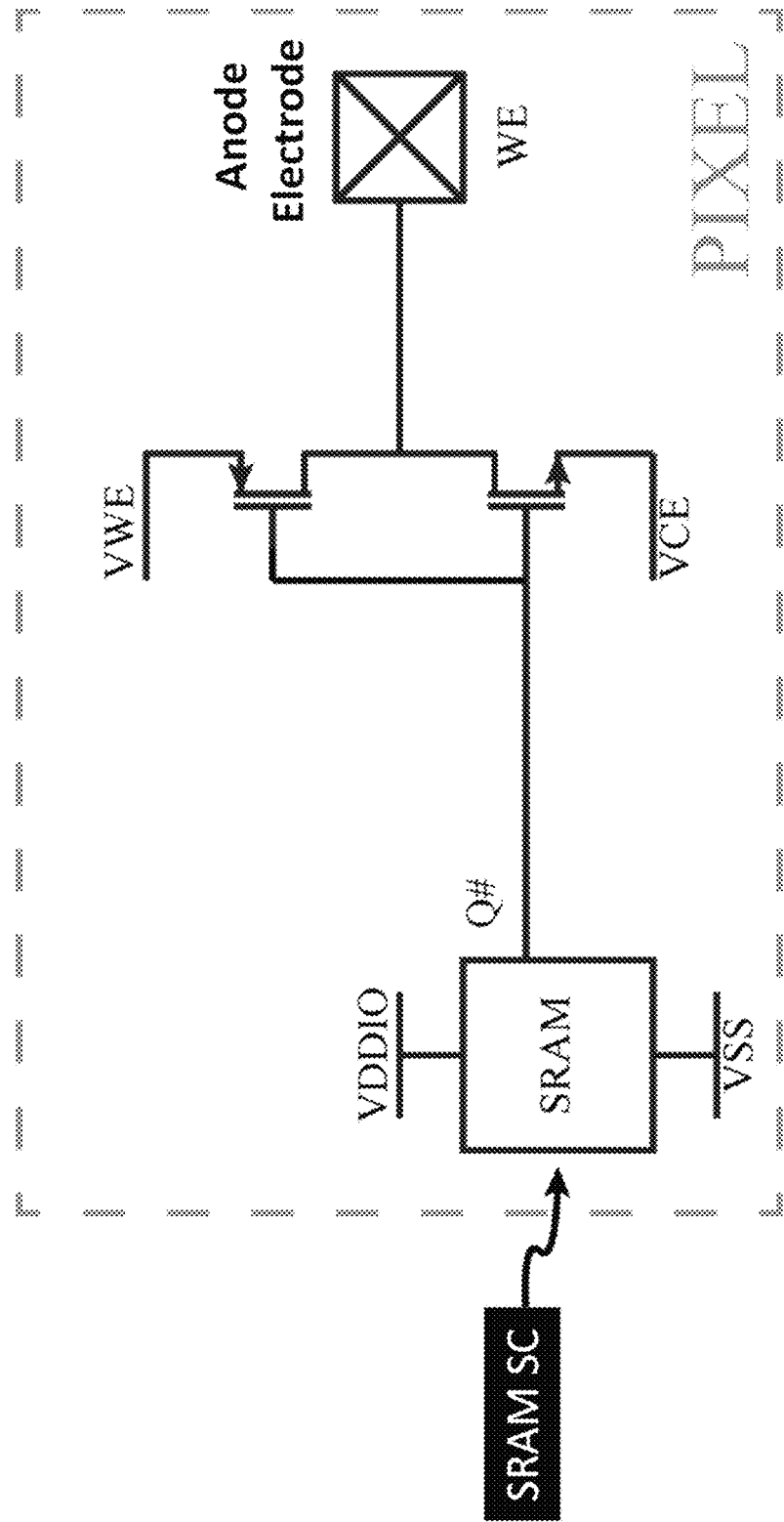
FIG. 42 illustrates a basic control circuit for a synthesis pixel, in accordance with various exemplary embodiments.

Turning now to FIG. 42, illustrated is an exemplary embodiment of a functional circuit schematic for synthesis pixel 120 circuitry indicated in the right side of FIG. 41A, having no monitoring function. In this exemplary embodiment, for state control functionality synthesis pixel 120 provides a memory element, shown as a static random-access memory (SRAM) bit. In other exemplary embodiments, this can comprise a dynamic random-access memory (DRAM) bit, a magnetic random-access memory (MRAM) bit, or other suitable component. The output of the memory cell is connected to a pair of opposing switches that connect the anode electrode node shown (WE) to either the global voltage supply level $V_{WE}$ for an "on" or acid generating state, or to the global voltage supply level of the cathode, $V_{CE}$, to achieve the off-state. In some exemplary embodiments, the supply voltage of the memory cell ($V_{DDIO}$) can be set to a different value from the global supplies $V_{WE}$ or $V_{CE}$, for example via a level shifter applied to these voltages. The input arrow SRAM SC indicates the programming of the SRAM memory bit by use of the chip array State Control circuitry. In this exemplary embodiment, the pixel cathode (Counter Electrode) is maintained at a common global value, $V_{CE}$, when activated for acid removal, and there is therefore no internal control switch for the cathode in this pixel circuit (unlike the illustration in FIG. 41A).

Figure 43:
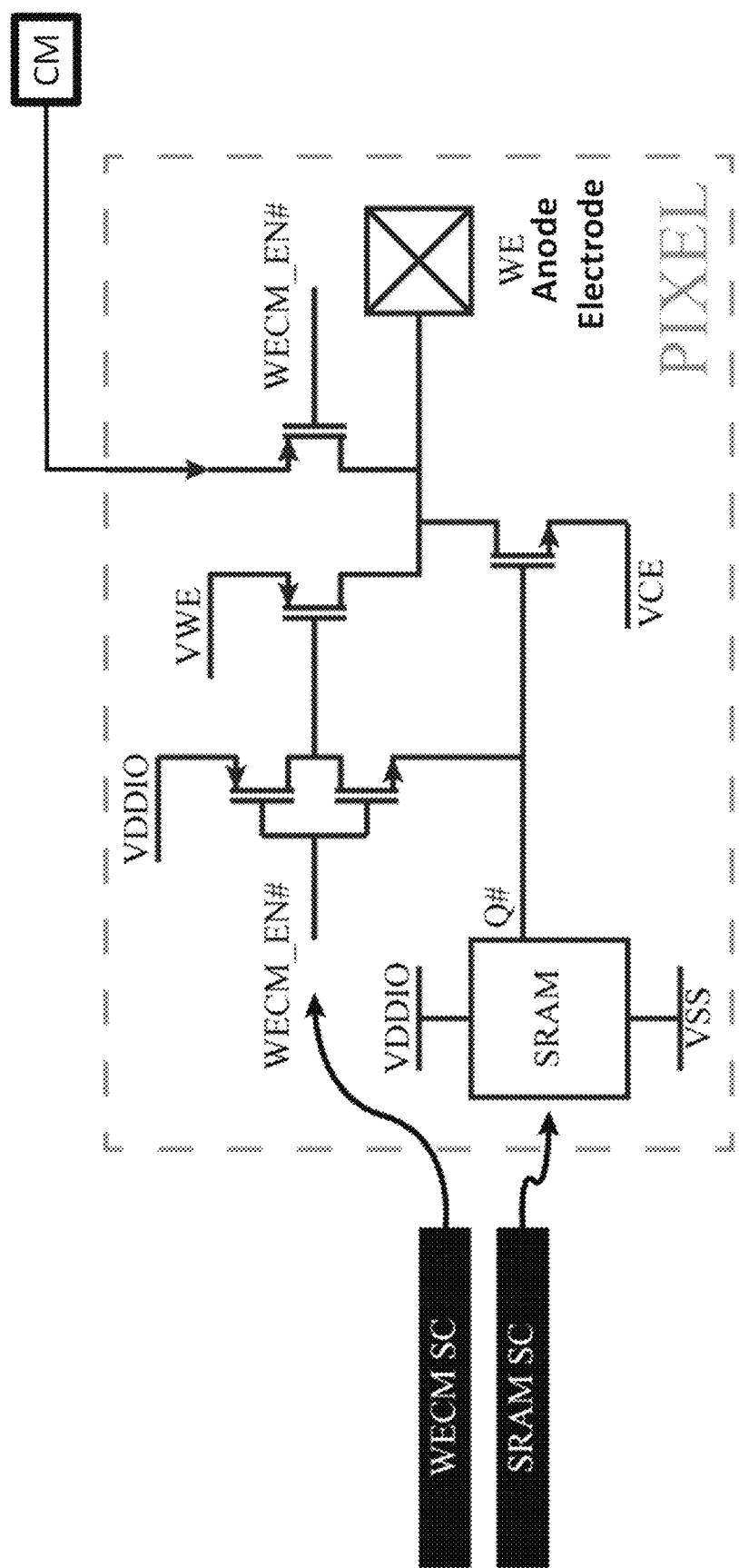
FIG. 43 illustrates a control circuit for a synthesis pixel with the addition of a monitoring circuit, in accordance with various exemplary embodiments.

With reference now to FIG. 43, illustrated is an exemplary embodiment of a functional circuit schematic for synthesis pixel 120 circuitry indicated in the right side of FIG. 42B, in which there is current monitoring (CM) function to monitor anode (WE) current. The schematic is an extension of the basic pixel schematic of FIG. 42, with the addition of a circuit that functions to switch the anode (WE) into an external, shared, off-pixel current meter circuit (CM). As illustrated, the state control input WECM SC controls the switch control WECM_EN#, which when in the on state decouples the WE electrode from the global supply voltage $V_{WE}$ and instead engages it into the external current meter CM. In some exemplary embodiments, this may be applied to monitor a single synthesis pixel 120, or in other exemplary embodiments, to monitor the net current of an entire row of synthesis pixels 120. In exemplary embodiments, readout of the monitor measurements is provided by the chip column parallel readout circuitry. The remainder of the pixel circuit may be as described above and illustrated in FIG. 42.

Figure 44:
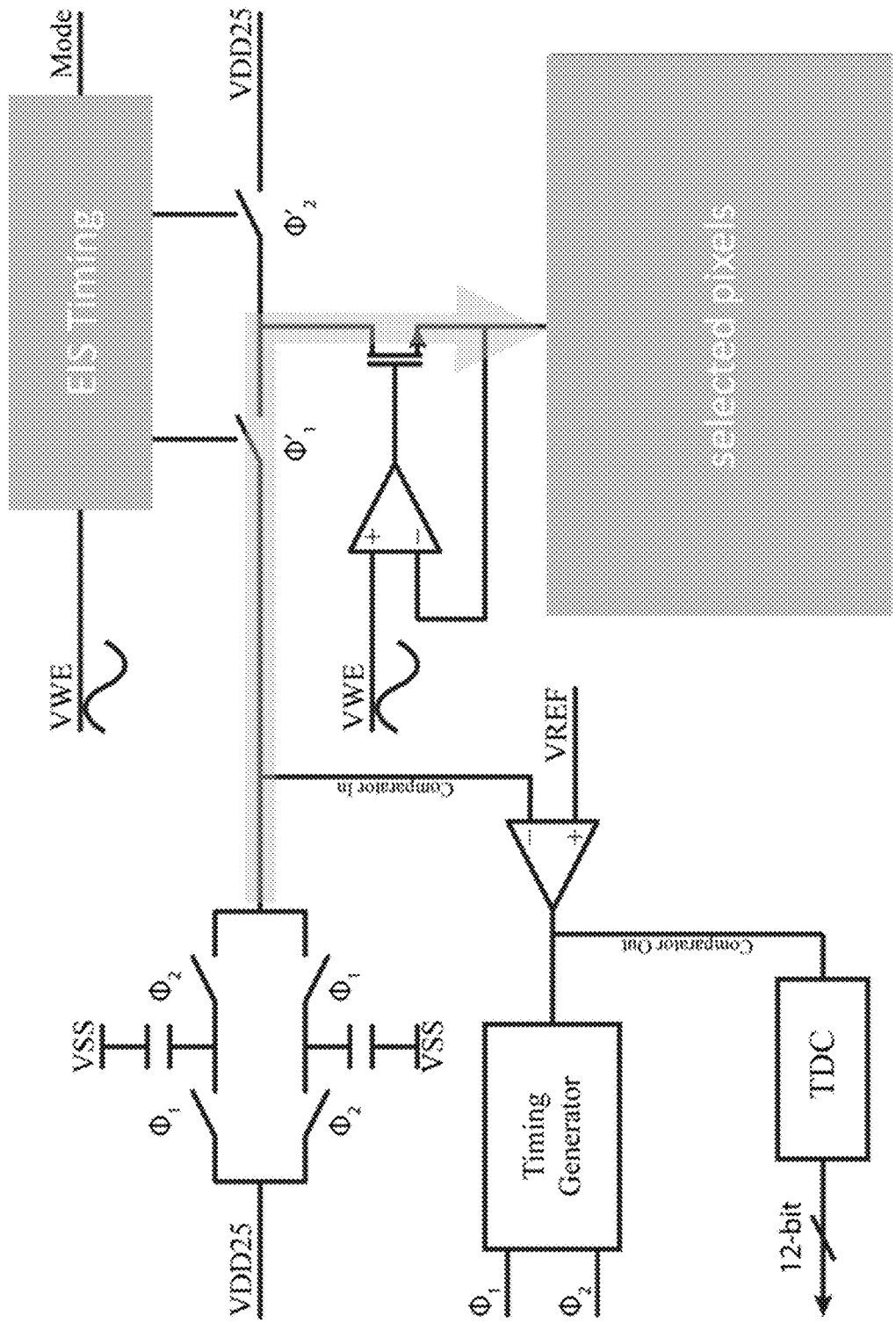
FIG. 44 illustrates an exemplary embodiment of a monitoring circuit, in accordance with various exemplary embodiments.

Turning to FIG. 44, illustrated is an exemplary embodiment of a synthesis monitoring circuit, such as may be generally used in FIG. 43 in the role of the current monitor (CM), or in the role of the monitor circuit indicated in FIG. 41B. The block diagram shown depicts a circuit to monitor the current as well as the impedance from a synthesis pixel 120 anode, or the collective anodes of a selected group of synthesis pixels 120 (such as, in exemplary embodiments, a row or column of pixels). The circuit shown is operable as an integrator where the current from the from the selected synthesis pixel 120 anodes is integrated on a selected capacitor (from the pair in upper left) and compared against (via Comparator In line, middle) a reference voltage, VREF. A local feedback loop regulates the voltage applied to the selected synthesis pixels 120, to either the global voltage supply $V_{WE}$ for current monitoring, or also to sinusoidal signal modulation near this voltage, which when applied provides measurement of impedance. The illustrated timing generator toggles between two integrating capacitors to allow one to be reset while the other is used for integration, so as to provide a readout that is continuous using two clocks $F_1$ and $F_2$. In various exemplary embodiments, a suitable time to digital converter (TDC) (for example, with a 12-bit accurate output) is used to measure the integration time for the current monitoring and electrochemical impedance spectroscopy (EIS) measurement modes. From the disclosure of the various exemplary monitoring circuits herein, various approaches may be utilized to implement the functional blocks disclosed, and all such variations are considered to be within the scope of the present disclosure.

Figure 45A:
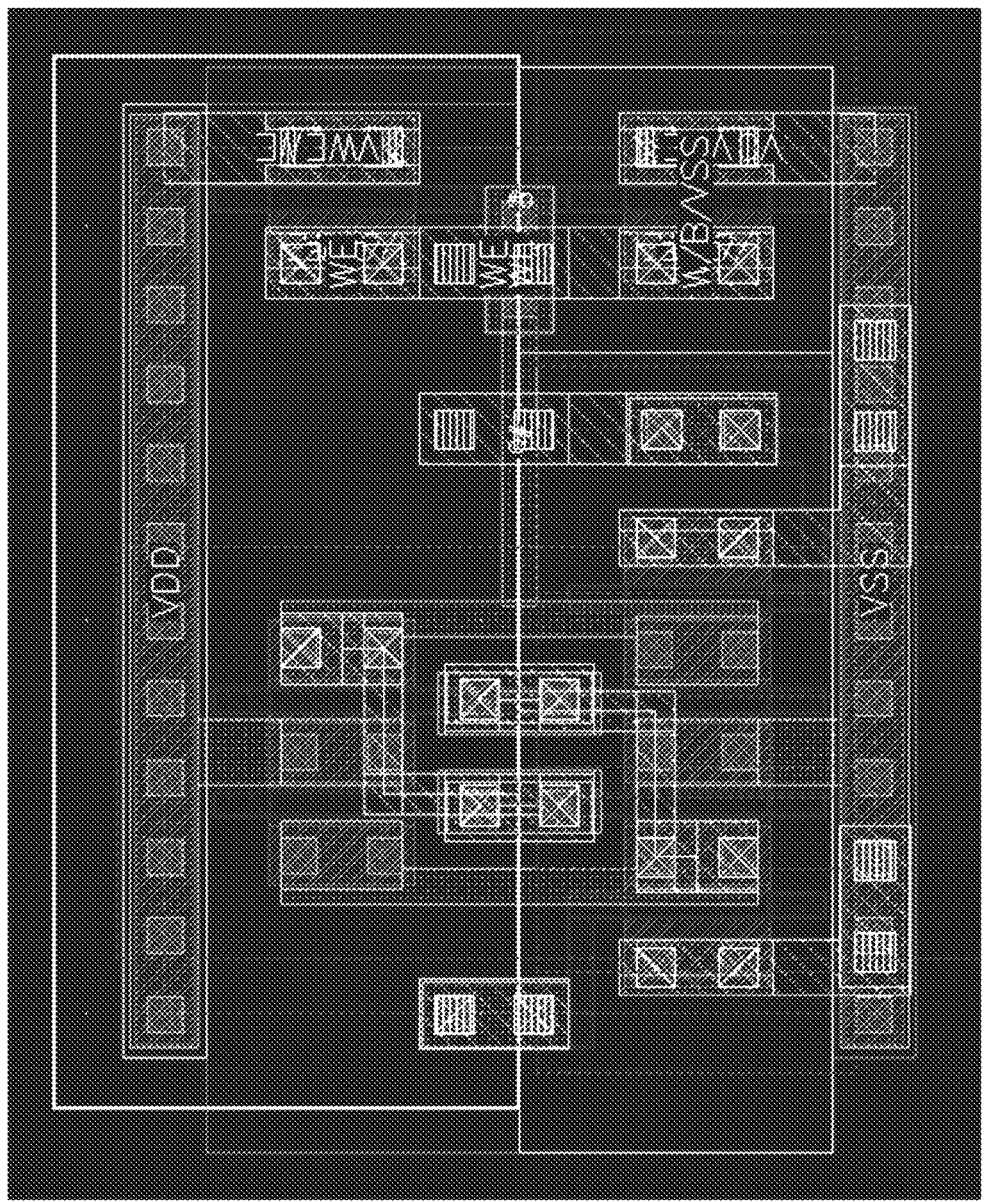
FIG. 45A illustrates an integrated circuit layout for a synthesis pixel configured absent a current monitor, in accordance with various exemplary embodiments.
Figure 45B:
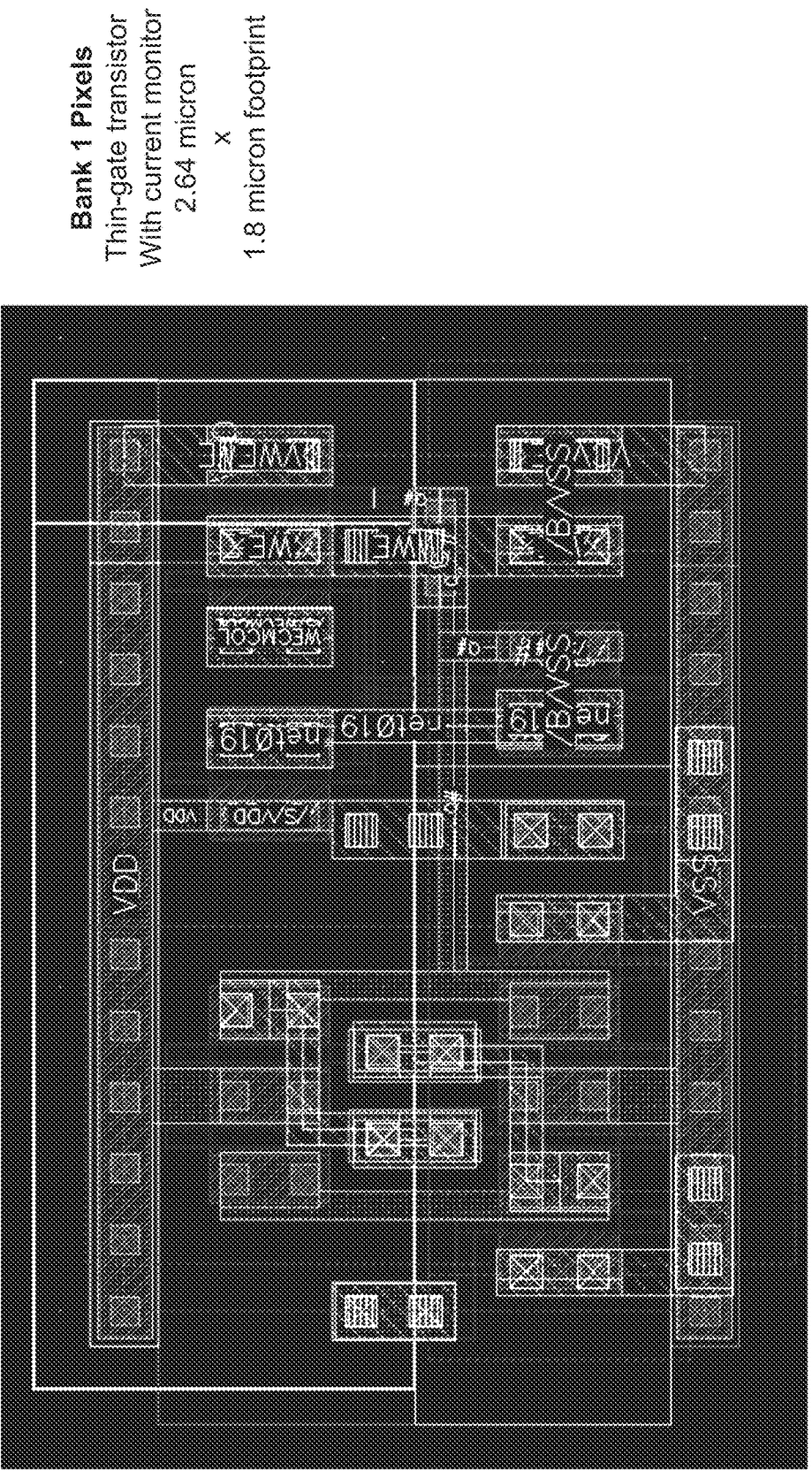
FIG. 45B illustrates an integrated circuit layout for a synthesis pixel configured with a current monitor, in accordance with various exemplary embodiments.
Figure 45C:
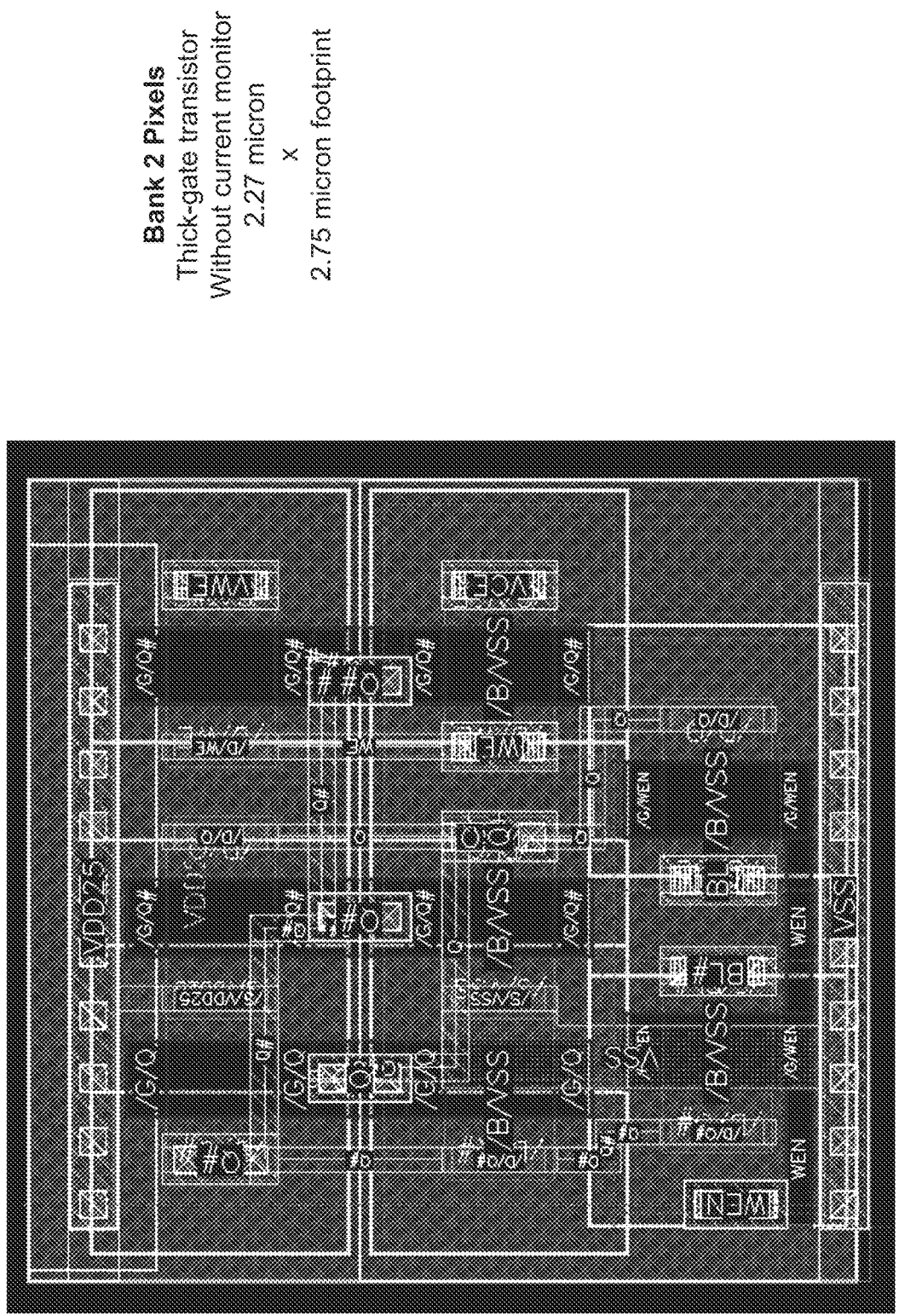
FIG. 45C illustrates an integrated circuit layout for a synthesis pixel configured absent a current monitor, in accordance with various exemplary embodiments.
Figure 45D:
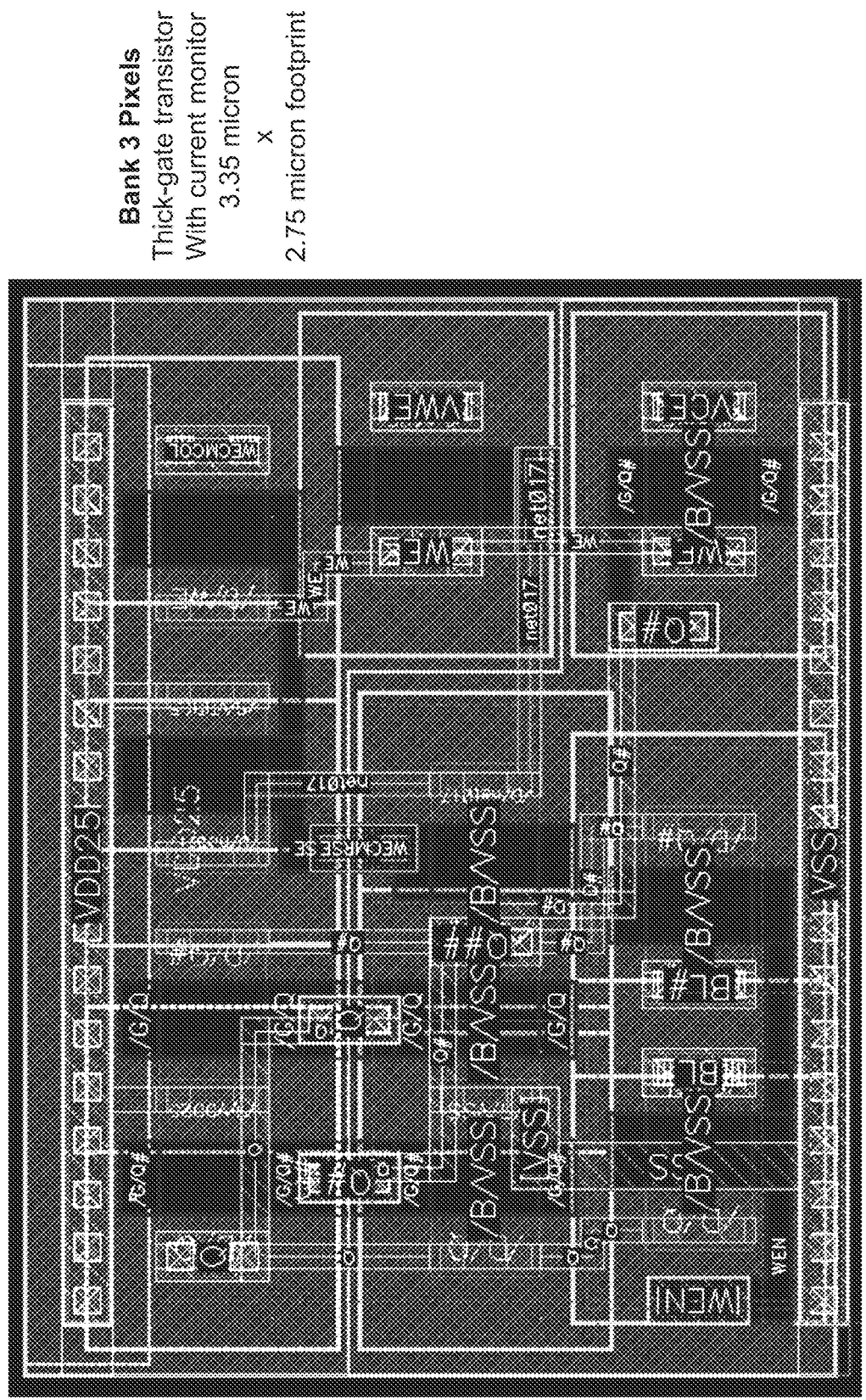
FIG. 45D illustrates an integrated circuit layout for a synthesis pixel configured with a current monitor, in accordance with various exemplary embodiments.

FIGS. 45A, 45B, 45C, and 45D illustrate exemplary embodiments of detailed integrated circuit layouts for various synthesis pixel 120 circuits of the forms disclosed, as implemented in a 65 nm CMOS process node. FIGS. 45A and 45C illustrate layout for synthesis pixels 120 with no current monitoring capability (without Current Monitor), with their respective pixel circuitry layout dimensions indicated, and in variants using thin-gate or thick gate transistors. FIGS. 45B and 45D illustrate layouts that include support for off-pixel (shared) current monitoring (with Current Monitor), with indicated dimensions. The dimensions demonstrate that synthesis pixel 120 circuitry can be placed at a 1 micron scale pitch. Smaller synthesis pixel 120 circuits than those shown may also be realized, for example in 65 nm CMOS or in finer CMOS nodes, and the foregoing exemplary illustrations are not meant to imply limits on synthesis pixel 120 size. In various exemplary embodiments, thick-gate devices allow for a $V_{WE}$ and/or $V_{CE}$ to be higher than the nominal 65 nm supply voltage limit of 1.2 V. This example illustrates that such synthesis pixels 120 can readily have a pitch of several microns in 65 nm CMOS. Moreover, exemplary circuitry area penalty for having exemplary current monitor circuitry (for off-pixel shared current monitoring) is indicated, showing it is a modest area multiplier cost in the range of between about 1.2× and about 1.5×. Circuits shown labeled as Bank 1, Bank 2, and Bank 3 refer to actual pixel layouts for synthesis pixels 120 in the banks shown in the DNA synthesis chip 100 illustrated in FIG. 49.

Exemplary DNA synthesis chips 100 are configured with surface electrodes that are used for the anode, cathode, and in exemplary embodiments, additional monitoring electrodes. In exemplary embodiments, these surface electrodes are fabricated at a foundry, using standard semiconductor fabrication processes, and are connected using standard vias in DNA synthesis chip 100 to pixel circuitry implemented at lower levels of the chip. In other exemplary embodiments, such electrodes may also be fabricated by additional post processing steps, such as through additional etching and deposition processes, which may remove sacrificial materials, and add desired electrode materials in the desired electrode geometries. In exemplary embodiments, well structures and other disclosed surface structures may be produced through such post-processing steps.

Figure 46:
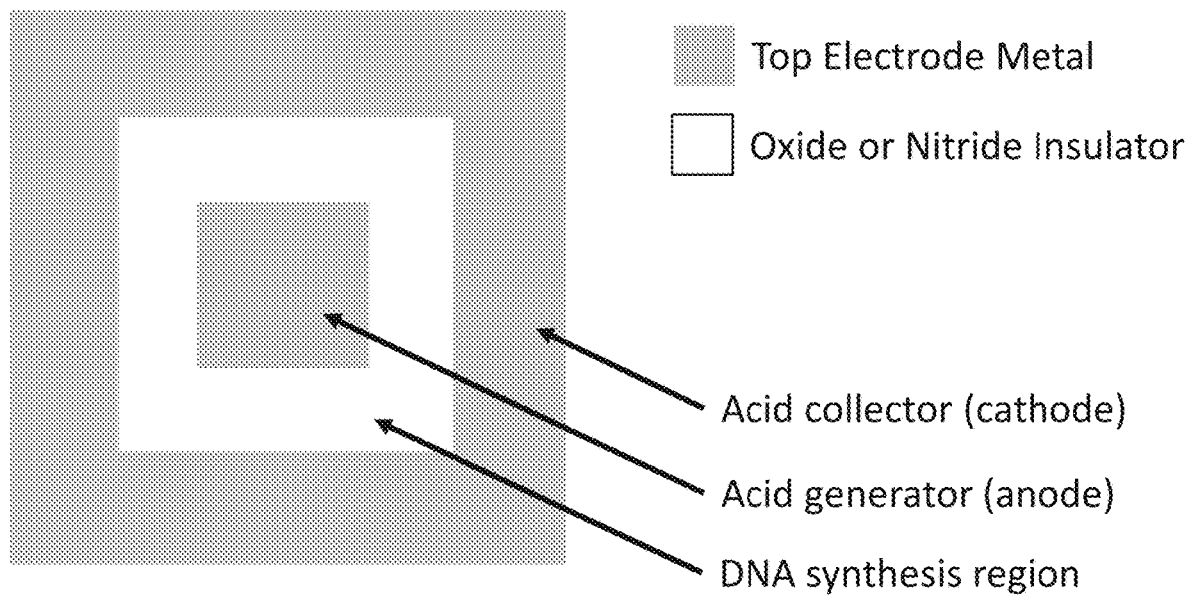
FIG. 46 illustrates an exemplary planar electrode architecture for a synthesis pixel, in accordance with various exemplary embodiments.

Turning now to FIG. 46, illustrated is an exemplary embodiment of synthesis pixel 120 anode and cathode geometry, for a planar electrode geometry. The anode takes a form of an inner electrode and the cathode takes on a form of a surrounding outer electrode. An insulating layer, which in exemplary embodiments may be an oxide or nitride layer as are commonly available insulators in CMOS devices, is used to provide insulating separation between, and a substrate for, such electrodes, and also provides the exposed area which may be functionalized to support the DNA synthesis, such as by silanization or other suitable process. In exemplary embodiments, these electrodes are made of platinum, palladium, or iridium, or may be made of other suitable metals, such as gold, and subsequently may be plated or coated with these suitable materials.

Figure 47:
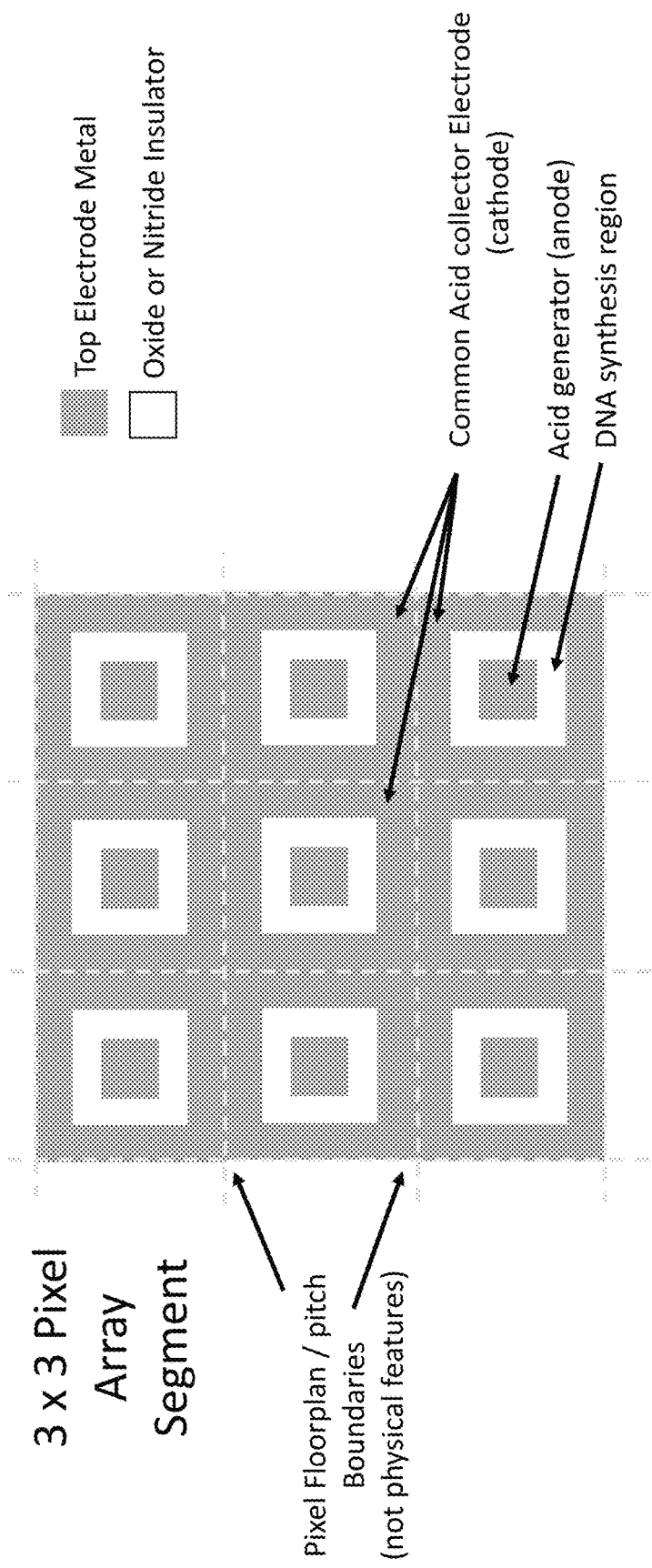
FIG. 47 illustrates use of shared cathodes across groups of synthesis pixels, in accordance with various exemplary embodiments.
Figure 48:
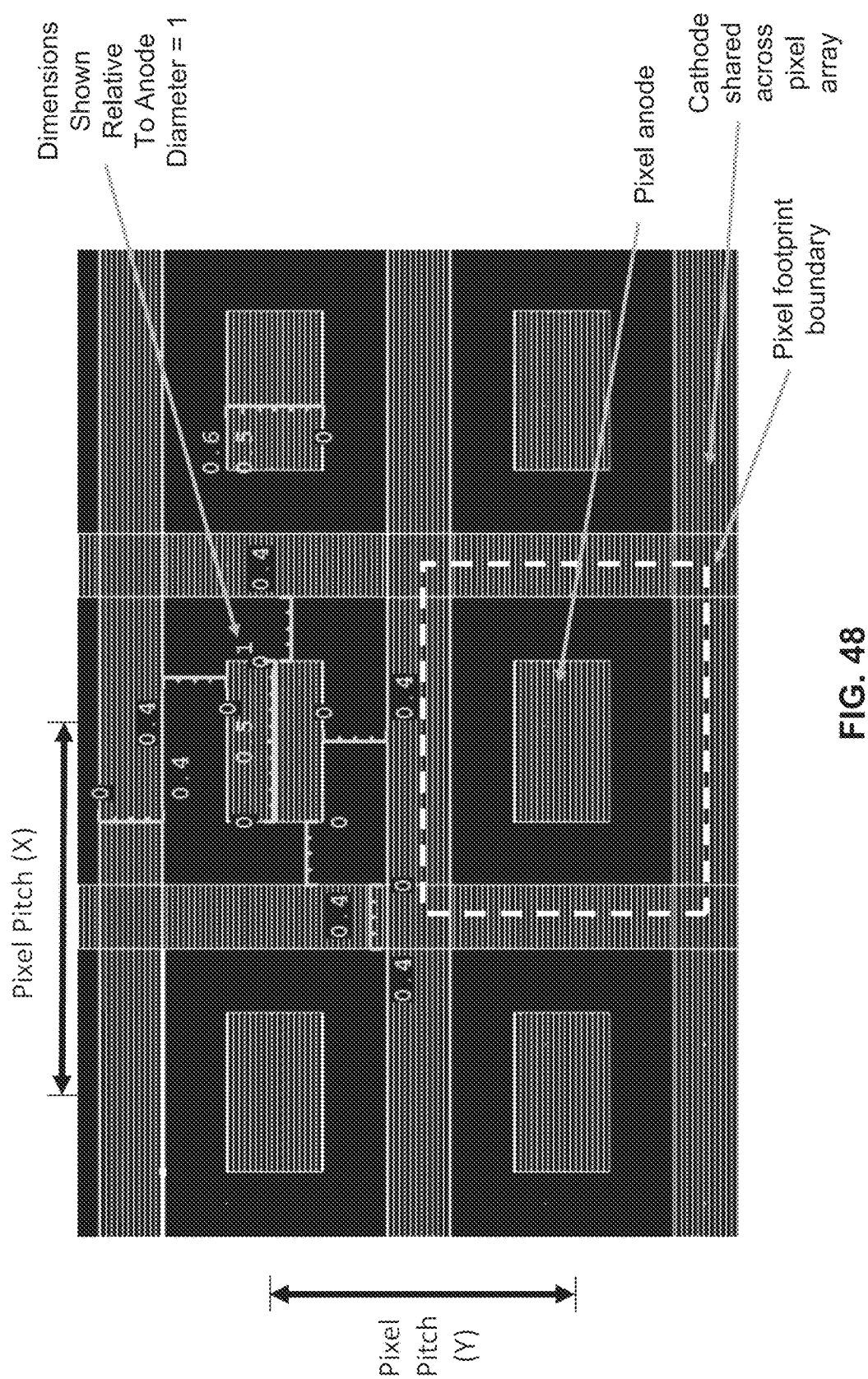
FIG. 48 illustrates an exemplary layout of a geometry of pixel electrodes in an array utilizing a shared cathode, in accordance with various exemplary embodiments.
Figure 49:
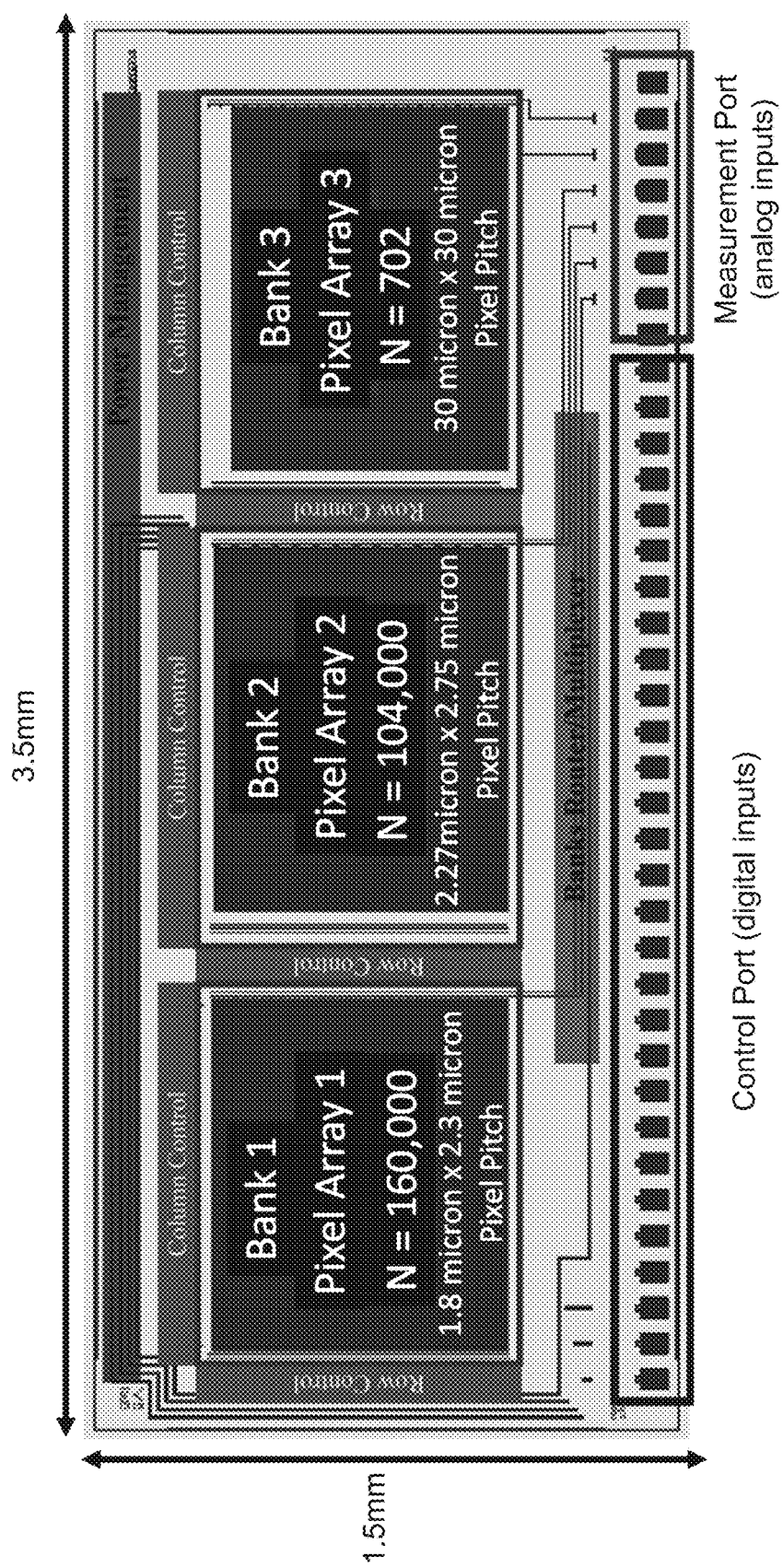
FIG. 49 illustrates a floorplan of an embodiment of a CMOS synthesis chip, in accordance with various exemplary embodiments.

With reference to FIG. 47, illustrated is an exemplary embodiment of the synthesis pixel 120 electrodes comprising a shared cathode continuously connected between pixels and common to all the synthesis pixels 120 of the array 110 (or the all the pixels in a certain region). In such embodiments, synthesis pixels 120 do not need internal control over the cathode, and it may instead have a global control. FIG. 48 illustrates exemplary surface feature layout for an exemplary embodiment of synthesis pixels 120 with shared cathodes, which corresponds to the pixel electrode layout for the CMOS chip depicted in FIG. 49 and the pixel circuits indicated in FIG. 47. FIG. 49 illustrates the floorplan for an exemplary embodiment of a CMOS DNA synthesis chip 100, which is an exemplary embodiment of the chip architecture illustrated in FIG. 40. The illustrated exemplary embodiment of DNA synthesis chip 100 comprises three major synthesis pixel 120 sub-arrays, with separate row and column control, and other major functional blocks (power, router, ports) as indicated, and utilizes synthesis pixels 120 with circuit layouts shown in FIGS. 45A, 45B, 45C, and 45D, as labeled there by Bank 1, Bank 2 and Bank 3 pixels. The size and pitch of the pixel subarrays are as indicated in FIG. 49. For example, the smallest pitch bank has 160,000 pixels, with pitch 1.8 microns×2.3 microns. This illustrated embodiment of DNA synthesis chip 100 was fabricated and utilized for various experiments and demonstrations described further hereinbelow.

Figure 50:
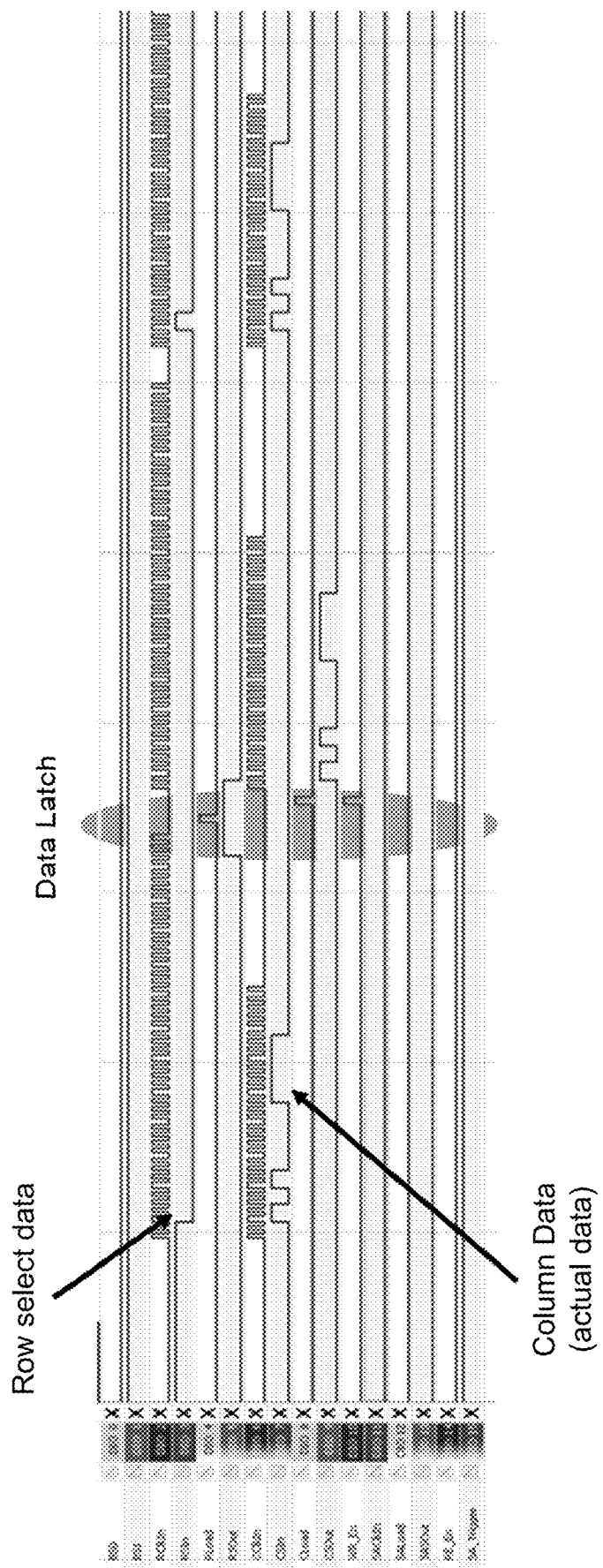
FIG. 50 illustrates an exemplary a timing diagram for control of synthesis pixels on a pixel array chip, in accordance with various exemplary embodiments.

Chip Timing and Operation: With reference now to FIG. 50, illustrated is an exemplary embodiment for a global timing diagram for the control of DNA synthesis chip 100 embodiment illustrated in FIG. 49. The timing indicated is as follows: Bank select (BS0 and BS1) select between different banks (arrays) of synthesis pixels 120 on the chip. The row signals are loaded with the input (Rsin), clock (RSClkin), and latch (Rload) signals. The signals can also be read back from the row decoder via the output (Rsout). The column decoder is clocked via similar signals (Csin, CclkIn, Cload, and Csout). The write enable (WR_En) loads the (anode on/off) state data into the synthesis pixels 120. Reading data from synthesis pixels 120 is controlled via the Sense Amp signals, specifically the clock (SAClkIn), load (SALoad), output (SAOut), and trigger (SA_Trigger). In this exemplary example, data is latched into synthesis pixels 120 at the annotated Data Latch event.

From the foregoing disclosures and illustrations of DNA synthesis chip 100 and related synthesis pixel 120 design and operation, it will be appreciated that there are many variations in method and details of methods possible, and all such variations and details are considered to be within the scope of the present disclosure.

Figure 51:
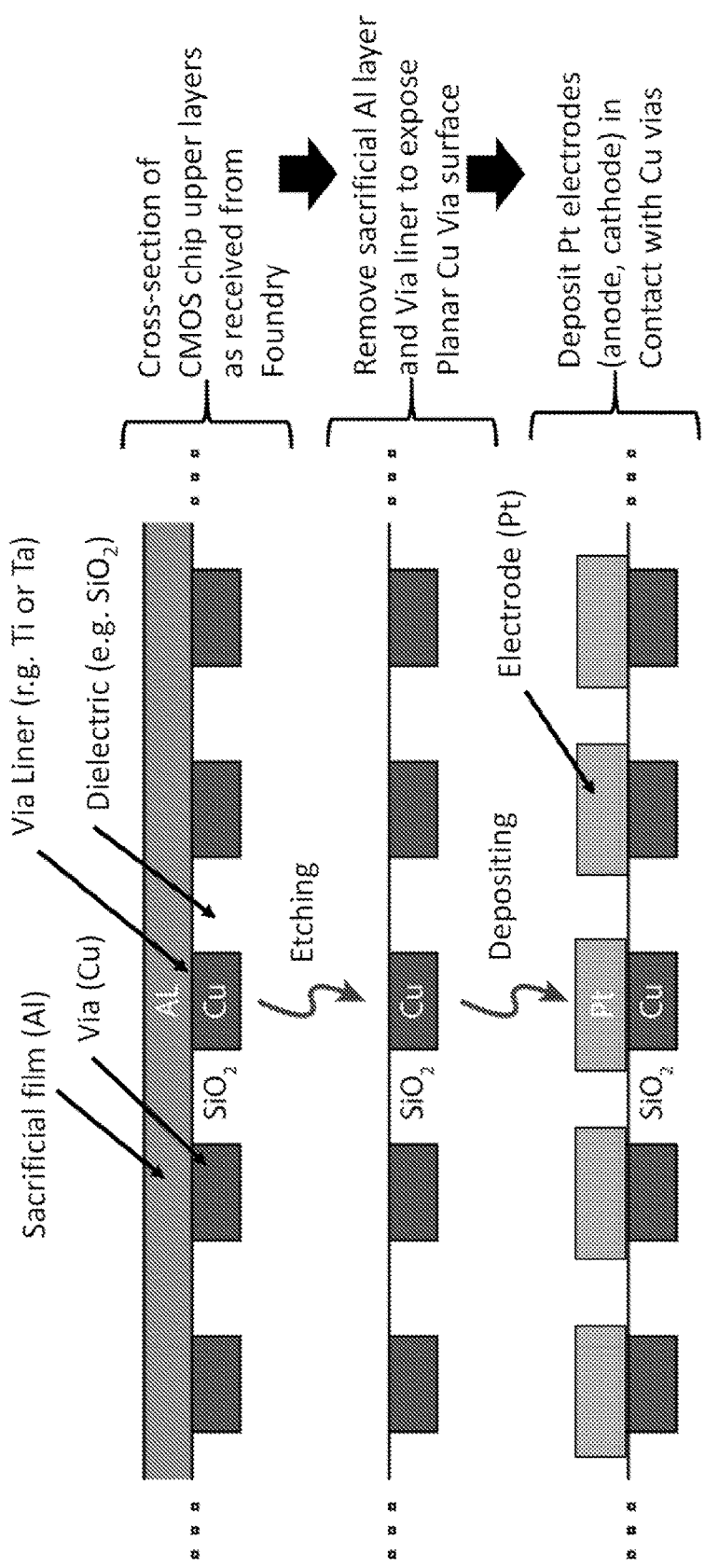
FIG. 51 illustrates an exemplary method of fabricating metal electrodes on a CMOS chip, in accordance with various exemplary embodiments.

Electrode Post-Processing: FIG. 51 illustrates a method for fabricating synthesis pixel 120 electrodes (anode and cathode) starting from a standard CMOS chip material stack as produced by a commercial foundry, in accordance with various exemplary embodiments. In an exemplary embodiment, the foundry process is a 65 nm CMOS process. As indicated in FIG. 51, the CMOS foundry chip is designed and fabricated such that exposed on the top layer of the chip is a sacrificial layer, which may conveniently be the metal used for pads or interconnects. As shown, in this case it is an aluminum layer, which is the CMOS interconnect metal for this CMOS node. Immediately under this is a via layer that provides the planarized vias that that will ultimately be connected to the anode and cathode, to form the desired anode and cathode circuits as disclosed above and as illustrated in FIGS. 41A through 44. In an exemplary embodiment, the CMOS via metal is copper (Cu). In typical CMOS foundries, there will also be a thin liner material protecting the via surface, such as titanium or tantalum, as indicated. In a first step, selective etching processes are performed to remove the sacrificial Al, and then another selective etching step is performed to remove the exposed Ti via liner, leaving exposed the planarized Cu via faces and the planarized layer. Then, through standard patterning and metal deposition processes, the metal electrodes (anode and cathode) are formed with the desired geometry, in contact with appropriate Cu via(s) as desired. In exemplary embodiments, as shown, the electrode metal may be platinum.

Figure 52:
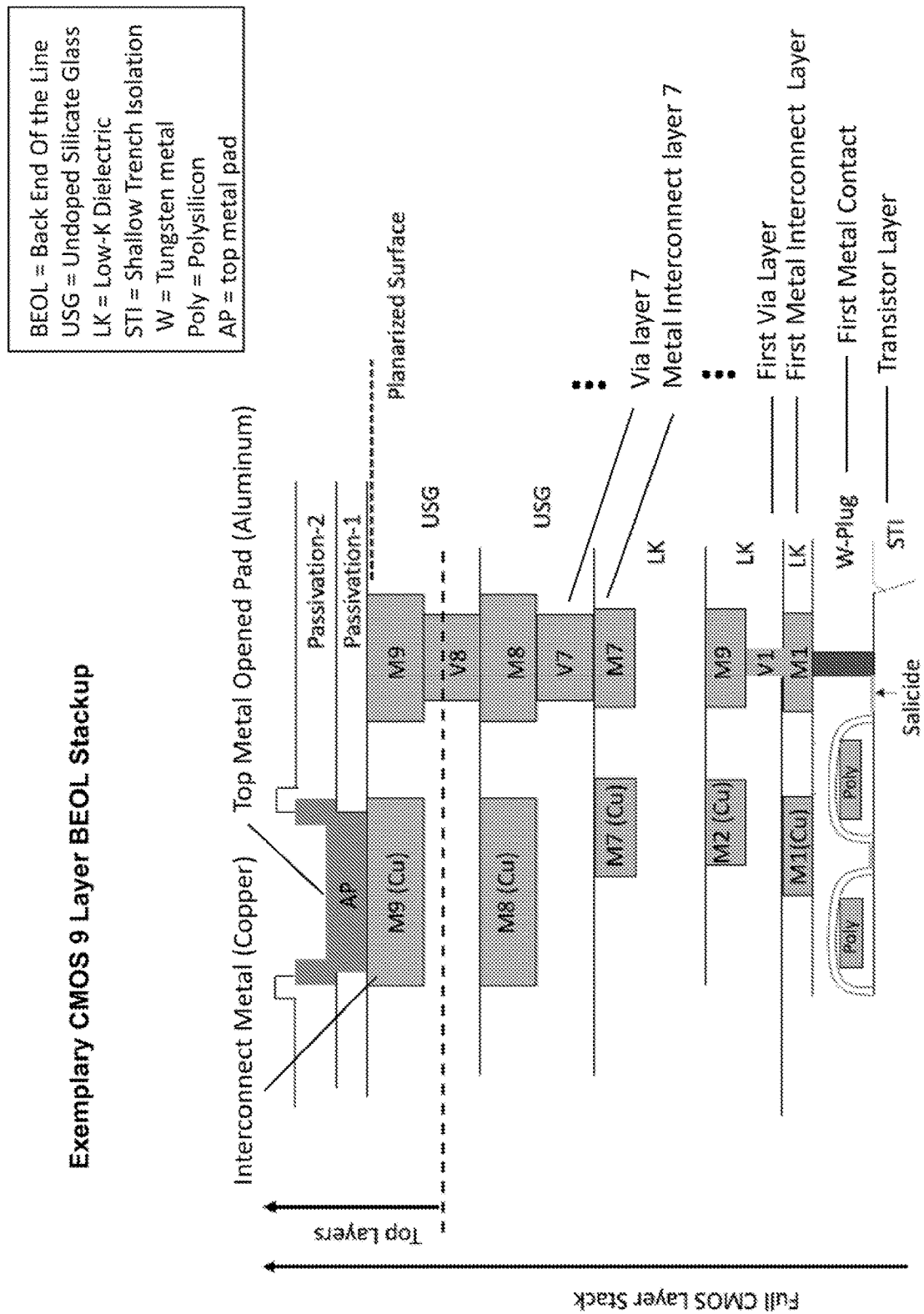
FIG. 52 illustrates an exemplary material stackup for a CMOS chip, with upper sacrificial metal layers and vias that provide for electrode fabrication, in accordance with various exemplary embodiments.
Figure 53A:
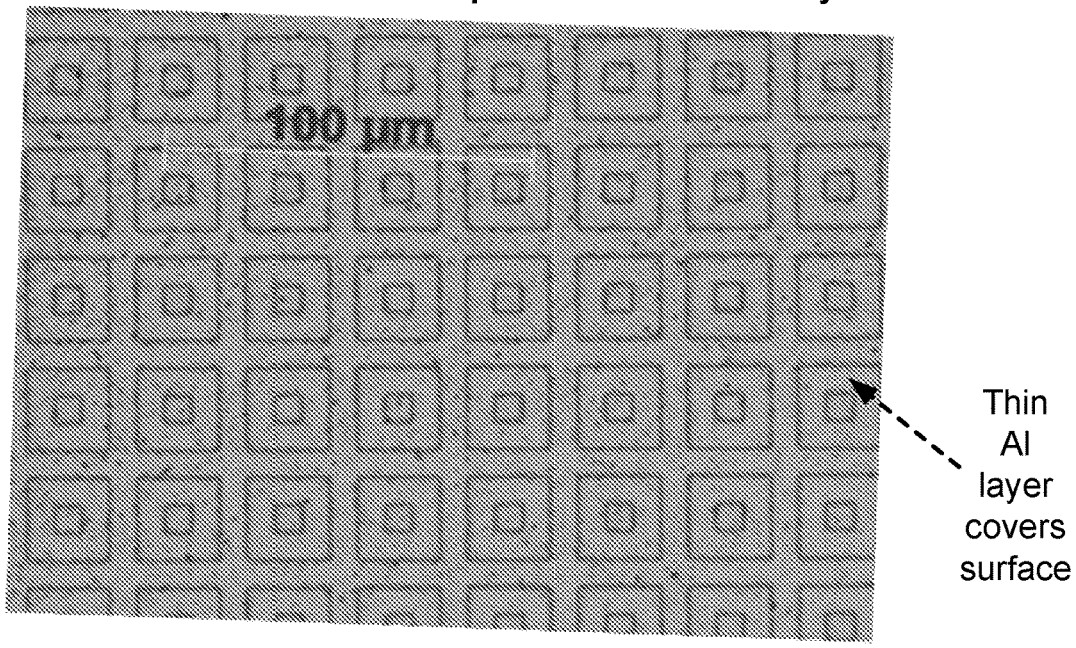
FIGS. 53A, 53B, 53C, 53D, 53E and 53F illustrate stages of an exemplary embodiment of electrode fabrication post-processing, in accordance with various exemplary embodiments.
Figure 53B:
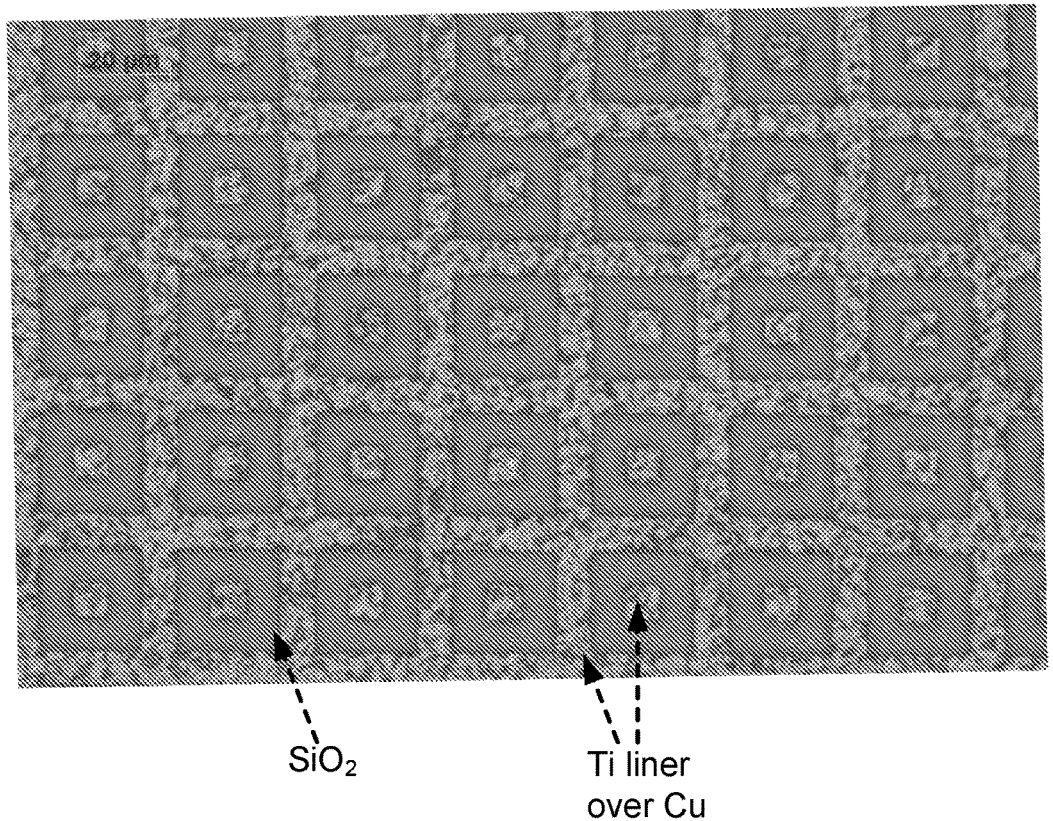
Figure 53C:
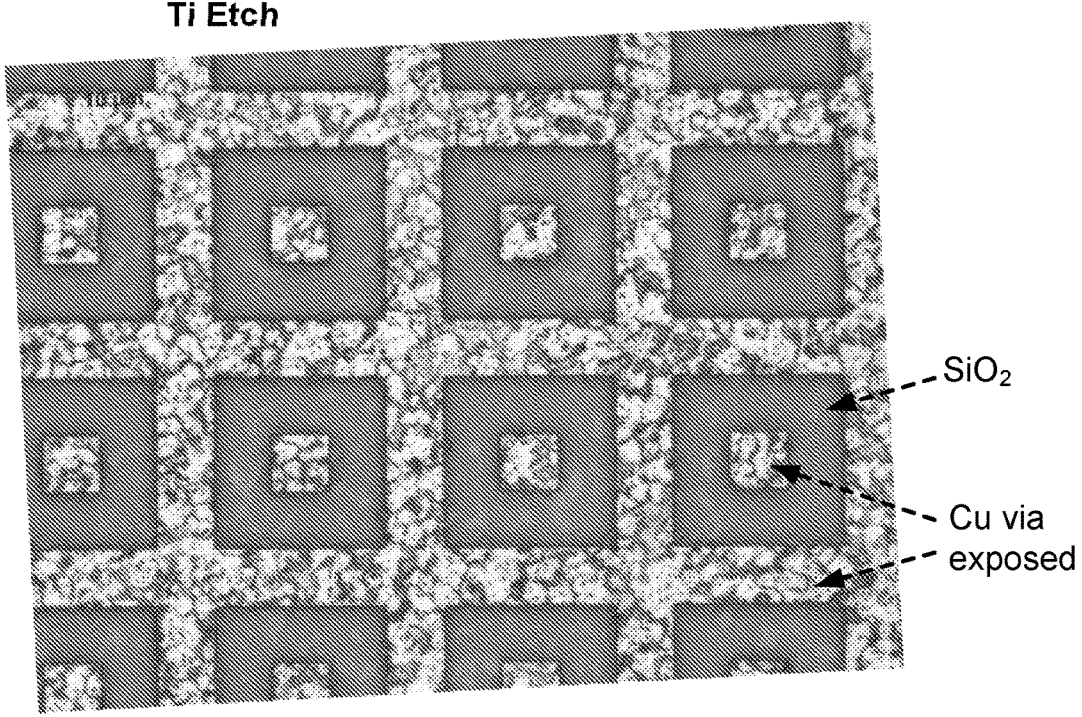
Figure 53D:
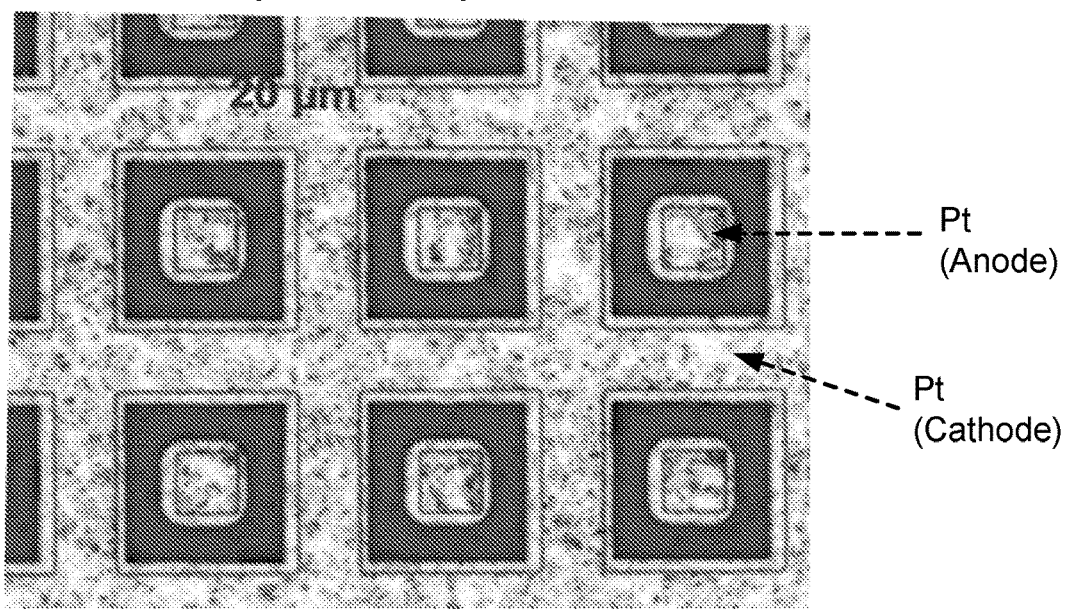
Figure 53E:
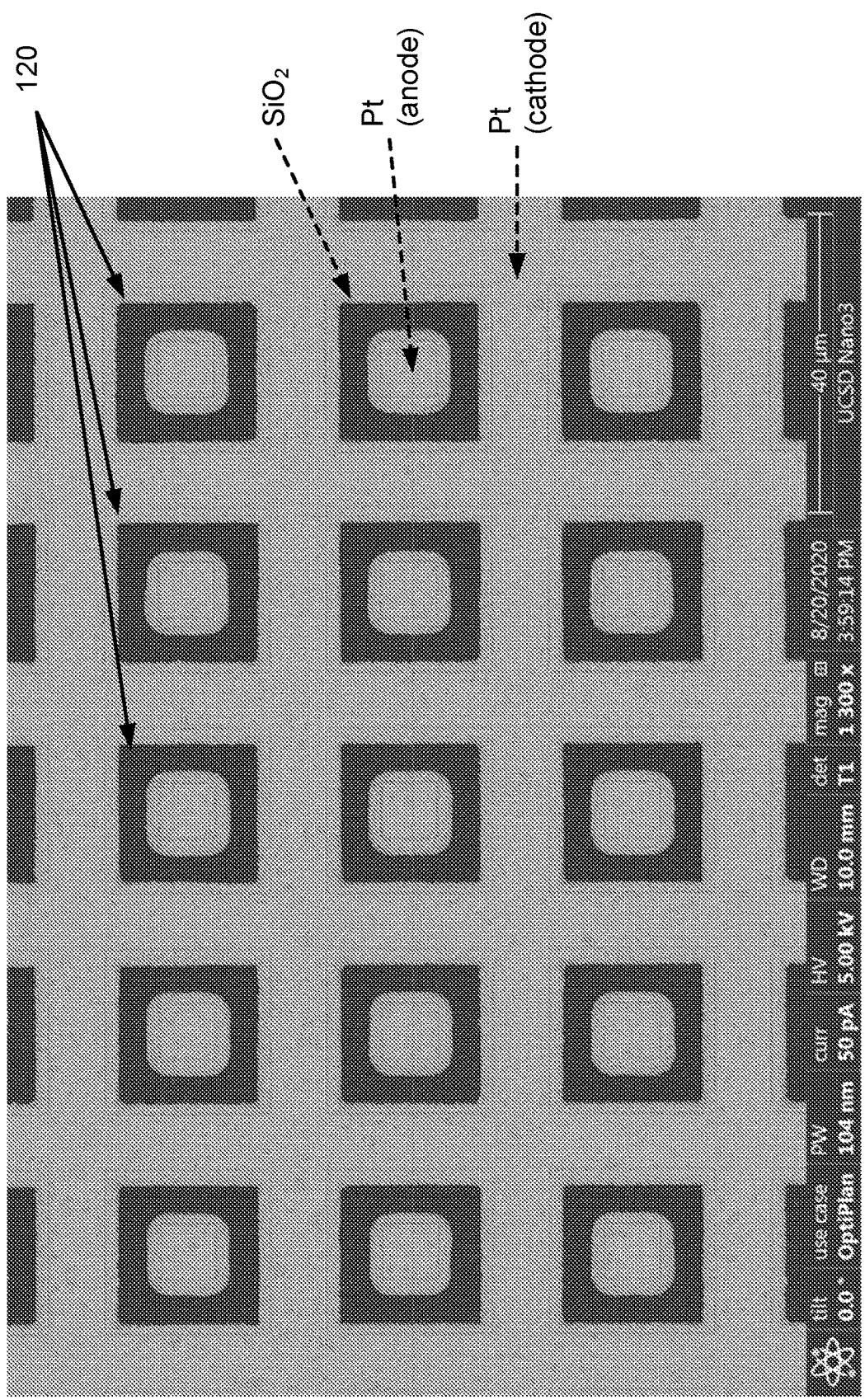
Figure 53F:
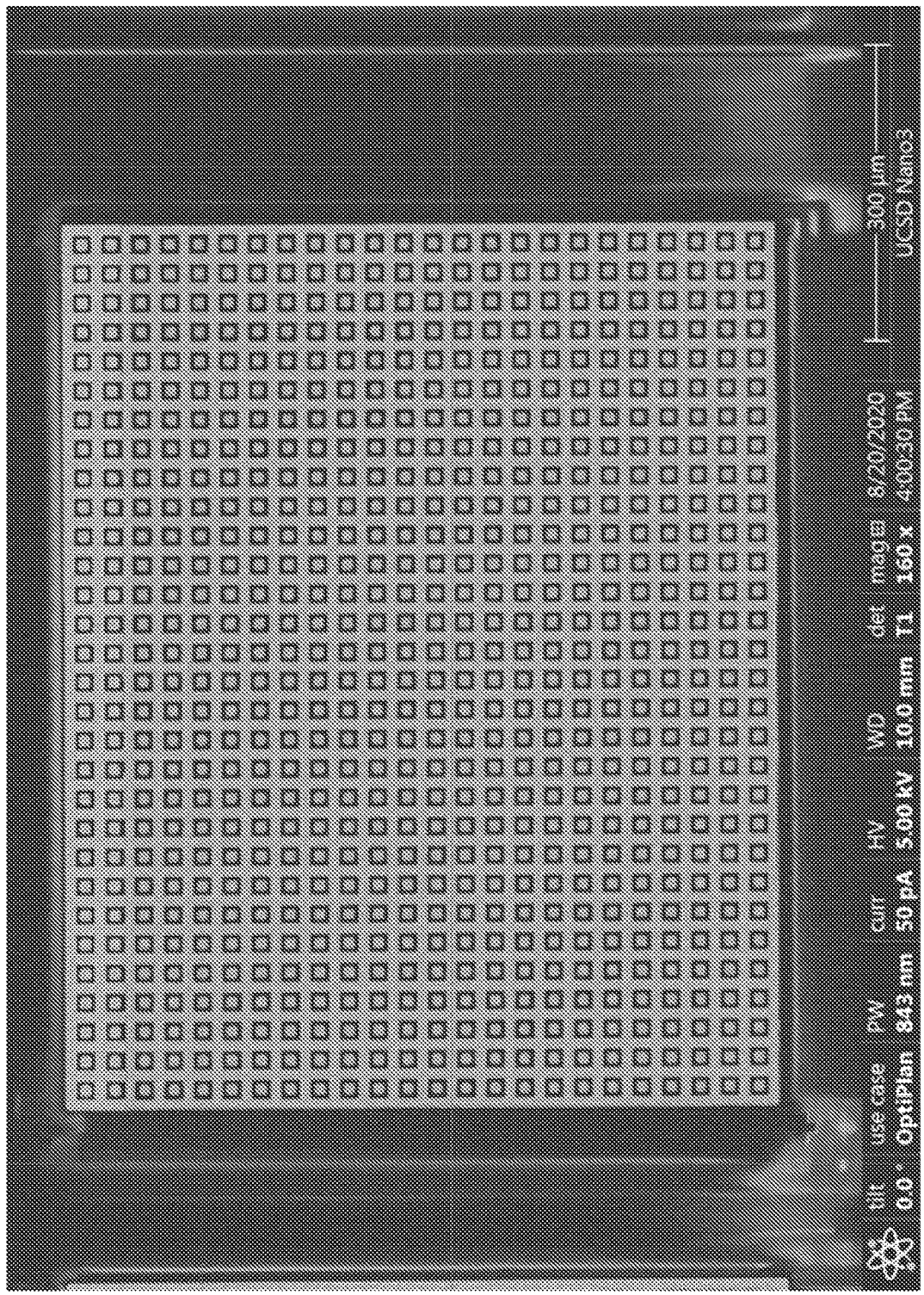
Figure 54A:
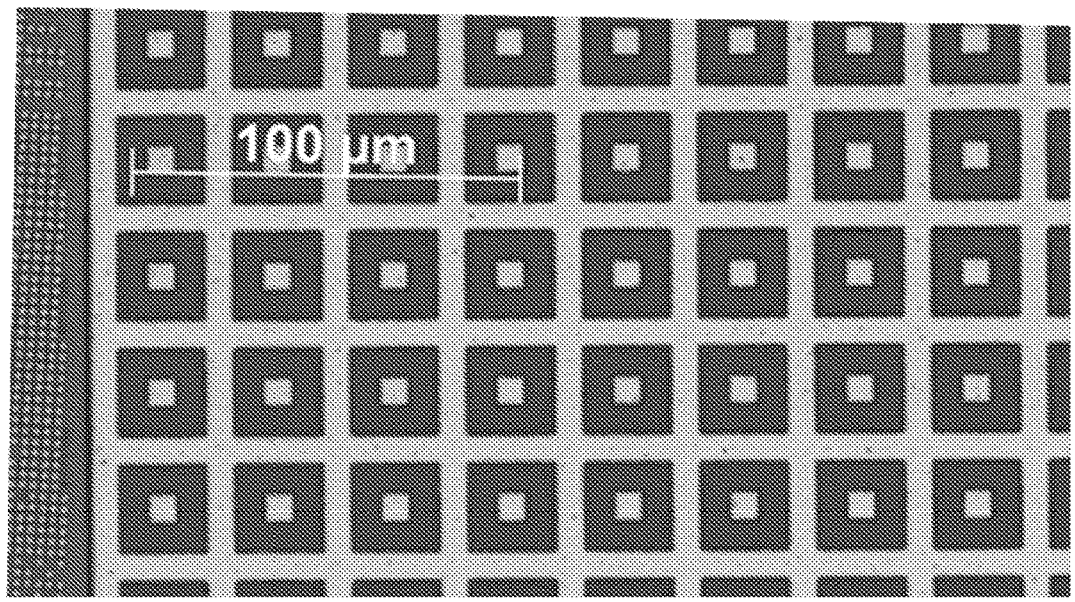
FIGS. 54A and 54B illustrate exemplary electrodes on a post-processed chip, in accordance with various exemplary embodiments.
Figure 54B:
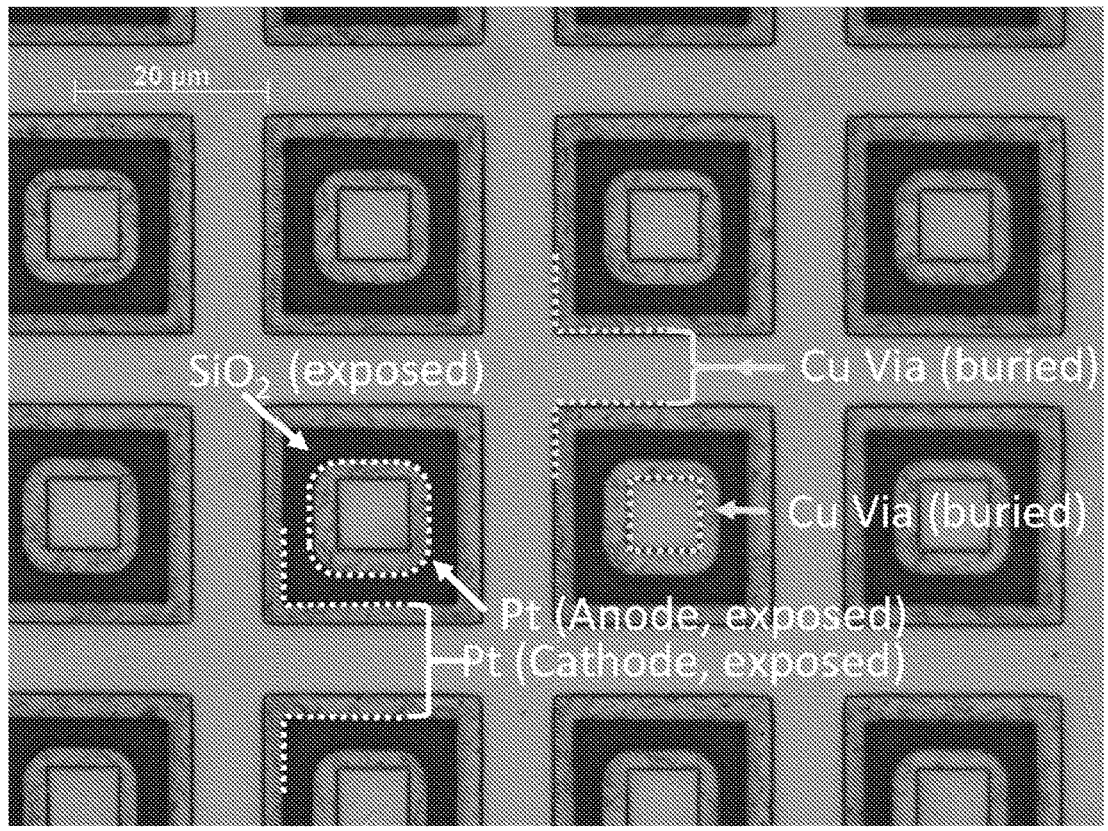

FIG. 52 illustrates a schematic of an exemplary CMOS foundry material stack for a 65 nm CMOS process, having 9 total layers on the Back End Of the Line (BEOL) processing. The location of the sacrificial Al and Cu vias, and the planar via interface indicated FIG. 51, are highlighted in the stackup shown in FIG. 52. FIGS. 53A through 53E illustrate the result of exemplary process steps as performed for DNA synthesis chips used for the exemplary work described below. In FIG. 53A is a top-down view in an SEM image showing a region of the pixel array 110. The surface material is micron-thick aluminum, and the SEM image also shows the dark boundaries of the Cu via regions buried below. In FIG. 53B is illustrated the surface after a selective Al etch is applied. The exposed surface is now planarized, with regions of $SiO_2$ dielectric, and regions of Cu via covered by a thin Ti liner. FIG. 53C shows the result after a selective Ti etch to remove the liner, so that planarized Cu is exposed. FIG. 53D shows the result after patterned Pt has been deposited onto the anode and cathode regions. FIG. 53E shows SEM images of the finished synthesis pixels 120, and FIG. 53F shows the entire pixel array 110. FIG. 54A shows an additional SEM image view of finished synthesis pixels 120 in at least a portion of the array 110, and FIG. 54B shows a close-up view annotating features visible in the SEM image. The exposed surface is the Pt anode (central rounded squares with dashed boundary superimposed) and shared cathode (grid of wide lanes with dashed boundary superimposed), separated $SiO_2$ dielectric zones intended for synthesis (dark rectangular ring regions). The boundaries of the Cu via regions buried beneath the Pt are also visible as dark lines recessed from the boundary of the Pt electrodes.

From the foregoing disclosure of the endpoint and exemplary approaches for fabricating the anode and cathode electrodes, it will be appreciated that there are many variations in method and details of such methods suitable, to achieve fabrication of similar or comparable pixel electrode structures on DNA synthesis chips, and the present disclosure contemplates all such suitable approaches and techniques. This includes methods for making the desired final electrode structures on the synthesis pixels that may be performed entirely within an industrial CMOS foundry, which is an exemplary embodiment, or methods that may be performed outside such foundries, such as for using processes or tools or materials not readily available in commercial CMOS fabrication lines.

Synthesis Chip Flow Cell and Supporting System Hardware

For DNA synthesis chip 100 operation, in exemplary embodiments DNA synthesis chip 100 is packaged into a flow cell, which provides an interface to a fluidic control system to supply liquid reagents for the synthesis chemistry cycles, and also provides connections to an electrical control system that operates DNA synthesis chip 100, and transfers monitoring data off DNA synthesis chip 100.

Figure 55:
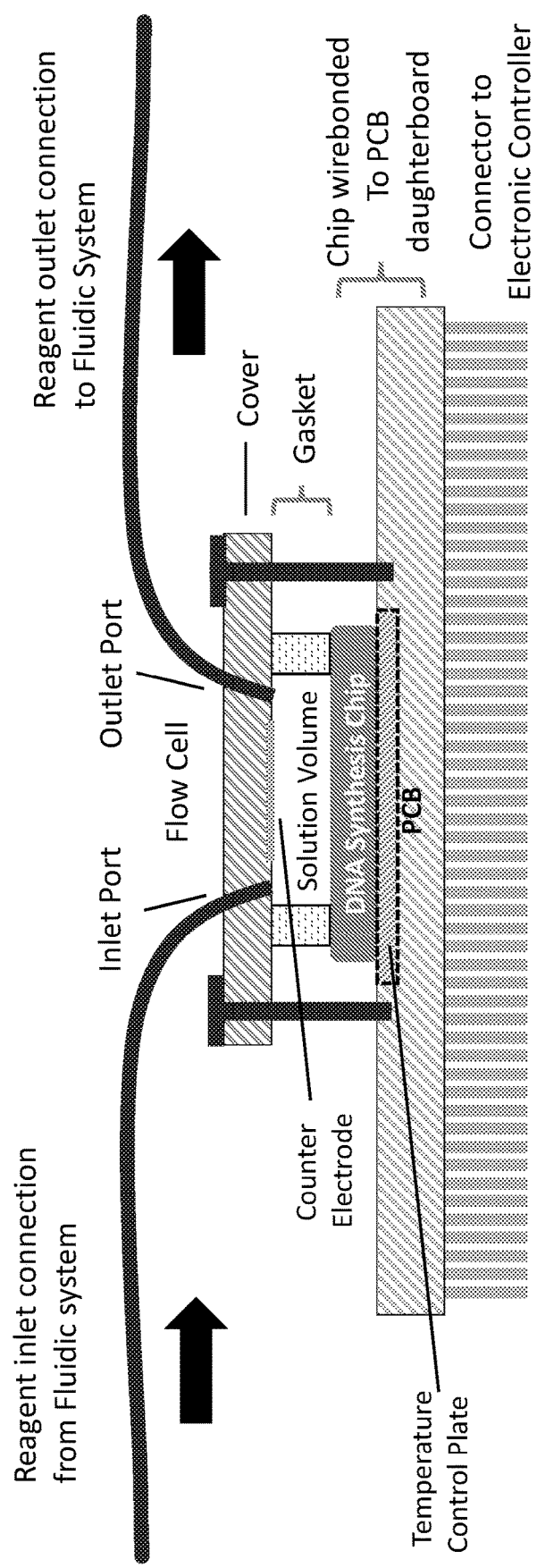
FIG. 55 illustrates an exemplary flow cell to support the operation of an exemplary DNA synthesis chip, in accordance with various exemplary embodiments.

Flow Cell: FIG. 55 illustrates an exemplary embodiment of a chip flow cell. As shown, the DNA synthesis chip is wirebonded to a daughterboard printed circuit board (PCB), with partial encapsulation to expose the top surface of the chip comprising the pixel array 110 portion of the chip to the environment. A flow cell is formed that comprises a cover pressed on a compliant gasket sitting on the chip surface, to provide a spacer and fluidic seal that defines the solution volume of the flow cell, and with the cover providing inlet and outlet ports that connect to the fluidic control system. All flow cell materials in contact with solution are compatible with the solvents that are used during acid generation, such as acetonitrile, and also compatible with the resulting highly acidic environment resulting from the acid generation phases of the chip. Examples of such compatible materials include perflouroelastomers (such as Kalrez brand offered by DuPont) for the gaskets, and polyetheretherketone (PEEK) or glass for the flowcells. In exemplary embodiments, inner surfaces of the flowcell that contact solution, such as the bottom of the cover, are coated with platinum or other suitable electrode metal to provide a large area electrode in contact with the solution, which can be used to set the solution potential, preferably with this electrode acting as the counter electrode of, and under the control of, a potentiostat that controls the solution potential. The synthesis chip exposed surface acts as the lower surface boundary of the flow cell solution volume. As illustrated, the chip wirebonded to the daughterboard PCB provides an electrical connector between the chip pinouts and the motherboard that supports the system electrical supporting hardware. In exemplary embodiments, the wirebonded chip PCB is mounted on a temperature control plate, such as the plate of a Peltier device, to set the temperature of the chip and flow cell and thereby maintain thermal control for the temperature-sensitive chemistry processes of DNA synthesis, and for the temperature sensitive aspects of the electrical and fluidic elements of the system.

Figure 56A:
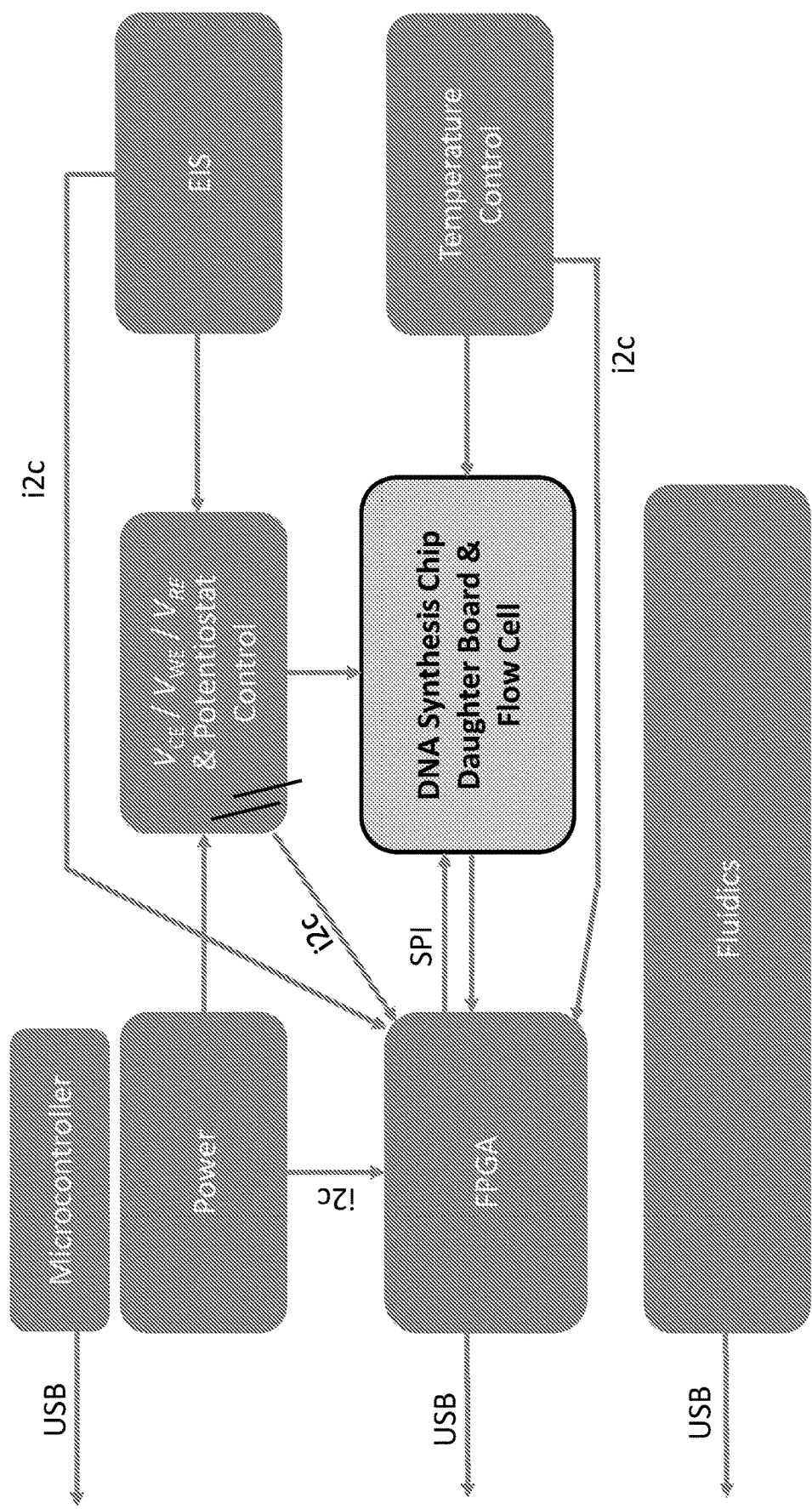
FIG. 56A illustrates an exemplary architecture of a system supporting a DNA synthesis chip, in accordance with various exemplary embodiments.
Figure 56B:
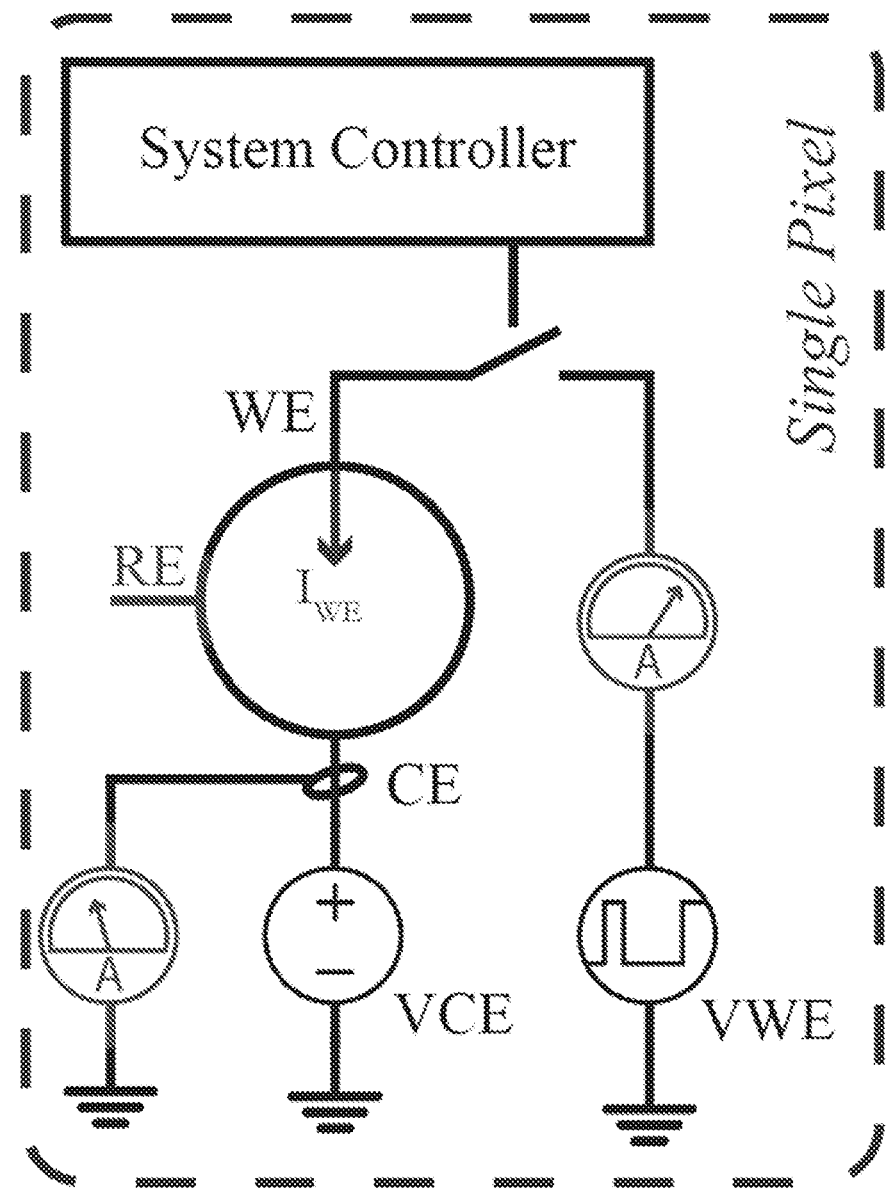
FIG. 56B illustrates a pixel-level view of functions of a system supporting a DNA synthesis chip, in accordance with various exemplary embodiments.

Supporting System Hardware: FIG. 56A illustrates a block diagram for exemplary embodiments of a supporting hardware system that provides electrical, fluidic, and thermal control of DNA synthesis chip 100 and associated flow cell. As indicated, an exemplary platform consists of a DNA synthesis chip 100 and flow cell controlled via a digital interface, which in exemplary embodiments is performed by a field programmable gate array (FPGA). However, any suitable digital interface may be utilized, as desired. The exemplary hardware also supports programmable working, counter, and reference electrode voltages ($V_{WE}$, $V_{CE}$, $V_{RE}$) relevant for the electronic acid generation and operation of a potentiostat, and provides the ability to monitor electrochemical impedance spectroscopy (EIS) off-chip. In some exemplary embodiments, a temperature of DNA synthesis chip 100 is controllable, as indicated. The housekeeping control of the voltage generation, EIS, and temperature controller in exemplary embodiments is accomplished via suitable hardware, for example a microcontroller over a serial peripheral control interface (such the SPI or i2c standards). In various exemplary embodiments, the microcontroller, FPGA, and fluidics communicate with a host computer via USB or other suitable protocol. In some embodiments, the microcontroller and FPGA have a bidirectional communication interface. The working electrode (WE) voltage can also be pulse width modulated (PWM), to further control the amount of acid generated during acid generation phases of operation. FIG. 56B illustrates a view of the relation of this supporting system to certain pixel-level operations on DNA synthesis chip 100. As indicated in FIG. 56B, the system controller supplies the voltages $V_{WE}$ and $V_{CE}$ that control the acid generation process over time (and corresponding modulation of these applied voltages over time), and monitors the external solution phase Reference Electrode for potentiostat control of the global solution potential of the flow cell, and also engages the measurement of the Working Electrode (anode, acid generation electrode) and Counter Electrode (cathode, acid removal) current or impedance to support synthesis monitoring functions.

In addition to the foregoing exemplary embodiments of DNA synthesis chip flow cell and system support hardware, many variations and details of implementation may be utilized without departing from the scope of the current disclosure.

Chip-Based DNA Synthesis Systems

Figure 57:
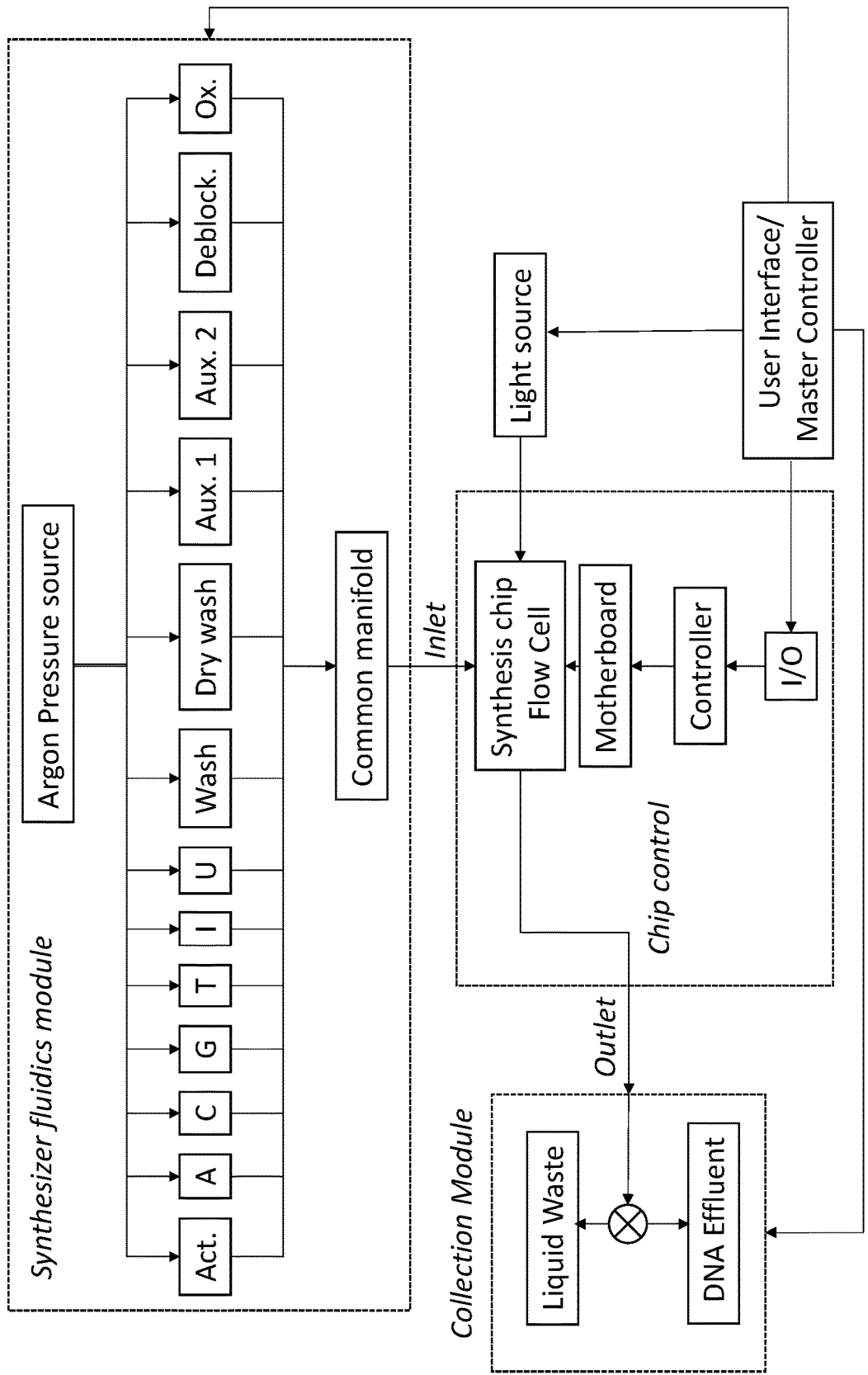
FIG. 57 illustrates a system diagram for a DNA synthesis instrument that operates a single chip, in accordance with various exemplary embodiments.

In exemplary embodiments, DNA synthesis chip 100 and supporting system hardware disclosed are embedded in complete systems that perform automated DNA synthesis. FIG. 57 illustrates one such exemplary embodiment, showing the schematic for a single-chip DNA synthesis system. As shown, reagent delivery is performed with a fluidics module consisting of reservoirs pressurized with an inert gas source, such as argon, and a manifold to regulate reagent delivery to DNA synthesis chip 100, including mixed reagents. In the example shown, reagent reservoirs are provided for (from left to right) the activation solution used for acid generation (Act.), 6 amidite bases (A, C, G, T, U, I (Inosine)), a wash solution, a dry wash, two auxiliary reagent reservoirs, and the deblock solution and Oxidizer (Ox.) solution such as are utilized in the phosphoramidite synthesis method. Moreover, exemplary embodiments may utilize a greater or lesser number of reagent reservoirs than shown. DNA synthesis chip 100, and corresponding flow cell, and chip control system such as that disclosed previously obtains control signals from a user interface or master controller shown, which also serves to synchronizes fluid delivery to the chip and the voltage applications and other chip functions for the synthesis cycles. In exemplary embodiments, this master controller is in common with the chip controller, or may be a separate controller, or may be an external computer. Some exemplary embodiments include a light source module as shown, to remove synthesis products from DNA synthesis chip 100 by photolysis of the linkers that tether the DNA synthesis products to the solid support surface. The exemplary system has a fluidic collection module for collecting waste reagents, or collecting effluent carrying the released DNA fragments post-synthesis, under the control of the controller.

Figure 58:
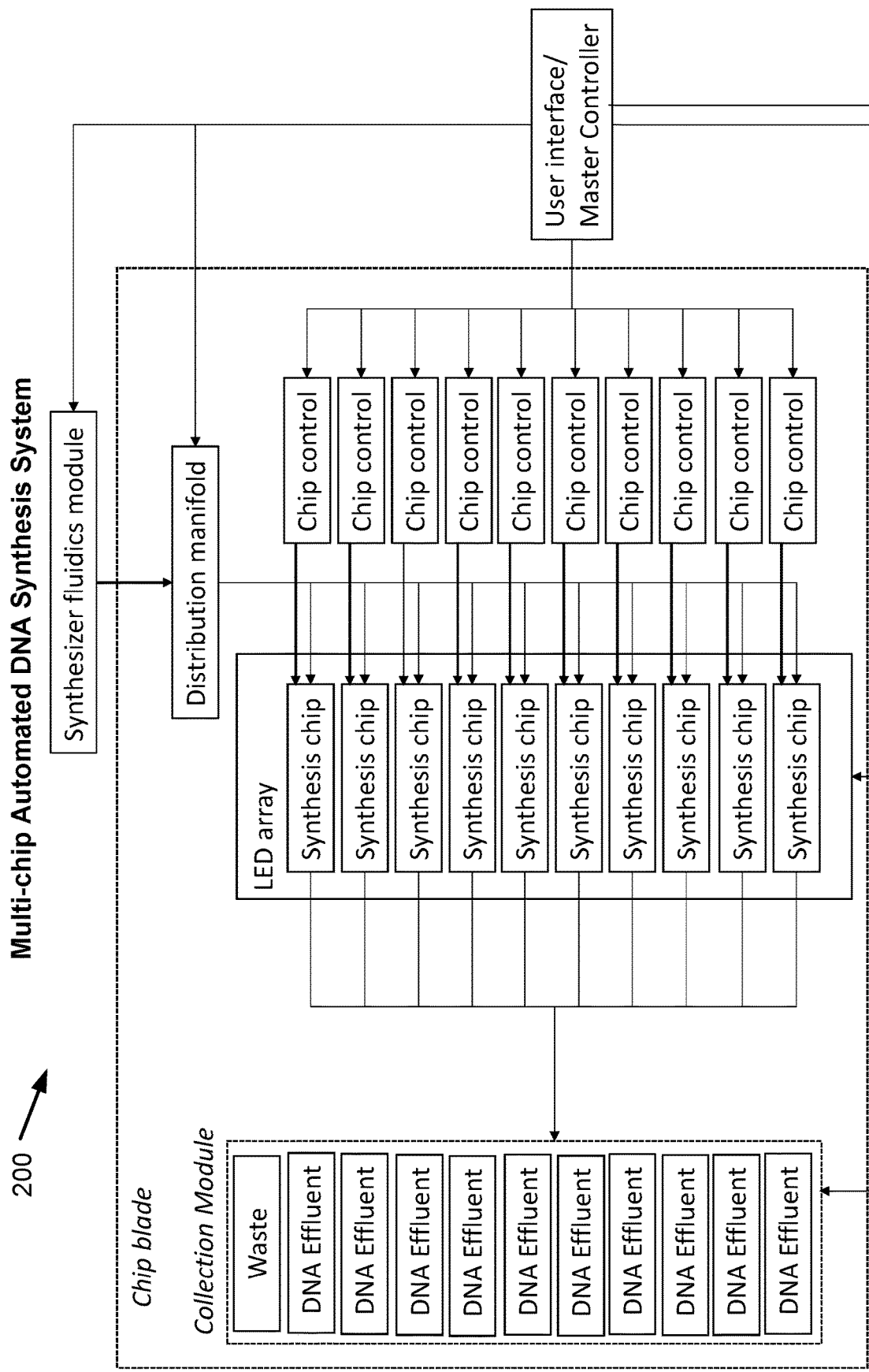
FIG. 58 illustrates a system diagram for a DNA synthesis "blade" instrument with a scalable architecture for running multiple chips, in accordance with various exemplary embodiments.

In various exemplary embodiments, an automated DNA synthesis system 200 may comprise multiple DNA synthesis chips 100 in a single device. FIG. 58 illustrates one such exemplary embodiment, showing the high-level schematic for a multi-chip DNA synthesis "blade server". Multiple DNA synthesis chips 100 may be supported by installing an additional distribution manifold in the fluid pathway between the fluidics module and the multitude of DNA synthesis chips 100. This enables addressability at the individual chip 100 level for circumstances requiring selective reagent deliveries or selective elution of products. Moreover, in exemplary embodiments that use light for product removal, an LED array can provide the selective illumination capability. As shown, each DNA synthesis chip 100 is configured with its own chip controller and independently addressable fluidics, which provides for independent operation of each chip 100. In other exemplary embodiments, a single common controller may provide control signals and voltages for all DNA synthesis chips 100. A fluidic collection module, under control of the controller, collects waste solution, and also selectively collects released DNA from each DNA synthesis chip 100 in respective collection pools. In other exemplary embodiments, a common fluid drive may supply identical liquid reagents to all chips 100. In such exemplary embodiments configured with common chip control and common fluidics, chips 100 may be configured to function as distributed pixel arrays, that conceptually may be organized into one large virtual pixel array in one large virtual flow cell. Moreover, in exemplary embodiments there may be a single collection pool for DNA effluent from all DNA synthesis chips 100. In exemplary embodiments, physical layout of the multiple DNA synthesis chips 100 in the blade may be as a linear array of chips, as laid out in the illustration, or may be in a rectangular array, or may by in a multi-plane stack of rectangular arrays. In exemplary embodiments, the multi-chip blade system 200 may have capacity for up to 10 chips, up to 100 chips, up to 1000 chips, up to 10,000 chips, or even more.

Figure 59:
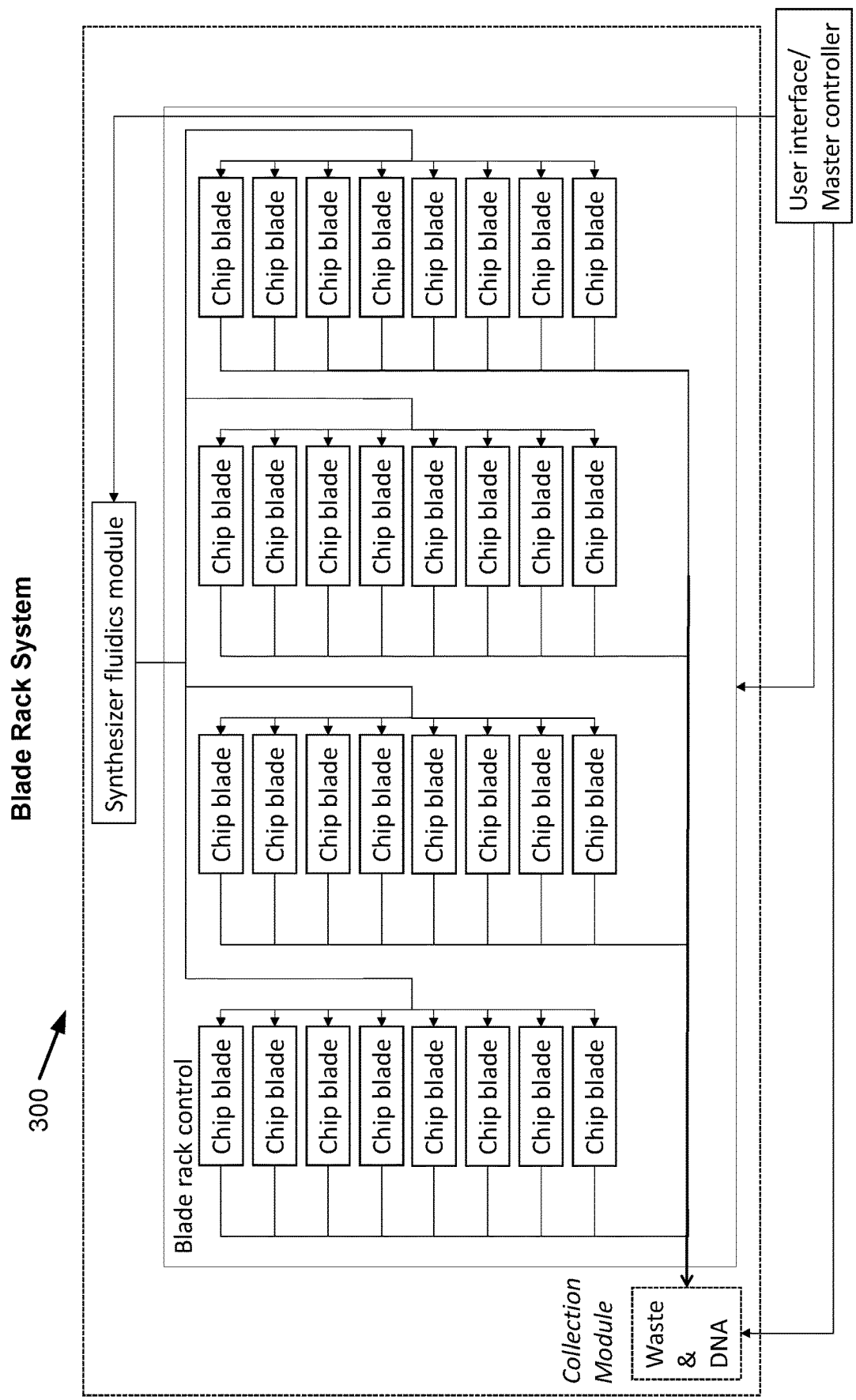
FIG. 59 illustrates a system diagram for a scalable blade server cluster architecture for running multiple synthesis blade server instruments in a rackable format, in accordance with various exemplary embodiments.

In various exemplary embodiments, the multi-chip blades can be configured into a rack mounted multi-blade system 300 for greater scalability and high-density DNA synthesis. FIG. 59 illustrates the schematic for such an exemplary embodiment. As shown, in an exemplary embodiment, one master fluidics module may drive an entire rack of chip blades. The illustration depicts a rack driving 32 blades. Such a rack mounted system, in exemplary embodiments, may support up to 8 blades, up to 16 blades, up to 32 blades, up to 64 blades, up to 128 blades, or even more in a single rack mounted system.

Figure 60:
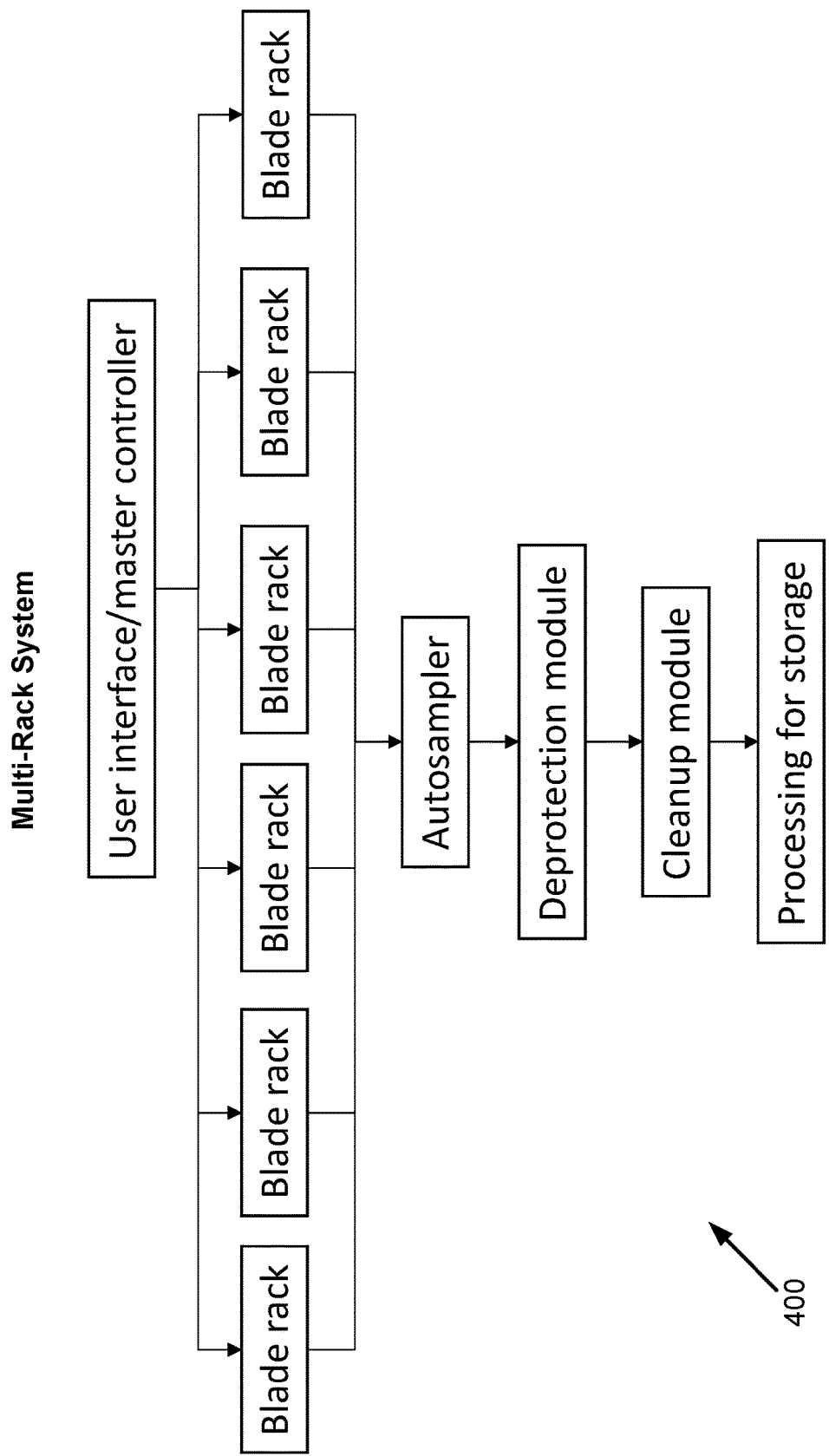
FIG. 60 illustrates a system diagram for a scalable multi-rack architecture for running multiple racks of blade DNA synthesis servers, in accordance with various exemplary embodiments.

In exemplary embodiments, even greater scalability and density may be provided by organizing rack-mounted blades into a multi-rack system. FIG. 60 illustrates the high-level organization of such a multi-rack system 400. In the exemplary embodiment shown, the organization is such that the synthesis products from multiple racks may be processed by collecting them in an autosampler prior to final bulk post processing. In exemplary embodiments, the autosampler serially collects the products into separate tubes, as output separately from the racks, or as output separately from the blades of the racks, or from the chips of the blades of the racks. The resulting collected product samples in the autosampler undergo individual bulk deprotection and cleanup steps, as well as processing to prepare the DNA for physical storage, such as in a freezer or refrigerator, or dried down or lyophilized for dry room temperature storage. In other exemplary embodiments, bulk deprotection and cleanup steps may be performed upstream of the autosampler, with only the preparation for storage performed post autosampler.

Storage of Digital Data in DNA

Figure 61:
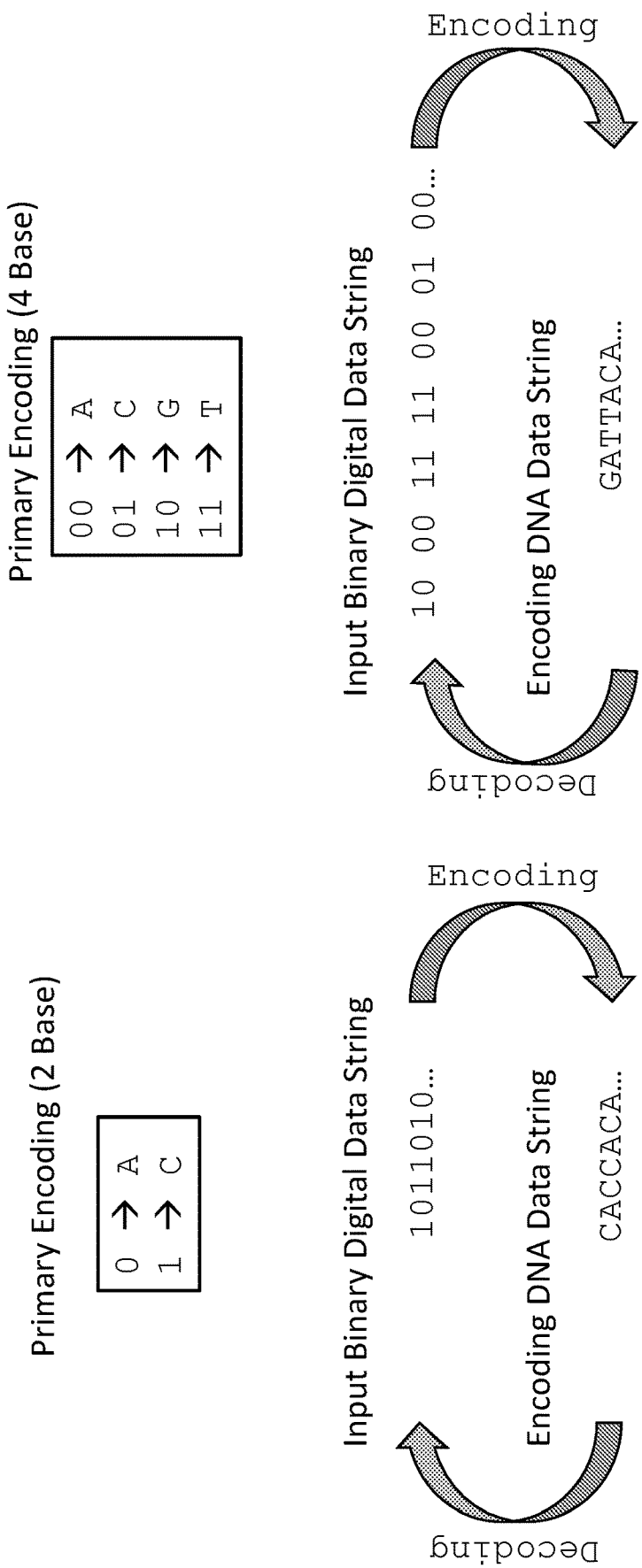
FIG. 61 illustrates encoding binary digital data into DNA sequence information, in accordance with various exemplary embodiments.

Exemplary DNA synthesis chips disclosed herein, such as DNA synthesis chip 100, can be used for systems and methods to store digital data in DNA in accordance with various exemplary embodiments. The use of DNA for data storage generally utilizes an encoding and decoding scheme that can be used to convert a digital data string into a logical DNA sequence string or multiple strings (encoding), and to convert such DNA sequences back to a digital data string (decoding). For the sake of illustration, two simple encoding schemes are shown in FIG. 61. In the first scheme at left, for encoding binary digital data, any two of the DNA bases, such as A and C, can simply be used to represent the binary 0 and 1 as the primary encoding, thus using 2 bases. In that case, in such a 1-for-1 code, for example, the 7 bit binary string 1011010 encodes into the 7 base DNA sequence CACCACA, and vice versa for decoding. However, because a DNA sequence provides 4 logical symbols, instead of just two for binary strings, it is possible to let each base represent 2 bits, as shown in the primary coding scheme at right in FIG. 61. This results in more compact encoding, for example using the encoding there, the 14-bit binary string 10 00 11 11 00 01 00 . . . encodes into 7 letter DNA sequence GATTACA.

Figure 62:
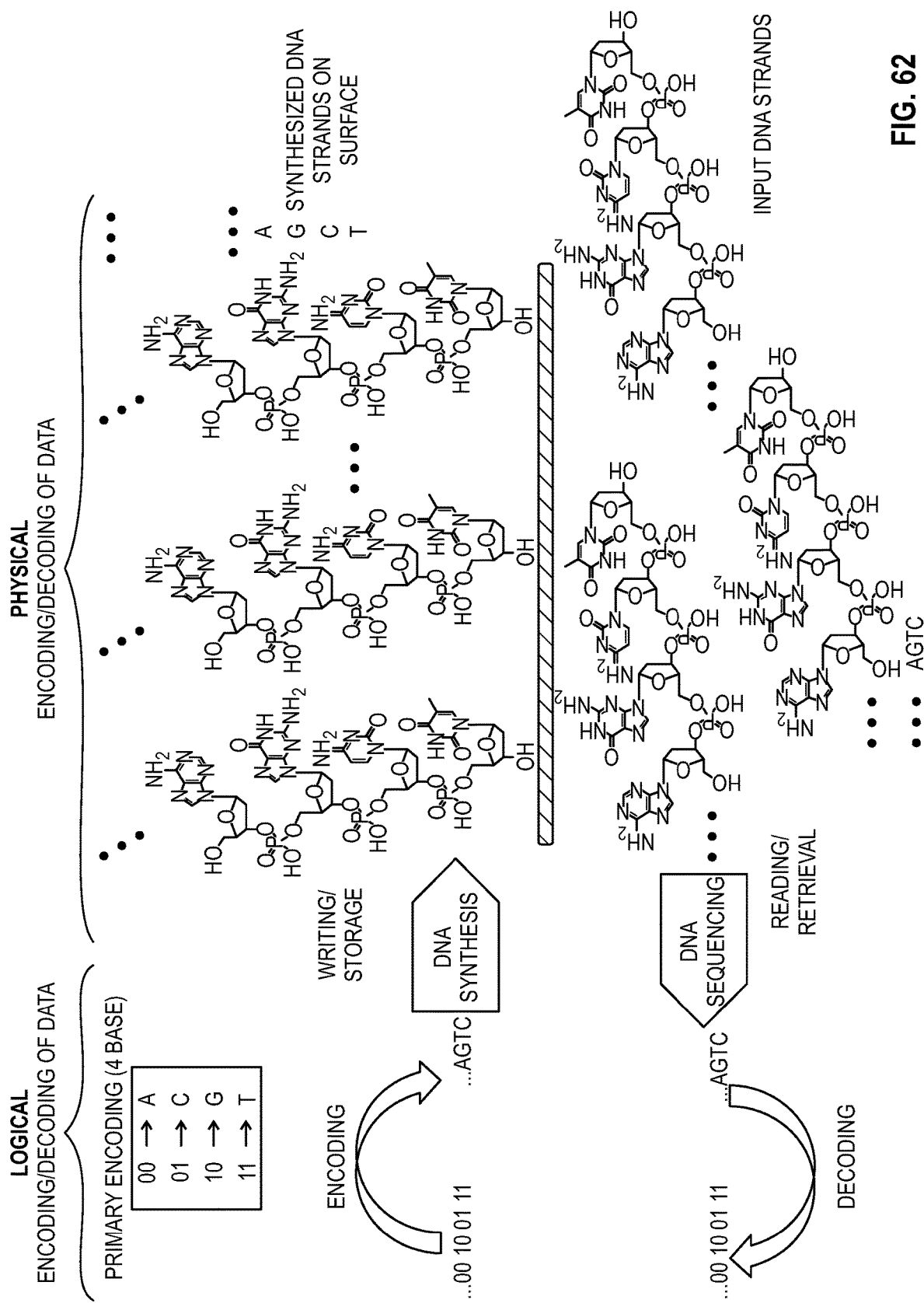
FIG. 62 illustrates logical and physical aspects of using DNA to store digital data, in accordance with various exemplary embodiments.

Once a suitable encoding scheme is provided to define the logical translation process, the actual storage and retrieval of digital data using DNA involves the physical synthesis of DNA sequences for the physical encoding, or writing, and the sequencing of DNA for the physical retrieval, or reading. This is illustrated in FIG. 62, which shows that writing or storing data into DNA starts with the logical encoding of data into DNA sequence, followed by the physical synthesis of the DNA strands, while data retrieval or reading starts with the physical process of sequencing DNA, combined with the logical decoding of sequence data.

Figure 63A:
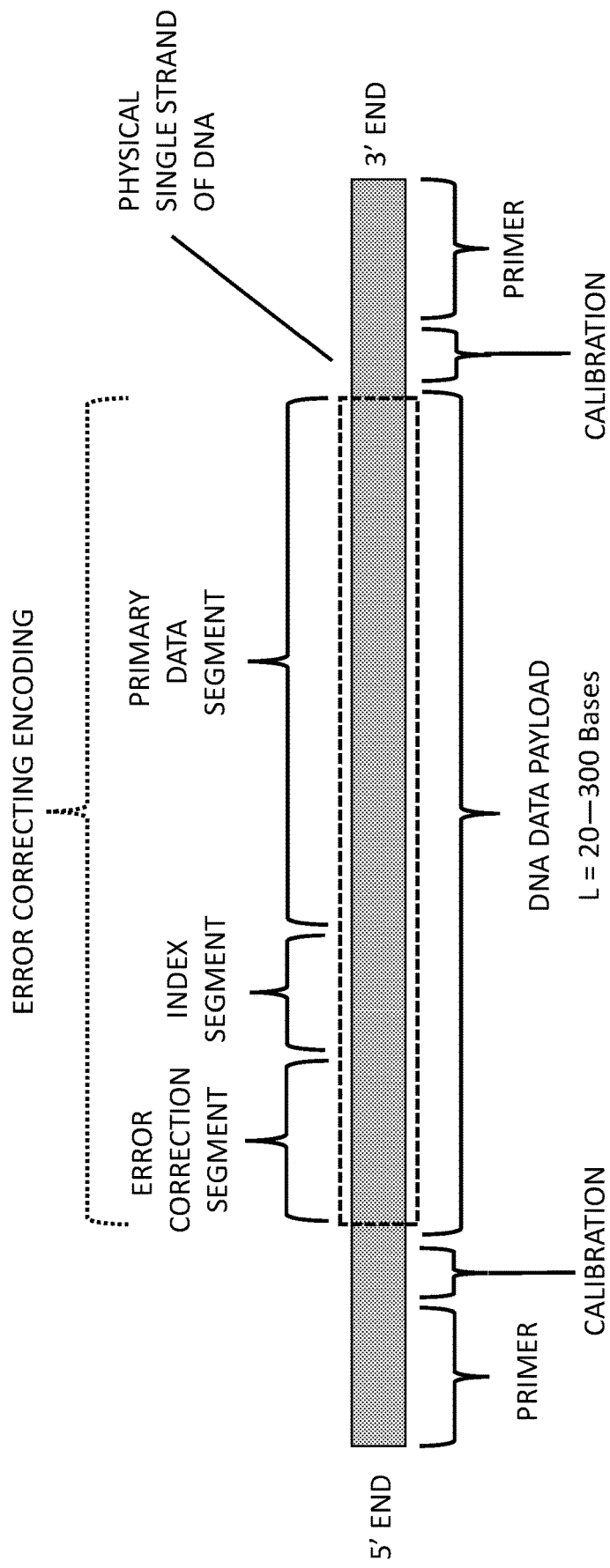
FIG. 63A illustrates organization of physical DNA strands for digital data storage and retrieval, in accordance with various exemplary embodiments.

In various exemplary embodiments implementing storage of digital information in DNA, the physical DNA strands utilized may benefit from additional elements and specifications that make the relevant processes more accurate, efficient, flexible, convenient, robust, and/or economical. FIG. 63A illustrates an exemplary embodiment of a logical structure of a DNA strand to be used for DNA data storage. The single physical strand is indicated as having a 5' end and a 3' end. In exemplary embodiments, the ends of the strand are devoted to primer sites, which may be used, for example, for PCR amplification and selection of such strands from a pool, or to replicate stored data. Such primers may also be used as priming sites for the sequencing (read) of the DNA, in certain exemplary embodiments wherein a sequencing method utilizes a priming site. Moving inward on the strand from such sites, various exemplary embodiments may comprise additional sequence segments, indicated in FIG. 63A as calibration segments. One such use for such segments, in exemplary embodiments, is for calibration of a sequencing method that reads the DNA data, for example in cases where known sequencing at the start and end of the read may improve reading accuracy and assist in correcting errors that arise in the reading process. In other exemplary embodiments, such added physical sequence elements may be useful depending on the diverse details of the synthesis and sequencing and storage processes, such as, for example, enzymatic restriction or digestion sites that can be used to remove primers. In various exemplary embodiments, as shown, these regions flank the data payload, which contains all the sequence specific to the data stored in the DNA. Moreover, in exemplary embodiments, as indicated, this payload contains segments that hold error correction data, index data, and primary data. In exemplary embodiments, there is a primary data segment, which represents a segment of the input digital data string, such as for example, an encoding sequence as in FIG. 61. In exemplary embodiments, the primary data segment utilizes an index, which indicates the location of the primary data segment within the entire input digital data string, and this index is also part of the data payload in the DNA strand. In exemplary embodiments, the combined index and data segment are subjected to an error correcting code (ECC), which has additional overhead sequence that may be stored in another data segment. This error correcting code can be used to correct for the errors in retrieved DNA sequences, for example errors that may result from errors in the physical synthesis of the desired sequence strand during writing, errors that may result from handling and storage of DNA, such as from related processes such as making PCR copies, or DNA damage (such as deamination of C, which results in C→U/T errors), and from errors from the physical sequencing process used to read retrieved sequence strands. In exemplary embodiments, as indicated by the dashed upper bracket of FIG. 63A, the extra sequence utilized for error correction may be distributed throughout the data payload itself (or even across data payloads of multiple DNA strands), rather than simply being confinable to a segment of the payload as extra informational bases, and the ECC payload may not even include any of the original string explicitly, such as in the use of Hamming distance codes. In other exemplary embodiments, the error correction sequence "overhead" may reside in a well-defined segment of the payload, such as in the use of one or more "parity bits" or "parity bases", or in the use of repetition codes, where the desired string is simply repeated one or more times.

In various exemplary embodiments, the length of a data payload is in the range of 1-400 bases, and preferably in the range of 1-200 bases. The length of the primer segments are preferably in the range of 10-30 bases, and the length of the calibration sequences are preferably in the range of 4-16 bases. However, any suitable lengths may be utilized, as desired. In addition, in exemplary embodiments, in the physical DNA storage material, it is preferable to have multiple copies of the same physical strand, to overcome potential losses from physical handling and processing of the DNA during synthesis, release, storage, access, and/or sequencing, and to overcome limitations of random sampling when sequencing the fragments for retrieval. For example, in various exemplary embodiments, there are expected to be at least 10 copies, at least 100 copies, at least 1000 copies, at least 10,000 copies, at least 100,000 copies, or even more copies of each such logical DNA data-carrying fragment. From the exemplary embodiments directed to organization of DNA disclosed herein, it will be appreciated that many variations and details exist to achieve these same or similar ends, and all such variations and details are considered to be within the scope of the present disclosure. Moreover, in certain exemplary embodiments wherein a digital data stream is rendered into a set of such storage sequences, such sequences will have similar or identical length, and similar or identical lengths of the sub features such as primers, calibration sequences, and data payload and segments thereof.

Figure 63B:
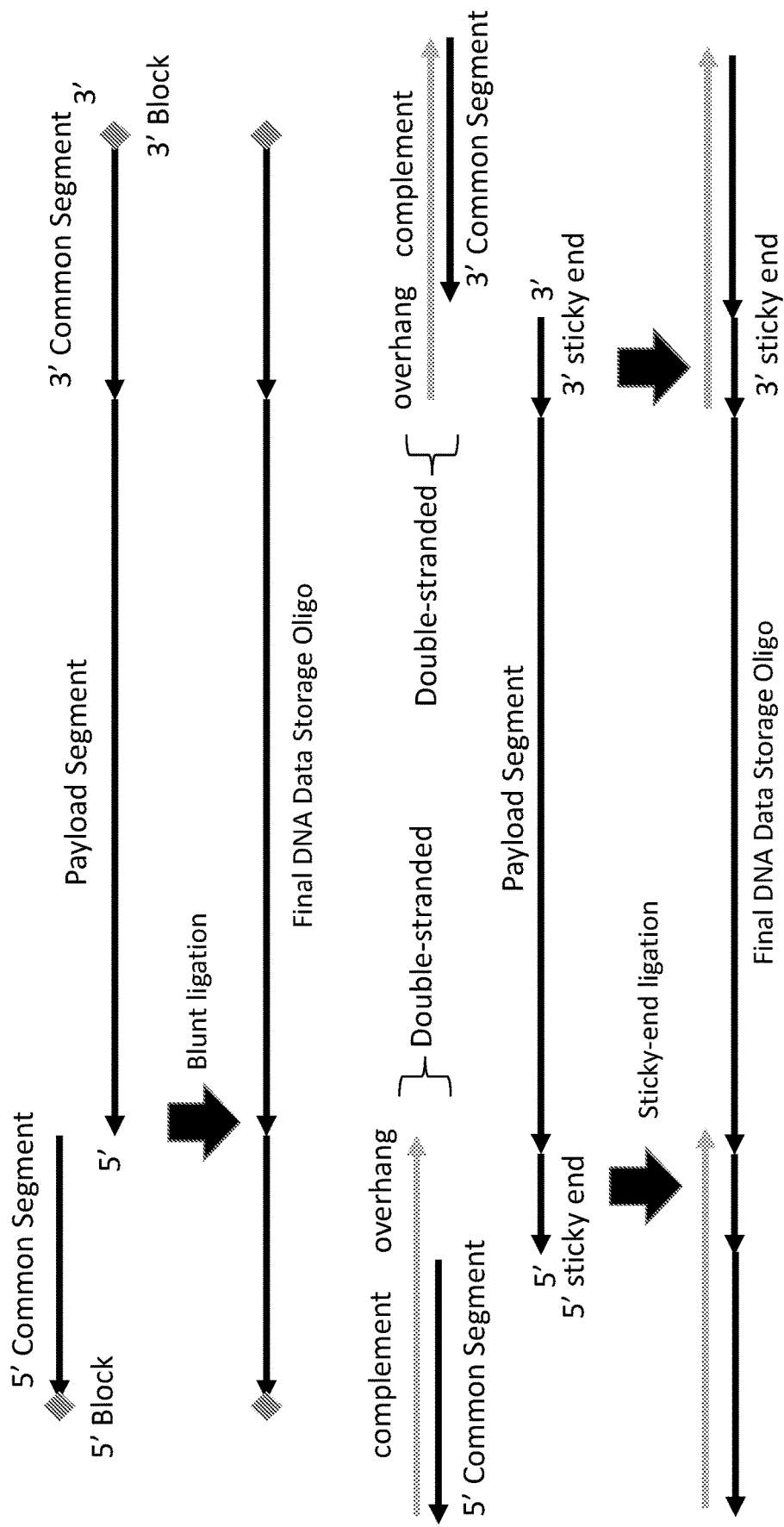
FIG. 63B illustrates ligation strategies for adding the common sequence elements to the ends of DNA data storage payload segments, for efficient synthesis of DNA data storage strands, in accordance with various exemplary embodiments.

Efficient Construction of Common Sequence Elements in DNA Data Storage Oligos: In various exemplary embodiments, left and right constant (or common) elements of the DNA strand architecture as illustrated in FIG. 63A—such as, in exemplary embodiments, the left and right primer and calibration segments—can be added by efficient "pre-assembled" approaches rather than by direct base by base synthesis. For example, in various exemplary embodiments wherein synthesis starts at the 3' end and proceeds to the 5' end, the 3' constant DNA segment may be provided as part of the surface functionalization. Moreover, in some exemplary embodiments the 5' constant segment may be provided as a complete strand segment coupled to the deprotected group of the growing strand, via use of the same coupling chemistry as for the individual base additions. Additionally, in exemplary embodiments, either of the constant termini segments may be attached by ligation chemistry post synthesis, for example as indicated in FIG. 63B. In exemplary embodiments, this may be enzymatic ligation. In one such exemplary embodiment, shown in the upper portion of FIG. 63B, the 3' termini provided on the synthesized strand is blocked or not phosphorylated, such that it cannot undergo standard enzymatic DNA ligation, and the 5' constant segment can then be added by single stranded blunt end ligation post synthesis, such strands having their 3' end ligatable, but their 5' end blocked or not phosphorylated or otherwise not ligatable, so that only the desired ligation can occur, of the common segment to the strand 5' end, and no unwanted ligations involving the common segments or payload segments can occur.

In other exemplary embodiments, for example as shown in FIG. 63B (lower portion), the ends to be ligated (3', 5', or both) can be provided with a short sequence segment to support the well-known method of "sticky-end" enzymatic ligation of DNA, and for this pre-fabricated terminal segments may be provided in suitable double stranded form with complementary sticky-end overhang, to support such ligation. In an exemplary embodiment, the short sequence segment for this overhang is a single terminal A or T, and the well-known T-A ligation method can be used to add the constant segment, provided in an at least partially double stranded form, with the appropriate complementary overhang (T-overhand for A at terminus, A-overhand for T at terminus). In other such exemplary embodiments, the overhang may be longer, for example 2-bases, 3-bases, 4-bases, 5-bases, 6-bases, or even longer. Moreover, in exemplary embodiments where both constant ends are ligated on, such overhangs may be sequence specific for the 5' and 3' ends of the synthesized strand, such that the desired 3' and 5' constant segments more efficiently and selectively ligate to the respective desired ends. For example, the synthesized segment may be configured with "AA-3'" as its 3' end, and "5'-CC" as its 5' end, the sticky end overhang being "5'-TT" for the 3' end segment, and "GG-3'" for the 5' end segment. In still other exemplary embodiments, either of these common end segments may be added by direct synthesis, but by using just the series of base additions required for the sequence (i.e., just n coupling cycles of the desired bases in series, to achieve the same n bases sequence at all pixels, rather than the 4n coupling cycles that would normally be used to synthesize arbitrary independent n-mers at the pixels). In exemplary embodiments, these common cycles may further be performed by using global chemical deprotection by flowing in the deprotecting acid globally, rather than by using electrochemical voltage-drive acid (or H+) generation.

Molecular Barcodes: In various exemplary embodiments, calibration segments may include a segment of length k bases that is a randomly synthesized k-mer sequence at the single molecule physical level, serving as a "molecular barcode." In exemplary methods for retrieving data, this molecular barcode serves the purpose of verifying that there were distinct molecular source molecules for what otherwise (aside from this k-mer) are identical or highly similar sequence reads, post read-out, in contrast to being reads of replicates of the same source molecule that arise from PCR copies derived from the same initial template molecule. Accordingly, in exemplary embodiments, such a molecular barcode random k-mer segment is generated by performing k rounds of base coupling with a pool of mixed bases of amidites (or, so-called N pool, for all 4 bases mixed, preferably at equal concentrations, or any other degenerate mixture of multiple amidite bases, preferably at equal concentrations, or at unequal concentrations). Via this exemplary approach, even within a single pixel site, a multiplicity of strand molecules synthesized there, which are typically intended to have identical sequence subject only to deviations from synthesis errors, are instead in this case intended to receive different random k-mers that distinguish the individual molecules, in the fashion in which they randomly receive one of the $4^k$ possible random k-mers (or otherwise sequences randomly drawn from the pools provided). Thus, if a duplicated sequence is read out from a pixel's products, after being subject to a PCR amplification process, it can be flagged as being a duplicated read and discarded, which capability is essential for some forms of post-read error correction, and in exemplary embodiments this would be an incorrect judgement only $(¼^k)^{th}$ of the time, and therefore only sacrifices a small fraction of the data. For example, if k=3 random bases are used as a molecular barcode, only 1/64 ($¼^3$) of the read out sequences would be incorrectly discarded.

Figure 64:
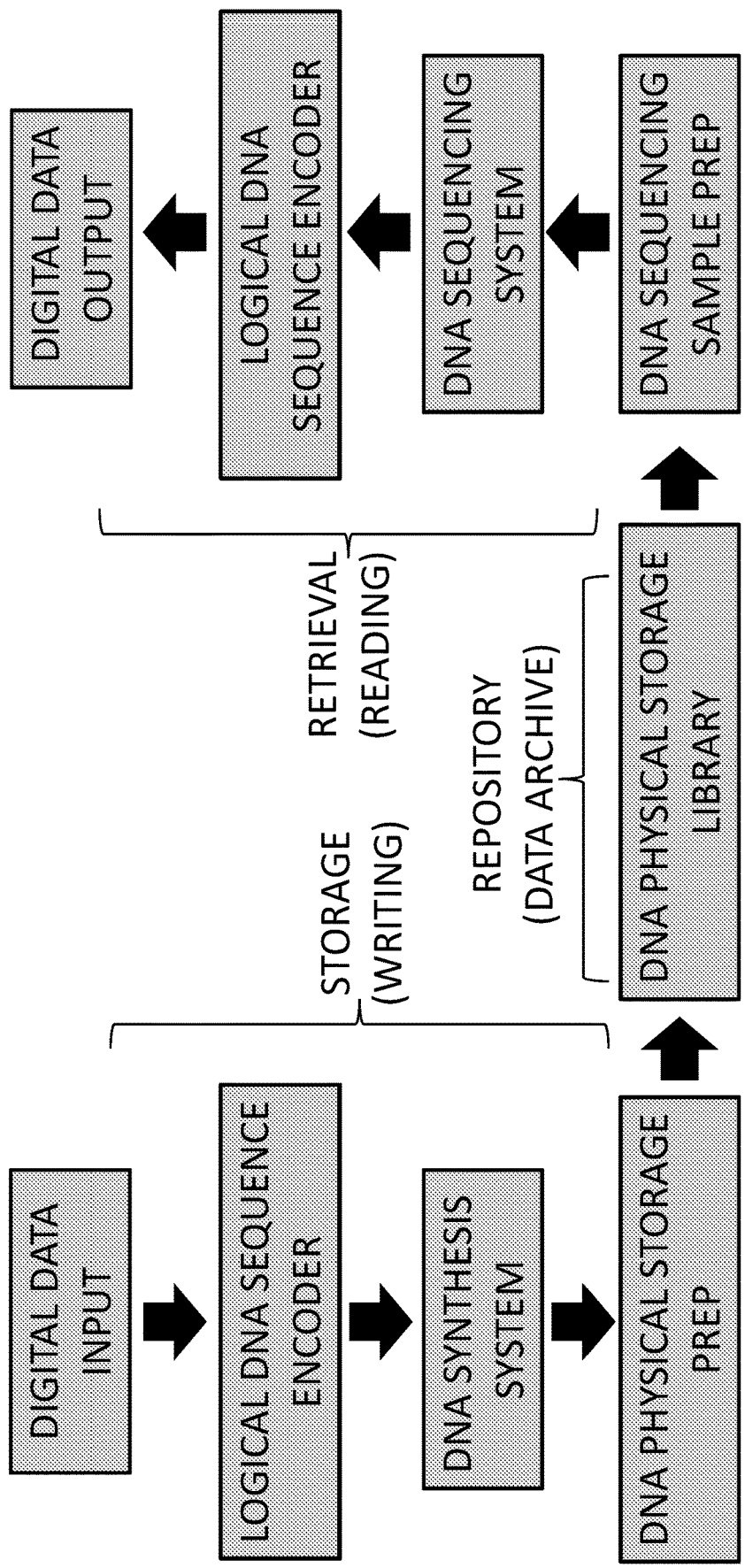
FIG. 64 illustrates an exemplary total system for DNA digital data storage, in accordance with various exemplary embodiments.

Turning now to FIG. 64, according to various exemplary embodiments a total DNA data storage system 500 supporting both storage and retrieval of digital data is illustrated. As shown, the system comprises components for providing input digital data, which is then transformed into a set of desired logical DNA sequences by the encoding system. These desired sequences are provided to a DNA synthesis system, which produces the resulting physical DNA sequences. These sequences typically undergo various preparations for physical storage, such as organization of fragment pools into tubes, containers, or other physically discrete separations; addition of stabilizing reagents; drying down; and so forth. Collectively, this series of steps constitutes a storage process or "writing" of data into DNA. The resulting physical DNA is then passed to the physical storage library, which may include a system for managing tubes, managing sub-sampling from tubes, as well as control of environmental parameters (such as temperature and light levels). This system constitutes the DNA data repository or "data archive." When it is desired to recover the digital data in a standard format, suitable DNA samples from the repository are provide to a sample prep system, which performs processes associated with preparing the DNA for sequencing, such as reconstituting in solution, possible PCR amplification of the data segments of interest, and the like. This material is passed on to the DNA sequencing system, which sequences the DNA fragments, and provides output as a set of logical DNA sequences (and affiliated information, such as quality scores or measurement confidences on the read bases). These logical sequences are then converted by the decoder system from a DNA sequence back to the desired digital data format. Collectively, this series of steps constitutes the data retrieval process or reading of digital data from DNA.

In exemplary embodiments, the total DNA storage system 500 of FIG. 64, or in particular the data storage subsystem thereof, comprises a DNA synthesis chip system in the DNA synthesis system indicated. In exemplary embodiments, the system so comprised may be a single chip synthesis system, such as in FIG. 57, or a multi-chip system 200 such as in FIG. 58, or a blade rack system 300 such as in FIG. 59, or multi-rack system 400 such as in FIG. 60. In various exemplary embodiments, in exemplary methods of use of such a chip-based system, the respective entire target sequences such as in FIG. 63A may be synthesized on individual pixels on the synthesis chip, or may be replicated across multiple pixels. In other exemplary embodiments, any or all portions of the sequence of FIG. 63A that are common and not varying between sequences, such as in exemplary embodiments the 5' or 3' end primers and calibration sequences, may be added by bulk ligation methods post on-chip synthesis on the pool of synthesized fragments, with just the independent data payload segment synthesized on respective independent pixels on chip, so as to reduce the number of cycles of on-chip synthesis utilized. In other exemplary embodiments, the starting material for on chip synthesis may be the common sequence elements of one end, such as the 3' end calibration and primer segment (for synthesis that proceeds in the 3' to 5' direction, such as using common protected phosphoramidite reagents), so as to reduce the number of cycles of on-chip synthesis utilized.

Figure 65:
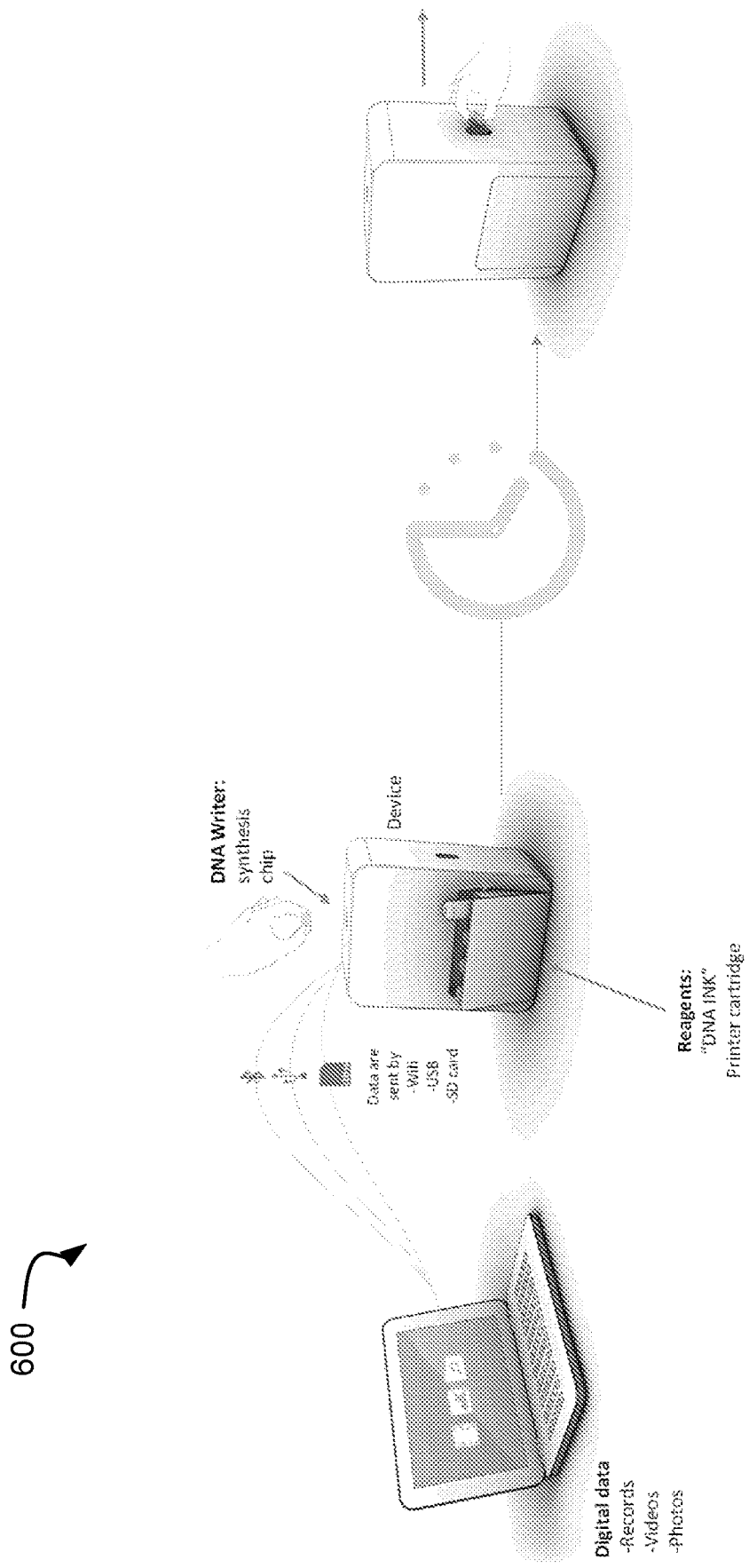
FIG. 65 illustrates an exemplary system and method for the storage of digital data into DNA for personal use, in accordance with various exemplary embodiments.
Figure 66:
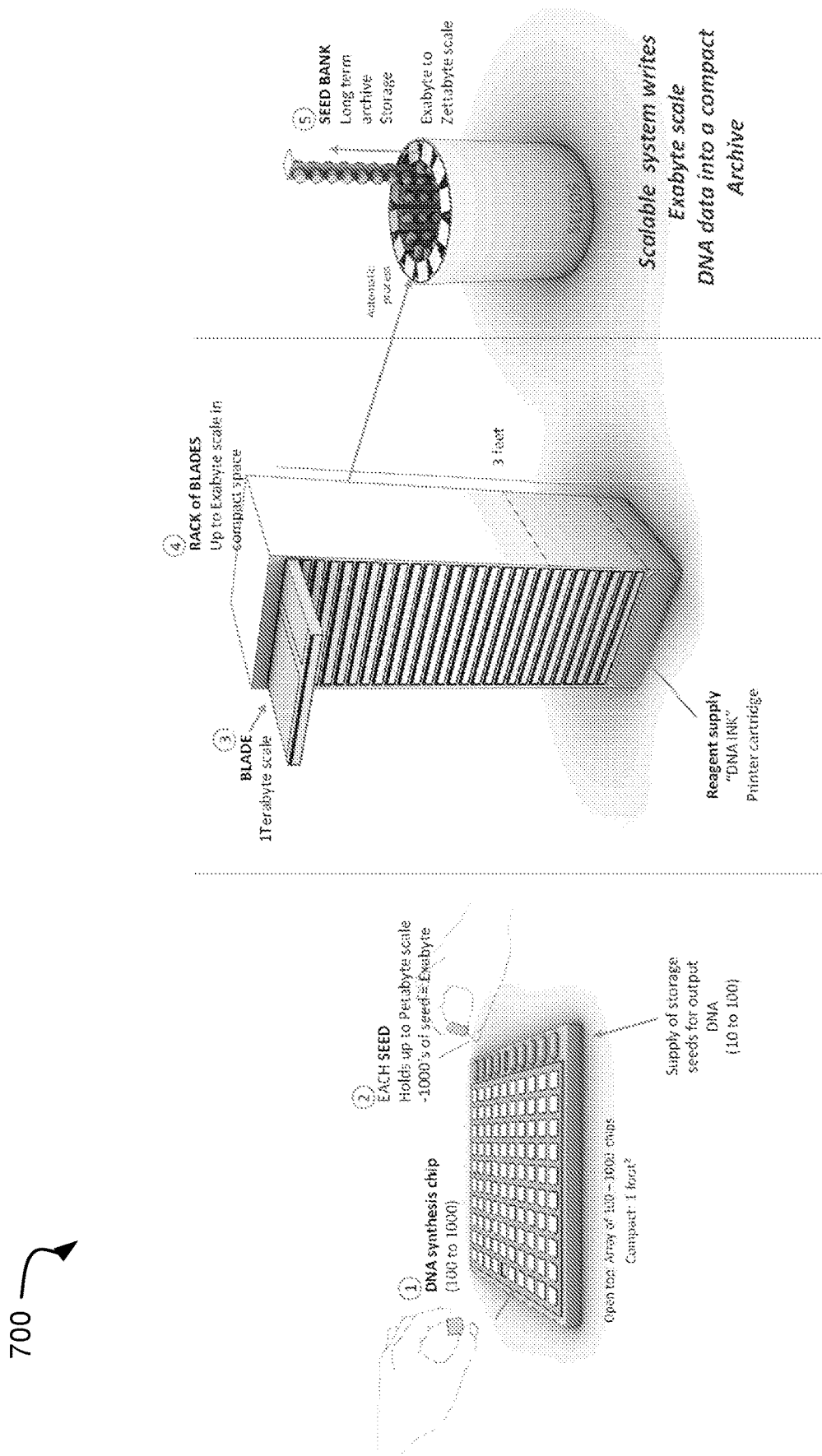
FIG. 66 illustrates a system and method for the high-capacity storage of digital data into DNA, using a scalable blade server system, and a "seed bank" repository for archival storage, in accordance with various exemplary embodiments.

With reference now to FIG. 65, in accordance with various exemplary embodiments is illustrated a Personal DNA Data Storage System 600, for example intended for use in the home, office, or school. As indicated, a source of initial digital data input may be a personal computer (such as via a wi-fi or Bluetooth connection), a memory stick device, or the like. The integrated instrument shown includes DNA encoding software, as well as a single-chip DNA synthesis chip system, and a DNA physical storage prep system. In operation, system 600 is provided with a CMOS synthesis chip as shown, and loaded with liquid reagent supplies as shown. In operation, the digital data is encoded using internal computing hardware, algorithms, and software (including the use of an error correcting code for the encoding), the target sequences are synthesized on chip, such as through any of the cyclical electrochemistry processes disclosed herein (and possibly producing errors from synthesis). Using internal fluidics, the finished strands are released from the synthesis chip, collected, and deposited into a capsule (in respective exemplary embodiments encapsulated in a dry or liquid form), with the resulting capsule, or storage "seed pod" returned to the user. As indicated, the time utilized for synthesis and post-processing preparation is, in exemplary embodiments, 4 hours or less, to support the personal use case. In exemplary embodiments, the time utilized depends at least in part on the base length of the DNA fragments being synthesized, such as 50-mers, or 100-mers, or 200-mers, and may be less than 6 minutes per base, less than 3 minutes per base, less than 1 minute per base, less than 30 seconds per base, or less than 10 seconds per base depending on the embodiment and associated configuration. In exemplary embodiments, system 600 can store data on the megabyte, gigabyte, terabyte, or multi-terabyte scale.

In accordance with various exemplary embodiments, a Server DNA Data Storage System 700, intended for scalable, high-capacity storage for example for data storage clouds, or large-scale data archival storage, is illustrated in FIG. 65. As illustrated, a multi-chip server blade is populated with DNA synthesis chips, and a supply of DNA data storage "seed pods" that hold the DNA material for storage. The blades populate a rack system (and, in various exemplary embodiments, a multi-rack system). A common reagent supply may supply the entire rack or racks, or multiple reagent supplies may be utilized, as desired. In certain exemplary embodiments, this may include reagents utilized to refurbish chips and recycle them for re-use to synthesis new oligos. After chip synthesis is completed, the DNA material is post-processed and transferred to storage seed pods, and through an automated process transferred to a storage repository "seed bank" for high density archival storage. In various exemplary embodiments, system 700 can be configured and/or scaled to store data on the petabyte, exabyte, zettabyte, and/or yottabyte scale, as desired.

In light of the foregoing exemplary DNA data storage systems, it will be appreciated that many variations and details of implementation may be utilized, and all such variations and details are considered to be within the scope of the present disclosure.

DNA Data Storage Methods

Exemplary embodiments provide methods for using DNA synthesis chip systems to store digital information in DNA strands. Such exemplary methods enable highly efficient and rapid approaches for decomposing a given digital data string into short DNA strands, and rapidly and efficiently synthesizing such strands on a chip-based system, and benefiting from the unique attributes of chip-based synthesis.

Figure 67:
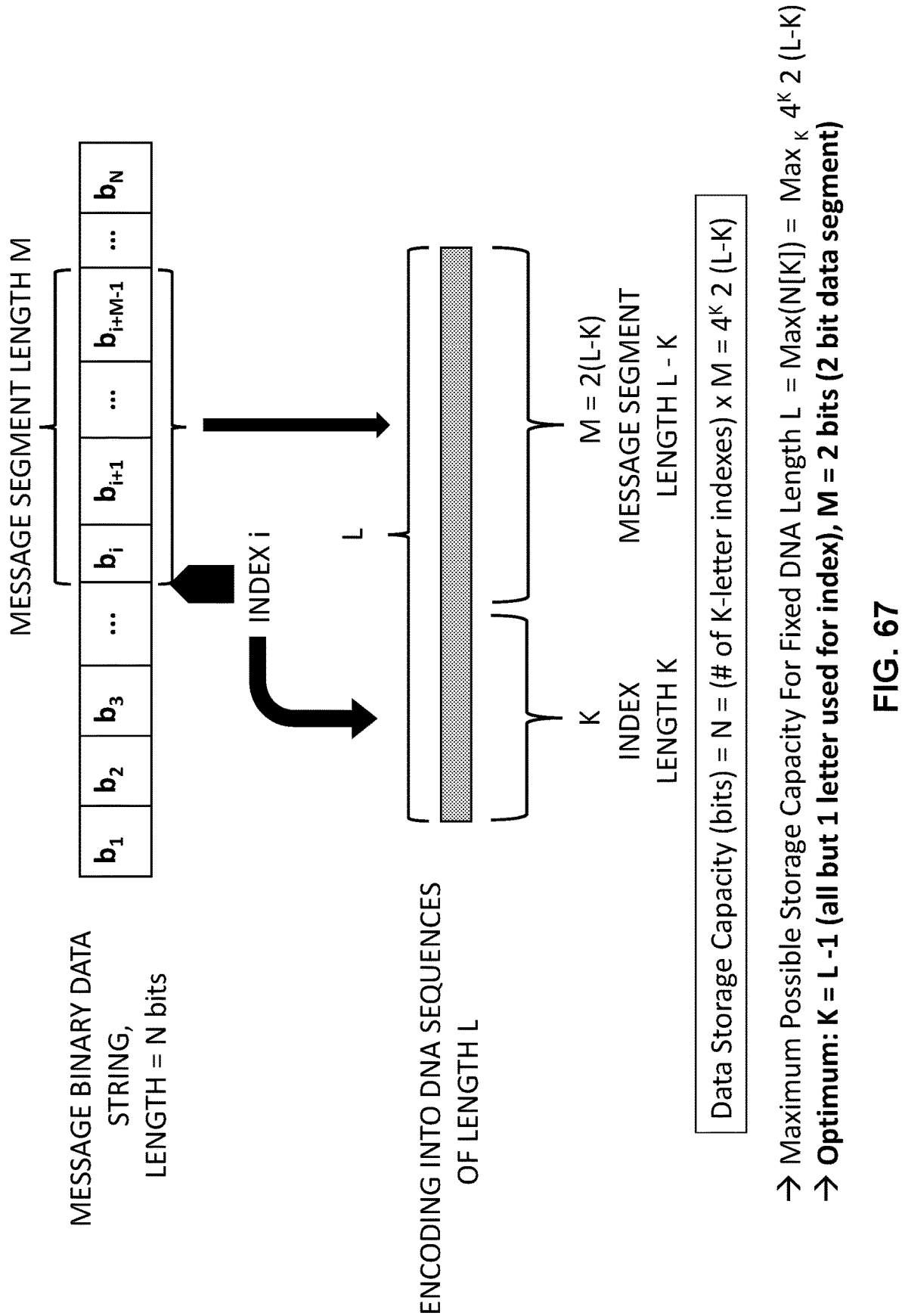
FIG. 67 illustrates storage of binary data strings in DNA by decomposition into indexed data segments, and relation between the size of the binary string that can be stored and the data architecture of the DNA segments, in accordance with various exemplary embodiments.

In an exemplary embodiment, as illustrated in FIG. 67, a digital bit string of length N is to be encoded into DNA. N may be large, for example the total number of bits in the string being on the scale of a megabit, gigabit, terabit, petabit, exabit, zettabit, or even more. In this exemplary embodiment, it is provided that the DNA data payload segments will all be of the same length in bases, L. The long data string is broken into many segments of equal size M bits (with padding of the final partial segment if desired). The index for each segment, which is the index, i, of the bit $b_i$ at start of the corresponding data segment in the string, is encoded using K bases of the DNA payload, and the bit date segment of length M is encoded in the remaining L−K bases for the data segment. For example, in the case of encoding 2 bits per base as in the example code in FIG. 61 (note: other preferred encoding schemes may average less than 2 bits per base in the message segment, and consideration here apply similarly, if "2" is replaced by a lower density, c<2), the relation between number M of bits in the segment and number L−K of bases, will M=2(L−K) (i.e., 2 bits per base). The total number of distinct indexes that can be encoded in the K-base index segment using all 4 symbols {A,C,G,T} is $4^K$. Therefore, the maximum total size of the bit string, N, that can be stored into DNA payloads this way is the number of indexed payloads, $4^K$, times the size of each segment in a payload, M=2(L−K), or N=$4^K$ 2 (L−K).

Using this general formula for the storage capacity of this exemplary method, two important optimal storage formats within this framework can be identified:

Maximal Data Storage Capacity Mode: In this scenario, the goal is to maximize the storage capacity of the method, N bits, as a function of the choice of index size, K letters, for a given length of DNA sequence, L. The reduces to the problem of solving for $N_{MAX}=Max_K 4^K 2(L-K)$.

Figure 68:
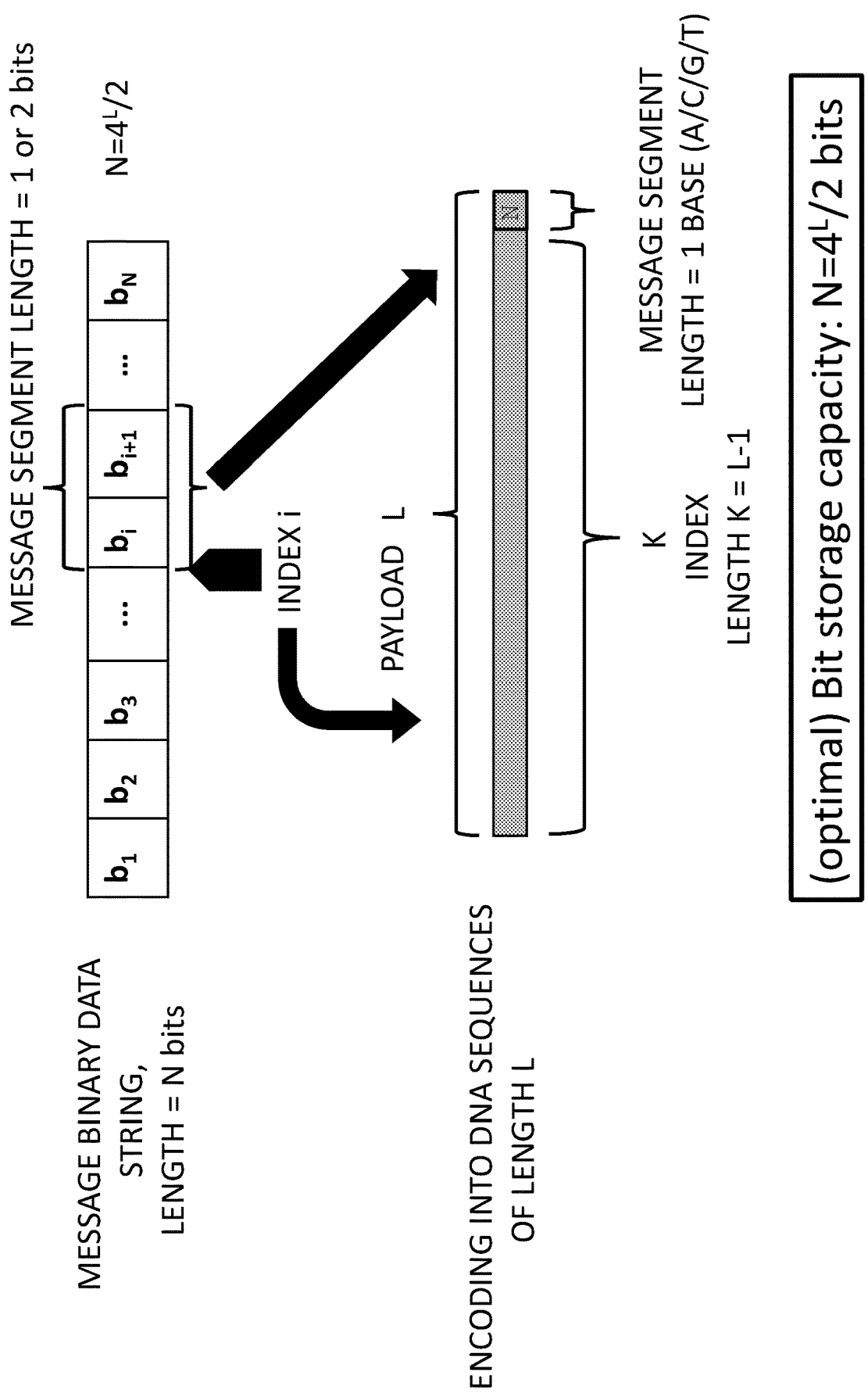
FIG. 68 illustrates an optimal method of decomposition of a binary data string into index and data segments for storage in DNA, optimized to store the largest message string using strands of a given length, in accordance with various exemplary embodiments.

The maximizer of this occurs at K=L−1, in which case L−K=1 so that M=2 bits is the data segment, and $N_{MAX}=4^L/2$ bits. This special mode for storing the largest amount of data is illustrated in FIG. 68, which highlights that just a single letter of the DNA data payload stores the message segment, which is just 2 bits, and the entire remainder of the length L DNA payload is used to store the index. For example, in this optimal method, a DNA data payload of the listed lengths has the following storage capacities (and Byte measures at right)

| Length of DNA Payload L | Storage Capacity N/bits (Bytes) |
|---|---|
| 11 | 2 $10^6$ (0.25 MB) |
| 16 | 2 $10^9$ (0.25 GB) |
| 21 | 2 $10^{12}$ (0.25 TB) |
| 26 | 2 $10^{15}$ (0.25 PB) |
| 31 | 2 $10^{18}$ (0.25 EB) |
| 36 | 2 $10^{21}$ (0.25 ZB) |
| 41 | 2 $10^{24}$ (0.25 YB) |

In exemplary embodiments with error correction, a portion the DNA payload is allocated to error correction; therefore, the number of payload bases utilized above for the same capacities shown would increase. In various exemplary embodiments, this increase for error correction is up to 25% of the size, up to 50% of the size, up to 75% of the size, up to 100% of the size, or up to 200% of the payload sizes shown above.

One benefit of this exemplary method is that relatively short (and therefore easier to accurately synthesize at higher yield) payloads provide massive data storage capacity. For an extreme example, estimates of the totality of digital data in the world circa 2021 are around 1 zettabyte (ZB), which could be stored using just 37-mers payloads in this exemplary framework.

Figure 69:
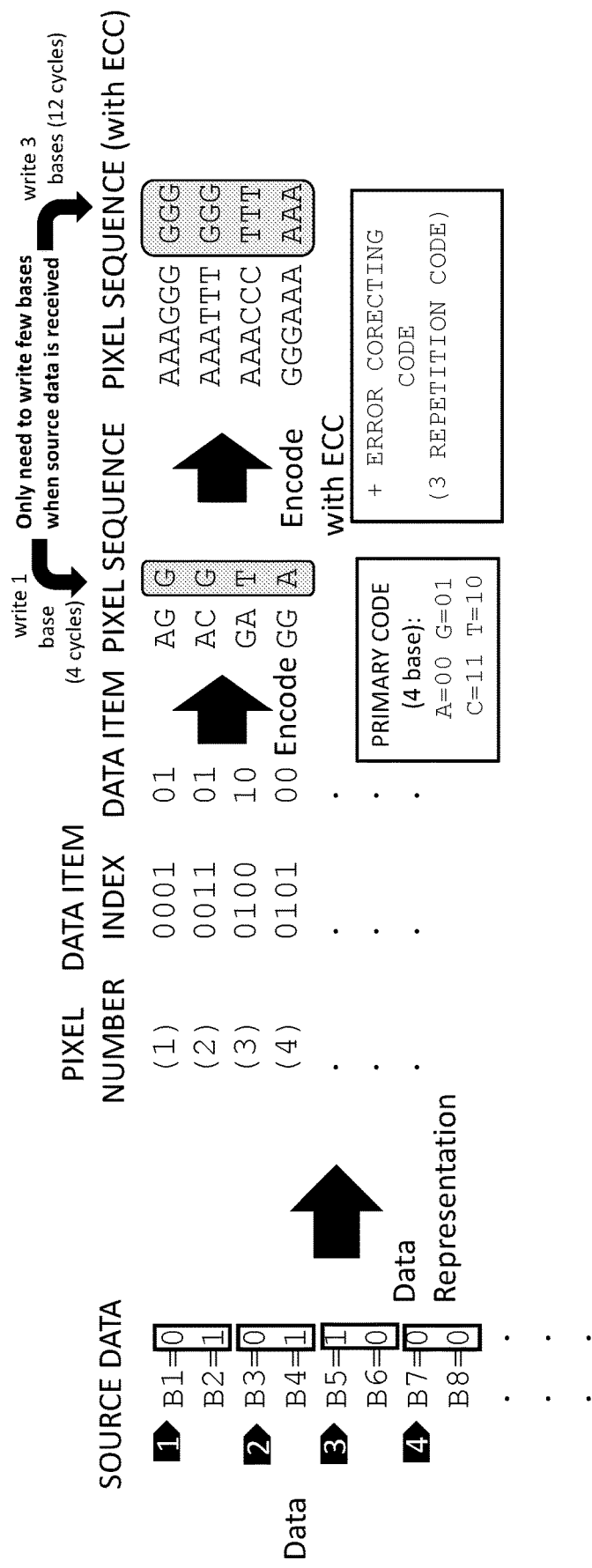
FIG. 69 illustrates an optimal encoding scheme for length of message, and an associated rapid writing mode for a DNA synthesis chip and including error correction, in accordance with various exemplary embodiments.

Turning now to FIG. 69, in accordance with various exemplary embodiments is illustrated an example of using this optimal encoding scheme to encode a binary input string "message." The input bit string is shown at left, with the first four index locations and 2-bit data segments highlighted. The N DNA payloads str synthesized at N pixels, and the pixel numbers and their respective payloads are shown, with first the index value (in binary) and the payload data segment (2 bit) shown, followed by the DNA encoded form of this binary data for each pixel, using here the primary code shown to encode both the index segment (2 bases) and the data segment (1 base, highlighted in the middle grey vertical box of FIG. 69). In various exemplary embodiments, it is desirable to have an error correcting code (ECC) applied to these DNA sequence payloads. In certain exemplary embodiments, a suitable ECC can be applied separately to the index segment, and a different suitable ECC can be applied to the single-base data segment. For purposes of illustration here, a simple triple repetition code is used—i.e. each letter is repeated three times (highlighted in the right grey vertical box of FIG. 69). This approach provides the general power to correct any single base error in this data segment (i.e., any 1-letter insertion, deletion, or substitution), or any single base error in the index segment. It will be appreciated that many other error correction encodings of this type (i.e., use of separate ECC on the index and on the single data segment base) may be utilized, and all such variations are considered to be within the scope of this disclosure. For example, instead of triplet repetition of the 4 possible bases, yielding the code words AAA, CCC, GGG, TTT, in other exemplary embodiments any 4 triplet words from the 64 total DNA sequence triplets could be used as the ECC code words instead, allowing single letter correction, as long as they are chosen so the edit distance between any two of them is greater than 2 (for the edit operators of one base insertion, deletion, or substitution). Many such compatible 4 word sets are possible. It will be appreciated that this is an optimal error correction code in this framework, because such 1 letter correction is not possible using less than three letter code words. Moreover, more powerful ECC capabilities may be utilized in various exemplary embodiments, for example longer repetition codes, the use of hamming codes tolerant of a large number of edits, and the like, to encode the 4 one base states used for the 1 base data segment (highlighted in the grey vertical box in the middle of FIG. 69).

Chip Rapid Writing Mode: A exemplary embodiment of a method for use on a DNA synthesis chip is a rapid writing mode, also illustrated in FIG. 69. As illustrated therein, the indexes assigned to pixels are universal, and do not contain information about the input data. Therefore, in these exemplary embodiments, the DNA index segments are pre-synthesized on the pixels of a chip (or chips), which can be done in any standardized order. For example, in an exemplary embodiment, the pixels on the chip (or chips) may be numbered 1 through $N=4^K$, and the successive 2K-bit binary numbers from 1 to N can be encoded in K letters of DNA, with the primary binary encoding shown in FIG. 69. With the indexes pre-synthesized on the chip or chips, writing the input message binary string consists of just writing a single letter across all the pixels of the chip or chips. This is therefore rapid, because it utilizes just 4 deprotection cycles of synthesis on the chip. Even in the case of using the triplet repetition code shown (or any other 3 letter ECC), the message specific writing is just the final 3 bases after the indexes, and again this utilizes just 12 deprotection cycles, no matter how large the message is, and now providing such error correction. It will be appreciated that even more powerful error correction can be used in certain exemplary embodiments, for example to guard against even less likely multi-error data failures, but in any case, it is a relatively small and fixed amount of writing effort, that is completely independent of the size of the message data. Stated another way, it will be appreciated that exemplary systems and methods provide for writing of arbitrarily large amounts of message data within a specified number of deprotection cycles. Additionally, in other exemplary embodiments, more generally, instead of the index code words just being encodings of the 2K-bit binary numbers for 1 through $N=4^K$, the code words that are pre-synthesized can in general be any $N=4^K$ DNA codewords of length J, J>K, selected from $4^J$ total such words, and used as the index keys, and pre-synthesized at the pixels. Such codewords in certain exemplary embodiments further have an error correcting code applied to them, and the $N=4^K$ ECC-protected index code words are what is pre-synthesized at the pixels. In various exemplary embodiments, the ECC protection on the index code words can be made as strong as desired (i.e., the probability of multiple errors resulting in lost data can be as low as desired).

Figure 70:
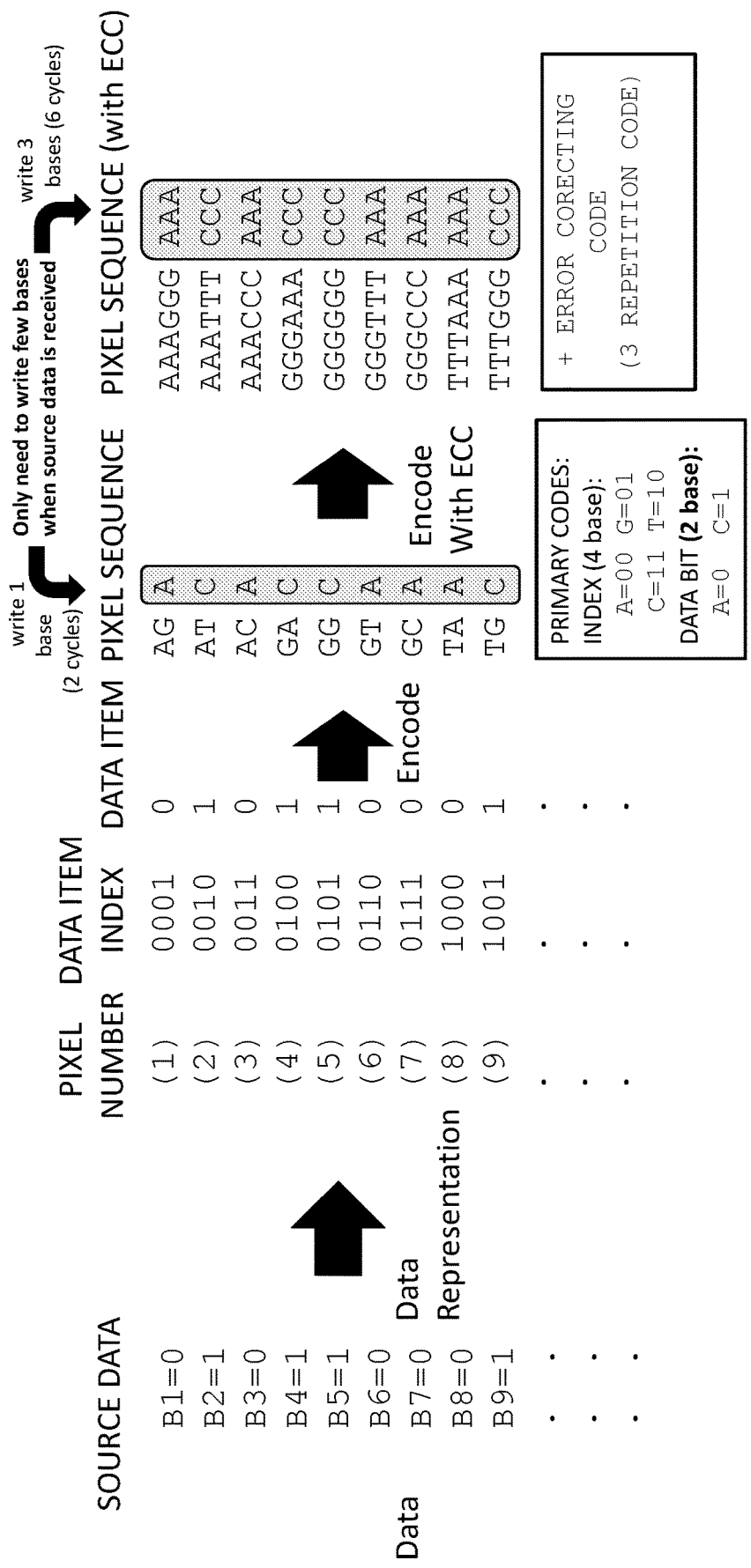
FIG. 70 illustrates a rapid writing mode for a DNA synthesis chip, using two bases for the data segment, and including error correction, in accordance with various exemplary embodiments.

FIG. 70 illustrates another exemplary embodiment of similar chip rapid writing mode, but in this embodiment the index set used points to each and every successive binary bit in the input string, and therefore the data segment is just the single binary bit pointed to, and this data segment bit is encoded using just two bases (e.g., A=0 and C=1 shown) (with the index encoded with a 4 base primary encoding). This approach provides a further speed advantage in that just A or C is written to write the message of any size, i.e., just two deprotection cycles on the chip, thereby reducing the time. Even if a triplet (or longer, m) repeat code is used for error correction as shown, the time to write the message with this ECC is still just the time for six (or 2m) deprotection cycles. This exemplary embodiment makes a further "speed-space" tradeoff, because twice as many pixels ("more space") are used to index the input digital string, but with the advantage that the write speed is twice as fast ("faster speed").

Figure 71:
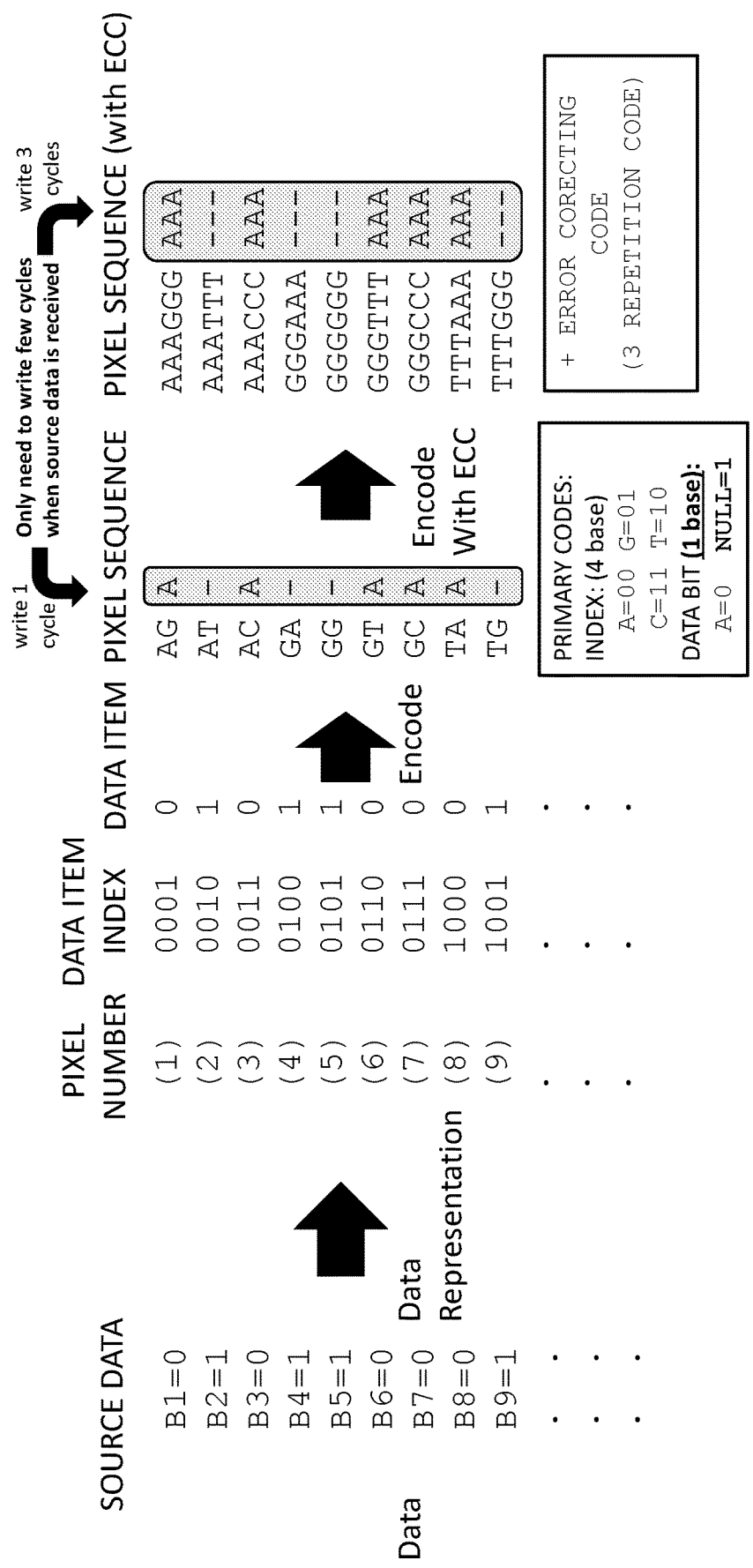
FIG. 71 illustrates a rapid writing mode for a DNA synthesis chip, using one base for the data segment, and including error correction, in accordance with various exemplary embodiments.

FIG. 71 illustrates another exemplary embodiment of a chip rapid writing mode, in which the index set used points to each and every successive binary bit in the input string, and in which the data segment is therefore just the single binary bit pointed to, and this data segment bit is encoded using just one base (e.g., A=0 and Null=1 shown) (with the index encoded with a 4 base primary encoding). Stated another way, one of the data states is encoded by not extending, which provides a further speed advantage in that just a single "A" is written to write the message of any size, i.e., just one deprotection cycle on the chip, thereby further reducing the time. Even if a triplet (or longer, m) repeat code is used for error correction as shown, the time to write the message with this ECC is still just the time for three (or m) deprotection cycles. This exemplary embodiment provides for the fastest possible rapid write, a single deprotection cycle on chip, to write a message of any size. In exemplary embodiments, this may be performed in less than 60 seconds, less than 10 seconds, or less than 1 second.

Figure 72:
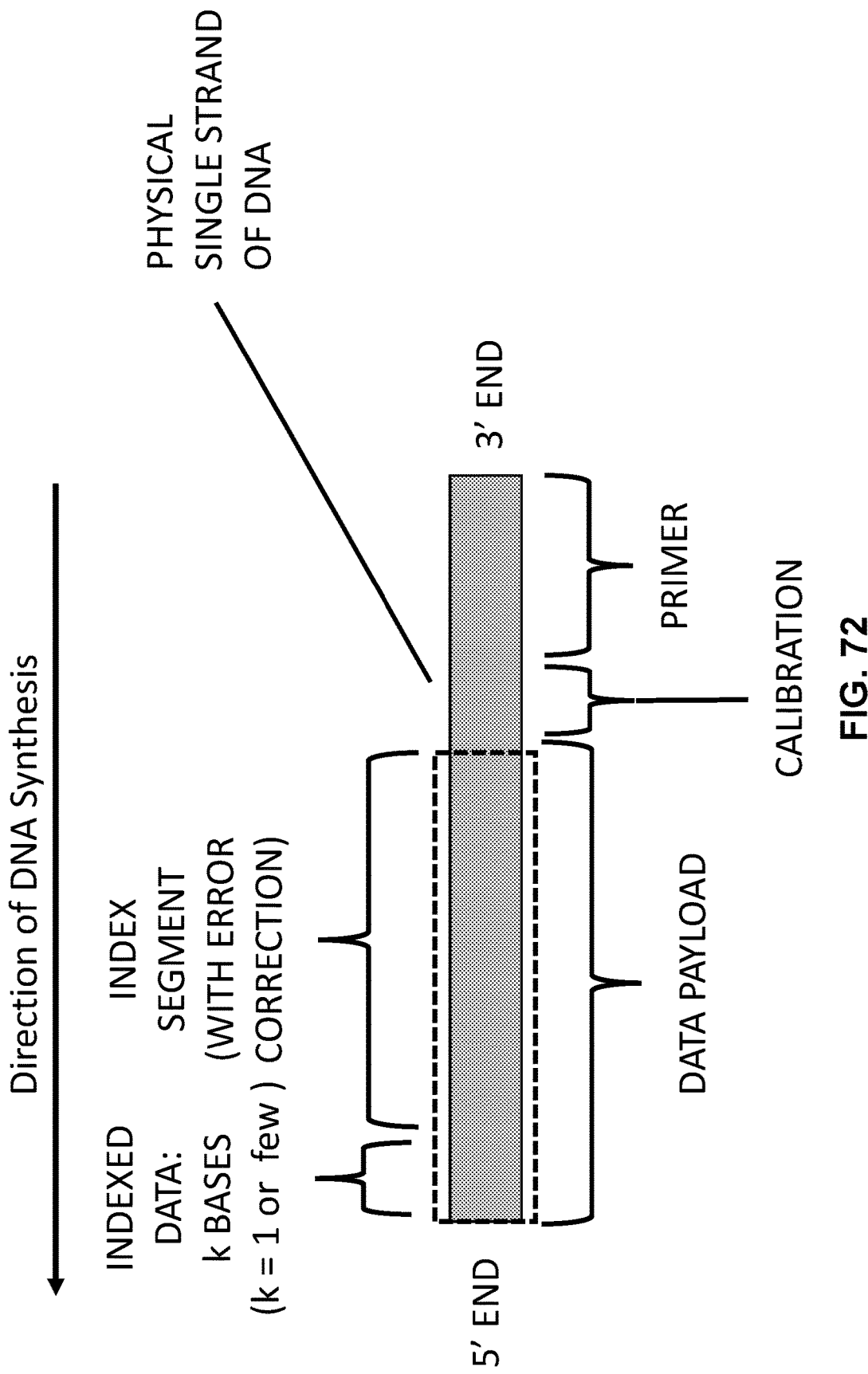
FIG. 72 illustrates logical structure of synthesized DNA strands for rapid writing modes for a DNA synthesis chip, in accordance with various exemplary embodiments.

FIG. 72 illustrates an exemplary embodiment of the format of the physical DNA strands used for exemplary rapid writing schemes and used for optimal data storage capacity. As shown, for synthesis in the 5' direction, the primer and calibration site can be synthesized first on chip, or synthesis can start from such premade common (to all pixels) DNA segments. Additionally, an index segment with ECC can be pre-synthesized on the chip or chips that provide the total number of needed index pixel sites. Then, upon receipt of a message binary string to be stored, the single or few (when ECC is used) bases needed can be written at the 5' end, thereby completing the write in the same time, regardless of size of message. In exemplary embodiments, a 5' end primer and calibration sequence are ligated in. Alternatively, these aspects can be synthesized on chip, which, while taking more time, is still a write time that does not increase no matter how large the message size.

In exemplary embodiments of the error correction for these chip rapid writing modes in which there is separate error correction applied to the index and the (one letter) data segment, it is further possible, in the message writing phase, to also write additional error correction data that informs on whether there are errors present in the combined index plus data segment.

Data Storage Density Considerations: It will be appreciated that, while exemplary foregoing approaches maximize the number of bits that can be stored in length L data payloads, such approaches do not maximize the density of data storage, i.e., the number of total bits stored per total DNA bases utilized. This quantity may be represented as:

$$\text{Storage Density} = (\text{total bit capacity})/(\text{total bases used})$$
$$= 4^K 2(L - K) \text{ bits} / (L 4^K \text{ bases})$$
$$= 2(1 - K/L) \text{ bits per base}$$

The maximum possible data density is 2 bits per base, reflecting the primary encoding used for this example. At this maximum, $K=0$ (i.e., no index is utilized) and the storage capacity is actually minimal and trivial, just a single strand of DNA, storing just 2 L bits. In contrast, at the maximum storage capacity found above, when $K=L-1$, the data density is $2/L$ bits per base, so this is lower than the maximum density by a factor of L. In various exemplary embodiments, a balancing approach is taken between the conflicting constraints for data density (bits per base) and data capacity (total bits). There is no simple optimization criteria to strike this balance; in some exemplary approaches, a cost function $C(K)$ may be utilized such that $C(K)=C(\text{Density}(K), \text{Capacity}(K))$. Utilizing such a cost function, it can be optimized to select the index size K that minimizes this cost. In some exemplary embodiments, this cost function is monetary cost of data storage; in other exemplary embodiments this cost function incorporates performance criteria such as write speed or access speed or read speed, or physical footprint considerations, or projected future capacity considerations. Moreover, this cost function can include, in various exemplary embodiments, any suitable criteria that influence the specific data storage requirements in question.

In the absence of a specific optimization criterion or criteria, an exemplary embodiment striking a balance is to devote half the length L of the DNA payload to the index ($K=L/2$), and the remaining half to the message segment, $L/2$ bases or $M=L$ bits. This exemplary embodiment is illustrated in FIG. 69, and the resulting storage density is 1 bit per base, and the storage capacity is $(L/2) 4^{(L/2)} = L 2^{(L-1)}$ bits, as illustrated by the following table showing the capacity of different payload lengths:

| Length of DNA Payload L | Storage Capacity N/bits (Bytes) |
|---|---|
| 11 | 1 $10^3$ (1 kB) |
| 21 | 2 $10^6$ (0.25 MB) |
| 31 | 3 $10^9$ (0.4 GB) |
| 41 | 4 $10^{12}$ (0.5 TB) |
| 51 | 5 $10^{15}$ (0.6 PB) |
| 61 | 6 $10^{18}$ (0.75 EB) |

In various exemplary embodiments, utilizing ECC would result in an increase of up to 50% of the size, up to 75% of the size, up to 100% of the size, or up to 200% of the size(s) shown above.

As disclosed above, in a chip rapid write mode, indexes can be pre-written onto the chip(s) to reduce the time utilized to write the message. In the current exemplary embodiment, that is the time required to write $L/2$ additional bases. Also as disclosed above for a chip rapid write mode, in exemplary embodiments a preferred error correcting encoding can be applied separately to the indexes and the message segments in such "fast" writing modes.

Index Composition and Pre-Synthesis: In exemplary embodiments for encoding data into DNA, an index segment and message segment storage DNA payload format are employed, as illustrated in FIG. 67. For an application where there are up to N indexes utilized, such index sequences are N distinct sequences. In various exemplary embodiments, all indexes have the same sequence length, k. In such cases, the indexes are a subset of the set of $4^k$ DNA distinct k-mers. In various exemplary embodiments, the indexes are any such subset for any k, such that there are enough indexes available (i.e., $N \leq 4^k$). In other exemplary embodiments, the subset of N index sequences can be chosen to be a small fraction of all k-mers, and the index sequences may be highly distinct sequences from one another, such that error(s) in an index are unlikely to result in a sequence that would be confused with another index. Thus, such index errors can be readily corrected. In other exemplary embodiments, indexes may be selected to provide for more efficient (rapid or cost effective) pre-synthesis of the index set on the chip or chip set to be used for synthesizing the DNA for the storage of the up to N message segments. For example, in a situation where the C and T bases are synthesized in oligos substantially more rapidly or at a lower cost, various exemplary embodiments would utilize indexes restricted to k-mers composed solely of C and T to take advantage of this.

In various exemplary embodiments, an index set is pre-synthesized on the chip(s) in a first phase of synthesis. This typically occurs entirely before beginning the message segment synthesis. In exemplary embodiments, this first phase may be performed using different synthesis conditions than for the message segment phase, or a different industrial workflow, to achieve advantages in cost or quality. For example, in certain exemplary embodiments, this index phase may be performed with synthesis conditions optimized for speed, or for economy of synthesizing the indexes, or for other desirable criteria. In various exemplary embodiments, an index set may be selected and/or created to provide for a desired level of error correction, such as selecting a set of N k-mers (where N is substantially less than $4^k$) that have an Edit Distance of >2m between any two indexes, so that up tom edits (errors) of types from {1-base substitution, 1-base insertion, 1-base deletion} can be corrected. In other exemplary embodiments, other sets of k-mer indices from within all k-mers can be selected and/or created to provide for other suitable means of error correction. From the exemplary methods disclosed, many other suitable forms of error correction may be understood, and all such suitable approaches are considered to be within the scope of the present disclosure.

In exemplary embodiments wherein an index set is pre-synthesized, with error correction capability, message segments can be provided with additional error correction capacity, for correcting errors in the message segment, or in the combined index and message segment, implemented in a manner such that this additional message content and error correction may be added on post-synthesis of the indexes. This approach provides for the ability to efficiently pre-synthesize indexes with error correcting encodings, and to layer on a further error correcting code for message plus index that can be synthesized in a second phase of synthesis, starting from the pre-synthesized indexes. Stated another way, in these exemplary embodiments error correction used in the index segments does not require knowledge of the associated message segment assigned to that index, but the error correction in the latter segment can incorporate knowledge of the index. For example, in an exemplary embodiment, message segments contain additional error correction content to help determine where the index sequence ends and the message sequence begins, to prevent ambiguities in this boundary that may result from sequence errors. In particular, if there have been insertion or deletion sequence errors, in an exemplary embodiment such content may determine whether these have occurred in the index segment or the message segment, or both.

Low Overhead Error Correction Schemes. In various exemplary embodiments, short oligo payloads are being used to encode information (for example, as illustrated in the two capacity tables above), thereby reducing the on-chip synthesis utilized. The capacity tables shown do not include any overhead of sequence that is used for error correction in the payload, which reduces the maximum capacity for a given length of payload. For such exemplary embodiments enjoying the benefits of shorter oligo payloads, it is desirable to utilize forms of DNA sequence error correction that do not impose overhead involving synthesizing substantially more bases.

Figure 73A:
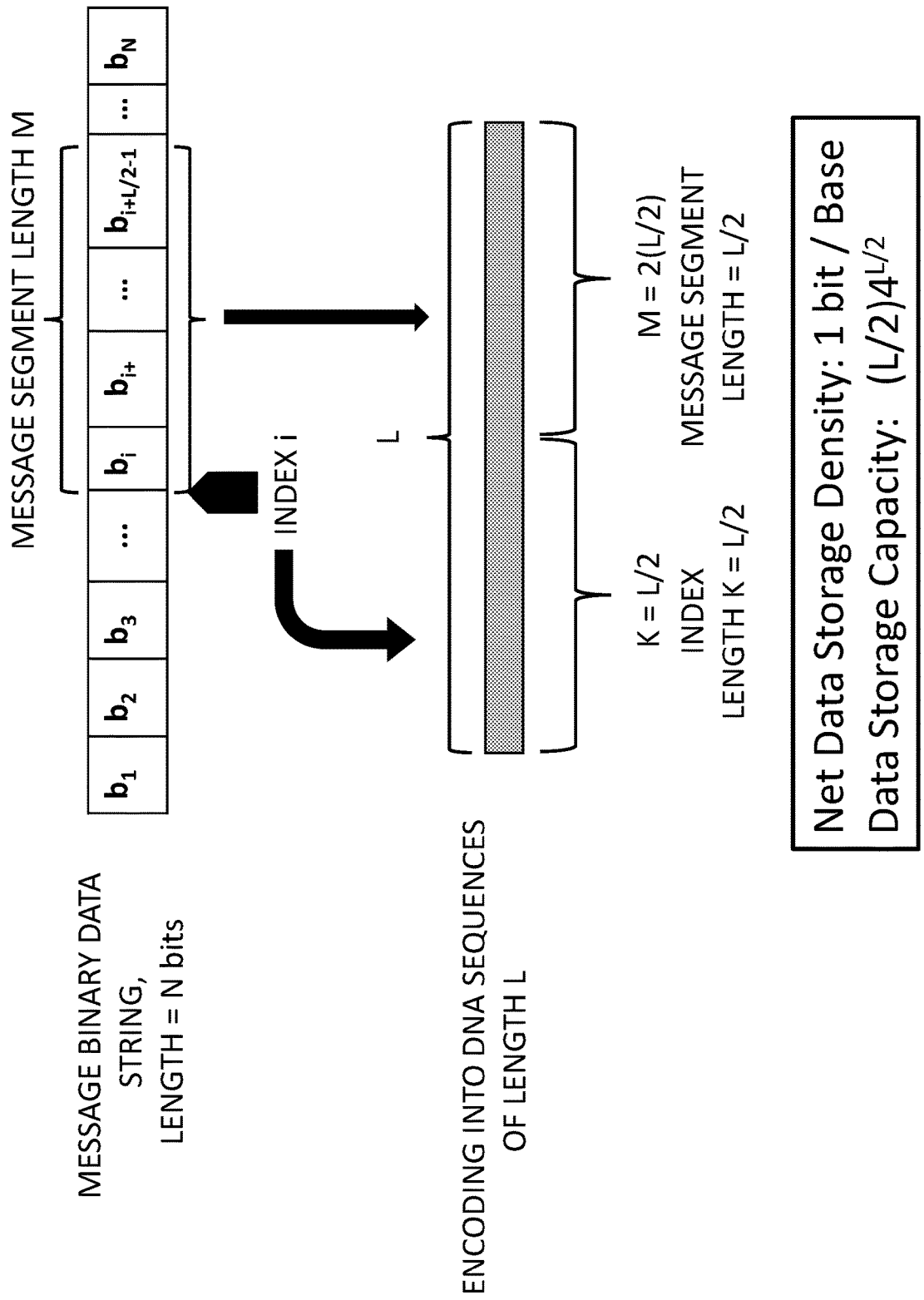
FIG. 73A illustrates data storage of a binary data string into DNA payloads with index and data segments for storage in DNA, using equal sized index and data segments, in accordance with various exemplary embodiments.
Figure 73B:
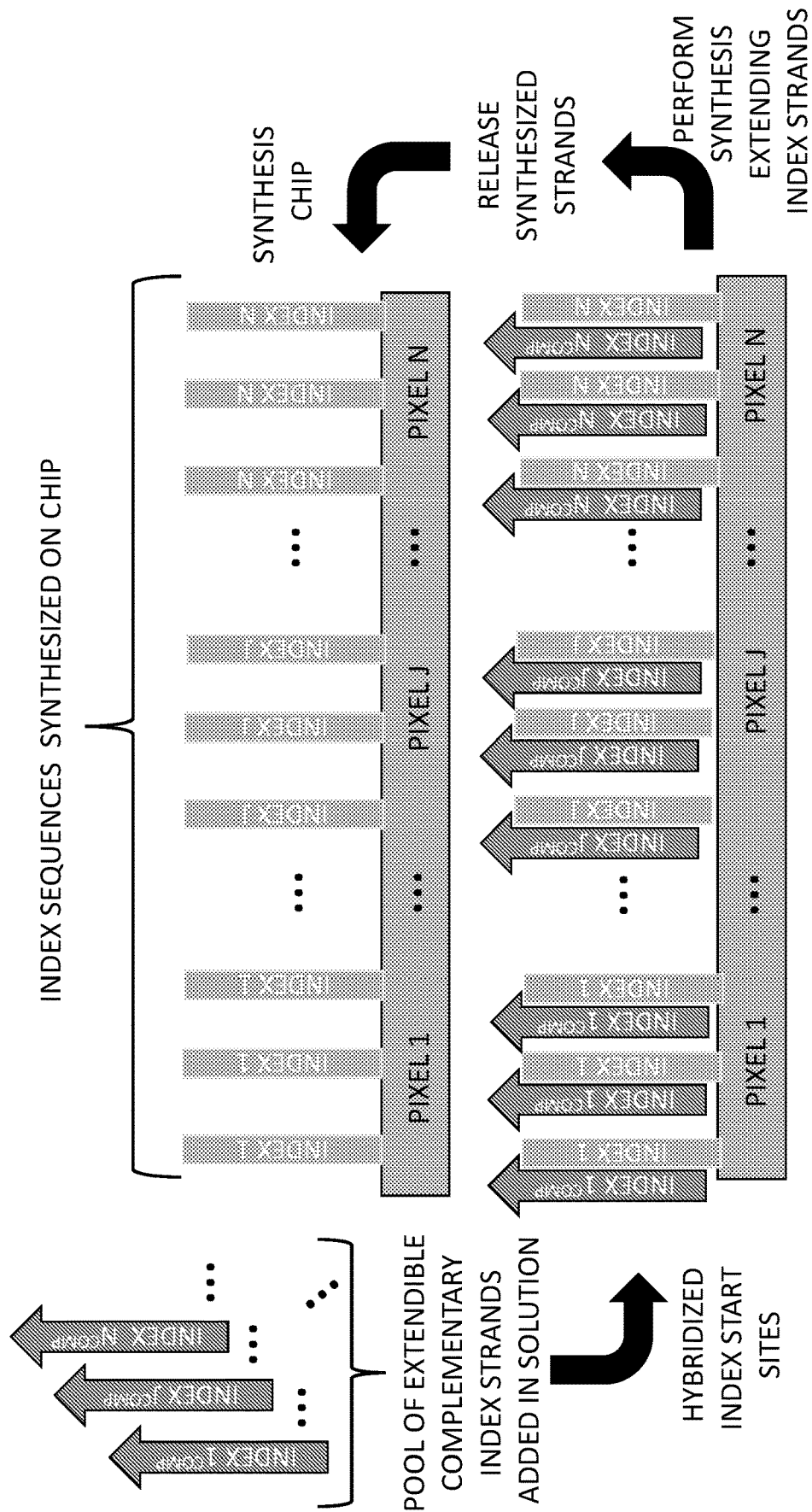
FIG. 73B illustrates re-use of chips with pre-synthesized indexes based on hybridization, in accordance with various exemplary embodiments.
Figure 73C:
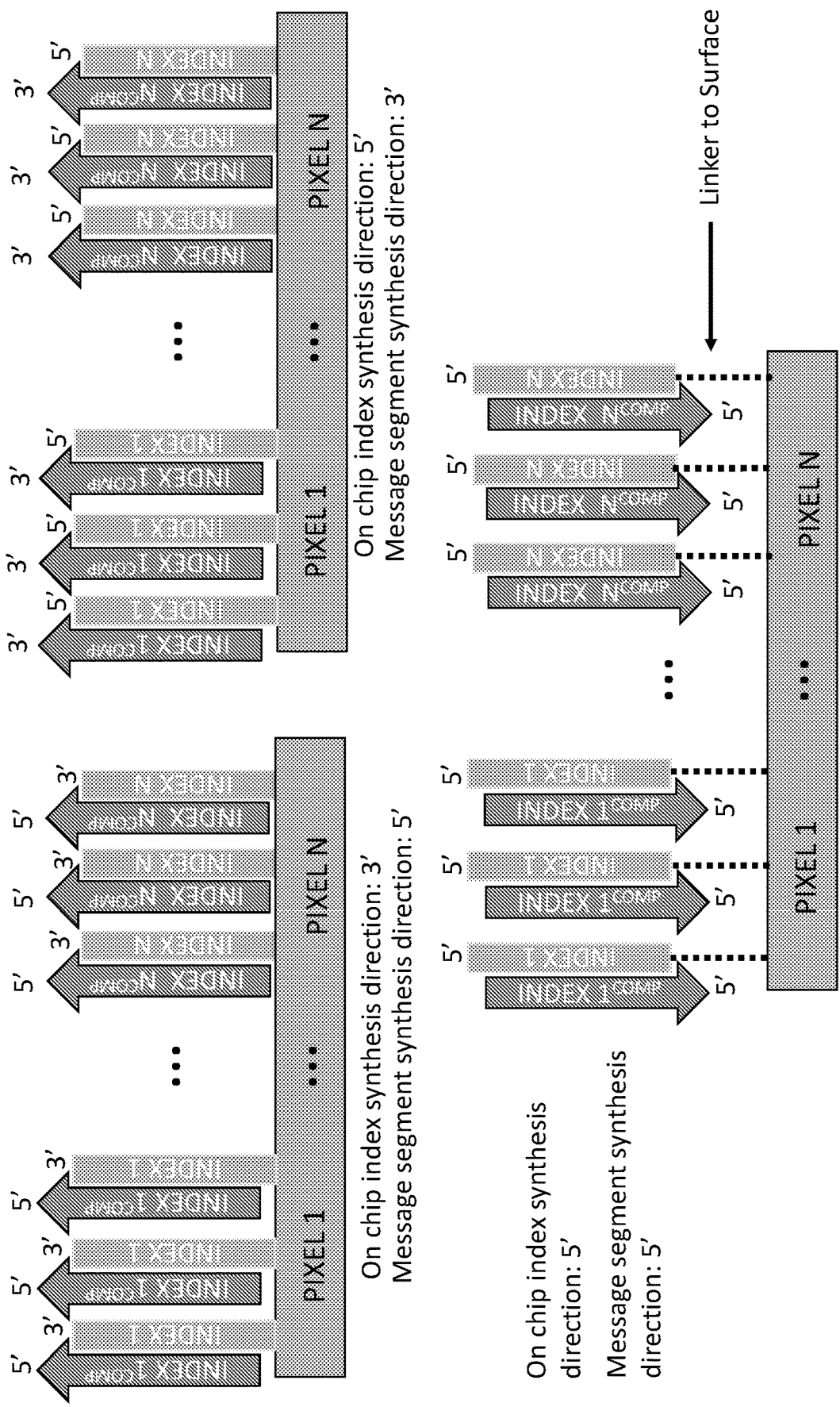
FIG. 73C illustrates re-use of chips with pre-synthesized indexes based on hybridization, with various orientations of synthesis, in accordance with various exemplary embodiments.

Coverage-based Error Correction. An exemplary embodiment of such a method of error correction—which requires no synthesis overhead at all—is illustrated in FIG. 73F. This embodiment utilizes coverage to correct errors. In a chip-based DNA data storage synthesizer as disclosed herein, for each target DNA sequence to be written, as provided by the DNA sequencer encoder of FIG. 64, a target sequence is assigned to one (or more) on chip synthesis pixels, and on any given pixel, multiple independent molecules are produced representing the target sequence. In exemplary embodiments, this may be 10, 100, 1000, 10,000, or even more independent molecules, representing the same target sequence. These independent molecules, in general, have statistically independent errors generated during synthesis. In subsequent handling, storage, retrieval, and/or sequencing readout of these molecules, such processes may result in further additional statistically independent sequence errors in the resulting retrieved sequences. In various exemplary embodiments, for each input sequence to be recovered, multiple such independently retrieved reads are obtained. In exemplary embodiments, at least 2, at least 3, at least 5, at least 10, at least 20, or even more such independent reads are obtained for each input sequence that is to be properly retrieved from the storage system. As illustrated in FIG. 73F, relative to the logical input sequence, these retrieved reads (5 reads total in the illustrated example), providing a "coverage" depth of 5 for the target sequence. The retrieved reads have various errors, such as multiple substitution errors (one letter changed to another), insertion errors (a letter inserted into the sequence), and deletion errors (one letter deleted from the sequence). In exemplary embodiments, these sequences are averaged together to produce a "consensus" sequence, that has averaged away independent errors. In various exemplary embodiments, the consensus sequence is constructed by the Median String Algorithm, or by approximations of this algorithm, or by generalizations of this algorithm to include available per-letter error likelihoods that may be used as weights within the edit distance metric utilized within the algorithm. Moreover, many other suitable consensus sequence algorithms are known and may be utilized, and all such suitable algorithms are considered to be within the scope of the present disclosure.

This consensus sequence becomes the recovered sequence, and recovered sequence is then further decoded by the decoder, individually or in combination with other such properly recovered sequences, as per the encoding/decoding method in use. In this way, coverage has been used to correct the errors, for example errors arising from synthesis as well as other processes of data storage and/or retrieval. It will be appreciated that, for coverage-based correction approaches, it should be possible to aggregate reads for the same target (i.e., the same index); this constraint means the targets should be distinct enough for there to be little ambiguity in the aggregation. In the case of short message segments, which lack sequence diversity, suitable indexes should thus be sufficiently distinct from one other. For example, in an exemplary embodiment wherein the index segments are all $4^k$ k-mers, and the message segment is a single base (as in FIG. 68), a substitution error in the index segment will result in the sequence of another index, thereby creating a spurious read that may be incorrectly aggregated as coverage for that other index. Thus, in various exemplary embodiments utilizing a coverage method, the index set used has the property that any two k-mer index segments differ in at least m of the k bases, for a difference parameter m>1. In some exemplary embodiments, m may be 2, 3, 4, 5, or up to 10. In these exemplary embodiments, this can be achieved by starting from an index set of size N that does not have the desired property, such as all $4^k$ k-mers, and appending to these indexes, as part of the data payload, j-mer sequences taken from all $4^j$ j-mers, such that the resulting N indexes so augmented now do have any two indexes differing in at least m positions. By setting such an m large enough (for example, between 1 and 50, or between 5 and 40, or between 10 and 30, or between 1 and 10), it can be assured that the aggregation of coverage for the coverage error correction, can have incorrect aggregations reduced to any desired low rate of occurrence. Thus, this appended j-mer, which may be appended at the start or end of the k-mer indexes, may function as a "disambiguation" tag to disambiguate coverage aggregation in the presence of errors, and this is created as part of the data payload. From the foregoing examples, it will be appreciated that many suitable methods for constructing such j-mer tags may be implemented, and all such approaches are considered to be within the scope of the present disclosure.

In various exemplary embodiments, one such preferred method, which is a greedy search method, is as follows: in the case of N indexes that require disambiguation, start with a candidate value for the j-mer length, $j=j_0$, and let U denote the universe of possible j-mers, which initially is al $4^j$ j-mers. Then, proceed to select any first such j-mer, $J_1$, from U, and then eliminate from U all j-mers that differ in less than m positions from $J_1$, and, so initiated, proceed to select additional $J_i$ from the remainder in U, and eliminate from U all j-mers that differ in less than m positions from $J_i$, for I=2, . . . , continuing in this manner until a $J_N$ is obtained (i=N), in which case the process may be halted, having produced enough j-mers to append one uniquely to each of the N indexes (in any order), or until the universe of candidate j-mers remaining, U, is empty (in which case, restart with j incremented to j+1, and U again reset to all j-mers, for this larger j). This process will eventually produce a suitable set of N disambiguation j-mers, mutually differing by at least m positions. Other such exemplary embodiments of construction methods can be done as disclosed below for constructing k-mers that have a mutual Edit Distance (see below) of at least 2m, including methods that also allow for sequence constraints, or, in exemplary embodiments, the entire N index set can be recoded into k-mers spaced by at least 2m, as disclosed below, and this can provide the disambiguation desired for use in various exemplary embodiments.

Consensus Sequence Methods. In exemplary embodiments where coverage is used to correct errors, an exemplary method of "averaging" the coverage to remove errors is to construct the Median String, which is a well-known method of averaging together strings in computer science. because computation of the exact Median String is NP-complete and therefore costly, in exemplary embodiments various known approximation algorithms for Median String may be used to form the consensus sequence. In exemplary embodiments for finding the consensus sequence, coverage sequences can undergo Multiple Sequence Alignment, which is a well-known method in bioinformatics of associating the letters of identifying common letters across multiple strings which may be related to each other through "editing operations" of insertions, deletions, and/or substitutions. Once such identifications are made across strings, it is possible to take a "vote" on the most likely letters of a common ancestor string, or otherwise use various well-known algorithms to construct a consensus sequence representing a "a common ancestor" that best explains the observed sequences, such as a maximum likelihood estimator for one sequence that would result in the others through such random errors, and an assumed random error model. From the principles disclosed herein, many such suitable methods and variations of methods for forming a consensus sequence from observed coverage sequences may be understood, and all such methods are considered to be within the scope of the present disclosure.

A benefit of the disclosed coverage methods is that no additional overhead is utilized in the data payload itself to support this form of error correction. In various exemplary embodiments, molecular barcodes (per-molecule random k-mers) as disclosed above are added to the independent molecules synthesized to provide the source of coverage. Such barcodes are used in the consensus generation process to eliminate possible PCR generated duplicates that do not derive from independently synthesized molecules, and which therefore create systematic error biases (errors that are not independent) in the coverage. In a preferred embodiment, for coverage molecules having the same barcode sequence, only one is selected and entered into a consensus generation algorithm, and the others are ignored. Such barcodes may, in exemplary embodiments, not incur any payload overhead because they may exist in the synthesis molecular start sites at the synthesis pixel, or may be ligated in post synthesis. Moreover, at the cost of overhead in the payload, in exemplary embodiments barcodes may be added directly as part of the data payload, by performing k steps of synthesis with a pooled mixture of the four phosphoramidite bases {A,C,G,T}. In various exemplary embodiments, the k-mer for barcoding utilizes k=1, 2, 3, 4, 5, or even more. Coverage-based error correction is independent of any other error correcting code that may be used in encoding the payload. Thus, in exemplary embodiments, coverage-based error correction may be used in combination with other forms of ECC used at the payload sequence level. In general, the level of error correction provided by a coverage of C is that an error would typically need to occur at least C/2 times at the same position to result in an incorrect vote. The probability of that occurring, for a per base error rate of p, p being much smaller than 1, and C>>1, is approximately $P=2^C_p{}^{(C/2)}$. For a typical error rate of synthesis of p=0.01, coverage of C=10 reduces the error probability per base to roughly $P=10^{-7}$. Coverage of C=5 reduces per base errors to a rate of $P=10^{-5}$, and coverage of C=3 reduces it to $P=3 \cdot 10^{-4}$.

Edit Distance-based Error Correction. With reference now to FIG. 73G, in various exemplary embodiments Edit Distance-based error correction methods are used for error correction. This form of ECC adds overhead to the DNA data payload of FIG. 67. FIG. 73G illustrates this class of methods for the case of encoding a desired set of N indexes into k-mer sequences that can be error corrected for up to m errors, if such indexes are corrupted by errors in the process of synthesis, storage, and/or sequencing retrieval. Moreover, the exact same method, more generally, can be used to encode any set of N data payloads into payload k-mer DNA sequences that can be error corrected up for up to m errors, if such DNA data payloads are corrupted by errors in the process of synthesis, storage, and/or sequencing retrieval. These approaches utilize the Edit Distance, which is a well-known mathematical distance function that defines the distance between any two character strings as the minimum number of string editing operations needed to transform one character string into the other (where the allowed editing operations are single character substitution, single character deletion, or single character insertion, relative to a given symbol set or alphabet from which the strings are composed). In the case of DNA sequences as strings, this alphabet set is {A,C,G,T}. For example, in the case of the DNA sequence strings GATTACA and GAATACCA, the Edit Distance is 2 (the two edits "substitute the first T to A", and "insert a C between C and A" shows it can be done in 2 edits, and exhaustive examination shows it cannot be done with a single edit; therefore, the minimum number of edits to transform one sequence to the other is 2). In general, the edit distance between any two such sequence strings or any lengths can be rigorously, exactly, and efficiently computed using well-known Dynamic Programming algorithms. In other exemplary embodiments, probability weights may be utilized for the different edits, i.e. probabilities for the different error modes of substitutions, insertions, and deletions, and therein the Edit Distance can be generalized to the number of edits in the most probable series of edits that transforms one string into the other. To utilize this for exemplary methods of error correction, as illustrated in FIG. 73G, consider a set of N indexes is desired such that for up to m errors corrupting such an index, these errors can be corrected (i.e., the intended un-corrupted index can be identified). As indicated, the set of all possible DNA sequence strings of any length, n, $0 < n < \infty$, can be thought of as points in an infinite dimensional space, where the different "dimension axes" are the letter options {A,C,G,T, "null"} for Base 1, Base 2, etc. of a sequence (allowing the "null" option with the convention that finite sequences are padded with "null" in all additional "unused" dimensions). This space is a geometric space, where the distance between points is the Edit Distance. Therefore, for a point S in this space, we have the concept of a (closed) ball of radium m (where m in $\{0, 1, 2 \ldots\}$ is a non-negative integer) centered at S, denoted Ball(S,m), which is all points in the space at distance≤m from S. Such balls of radius m are indicated conceptually by the dashed circles in FIG. 73G. Now consider there is provided a set of N points in this space, all of which are of the same length k (i.e., all are k-mer sequences) for some index length k, and such that the points $\{S_1, S_2, \ldots, S_N\}$ are mutually spaced apart as shown, such that for any two of these points, the respective balls of radius m do not intersect, i.e. Ball($S_i$,m) and Ball($S_j$,m) have no points in common, for any i≠j. In exemplary embodiments for indexes with ECC, these N k-mer DNA sequence—explicitly expressed as sequences $S_i = B_{i1} \ldots B_{ik}$, i=1 ... N, $B_{ij}$ in {A, C, G, T}—are used as N index sequences for the index segments of N payloads as in FIG. 67. In these embodiments, if such an intended index $S_J$ is retrieved as a sequence S, corrupted by up to m errors (note, this corrupted S need not be a k-mer, due to corruption by some numbers of insertions or deletions), then when S is compared to all admissible indexes $\{S_1, S_2, \ldots, S_N\}$, $S_J$ can be identified as the only index with distance m, while all others must be at a distance>m, due to the fact that the Balls of radius m around the indexes do not have any points in common. Accordingly, this provides an exemplary ECC method: for any corrupted index S, if there is an allowed index at distance≤m, correct S to this index, otherwise discard as corrupted beyond possible correction. This exemplary error correction method can only provide a wrong correction for an observed S that suffers from >m errors. Therefore, if m is made large enough, this can be reduced to any desired level of improbability, based on the probability of errors. Accordingly, in exemplary embodiments, if N payloads are to be retrieved with a mean coverage of C, the total number of reads to be decoded is R=NC, and m can be chosen to be large enough such that the expected number of wrong index corrections among the R read corrections, based on the probability of errors, is <1, or <0.1, or <0.001, or <0.0001, or <0.00001, or even lower.

In the foregoing example, it is assumed a suitable set of "well-spaced" k-mer points $\{S_1, S_2, \ldots, S_N\}$ is provided in the space of all sequences. In practice, an approach to identify such point sets is desirable. Accordingly, in exemplary embodiments such a point set is constructed by the following algorithm, given the number of indexes, N, desired, and the number of correctible errors, m, desired. In addition, there may be given constraints on the allowable sequences, and in that case denote the collection of any such desired logical constraints by C, where these are logical tests that are either true or false on a given sequence where "true" corresponds to an admissible sequence. In exemplary embodiments these may be constraints against sequence features that are considered to cause difficulty in DNA synthesis or DNA sequencing. Such sequence features may comprise GC content (i.e. an upper limit on % of sequence that is G or C), or words that are not allowed (such as runs of the same base longer than some allowed run length, i.e. homopolymer length limits, or motifs that cause issues such as promoting G tetrad formation), or limits on secondary structure (such as limiting self-complementary segment lengths that may form DNA hairpin duplexes, or limits on the melting points of DNA folding secondary structures, such as can be computed by secondary structure calculations applied to a sequence, or avoiding sequence similarity to primers that may be used in the system as in FIG. 63, so as to avoid mis-priming in PCR, or any such constraints on the individual sequences or constraints among a sequence and other sequences in a given set, such as too much mutual complementarity with another set of sequences, in particular such as other members of the set of indexes under construction. In various exemplary embodiments, construction also involves identifying a suitable length for the index strings, k, as well as the desired set of N k-mers, denoted $\Sigma = \{S_1, S_2, \ldots, S_N\}$. Starting with an initial trial for k, $k_0$, which is at least large enough such that k-mers provide N indexes (i.e. $N \leq 4^{k_0}$), an exemplary method carries out the following search: start from $\Sigma = \{\ \}$ (empty set). Select a k-mer S at random (i.e., a randomly generated k-mer sequence, with letters drawn from among all four bases at equal probability). If S satisfies all constraints, C, set $S_1 = S$, and add this to the set, $\Sigma = \{S_1\}$. Otherwise, generate another random trial. Continue until an admissible $S_1$ is found. If none is found, stop after a pre-set search limit of T total random sequence trial failures. In exemplary embodiments, this limit may be hundreds, thousands, millions, or billions of trials, or even more. Increase k to k+1 and repeat the search process in this larger k-mer set, with $\Sigma = \{\ \}$ (reset to empty set). At a stage at which Σ has less than N elements, generate another random k-mer, S, check that the constraints are satisfied (including if possible those that may involve the existing contents of Σ) and also check that the distance from S to any other point in Σ is >2m (note this ensures that Ball(S,m) cannot intersect Ball($S_j$,m) for any $S_i$ in Σ, since if there was a point s in both balls, S could be transformed to s in ≤m edits, and s could be transformed to $S_i$ in in ≤m edits, showing that S could be transformed to $S_j$ in ≤m+m=2m edits, contradicting the selection criteria of S). Add such a S to Σ as the next index. If the generated S does not satisfy the criteria, continue random trials of S, and stop after a pre-set search limit of T total random sequence trial failures, and in that case increase k to k+1 and repeat the search process in this larger k-mer set, with $\Sigma = \{\ \}$ (reset to empty set). Stop whenever Σ reaches the desired number of N members. This exemplary algorithm will eventually produce a k and a set of k-mers with high probability, unless the constraint set is overly restrictive. Moreover, this exemplary search process can also be repeated multiple times, because it is probabilistic and can produce more desirable outcomes (shorter solution k for the k-mers) upon different realizations. Also, in exemplary methods, efficiency of the search can be improved by eliminating Ball(S,m) from the search space of k-mers each time a new S is accepted into E. If the remaining search space becomes empty, increase k to k+1 and repeat the search process in this larger k-mer set, with $\Sigma = \{\ \}$. This is a more efficient means to detect that there will not be a full set of N indexes in a given set of k-mers.

Estimates of ECC Overhead. The exemplary search algorithm above determines the index length k as part of the search, for k-mers that provide a desired capacity for error correction. In various exemplary embodiments, it is possible to estimate the order of magnitude required for k, in terms of the desired number of indexes N and the desired error correction capacity m, at least in the case where there are no constraints C to complicate matters. With no error correction (m=0), note we need k=[$Log_4$ N] ([x] denotes rounding up the nearest integer≥x), in order to accommodate the number of indexes utilized by using all possible k-mer sequences to index N things. Any greater value of k used for indexing can be considered to have increased by the overhead of error correction to allow for the correction of up to m errors. An exemplary heuristic estimate for this overhead is that, at this minimal k, any index is one edit away from others, whereas the indexes are desired to be 2m edits apart. This criterion can be achieved by adding 2m extra bases to each index, and selecting them so that the sequence differs at all 2m bases from its nearby neighbors. Thus, this suggests the desire to add ~2m extra bases beyond the minimal number needed for k. For an alternative and more optimal heuristic estimate, other exemplary embodiments utilize information theory: to identify and correct an error in a k-mer utilizes $Log_2(k)$ bits of information to identify the location of the error in the k-mer, and approximately 3 bits of information to correct it (by specifying among the $2^3=8$ options, namely, 3 substitutions, 4 insertions, and 1 deletion for the correction). Thus, to do this for a total of m errors, each utilizes this much information, and therefore in total it utilizes m ($Log_2(k)$+3) bits of information to correct m errors. Converting these to DNA letters, at 2 bits per letter, the number of added letters of overhead, on information theoretic grounds, is approximately m (1.5+½ $Log_4(k)$) extra bases of overhead to correct m errors. Generally assuming that for a range of k of practical interest, $Log_4(k)$~3, this overhead estimate becomes ~3 m. For a more refined evaluation of the overhead utilized to correct m errors, let B denote the average number of elements in a m-ball Ball(S,m), and K denotes the total number of elements within distance m of all k-mers. Then, because N disjoint m-balls are desired for an exemplary well-spaced index set, the size K should allow for all these N disjoint sets of size B, i.e. K~NB. The number of elements in a ball Ball(S,m) can be difficult to count precisely, for example, because different series of up to m edits can produce the same point in the ball. However, the number of series of up to m edits applied to the center point k-mer S scales like the number of ways to choose m edit sites in the k-mer, $~k^m$, times the number of choices for the series of m edits, $L^m$ (L is the number of total edit operators), or $(kL)^m$. K in turn encompasses all possible m edits of k-mers, which is everything from (k−m)-mers to (k+m)-mers, which scales like $4^{(k+m)}$, thus, we need $4^{(k+m)}$~N $(kL)^m$. This implies that to highest order k~$Log_4$ N+m $Log_4$ L+m $Log_4$ k. In this case, the number of edit operations is L=8 (3 substitutions, 1 deletion, 4 insertions), thus we have k~$Log_4$ N+m (1.5+$Log_4(k)$), which is somewhat higher than the information theoretic minimum above, as expected. In simple terms, this sets an expectation, reflected in exemplary embodiments, that adding about ~(1.5+$Log_4(k)$) m~4.5 m letters to the minimal index length (and data payload) results in m letters of error correction in the index. Thus, these estimates overall suggest the addition overhead is about 3-4.5-fold times m. For example, for 20-mer indexes where correction of up to 5 errors is desired, we may expect to add 15-23 letters of ECC overhead. In contrast, correction up to just 2 errors utilizes 6-9 overhead bases. In light of the foregoing examples, many possible suitable algorithms, either variations on the above, or others suitable for constructing such well-spaced out point sets in string space, may be utilized and all such algorithmic approaches are considered to be within the scope of the present disclosure.

Error Correction of Indexed Message Segments. As illustrated in FIG. 63, in various exemplary embodiments error correction encompasses both the index segment, and the message segment of the data payload. The examples above directed to Edit Distance methods was presented in terms of finding a set of N k-mer indexes in which up to m errors can be corrected. As noted there, a same or similar Edit Distance correction method can be applied to the entire DNA data payload of length L, so as to be able to correct up to m errors in the entire payload. However, in these approaches, it is not generally possible to break the encoding strings {$S_1$, $S_2$, ..., $S_N$} into an index segment that can be prefabricated, independent of the message segments, such that they could be added at the time when the data is specified (e.g., such as for rapid writing modes disclosed above). Accordingly, in various exemplary embodiments, it is desirable to keep the ability to prefabricate the k-mer indexes, and add a distinct final message segment in a separate phase of synthesis. In these approaches, in exemplary embodiments, message segments can also be encoded into Edit Distance ECC sequences, to provide any desired level of error correction.

For example, consider a total of Q distinct message segments. If a message segment has a length J, this would be at most $Q=4^J$ distinct J-mers. In a rapid writing mode or optimum capacity mode, J may be 1, or at most a few bases, for example. In a balanced mode as illustrated in FIG. 73A, J may be in the range of 10-20 bases, for example. For any desired number of errors to correct in the message segment, $m_{MESS}$, as above there can be a $k_{MESS}$ such that all the Q message segments are encoded in these Q $k_{MESS}$-mer sequences, {$T_1, T_2, \ldots, T_Q$}. Then, the entire data payload of N indexes and the respective message segments can be encoded as the concatenation of the k-mer encoded indexes, and the $k_{MESS}$-mer encoded message segments, such that all payloads will have the form ST for some S in the code words {$S_1, S_2, \ldots, S_N$} and some T in the code words {$T_1, T_2, \ldots, T_Q$}. Upon retrieval of such a payload, (ST)', a variety of suitable heuristic or optimal alignment methods and hash-based indexed lookup methods may be used to align the possibly corrupted payload sequence (ST)' to the all possible ST pairs, allowing up to an edit distance of m on the S aligned k-mer portion, and of $m_{MESS}$ on the T aligned $k_{MESS}$-mer portion. In addition to the foregoing example, many suitable algorithms or variations on algorithms for an alignment method may be utilized, and all such algorithms are considered to be within the scope of the present disclosure. In other exemplary embodiments, a short message segment, such as 1 or a few bases, may be encoded by other ECC means, such as simple repetition codes. These approaches are compatible with the above composite ECC method, of using the Edit Distance ECC for the index set, and a repetition code ECC or other well known ECC for short messages, such as ECC methods for 1 to a few bases or bits, for the short message segment.

Note on error rates: In terms of probability of errors, at least for synthesis, the per base error rate may be, for example, on the order of about 1% for an optimized synthesis method. In exemplary chip-based synthesis approaches as disclosed herein, a dominant error mode is often single base insertions, for example resulting from acid leakage from an acid generating pixel to nearby pixels, producing unwanted deprotection of molecular strands at other pixels, and thus unintended incorporations of a base in those molecular strands (i.e., insertions). Other forms of error, such as those resulting in a deletion, due to incomplete deprotection, can be less likely if deprotection is driven to completion, and substitutions are much less likely, as these errors require multiple process errors to result in a net substitution. Moreover, in a k-mer with error rate p per synthesized base, the probability of exactly m errors is (k choose m) $p^m$ $(1-p)^{k-m}$. For p=1% error rate and various k and m from 0 to 6 errors, this is tabulated below.

| k-mer index | m errors in the k-mer | error rate p | Prob. of m errors |
|---|---|---|---|
| 15 | 0 | 0.01 | 8.60E−01 |
| 15 | 1 | 0.01 | 1.30E−01 |
| 15 | 2 | 0.01 | 9.21E−03 |
| 15 | 3 | 0.01 | 4.03E−04 |
| 15 | 4 | 0.01 | 1.22E−05 |
| 15 | 5 | 0.01 | 2.72E−07 |
| 15 | 6 | 0.01 | 4.57E−09 |
| 20 | 0 | 0.01 | 8.18E−01 |
| 20 | 1 | 0.01 | 1.65E−01 |
| 20 | 2 | 0.01 | 1.59E−02 |
| 20 | 3 | 0.01 | 9.61E−04 |
| 20 | 4 | 0.01 | 4.13E−05 |
| 20 | 5 | 0.01 | 1.33E−06 |
| 20 | 6 | 0.01 | 3.37E−08 |
| 30 | 0 | 0.01 | 7.40E−01 |
| 30 | 1 | 0.01 | 2.24E−01 |
| 30 | 2 | 0.01 | 3.28E−02 |
| 30 | 3 | 0.01 | 3.10E−03 |
| 30 | 4 | 0.01 | 2.11E−04 |
| 30 | 5 | 0.01 | 1.11E−05 |
| 30 | 6 | 0.01 | 4.67E−07 |

The foregoing illustration demonstrates that the ability to correct up to 5 errors drives index corruption rates to below 1 in 1 million levels. In various exemplary embodiments, combined with at least 5× coverage (as discussed above), the resulting systems and methods reduce corruption rates to about 1 in $10^{18}$ levels per base or beyond (i.e., approaching the rates sufficient to store exabytes of data with no expected recovery errors). Moreover, a desired error probability can be achieved through a variety of combinations of coverage-based error correction, with a coverage of C, and Edit Distance based correction of up to m errors, for C and m large enough. The overall scaling of the error rate from these combined effects scales like $p^{(m+C/2)}$, where p is the primary per base error rate, so that increasing m by 1 has comparable effect at error reduction as increasing coverage C by 2, and in any case, these techniques exponentially reduce the overall error rate, and thus provide efficient means to achieve arbitrarily low expected error rates in recovered data, at a cost of little (~3-4.5 m bases) or no payload sequence overhead.

Combined coverage and Edit Distance Error Correction. In many exemplary embodiments, exemplary methods of coverage error correction and Edit Distance error correction are combined, using coverage to correct aggregated reads from the same source (index) sequence, and using Edit distance ECC to correct errors in the indexes, and separately again on the message segments, or other ECC on the message segments. The use of Edit Distance correction on at least the indexes has the added benefit that the extra sequence diversity provides the distance between sequences needed to aggregate them properly (as coming from a common source sequence), prior to consensus correction, as disclosed above in the discussion of coverage-based methods. Thus, it is a benefit of combining exemplary coverage and distance methods that the distance encoded indexes are synergistic to successful coverage correction. Accordingly, in certain exemplary embodiments utilizing these combined methods, the coverage level C may be 2, 3, 4, 5, 6, 7, or up to 10, or up to 20, and them internal error correction capacity of indexes or payloads may be 2, 3, 4, 5, 6 or up to 10, or more. Exemplary error correction used on the short message segments may be m of 1, 2, or 3 for segments of 1 to a few, and similar to that for the index for longer segments. Additionally, in some exemplary embodiments, the short message segment may use a triplet repeat code, or other ECC suited to short strings of 1 to a few letters, such as up to 2, 4, 8, 16 or 32 DNA sequence letters. The table below illustrates a theoretical estimate of post-correction error rates, assuming a situation where the primary per base error rate for sequence is p (from all sources, writing, storing, and reading), all such errors are random and independent, a net m-Edit Distance ECC is used to perfectly correct payloads of length L having ≤m errors, and that all numbers of errors beyond this, ≥m+1 . . . L survive, and that then the minimal coverage level C is then used to correct remaining errors that occur at this residual rate, p' (which may be much less than p, since it is of the order of the probability of m+1 errors, $p^{(m+1)}$ times the resulting density of such m+1 errors in L, (m+1)/L), such that an error only survives if it aligns to provide an error in at least C/2 of the coverage of C at a certain base position. In various exemplary embodiments, error rates may be modeled as: the rate of surviving errors after the m-Edit Distance correction is p'=Sum[j=m+1, . . . , L; (j/L)(L choose j) $p^j$ $(1-p)^{(L-j)}$], and the rate of errors per base surviving coverage correction is Sum[j=C/2, . . . C; (C choose j) $p'^j$ $(1-p')^{(C-j)}$]; the length of the data payload segment with m-Distance error correction is approximately L=k+S+4.5m, where S is the base length of the message segments; the total indexing capacity is $N=4^k$, total storage capacity is N2S bits, or $Log_2$[N2S]/8 Bytes, the bit density per base is 2S/(k+S+4.5m), and the bit density per read out base is divided by C, 2S/(k+S+4.5m)/C. Survey: Error rates and storage capacity are summarized in the following tables, surveying L (synthesis length, derived), k+4.5m (index length, derived), S (length of message segment, 1, 2, 3, 5, 10, 20, 30, 50, 100), p=0.01, k (storage capacity, 10, 15, 20, 25, 30, 40), and m (error correction, 0, 1, 2, 3, 5, 10), and coverage (1, 2, 3, 5, 10, 20), and bit density per base, and per read bases.)

The tables below illustrate parameters that, as implemented in exemplary embodiments, provide for Exabyte storage capacity, Petabyte, and Terabyte, with less than one bit error. For Exabyte, the DNA payload (=on-chip synthesis length) can be as short as a 43-mer, and the message segments are just 4 bases. This utilizes high coverage (C=13) to eliminate errors. For more moderate coverage, payload lengths of lengths between 70 and 80 are utilized. For the Petabyte scale, it is possible to have payload lengths of about 39, and coverage of 11, or payload lengths in the low 50's, and coverage of 5. For the Terabyte scale, payloads in the low 30's are readily possible, with coverage of 9.

TABLE 1

Exabyte Scale Capacity with <1 bit error

| m | C | k | S | L Payload | bit/base | bit/base/read | Capacity (Byte) | Error rate (per base) |
|---|---|---|---|---|---|---|---|---|
| 2 | 13 | 30 | 4 | 43 | 0.19 | 0.014 | 1.2*10^(18) | 9.5*10^(−20) |
| 2 | 13 | 30 | 5 | 44 | 0.23 | 0.017 | 1.4*10^(18) | 1.3*10^(−19) |
| 2 | 15 | 30 | 10 | 49 | 0.41 | 0.027 | 2.9*10^(18) | 1.5*10^(−21) |
| 3 | 11 | 30 | 10 | 54 | 0.37 | 0.034 | 2.9*10^(18) | 8.2*10^(−21) |
| 4 | 9 | 30 | 10 | 58 | 0.34 | 0.038 | 2.9*10^(18) | 1.5*10^(−21) |
| 4 | 10 | 30 | 10 | 58 | 0.34 | 0.034 | 2.9*10^(18) | 2.9*10^(−21) |

TABLE 1-continued

Exabyte Scale Capacity with <1 bit error

| m | C | k | S | L Payload | bit/base | bit/base/read | Capacity (Byte) | Error rate (per base) |
|---|---|---|---|---|---|---|---|---|
| 5 | 7 | 30 | 5 | 58 | 0.17 | 0.025 | $1.4*10^{(18)}$ | $1.9*10^{(-21)}$ |
| 5 | 7 | 30 | 10 | 63 | 0.32 | 0.046 | $2.9*10^{(18)}$ | $9.2*10^{(-21)}$ |
| 7 | 5 | 30 | 10 | 72 | 0.28 | 0.056 | $2.9*10^{(18)}$ | $4.4*10^{(-21)}$ |
| 10 | 3 | 30 | 4 | 79 | 0.1 | 0.034 | $1.2*10^{(18)}$ | $1.4*10^{(-20)}$ |
| 10 | 3 | 30 | 5 | 80 | 0.13 | 0.042 | $1.4*10^{(18)}$ | $1.8*10^{(-20)}$ |
| 10 | 3 | 30 | 10 | 85 | 0.24 | 0.078 | $2.9*10^{(18)}$ | $5.9*10^{(-20)}$ |
| 11 | 3 | 30 | 10 | 90 | 0.22 | 0.074 | $2.9*10^{(18)}$ | $9.5*10^{(-22)}$ |

TABLE 2

Petabyte Scale Capacity with <1 bit error

| m | C | k | S | L Payload | bit/base | bit/base/read | Capacity (Byte) | Error rate (per base) |
|---|---|---|---|---|---|---|---|---|
| 1 | 15 | 25 | 4 | 34 | 0.24 | 0.016 | $1.1*10^{(15)}$ | $2.5*10^{(-17)}$ |
| 1 | 15 | 25 | 5 | 35 | 0.29 | 0.019 | $1.4*10^{(15)}$ | $3.1*10^{(-17)}$ |
| 1 | 15 | 25 | 10 | 40 | 0.51 | 0.034 | $2.8*10^{(15)}$ | $7.7*10^{(-17)}$ |
| 2 | 11 | 25 | 4 | 38 | 0.21 | 0.019 | $1.1*10^{(15)}$ | $1.0*10^{(-17)}$ |
| 2 | 11 | 25 | 5 | 39 | 0.26 | 0.023 | $1.4*10^{(15)}$ | $1.3*10^{(-17)}$ |
| 2 | 11 | 25 | 10 | 44 | 0.45 | 0.041 | $2.8*10^{(15)}$ | $5.0*10^{(-17)}$ |
| 3 | 9 | 25 | 10 | 49 | 0.41 | 0.046 | $2.8*10^{(15)}$ | $3.7*10^{(-18)}$ |
| 3 | 10 | 25 | 10 | 49 | 0.41 | 0.041 | $2.8*10^{(15)}$ | $7.3*10^{(-18)}$ |
| 4 | 7 | 25 | 10 | 53 | 0.38 | 0.054 | $2.8*10^{(15)}$ | $4.1*10^{(-18)}$ |
| 5 | 5 | 25 | 4 | 52 | 0.16 | 0.031 | $1.1*10^{(15)}$ | $4.1*10^{(-17)}$ |
| 5 | 5 | 25 | 5 | 53 | 0.19 | 0.038 | $1.4*10^{(15)}$ | $5.4*10^{(-17)}$ |
| 8 | 3 | 25 | 4 | 65 | 0.12 | 0.041 | $1.1*10^{(15)}$ | $2.2*10^{(-17)}$ |
| 8 | 3 | 25 | 5 | 66 | 0.15 | 0.051 | $1.4*10^{(15)}$ | $2.8*10^{(-17)}$ |
| 8 | 3 | 25 | 10 | 71 | 0.28 | 0.094 | $2.8*10^{(15)}$ | $8.9*10^{(-17)}$ |
| 9 | 3 | 25 | 10 | 76 | 0.26 | 0.088 | $2.8*10^{(15)}$ | $1.4*10^{(-18)}$ |
| 1 | 15 | 25 | 4 | 34 | 0.24 | 0.016 | $1.1*10^{(15)}$ | $2.5*10^{(-17)}$ |
| 1 | 15 | 25 | 5 | 35 | 0.29 | 0.019 | $1.4*10^{(15)}$ | $3.1*10^{(-17)}$ |
| 1 | 15 | 25 | 10 | 40 | 0.51 | 0.034 | $2.8*10^{(15)}$ | $7.7*10^{(-17)}$ |

TABLE 3

Terabyte Scale Capacity with <1 bit error

| m | C | k | S | L Payload | bit/base | bit/base/read | Capacity (Byte) | Error rate (per base) |
|---|---|---|---|---|---|---|---|---|
| 1 | 11 | 20 | 4 | 29 | 0.28 | 0.026 | $1.1*10^{(12)}$ | $1.0*10^{(-13)}$ |
| 1 | 11 | 20 | 5 | 30 | 0.34 | 0.031 | $1.4*10^{(12)}$ | $1.2*10^{(-13)}$ |
| 1 | 13 | 20 | 10 | 35 | 0.58 | 0.045 | $2.7*10^{(12)}$ | $2.9*10^{(-15)}$ |
| 2 | 9 | 20 | 5 | 34 | 0.29 | 0.033 | $1.4*10^{(12)}$ | $1.9*10^{(-15)}$ |
| 2 | 9 | 20 | 10 | 39 | 0.51 | 0.057 | $2.7*10^{(12)}$ | $6.6*10^{(-15)}$ |
| 2 | 10 | 20 | 4 | 33 | 0.24 | 0.024 | $1.1*10^{(12)}$ | $2.8*10^{(-15)}$ |
| 2 | 10 | 20 | 5 | 34 | 0.29 | 0.029 | $1.4*10^{(12)}$ | $3.7*10^{(-15)}$ |
| 2 | 10 | 20 | 10 | 39 | 0.51 | 0.051 | $2.7*10^{(12)}$ | $1.3*10^{(-14)}$ |
| 3 | 7 | 20 | 10 | 44 | 0.46 | 0.066 | $2.7*10^{(12)}$ | $2.5*10^{(-15)}$ |
| 4 | 5 | 20 | 4 | 42 | 0.19 | 0.038 | $1.1*10^{(12)}$ | $4.3*10^{(-15)}$ |
| 4 | 5 | 20 | 5 | 43 | 0.23 | 0.047 | $1.4*10^{(12)}$ | $5.6*10^{(-15)}$ |
| 4 | 5 | 20 | 10 | 48 | 0.42 | 0.083 | $2.7*10^{(12)}$ | $2.0*10^{(-14)}$ |
| 6 | 3 | 20 | 4 | 51 | 0.16 | 0.052 | $1.1*10^{(12)}$ | $3.6*10^{(-14)}$ |
| 6 | 3 | 20 | 5 | 52 | 0.19 | 0.064 | $1.4*10^{(12)}$ | $4.5*10^{(-14)}$ |
| 7 | 3 | 20 | 10 | 62 | 0.33 | 0.11 | $2.7*10^{(12)}$ | $2.2*10^{(-15)}$ |
| 1 | 11 | 20 | 4 | 29 | 0.28 | 0.026 | $1.1*10^{(12)}$ | $1.0*10^{(-13)}$ |
| 1 | 11 | 20 | 5 | 30 | 0.34 | 0.031 | $1.4*10^{(12)}$ | $1.2*10^{(-13)}$ |
| 1 | 13 | 20 | 10 | 35 | 0.58 | 0.045 | $2.7*10^{(12)}$ | $2.9*10^{(-15)}$ |

Chip-Level Indexing with Prefabricated Indexes. In various exemplary embodiments of DNA synthesis chips for DNA data storage systems, a chip having N pixels has a corresponding set of N k-mer index sequences $S=\{S_1, S_2, \ldots, S_N\}$ synthesized onto the N pixels of the chip, with index $S_i$ at pixel i, and synthesized using a disclosed electrochemical synthesis methods for such a chip, and produced in a first phase of synthesis synthesizing the k-mer indexes, and such that the message segments of DNA data payloads are synthesized in a second phase of synthesis, extending from these indexes. A chip with this index set S pre-synthesized on the pixels in the prescribed order may be referred to as an "S-chip." In exemplary embodiments, a message to be stored does not have to be specified until the second phase of synthesis on the S-chip. In exemplary embodiments for DNA data storage applications, an S-chip is mass produced in a multiplicity of copies. In exemplary embodiments, this mass production may be performed using more efficient industrial processes than are used on DNA data storage synthesis systems running S-chips, such as having high volume flow cells containing many chips undergoing index synthesis, and such as reusing or recycling reagents for such chips, or such as performing reagent exchange by moving the chip from reagent vat to reagent vat, rather than by pumping reagents into flow cells (i.e., chip physical transfer for chemistry cycles instead of solution transfer). In some exemplary embodiments, presynthesized indexes S are indexes that comprise error correcting codes. In exemplary embodiments, presynthesized indexes S are indexes that comprise error correcting codes using the Edit Distance methods, allowing corrections of up to m errors, m>0, as disclosed above and in FIG. 73G. In exemplary embodiments, the S-chips use an index set composed of short k-mer indexes, for example of length k less than 10, less than 15, less than 20, less than 25, less than 30, or less than 40, or less than 50. Moreover, in exemplary embodiments, the S-chip is provided with an external "volume" index set of sequences and associated physical oligos, $V=\{V_1, V_2, \ldots, V_i, \ldots, V_Z\}$, of size Z, which in exemplary embodiments are synthesized by other suitable approaches, such as classical DNA synthesis or in other contexts on chip, and a mechanism for joining in these volume level index oligos to the payload products from the S-chip. Additionally, in exemplary embodiments a volume index is joined by ligation to the pooled products post synthesis, or by inclusion of the volume index in the chip start site functionalization of an S-chip, such that subsequent synthesis includes these segments in the resulting products. In such exemplary embodiments, the provided volume index set is a set of h-mer indices $V=\{V_1, V_2, \ldots, V_i, \ldots, V_Z\}$ of size Z, and without substantial limit in the number of such indexes, through choice of large enough h-mer lengths. In exemplary embodiments, the volume index set V comprises error correction in the choice of these sequences. In exemplary embodiments directed to data storage methods, through the use of these exemplary volume indexes, replicates of the S-chip can be used to perform synthesis of payloads for the storage of data with no capacity limit on the amount of data to be so stored, by combining the limited indexing capacity, N, of the S-chip, with the unlimited indexing capacity, Z, of the volume index set V. In an exemplary embodiment of such a method for storing unlimited data in DNA, a DNA storage system is populated and repopulated as needed by S-chips, that are either pre-functionalized by per-chip volume indexes of $V_1, V_2, \ldots$, or are post-ligated with such volume indexes, for any number of desired volume indexes, such that the finished products of S-chip message synthesis and volume indexing are messages that can be designated (indicating the affiliation of indexes and message segments, but not implying the physical oligo structure) $V_iS_jM_{ij}$, for $i=1\ldots$, and $j=1\ldots N$, where $M_{ij}$ are the message segments synthesized at pixel index $S_j$ of the chip affiliated with the volume index Vi. The total size of a message that can be stored in these embodiments is therefore up to the size of NZ, and thus has no limit related to (i.e., is independent of) the S-chip index set size N, because the volume index size Z can be chosen to be as large as desired, without limit. In other exemplary embodiments, the indexes of S need not be k-mers of the same length k, and there can be any lengths, such as length $k_i$ for index $S_i$, where $k_i$ are in some range, $k_{min} \leq k_i \leq k_{max}$.

Chip-set and blade-level indexing prefabricated indexes. In various exemplary embodiments of DNA synthesis chips for DNA data storage systems, there is an index set $S=\{S_1, S_2, \ldots, S_N\}$, and there is a "chip-set" of P synthesis chips of the same design and form and type, i.e. manufactured copies of the same chip, which have a total of N pixels, and the pixels across the P chips have been numbered i=1 . . . N in a standardized scheme, and the indexes are pre-synthesized onto the N pixels of these chips, with index $S_i$ at pixel i, and synthesized using exemplary disclosed electrochemical synthesis methods for such chips, and produced in a first phase of synthesis synthesizing said k-mer indexes, and such that the message segments of DNA data payloads can be synthesized in a second phase of synthesis, extending from these indexes. The chip-set with said index set S presynthesized ion onto the pixels of the P chips in the prescribed order and spatial layout may be referred to as the "S-chip-set", and this is described as a chip-set with pre-synthesized indexes. The S-chip-set has associated embodiments and methods that carry over directly from those disclosed above for the S-chip, and all such suitable disclosures are encompassed here, without directly repeating them. In exemplary embodiments, the S-chip set may be the chip set for a blade of a multi-chip or rack-mounted DNA data storage system.

Unlimited Data Storage Capacity with Short On-Chip Synthesis. In various exemplary embodiments, data payloads synthesized on chip have their unique on chip, per pixel indexes, which are unique across all pixels on a chip, chip-set, or blade of chips, and such payloads are then further affiliated with additional index segments that provide a common index at the whole chip-level, whole chip-set-level, or whole blade-level, where such indexes are not synthesized on chip. Moreover, in exemplary embodiments, such common indexes are added by ligation post-synthesis, preferably off-chip after fragments are released, or in other exemplary embodiments, these common indexes are functionalized onto the chip or chipset to provide start sites for synthesis at their termini, such that the result is the payload is that synthesized onto them, starting from their termini, and resulting in a DNA strand comprising the common index. Such common indexes fabricated outside of on-chip synthesis may be thought of as providing a volume-level index for storage volumes, where such volumes in exemplary embodiments are all the DNA payload products from a single chip, a multi-chip set, or a blade of chips. Because the capacity of these external volume indexes is effectively unlimited, in these exemplary embodiments there is no limit to the storage capacity of what can be generated by synthesis chips, even when the length of the DNA data payloads is kept bounded, and in exemplary embodiments, relatively short. In exemplary embodiments comprising such volume indexing systems, the storage capacity is essentially unlimited (such as exceeding any of TB, PB, EB, ZB or YB capacity), while the on-chip data payloads synthesized have lengths less than or equal to 15 bases, less than or equal to 20, less than or equal to 25, less than or equal to 30, less than or equal to 35, less than or equal to 40, less than or equal to 50, or less than or equal to 60 bases. In addition, in various exemplary embodiments, this can be accomplished while controlling the total number of bit errors expected per EB to be <100, <10, <1, <0.1, or <0.01, or <0.001, with payload lengths that are less than or equal to 20 bases, less than or equal to 25, less than or equal to 30, less than or equal to 35, less than or equal to 40, less than or equal to 45, less than or equal to 50, or less than or equal to 60 bases. In such exemplary embodiments, combinations of coverage-based error correction and edit distance-based error correction are used to control error rates while keeping data payloads short.

Chip Reuse for Digital Data Storage. In exemplary embodiments comprising chip-based DNA synthesizers for DNA data storage applications, chips are reused for synthesis and undergo various levels of refurbishing in place to restore them for a next round of DNA payload synthesis. In exemplary embodiments, after each application of a chip to synthesize a set of DNA data payloads, such products are released and the chip undergoes a standard in-line prep for a next round of DNA strand synthesis, which includes a quality assessment prior to initiating the next round of synthesis. In exemplary embodiments, these processes are fully automated and occur in-place on the instrument or blade. If a chip fails this quality assessment, the chip may, in exemplary embodiments, undergo a repetition of the prep process, or may undergo a more extensive refurbishing process, or may be retired from use. In exemplary embodiments, each chip of the system, such as in a single chip or multi-chip blade system, also has its synthesis performance monitored in real time, either during synthesis or in a pre-synthesis assessment, for example by monitoring diverse synthesis quality parameters that can be monitored with the on-chip monitoring, such as current to anodes during acid generation, impedance spectroscopy of products, or the like. If such monitoring indicates chip performance not meeting a desired specification, the chip is taken off-line, to undergo a more extensive cleaning and re-functionalization process. The standard prep protocol, in exemplary embodiments, may include any of the cleaning and re-functionalization processes as disclosed below. Additionally, when a significant decline in performance is detected, or in other exemplary embodiments at a pre-scheduled time, the chip is taken off-line from synthesis, while remaining in place in the instrument, or blade, either after a synthesis run is complete and products are released, or, if during synthesis, the sequences in process may be released and discarded, and such sequences assigned to a future chip run of the same or another chip. Once offline, while still in place, the chip undergoes a series of cleaning and re-functionalizing processes. In exemplary embodiments, cleaning processes may be to clean the metal electrodes, or may be to clean the surface or region where DNA synthesis occurs, such as for example cleaning an oxide or nitride surface on which the synthesis is performed. Depending on the composition of the electrodes and DNA synthesis region and matrix, many such possible cleaning protocols are known which may be used in these steps, including electrochemical cleaning methods for the electrodes, which may involve sweeping the voltages on anode and cathode in suitable cleaning solutions, as well as chemical cleaning with acids or bases or other cleaning solutions. Many such suitable cleaning procedures are known and are considered to be within the scope of this disclosure.

Additionally, in exemplary embodiments, such cleaning treatments may involve light exposure or UV exposure, using onboard sources, to clean surfaces or to cleave specific photo-cleavable groups. In certain exemplary embodiments, the DNA synthesis region is cleaned to recover the starting oxide or nitride surface, and then reagents are added to re-functionalize the surface with suitable synthesis starting sites, such as for example silanizing the surface, or oxidizing the surface, or depositing other matrices to be used for initiating DNA synthesis. In exemplary embodiments, light exposure or UV exposure, using on-board sources, may be part of a re-functionalization process, such as for curing or crosslinking various materials. In exemplary embodiments, the re-functionalization may include redeposition of chip specific oligomers, such as chip-wide DNA indexes or DNA primers (or precursors of such, such as may be chemically protected or modified to be compatible with the synthesis process), that are integral to the start sites for synthesis, and such that these oligomers contribute to the resulting oligo part that comprises the DNA payload, such as providing for the addition of chip-wide primers or indexes. When the cleaning and re-functionalization process(es) are complete, the chip may undergo a quality assurance test, using on chip monitoring systems, and once this test is passed, the chip may be returned to online status, to engage in a next synthesis process for a next set of DNA payload synthesis, either asynchronously, or synchronously with other chips in an associated system or blade. In exemplary embodiments, such inline re-use processing may be repeated on a chip to reuse the chip for as many runs as needed, for example up to 2 times, up to 3 times, up to 5 times, up to 10 times, up to 20 times, up to 50 times, up to 100 times, or up to 5000 times, or even more, until such chip fails the reuse recycling process quality tests, or until it reaches a pre-determined lifetime of re-use cycles. In exemplary embodiments, the chips on a data storage synthesis system only have to be accessed and replaced, loaded, or off-loaded infrequently, preferably at intervals of greater than 1 day, greater than 3 days, greater than 7 days, greater than 14 days, or greater than 30 days, or greater than 60 days.

Chip Index Reuse for Digital Data Storage. In exemplary embodiments utilizing index sets pre-synthesized for single chips or chip sets, the index sets may be re-used, such that in subsequent re-use cycles for the chip, the index sets are restored to their initial state, without being re-synthesized. Various exemplary embodiments for index re-use are illustrated in FIGS. 73B, 73C, 73D, and 73E. FIG. 73B illustrates exemplary embodiments where the N index oligos synthesized on the pixels of a chip or chip-set are used as hybridization targets for a pool of complementary oligos, complementary to the index oligos, applied in solution to the chip or chip set, such that the oligos are allowed to hybridize to their complements on chip. These oligos further have an extendible end, on which synthesis can start. Post synthesis, the hybridization is melted by chemical or thermal means, to release the synthesized oligos, leaving the index oligos on chip ready for another round of synthesis. Moreover, in exemplary embodiments, these oligos may also provide a cleavable conjugation group such that they can be conjugated in place for stability, and cleaved for removal post synthesis. As shown in FIG. 73C, in exemplary embodiments, orientation of the 3' and 5' ends may be arranged so as to ensure the synthesis of the hybridized start site is facilitated: as shown in FIG. 73C upper left, the on chip pre-synthesized indexes may be synthesized using an alternative chemistry that extends in the 3' direction, such that the incoming oligo can have its 5' end directed away from the chip, to facilitate standard 5'-direction synthesis. Or, as shown at the upper right, the on-chip oligos may be synthesized in the standard 5' direction, and the encoding oligos have their 3' end directed away from the chip, to set up for using an alternative chemistry that extends in the 3' direction. Such chemistries based on phosphoramidite synthesis that extend in the 3' direction are well known in the context of standard phosphoramidite synthesis, and from the disclosures herein, it would it will be appreciated that these may be modified to make use of on-chip electrochemical synthesis as disclosed herein to drive the deprotection for such 3' directed synthesis chemistries, and thereby be able to perform them on chip as set forth for these exemplary embodiments with on chip 3' directed synthesis. In yet another exemplary embodiment, as shown at the bottom of FIG. 73C, only standard 5' directed synthesis is used on chip for the oligos, and to extend the hybridized start sites, and to avoid steric hinderance on the surface, in exemplary embodiments a long linker is used between the on-chip oligo synthesis and the surface, such that when the incoming oligo is hybridized, there is provided for a space between the 5' extendible end and the surface, via the long linker, which allows for efficient 5' directed synthesis on the hybridized oligos.

Figure 73D:
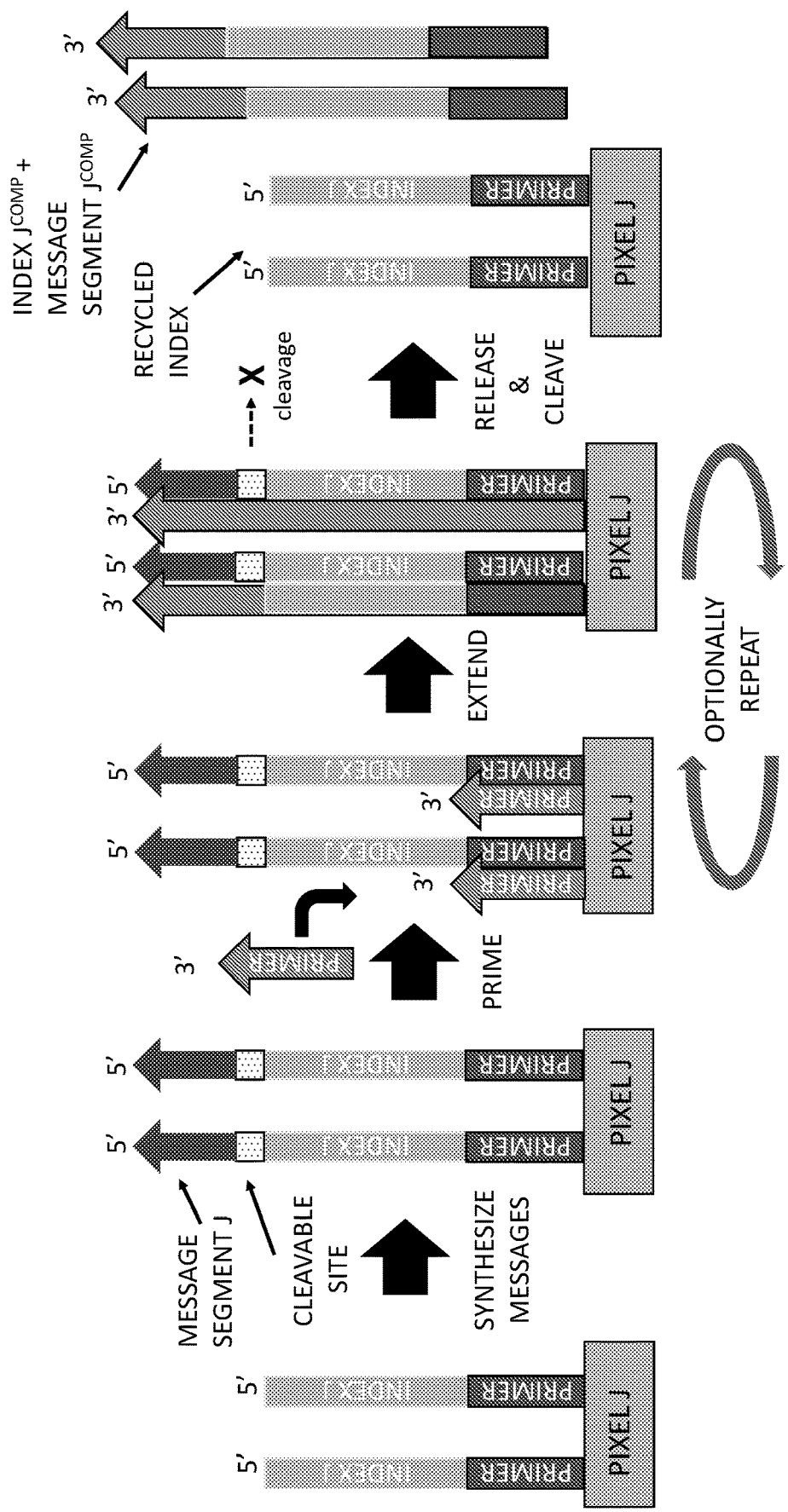
FIG. 73D illustrates re-use of chips with pre-synthesized indexes based on polymerase extension of a universal primer, in accordance with various exemplary embodiments.

With reference now to FIG. 73D, another exemplary embodiment of on-chip index re-use is illustrated. As shown, there is a universal primer oligo on the chip, from which the index extends, and which in exemplary embodiments may have been deposited as part of functionalization of the surface or may have been pre-synthesized on chip along with the index. Synthesis of desired messages proceeds from these indexes, in which the first base has a cleavable site in the backbone, such as photocleavable or chemically cleavable, or heat cleavable or pH cleavable, or another cleavable site, and then the remainder of the payload, i.e., the message segment, is synthesized as shown. Then, the universal primer is introduced and allowed to hybridize as shown, oriented with 3' end for extension. Then, polymerase extension of the primer is performed, and such extended products are released as shown, thereby providing the effective product of the synthesis to be used for DNA data storage. In exemplary embodiments, this process of priming, extending, and releasing can be repeated multiple times, to produce a higher yield of product. Once the extension and release process is completed, the cleavable site is cleaved, and the primer-index strand is restored for a next round of message synthesis. In exemplary embodiments, this strand may be fully restored by a suitable chemical reaction to refurbish the 5' end for synthesis, which may include synthesis of a final base, which can comprise the cleavable site.

Figure 73E:
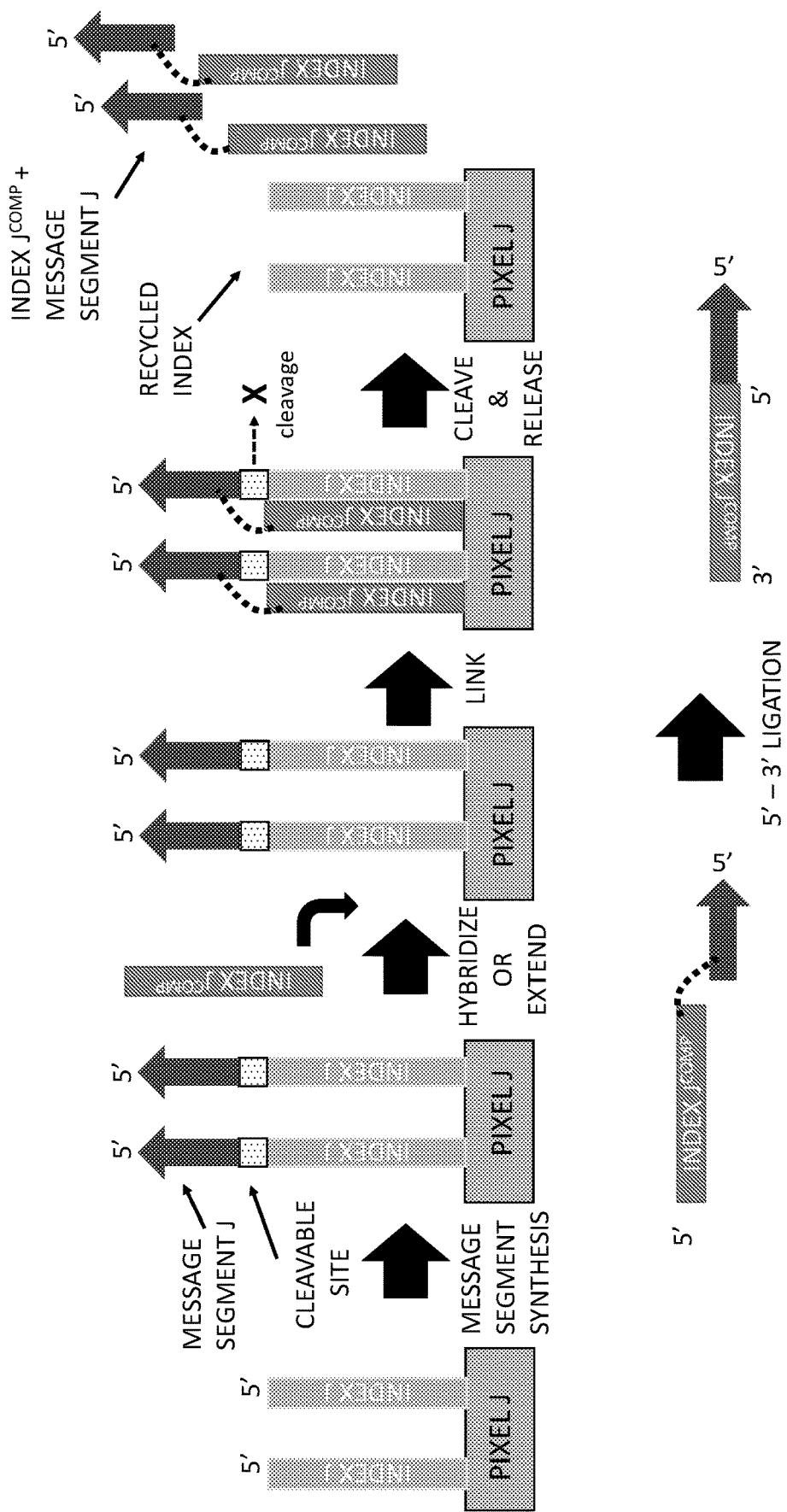
FIG. 73E illustrates re-use of chips with pre-synthesized indexes based on conjugation and ligation, in accordance with various exemplary embodiments.
Figure 73F:
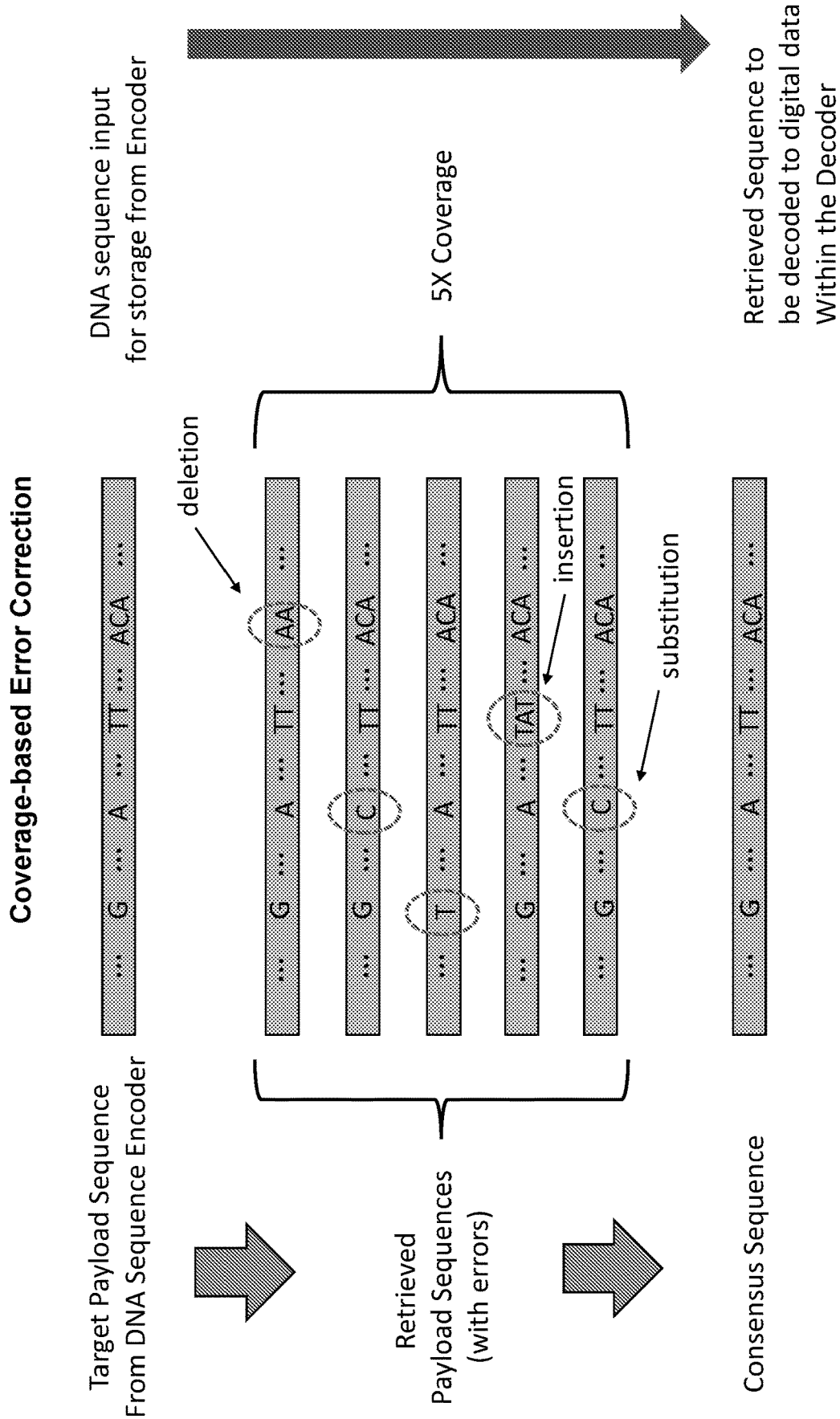
FIG. 73F illustrates a method of error correction using coverage and consensus sequence, in accordance with various exemplary embodiments.
Figure 73G:
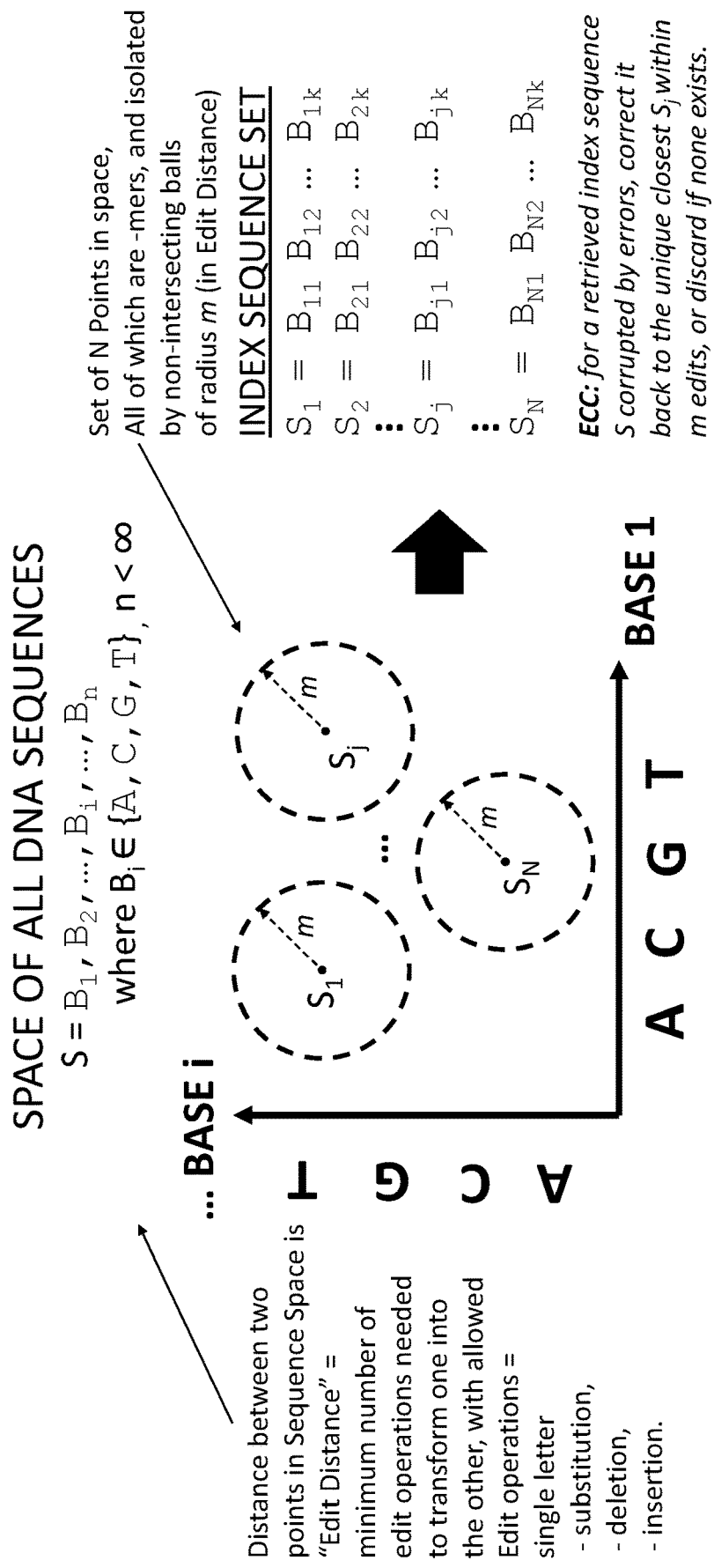
FIG. 73G illustrates a method of error correction suitable for handling up to m errors, based on edit distance, in accordance with various exemplary embodiments.

Turning now to FIG. 73E, yet another exemplary embodiment of on-chip index re-use is illustrated. As shown, the on-chip indexes are extended with a cleavable site before the first base, to have the desired message segments. Incoming complementary index oligos are hybridized to the indexes on chip. Such oligos are further functionalized such that via a linker, they can be conjugated to the message segment, which in exemplary embodiments is synthesized with a suitable cognate conjugation site. Then the cleavable site is cleaved, and the conjugated segments released. Post release, as shown in FIG. 73E bottom, for the pool of all such index-message constructs, the two linker-conjugated segments are ligated to form a single DNA segment comprising the index and message segment, resulting in the desired form for DNA data storage.

From the foregoing index re-use embodiments above, many variations, combinations, modifications, or alternatives for such methods of indexed chip may be understood, and all such are considered to be within the scope of the present disclosure.

Exemplary Chip DNA Synthesis Results and Reduction to Practice

This section presents certain exemplary experimental results directed to elements of the disclosure above for exemplary DNA synthesis chips and related systems and methods. The experimental results herein demonstrate reduction to practice of the fundamental aspects of CMOS chip DNA synthesis, using electrochemical acid generation for the deprotection steps, based on a quinone redox system for acid generation, and also demonstrate reduction to practice of exemplary acid localization methods, in particular use of the cathode for driving removal of acid, creating a controlled acid confinement zone, and eliminating pixel to pixel cross talk.

Figure 74:
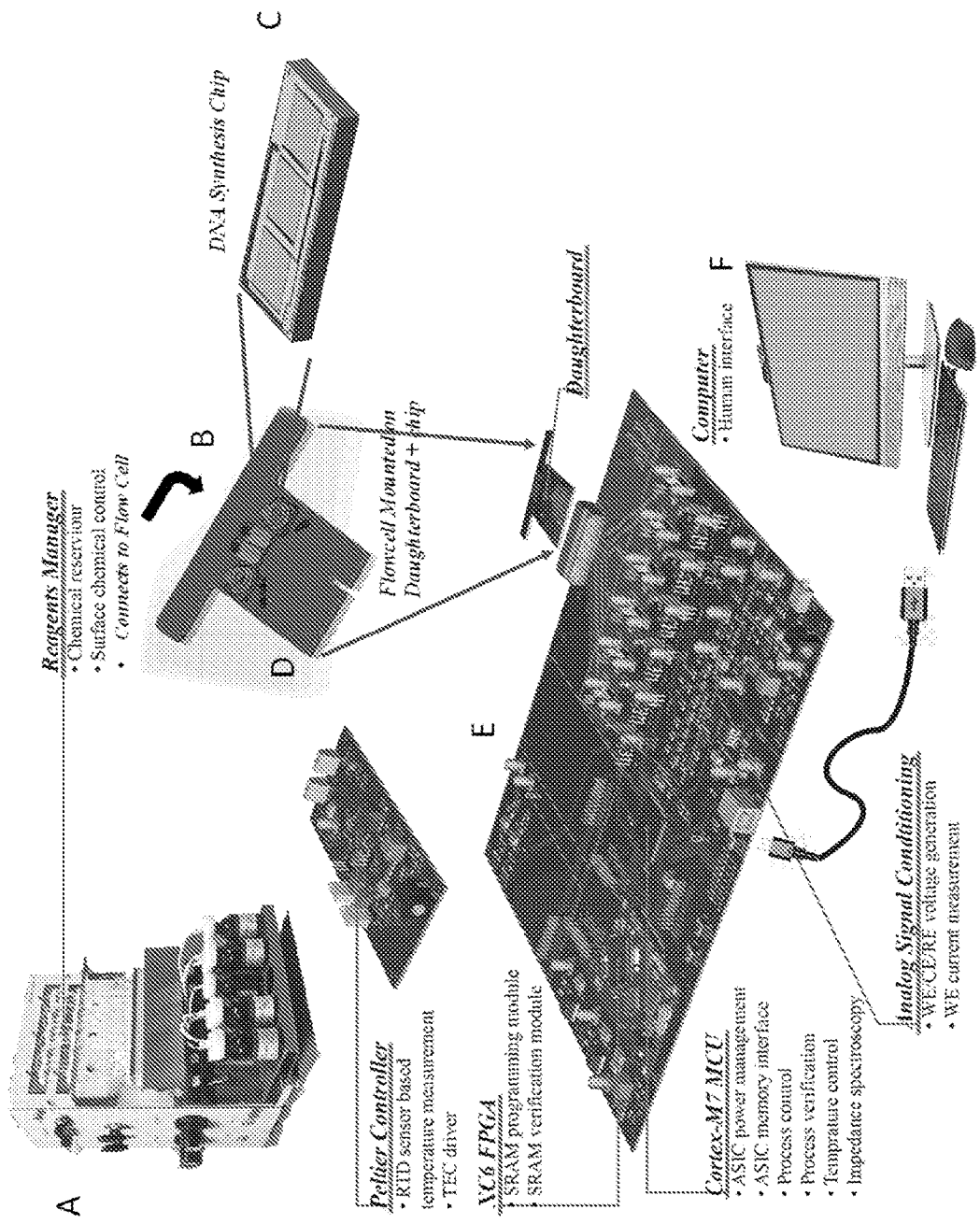
FIG. 74 illustrates a measurement system used to demonstrate DNA synthesis on a CMOS chip device, in accordance with various exemplary embodiments.
Figure 75:
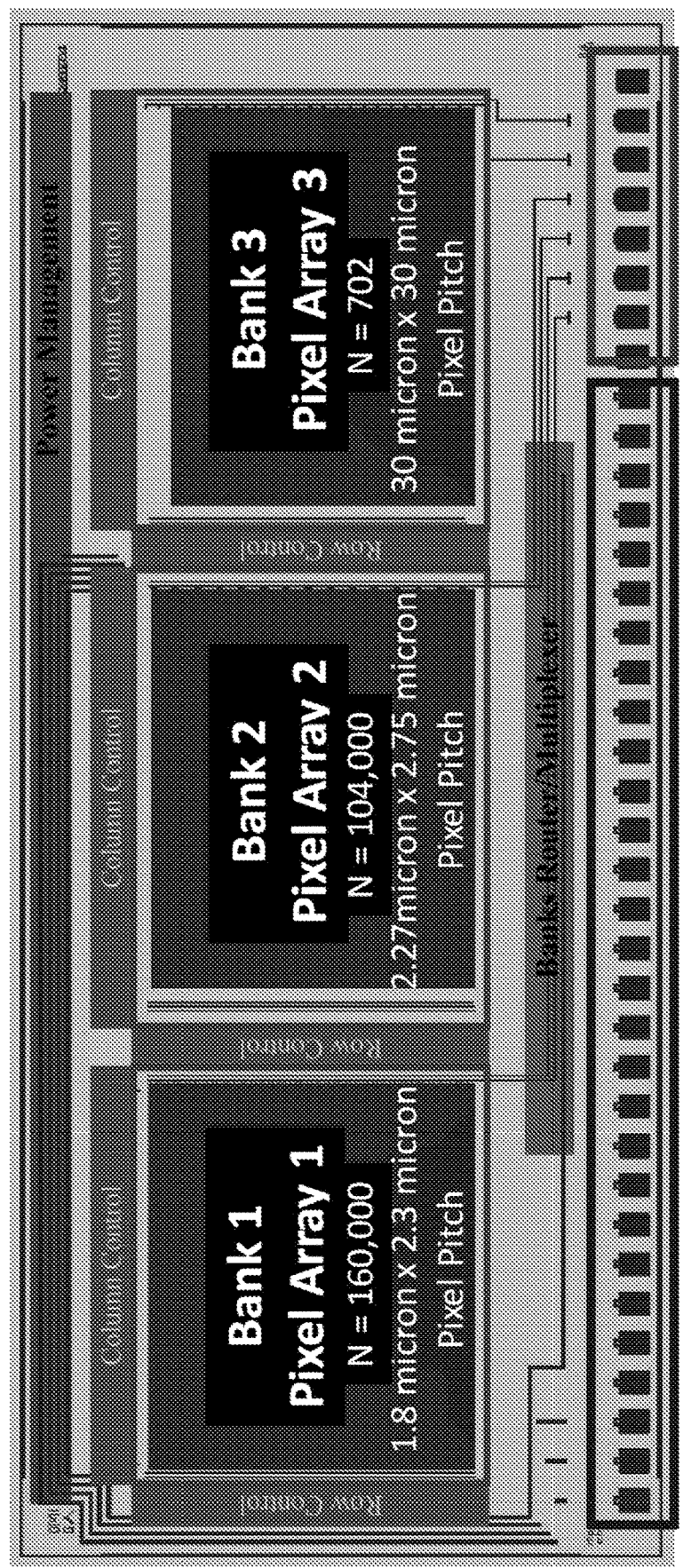
FIG. 75 illustrates a floorplan of an embodiment of a CMOS synthesis chip, in accordance with various exemplary embodiments.

With reference now to FIG. 74, illustrated are elements of an experimental measurement system used to demonstrate an exemplary DNA synthesis chip and functions thereof. This lab system includes a reagent dispensing fluids instrument (A), which drives a flow cell (B) containing a DNA synthesis CMOS chip (C), which is mounted on a daughterboard (D), all of which plugs into a supporting motherboard system (E), communicating with an external computer (F).

FIG. 49 illustrates an exemplary CMOS DNA synthesis chip used in these experiments. This chip has three-pixel arrays, Bank 1, Bank 2, and Bank 3, with respective progressively larger pixel pitches and surface electrode footprints of 1.8-micron×2.3-micron, 2.27-micron×2.75 micron, and 30-micron×30 micron. The number of pixels in each bank array are, respectively, N1=160,000, N2=104,000, and N3=720. The architecture of these pixels, and the chip, and the surface electrodes are reductions to practice of the pixel architecture set forth in FIGS. 42 and 45, the chip architecture set forth in FIGS. 40 and 50, and the pixel top layer planar electrodes as illustrated in FIGS. 54A and 54B.

Figure 76:
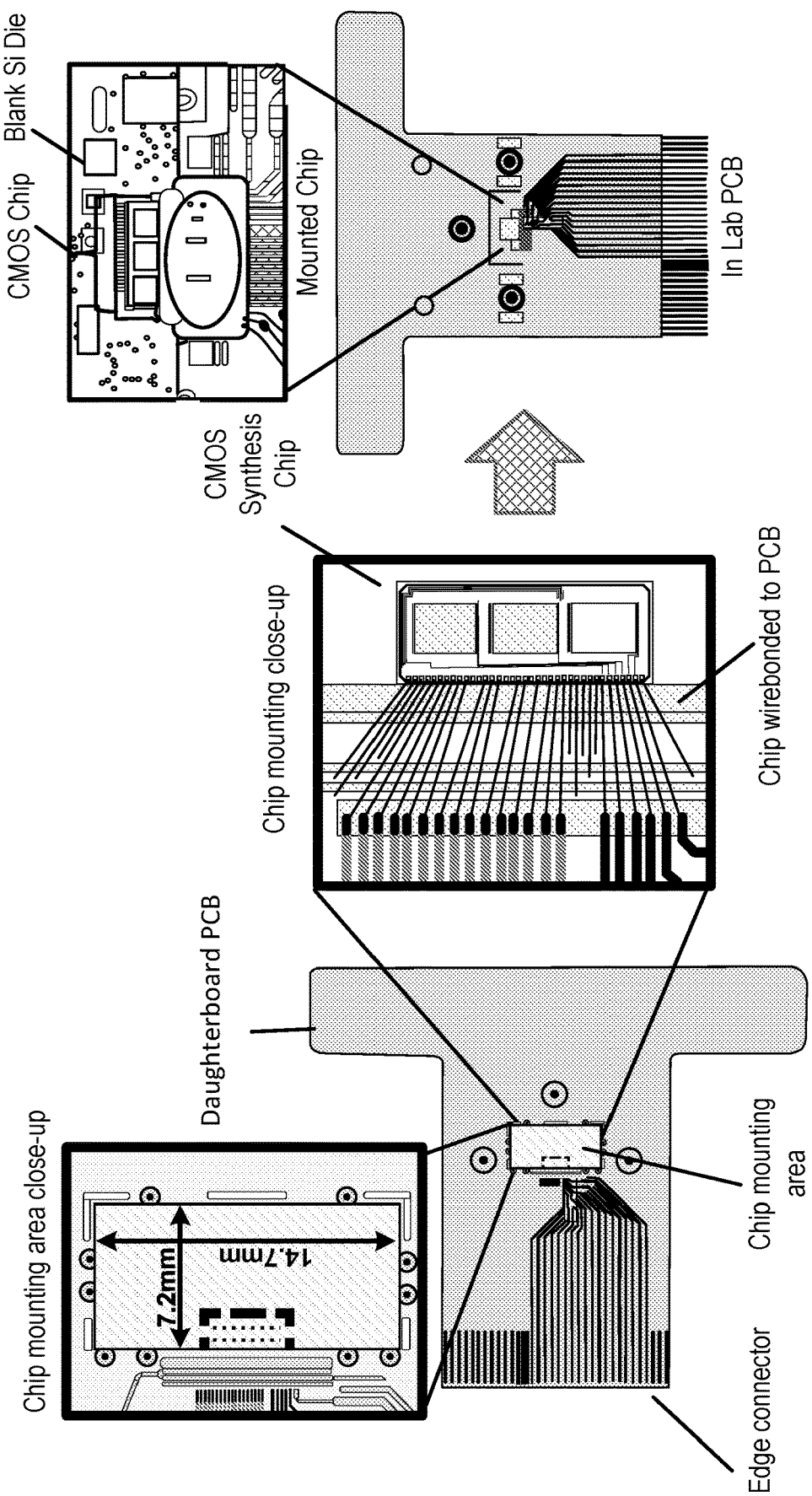
FIG. 76 illustrates a chip daughterboard used to demonstrate DNA synthesis on a CMOS chip device, in accordance with various exemplary embodiments.

FIG. 76 illustrates a daughterboard design used in experimental reduction to practice of certain embodiments, along with the chip mounting and wire bonding schema.

Figure 77:
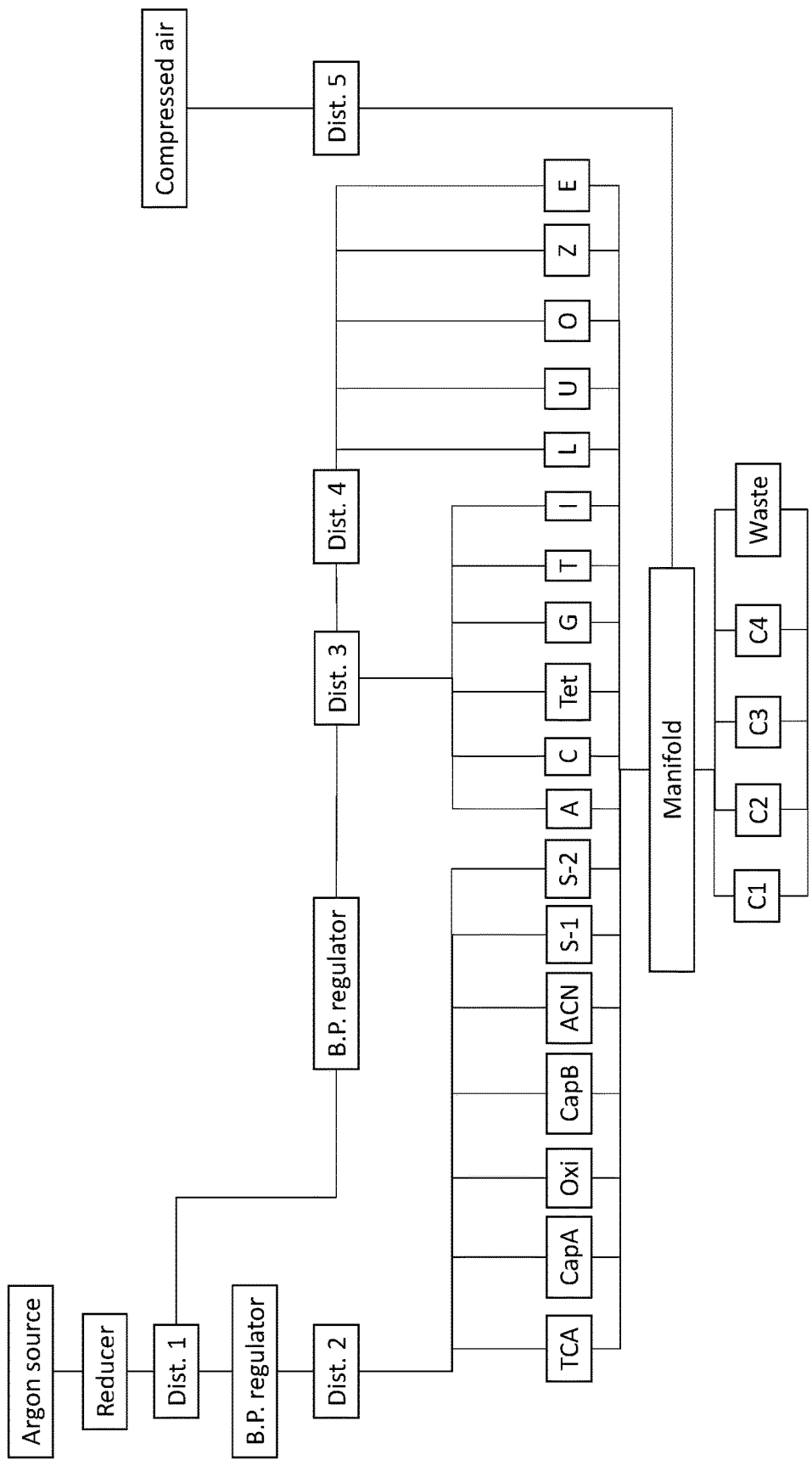
FIG. 77 illustrates a reagent delivery system used to demonstrate DNA synthesis on a CMOS chip device, in accordance with various exemplary embodiments.
Figure 78:
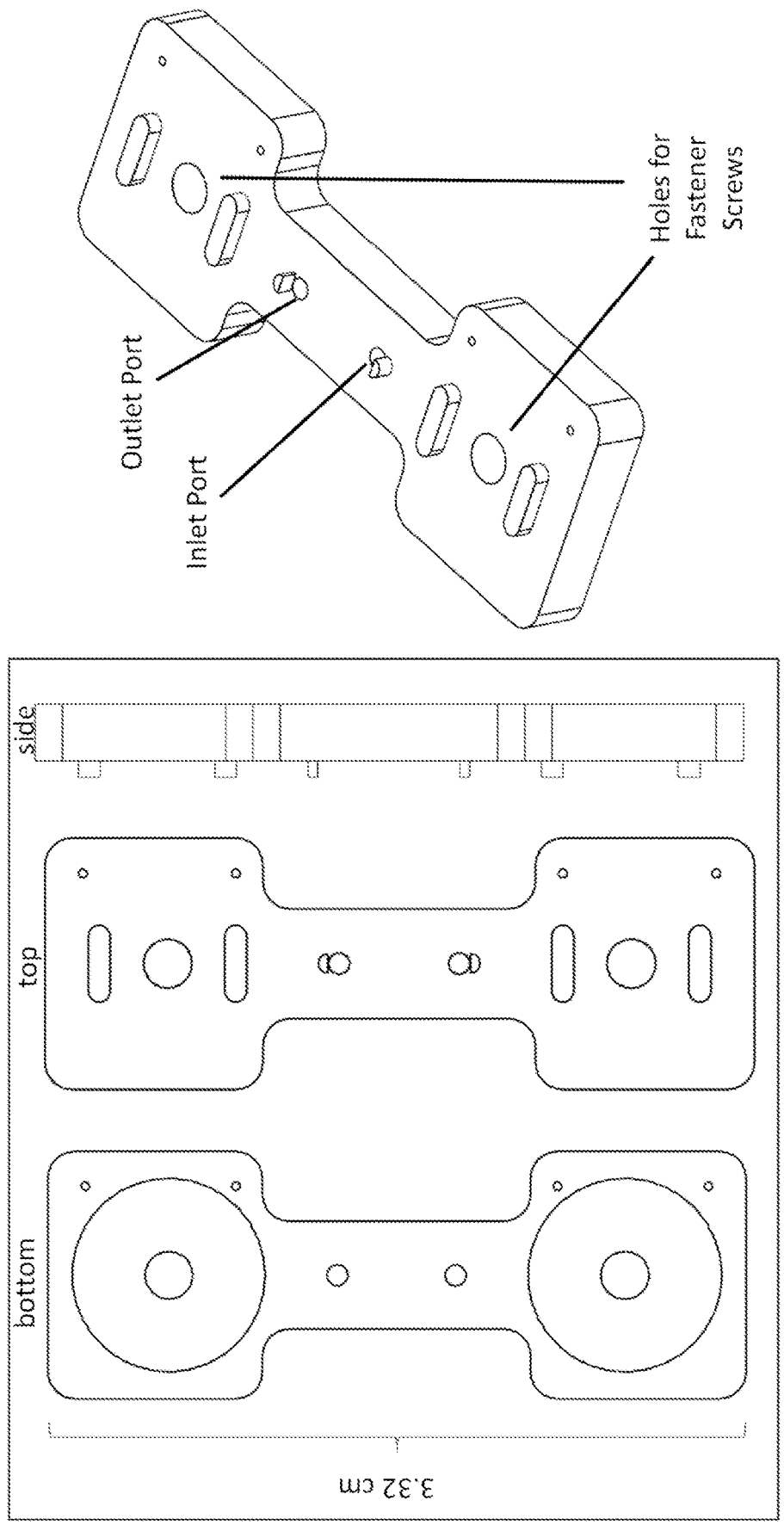
FIG. 78 illustrates a flow cell top-part design for a flow cell used to demonstrate DNA synthesis on a CMOS chip device, in accordance with various exemplary embodiments.
Figure 79:
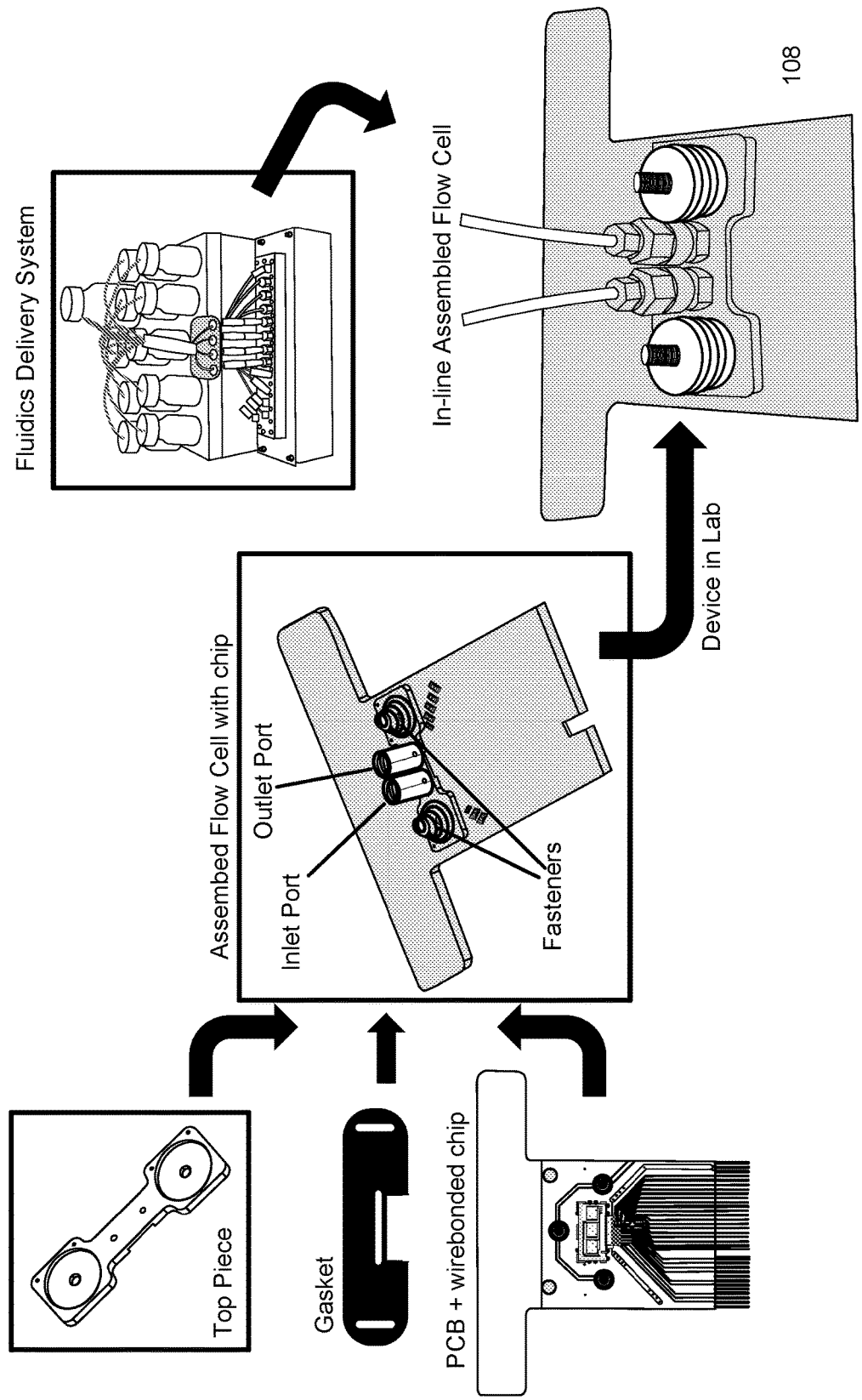
FIG. 79 illustrates an integrated flow cell used to demonstrate DNA synthesis on a CMOS chip device, in accordance with various exemplary embodiments.

FIG. 77 illustrates a reagent delivery fluidics system used in exemplary experiments, along with a schematic functional diagram of this system. This instrument is a commercially available DNA synthesizer for use with the standard phosphoramidite method, with custom modifications used to drive the experimental flow cell for the exemplary experiments. The fluidics system is a commercial K&A S-4 synthesizer. In the diagram, B.P. denotes "backpressure" and "Dist." denotes "distributor." The design of an exemplary flow cell top part is shown in FIG. 78, highlighting the inlet and outlet ports. FIG. 79 illustrates how this exemplary top part is mated to a gasket placed onto the chip mounted on the daughterboard, to form a completed flow cell, which is held together with fastening screws, and fitted with inlet and outlet ports for in-line fluidic connection to a reagent delivery system.

Figure 80A:
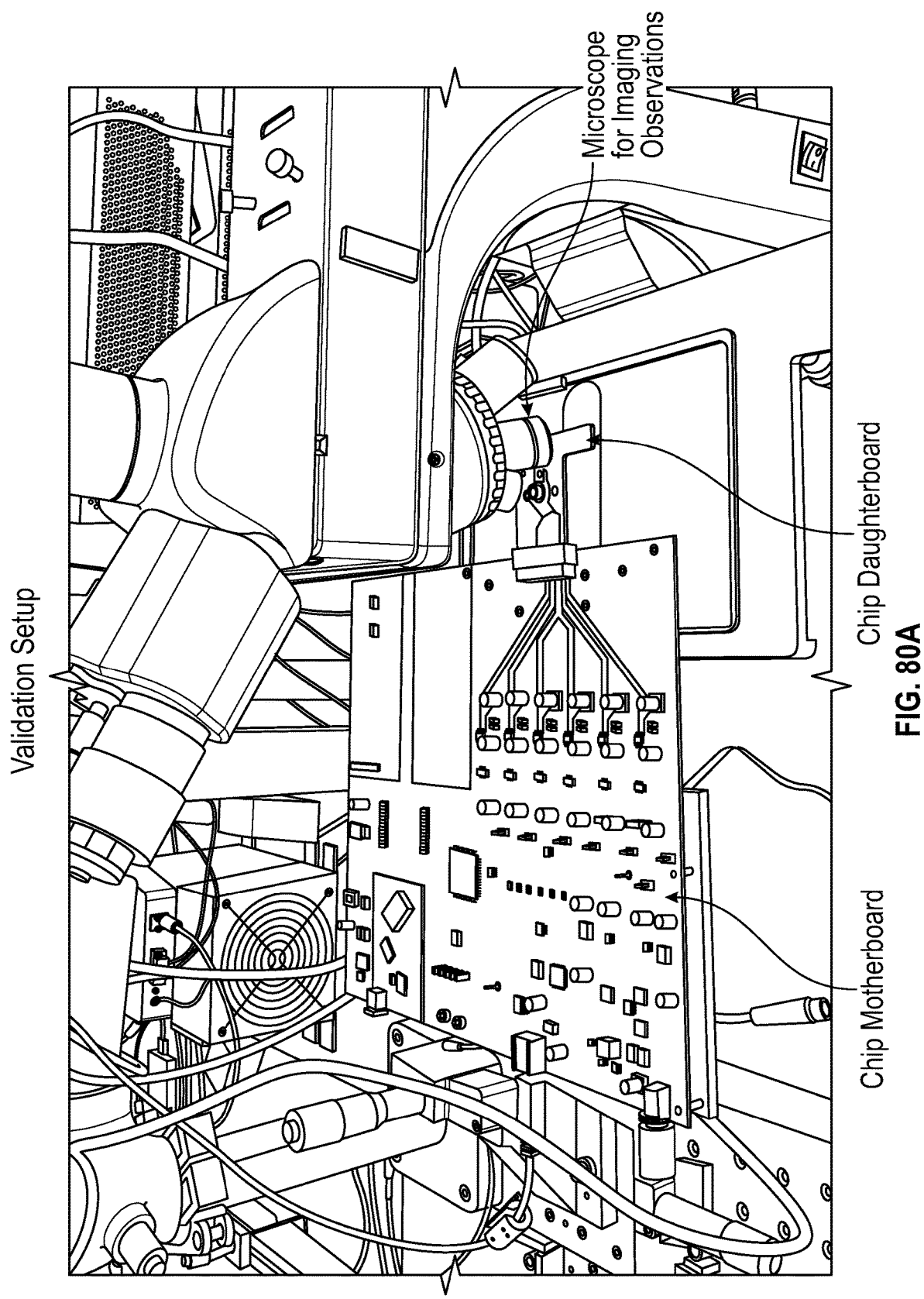
FIG. 80A illustrates an assemblage as used in the lab to demonstrate DNA synthesis on a CMOS chip device, with microscope attached for viewing, in accordance with various exemplary embodiments.
Figure 80B:
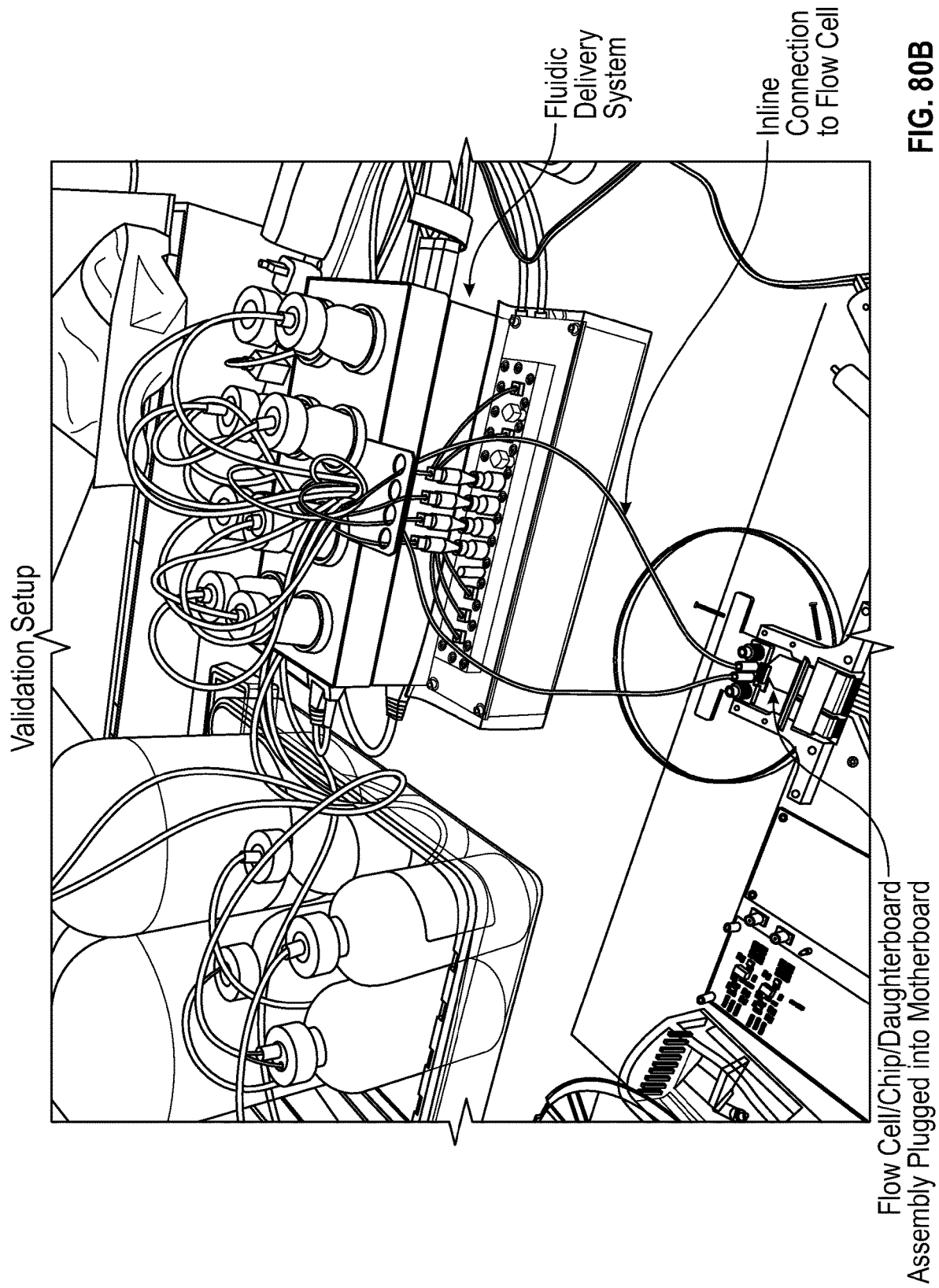
FIG. 80B illustrates an assemblage as used in the lab to demonstrate DNA synthesis on a CMOS chip device, with fluidic delivery system attached, in accordance with various exemplary embodiments.

FIG. 80A shows a complete assemblage as used in exemplary experimental work, in a configuration where an external microscope is mounted over the flow chip/cell area for imaging observations, such as may be done post-synthesis, or for intermediate observations during synthesis (the reagent delivery instrument is not hooked up in this configuration). FIG. 80B illustrates a completed assemblage as used in the exemplary experimental work, in a configuration where the chip flow cell is connected in-line with the fluidics delivery system, as is the case during synthesis reagent delivery cycles.

Figure 82:
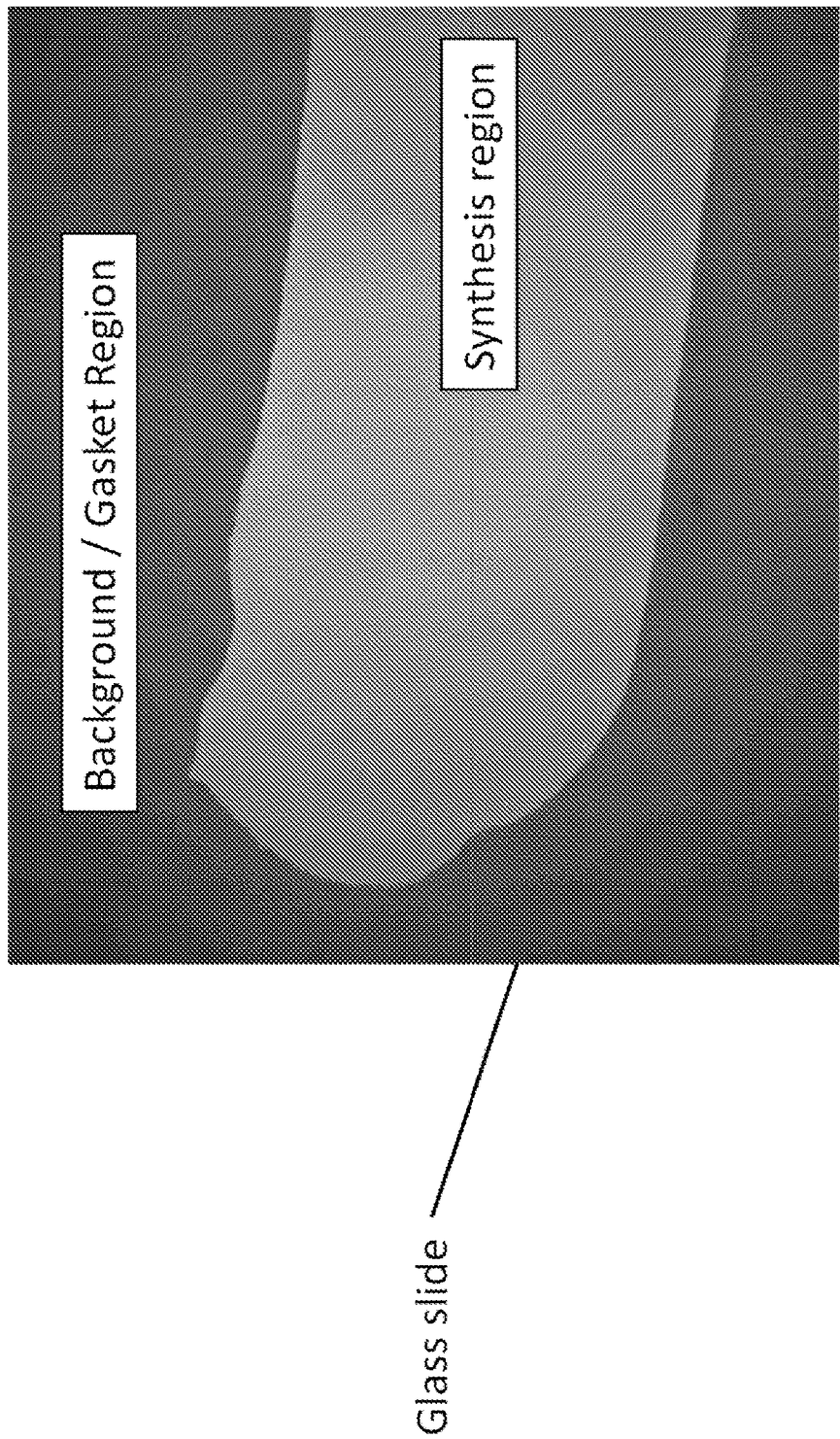
FIG. 82 illustrates a DNA synthesis result on a glass slide, in accordance with various exemplary embodiments.

Positive control experiments were performed to demonstrate the ability to perform standard synthesis on a silanized glass slide. This verified that the phosphoramidite reagents, reagent delivery, flow cell materials, and surface functionalization are all consistent with standard DNA synthesis chemistry. FIG. 81 illustrates an exemplary experimental reagent delivery protocol used to drive the standard phosphoramidite method chemistry with the reagent delivery system. In this protocol 'DCI' denotes dicyanoimidazole and 'DCA' denotes dichloroacetic acid. This protocol was applied to a silanized glass slide, to demonstrate the reference case of standard phosphoramidite method DNA synthesis (with the standard chemical acid deprotection). FIG. 82 illustrates results of one such exemplary experiment, where a 15-mer was synthesized on a glass slide. The synthesis product is visualized in FIG. 82 by hybridization of a complementary oligo that is labelled with a fluorescent dye, followed by fluorescent microscope imaging. This field of view shown depicts the edge of the gasket-covered (dark) area within the custom flow cell, and the bright area where the desired synthesis has occurred. Experimental Method: The experiment used hybridization of 5'-FAM-fluorescently labelled poly-$A_{15}$ oligonucleotide to a poly-$T_{15}$ sequence synthesized on a silanized glass slide. Silanization was conducted by immersing ArrayIt SMC2 slides in a solution composed of 95% ethanol, 5% water, 0.1% acetic acid, and an additional 2% v/v of a hydroxl bearing silane for 4 hours at room temperature. Slides were then rinsed in a solution of 95% ethanol, 5% water, 0.1% acetic acid for 10 minutes at room temperature, followed by 1 hour of incubation at 120° C. The slides were then left under vacuum at 120° C. overnight. DNA synthesis was conducted with a K&A S-4 synthesizer following the protocol in FIG. 81. Reagents were purchased from Glen Research (amidites, diluent, and deblocking solution) or Sigma Aldrich (oxidizer, part No. L060080). Amidites, activator, and acetonitrile were dried with trap packs (BioAutomation). After synthesis, the slide was treated with the 1:1 solution of ethylenediamine in ethanol for 50 minutes, then rinsed extensively with ethanol and water. Hybridization was conducted using 1 uM of oligonucleotide (Integrated DNA Technologies) in 20×SSC buffer (Sigma Aldrich) at RT for 30 minutes. The slide was then rinsed in 20×SSPE and imaged under a cover slip with an Olympus fluorescent microscope with a GFP filter.

Figure 84:
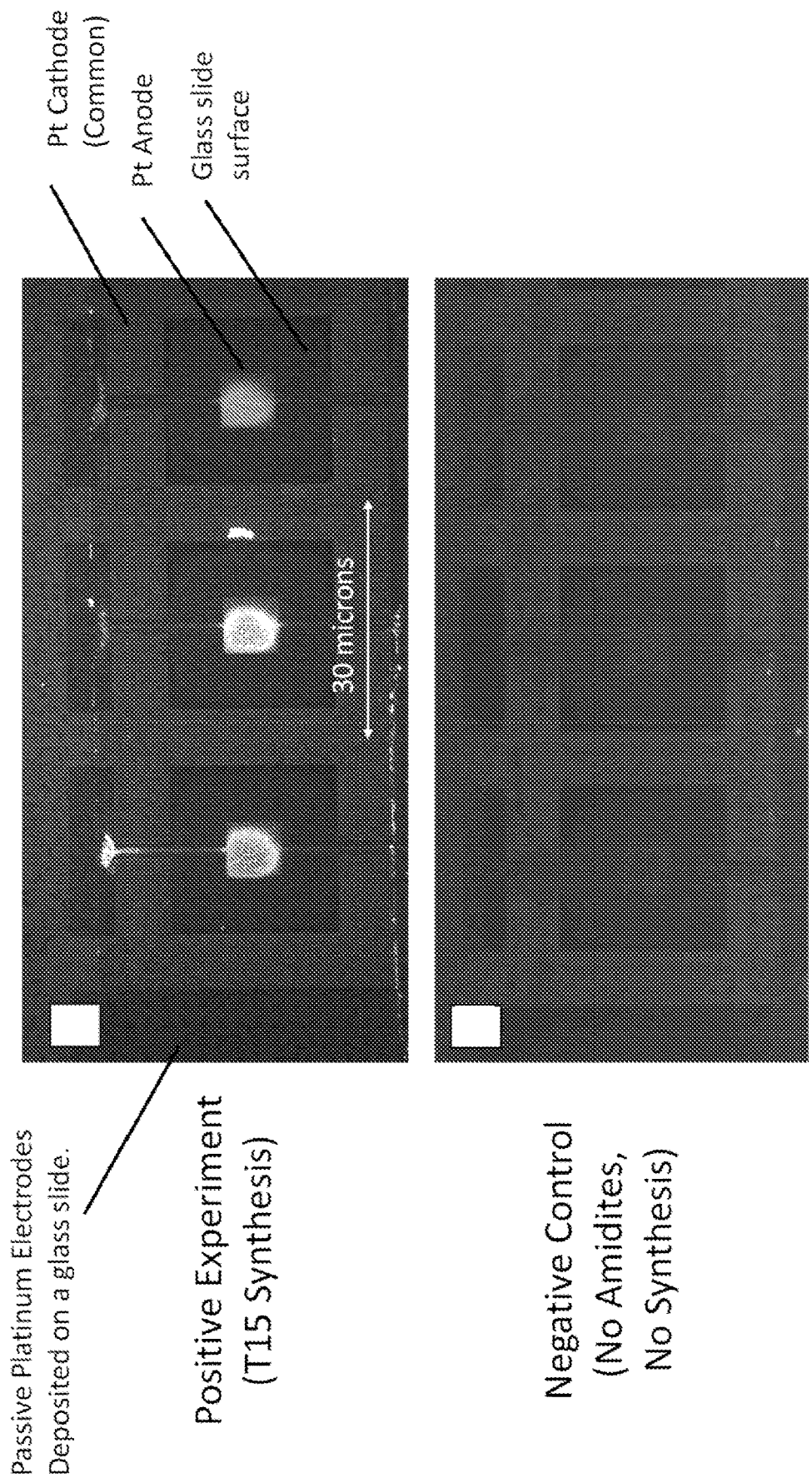
FIG. 84 illustrates an experimental result for electrochemical DNA synthesis on chip, in accordance with various exemplary embodiments.

FIG. 83 illustrates an exemplary experimental reagent delivery protocol used to drive the DNA synthesis with an electrochemical deprotection chemistry, with the reagent delivery system. In this example, the acid generation uses a quinone redox pair. In this protocol, 'TBAP' denotes tetrabutylammonium hexafluorophosphate. 'HQ' and 'BQ' denote hydroxyquinone and benzoquinone respectively, and 'DCI' denotes dicyanoimidazole. FIG. 84 illustrates results of one such exemplary experiment, where a 15-mer was synthesized on a passive electrode system, consisting of a glass slide with Pt cathodes and anodes deposited on it in the configuration shown, so as to drive electrochemical acid generation. The synthesis product is visualized by hybridization of a complementary oligo that is labelled with a fluorescent dye, followed by fluorescent microscope imaging. As shown in the upper panel, synthesis was achieved on the Platinum anode, while none occurs on the negative control below. Experimental Method: The synthesis product labelling is via hybridization of 5'-FAM-labelled poly-$A_{15}$ oligonucleotide to a poly-$T_{15}$ sequence synthesized on a passive electrode. The electrode was first treated with a UV/ozone cleaning for 30 minutes in a Helios 500 (UVO-TECH), rinsed briefly with water, and dried with an air stream prior to silanization. Silanization was conducted by immersing the electrodes in a solution composed of 95% ethanol, 5% water, 0.1% acetic acid, and an additional 2% v/v of a hydroxyl bearing silane for 4 hours at room temperature. Slides were then rinsed in a solution of 95% ethanol, 5% water, 0.1% acetic acid for 10 minutes at room temperature, followed by 1 hour of incubation at 120° C. The slides were then left under vacuum at 120° C. overnight.

The synthesis was conducted with a K&A S-4 synthesizer using the exemplary protocol in FIG. 83, before deprotection in 1:1 ethylenediamine:ethanol for 45 minutes and extensive rinsing with ethanol and water. Hybridization was conducted using 1 uM of oligonucleotide (Integrated DNA Technologies) in 20×SSC buffer (Sigma Aldrich) at RT for 40 minutes. The slide was then rinsed in 20×SSC and dried under an air stream prior to fluorescence imaging on a BZ-9000 (Keyence). FIG. 84, lower portion, shows a control sample generated using similar conditions as that in the upper portion, except that the amidite reservoir contained only acetonitrile during the synthesis step, so there is no synthesis product produced.

Figure 85:
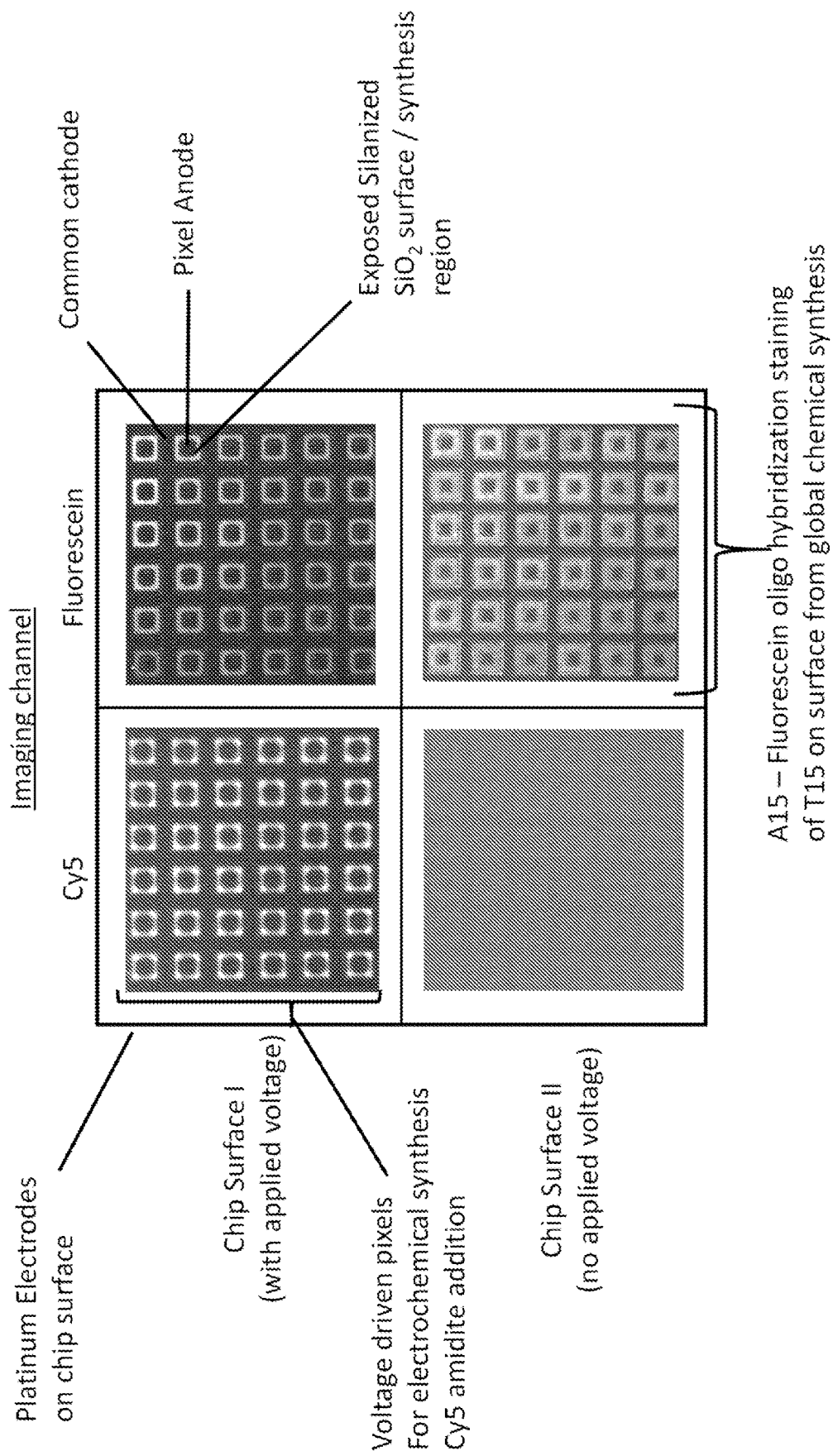
FIG. 85 illustrates results demonstrating electrochemical DNA synthesis on a CMOS chip device, in accordance with various exemplary embodiments.

FIG. 85 illustrates an exemplary on-CMOS chip demonstration of electrochemical deprotection (DMT removal) and synthesis of one base, a dye labeled amidite. Experimental Method: A 14 nucleotide sequence was synthesized on two separate silanized CMOS chip surfaces with a K&A S-4 using the exemplary protocol described in FIG. 81, for standard (non-electrochemical) synthesis, to serve as a synthesis control, and as a spacer to keep the subsequent Cy5-fluor away from the surface. Each CMOS chip surface then underwent three consecutive cycles of DMT-dT coupling and oxidation to produce a DMT-terminated surface. On Surface I, the flow cell was then flushed with a solution of 40 mM hydroquinone and benzoquinone and 100 mM tetrabutylammonium hexafluorophosphate (Sigma Aldrich) and 0.0015% (w/v) trichloroacetic acid (Fisher) in acetonitrile. Voltage was then applied to a subset of the features for 15 minutes before flushing the cell and replenishing the deblocking mixture. This process was repeated 3 times to encompass a range of voltages spanning 1.45 to 2.45 V. On Surface II, the flow cell was flushed with the same deblocking mixture as surface I and incubated in the same manner without application of voltage. A Cy5 amidite was then coupled to both surfaces (0.067 M, 4 min coupling time) before a >45 minute deprotection in an ethylenediamine:ethanol mixture. Each surface was then hybridized for 30 minutes with 1 uM 5'-fluorescein labelled-poly-A-15 oligonucleotide in 20×SSC and 0.1% Tween-20 at room temperature before a manual rinse in 1×SSPE and imaging on a Nikon Eclipse 50i with Cy5 and GFP filters. The images captured on the fluorescein channel indicate that the 15 nucleotide spacer was synthesized on both surfaces. By contrast, significant Cy5 signal was observed solely on the features of Surface I, indicating that the voltage generated sufficient acid to remove the DMT group and to allow fluorophore amidite coupling.

Figure 86:
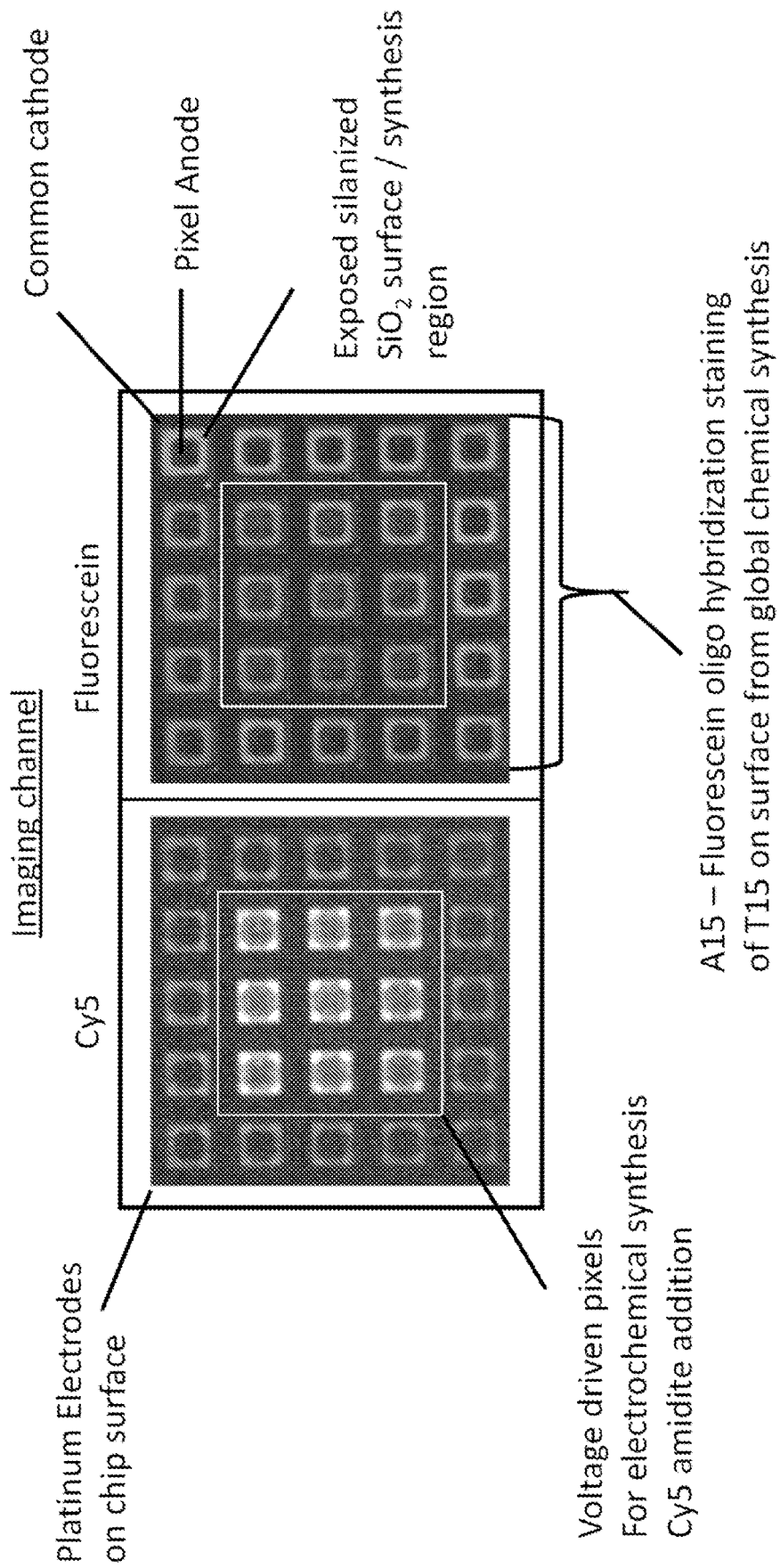
FIG. 86 illustrates results demonstrating electrochemical DNA synthesis with pixel localization on a CMOS chip device, in accordance with various exemplary embodiments.

FIG. 86 illustrates an exemplary on-CMOS chip demonstration of localized DMT removal, and synthesis of one base with a dye-labeled amidite, localized to desired set of pixels. This illustrates confinement of the electrochemical acid generation, and minimal cross talk from stray H+. Experimental Method: A 14 nucleotide sequence was synthesized on a CMOS chip surface with a K&A S-4 using the exemplary protocol described in FIG. 81, for standard (non-electrochemical) synthesis, to serve as a synthesis control, and as a spacer to keep the subsequent Cy5-fluor away from the surface. Three consecutive cycles of DMT-dT coupling and oxidation were then used to ensure a DMT-terminated surface. The flow cell was then flushed with a solution of 40 mM hydroquinone and benzoquinone and 100 mM tetrabutylammonium hexafluorophosphate (Sigma Aldrich) in acetonitrile. 1.85 V was then applied to the indicated 3×3 grid of features for 6 minutes before flushing the cell. A Cy5 amidite was then coupled to both surfaces (0.067 M, 4 min coupling time) before a >45 minute deprotection in an ethylenediamine:ethanol mixture. The chip was then hybridized for 30 minutes with 1 uM 5'-fluorescein labelled-poly-A-15 oligonucleotide in 20×SSC and 0.1% Tween-20 at room temperature before a manual rinse in 1×SSPE and imaging on a Nikon Eclipse 50i with Cy5 and GFP filters. The images captured on the fluorescein channel indicate that the control 14 nucleotide spacer was synthesized globally, while the Cy5 signal indicates the relative extent of electrochemically driven DMT removal. The localization of this Cy5 signal shows that acid confinement works, and there is limited pixel cross talk.

Figure 88:
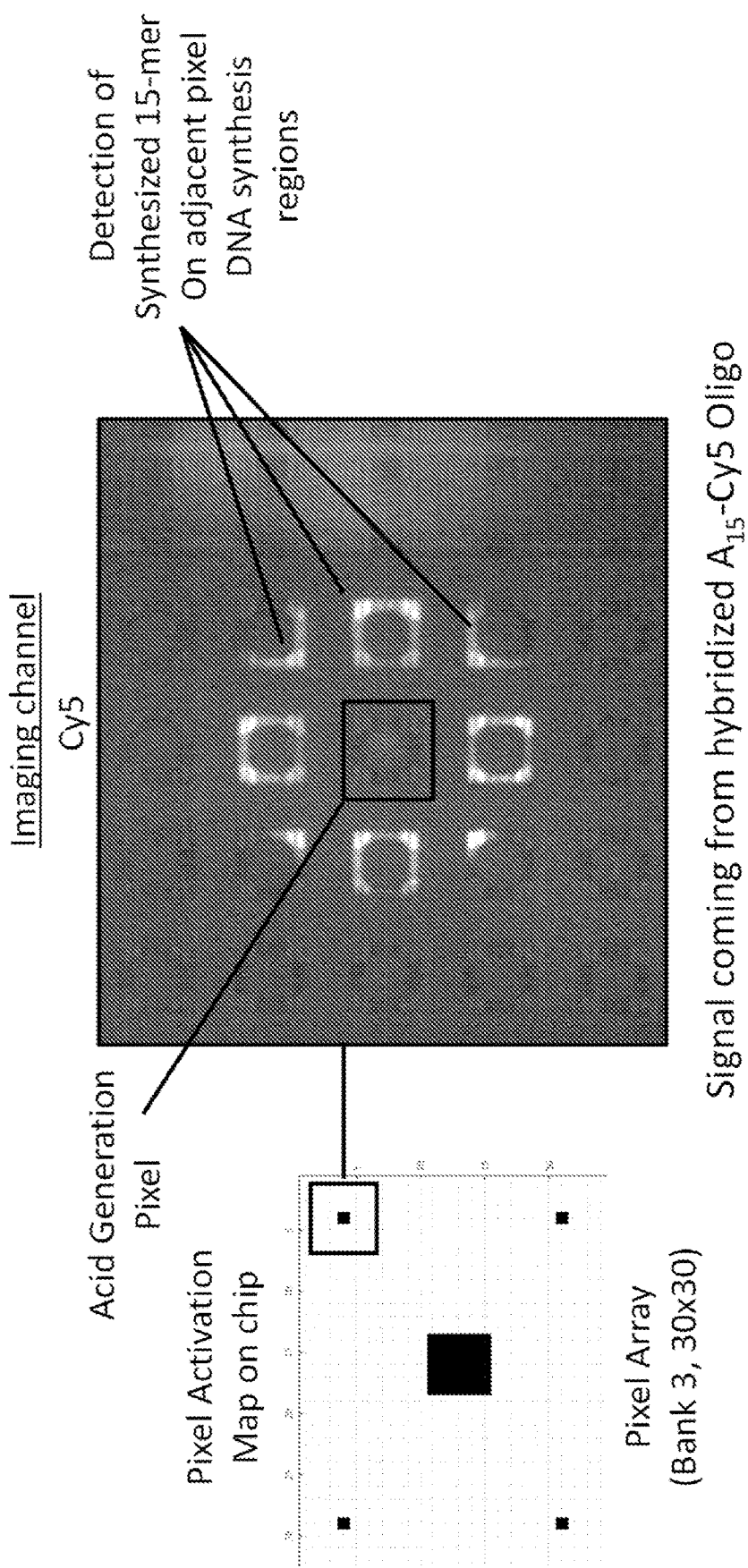

Localized electrochemical oligo synthesis on chip: This exemplary experiment demonstrated a complete reduction to practice of CMOS chip electrochemical oligo synthesis. FIG. 88 illustrates an exemplary demonstration of localized DNA oligo synthesis, using electrochemical synthesis. The inset (left) shows the activation map of pixels on the Bank 3 pixel array (30×30). To demonstrate localization of synthesis, electrochemical acid generation is applied only at a central 5×5 pixel array, and single pixels in the corners. A total of 15 synthesis cycles were performed, to synthesize the target oligo of $T_{15}$. The image inset (right) is a post-synthesis fluorescent microscopy image, showing a closeup around the corner synthesis pixel indicated in the activation map, imaging the result of hybridization of a 5'-Cy5-labelled poly-$A_{15}$ oligonucleotide to $T_{15}$ sequences synthesized on the chip. As shown, the hybridization signal, indicating successful synthesis of $T_{15}$ (or at least k-mers close to 15 in length) is localized to an approximately 1-pixel wide "halo" ring around the acid generation anode of the central pixel. The idealized synthesis pattern would be most intense in the central pixel DNA synthesis ring, with a limited (unwanted) halo in the synthesis ring areas of neighboring pixels. The actual observation shown has this halo, while the central pixel is dark. This pattern is the result of the detailed synthesis protocol, as well as the limitations of the hybridization reporter assay. Optimization of all the underlying synthesis reaction parameters and also the hybridization and imaging conditions, can be used to achieve and properly visualize the more idealized patterns. The full exemplary synthesis protocol used is shown in FIG. 87. The chip was first treated with a UV/ozone cleaning for 30 minutes in a Helios 500 (UVOTECH), rinsed briefly with water, and dried with an air stream prior to silanization. Silanization was conducted by immersing the chip in a solution composed of 95% ethanol, 5% water, 0.1% acetic acid, and an additional 2% v/v of a hydroxyl bearing silane for 4 hours at room temperature. The chip was then rinsed in a solution of 95% ethanol, 5% water, 0.1% acetic acid for 10 minutes at room temperature, followed by 1 hour of incubation at 120° C. and baking under vacuum at 120° C. overnight. The synthesis was conducted with a K&A S-4 synthesizer using the exemplary protocol in FIG. 87, where a subset of electrodes in the center and corners of the array were used for synthesis. The chip was then deprotected in 1:1 ethylenediamine:ethanol for 45 minutes and extensive rinsing with ethanol and water. Hybridization was conducted using 1 uM of oligonucleotide (Integrated DNA Technologies) in 20×SSC buffer (Sigma Aldrich) at RT for 30 minutes. The illuminated regions over the $SiO_2$ indicate the degree of localization achieved under these conditions.

In one exemplary embodiment, a DNA synthesis chip utilizes voltage-mediated acid generation based on electrochemical cycling of the redox couple hydroquinone (HQ) and tetrachloro-1,4-benzoquinone (TQ). HQ oxidation occurs at +0.8V (vs. Ag/AgCl) and TQ reduction at −0.25V (vs. Ag/AgCl). Thus, HQ is oxidized by applying >1.05V between the working electrode (WE) and counter electrode (CE), resulting in a TQ radical and two protons (H+). The subsequent acidification near the WE due to the proton release is sufficient to remove the dimethoxytrityl (DMT) protecting groups on the oligos and permit the next coupling step to occur. Importantly, the CE simultaneously reduces TQ, which consumes protons—thus controlling acid confinement. This allows localized selective deprotection of each oligonucleotide by activating individual pixels, enabling highly parallel synthesis. This exemplary redox system departs from previously reported couples that required >1.8V to cycle, thus limiting applicability of such older couples in advanced CMOS nodes. In contrast, the present DNA synthesis chip and redox system can be implemented in and utilized by CMOS nodes utilizing lower voltages, for example as low as 0.9 volts.

Architecturally, in this exemplary embodiment the DNA synthesis chip is arranged like an image sensor with 2D arrays of synthesis pixels, individually addressed and controlled by pitch-matched row- and column-level circuits. The synthesis pixel arrays share a serial interface to facilitate data/command exchange with an external FPGA. Each synthesis pixel contains a six transistor (6T) SRAM cell with all minimum sized devices for density reasons. The SRAM output is connected to drivers that apply either $V_{WE}$ or $V_{CE}$ to the WE to control localized acid generation. The CE is common to all pixels. Reading and writing the pixels follows traditional SRAM conventions. In this exemplary embodiment, three synthesis pixel variations are arranged in banks. Bank 1 operates from a 1.2V supply using only thin-gate oxide devices, limiting $V_{WE}$ while exhibiting the highest density (160 k pixels in 880×720 µm²). Banks 2 and 3 use I/O devices operating from $V_{DDIO}$, 2.5V, allowing higher redox voltages, such as the 1.8V needed for older redox couples. A level shifter in the row driver interfaces with these higher voltage synthesis pixels.

Continuing with this exemplary embodiment, the DNA synthesis chip was post-processed to deposit platinum electrodes. Each pixel defines the electrode geometry with the top metal layer where the WE are 1×0.6 µm², 1×0.6 µm², and 7.5×7.5 µm² for Banks 1, 2, and 3, respectively. Bank 3 has 15× larger electrodes to study acid diffusion and ease in imaging, but Banks 1 and 2 are sized in accordance with various preferred embodiments. Because µm-size features are too small to be directly patterned on the top metal of a CMOS process with passivation openings, a sacrificial aluminum (Al) structure—essentially a huge "bond pad"—was placed over the entire bank. Upon receiving the wafer, the Al was etched away, exposing the underlying tantalum diffusion barrier around the copper and the silicon dioxide between the CE and WE. The electrodes were then patterned with e-beam lithography (Banks 1 and 2) or photolithography (Bank 3). A film stack consisting of 10 nm (Bank 1 and 2) or 15 nm (Bank 3) chromium and 50 nm (Bank 1 and 2) or 500 nm (Bank 3) Pt was sputtered and lifted off. The electrodes are well-formed based on scanning electron microscope (SEM) images with no shorts between electrodes (see FIGS. 89 through 91B).

Continuing with this exemplary embodiment, the DNA synthesis chip is implemented in a 65 nm CMOS process occupying 4.79 mm² and consumes 6 mW. It is electrically controlled through an FPGA by MATLAB scripts that load in the pattern to be synthesized and then run through the appropriate fluidic cycles. Reagents are delivered through a K&A DNA synthesizer connected to a custom-designed flow cell with a Pt rooftop reference electrode (RE). The classic chemical deprotection step using trichloroacetic acid (TCA) was replaced by the aforementioned electrochemical protocol using $V_{WE}$=1.15V, $V_{CE}$=0V, and $V_{RE}$=0.3V for 60 s in equal parts HQ/TQ (20 mM). The electrodes were tested for stability by applying voltage while immersing the chip in acetonitrile and TCA for over 24 hours with no visible signs of degradation such as delamination or embrittlement.

As compared to prior CMOS approaches for DNA synthesis, this exemplary embodiment achieves numerous improvements over the art of record. For example, Bank 3 electrodes confine DNA synthesis to an area 10× lower than realized on prior CMOS approaches, while the pitch of Bank 1 synthesis pixels scales to >130 million sites on a full reticle chip, >100× any synthesizer previously reported in the literature.

Figure 89:
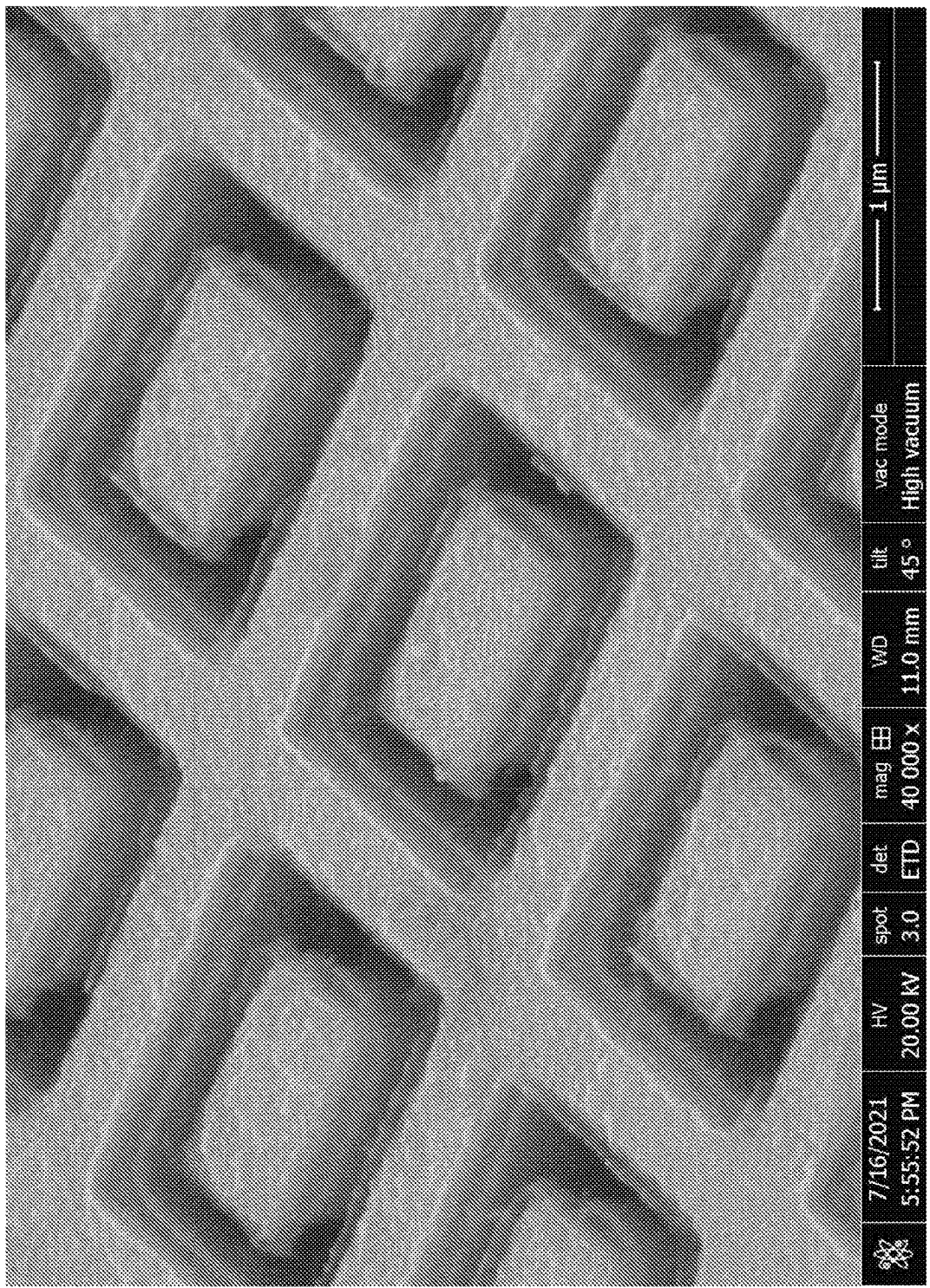
Figure 90:
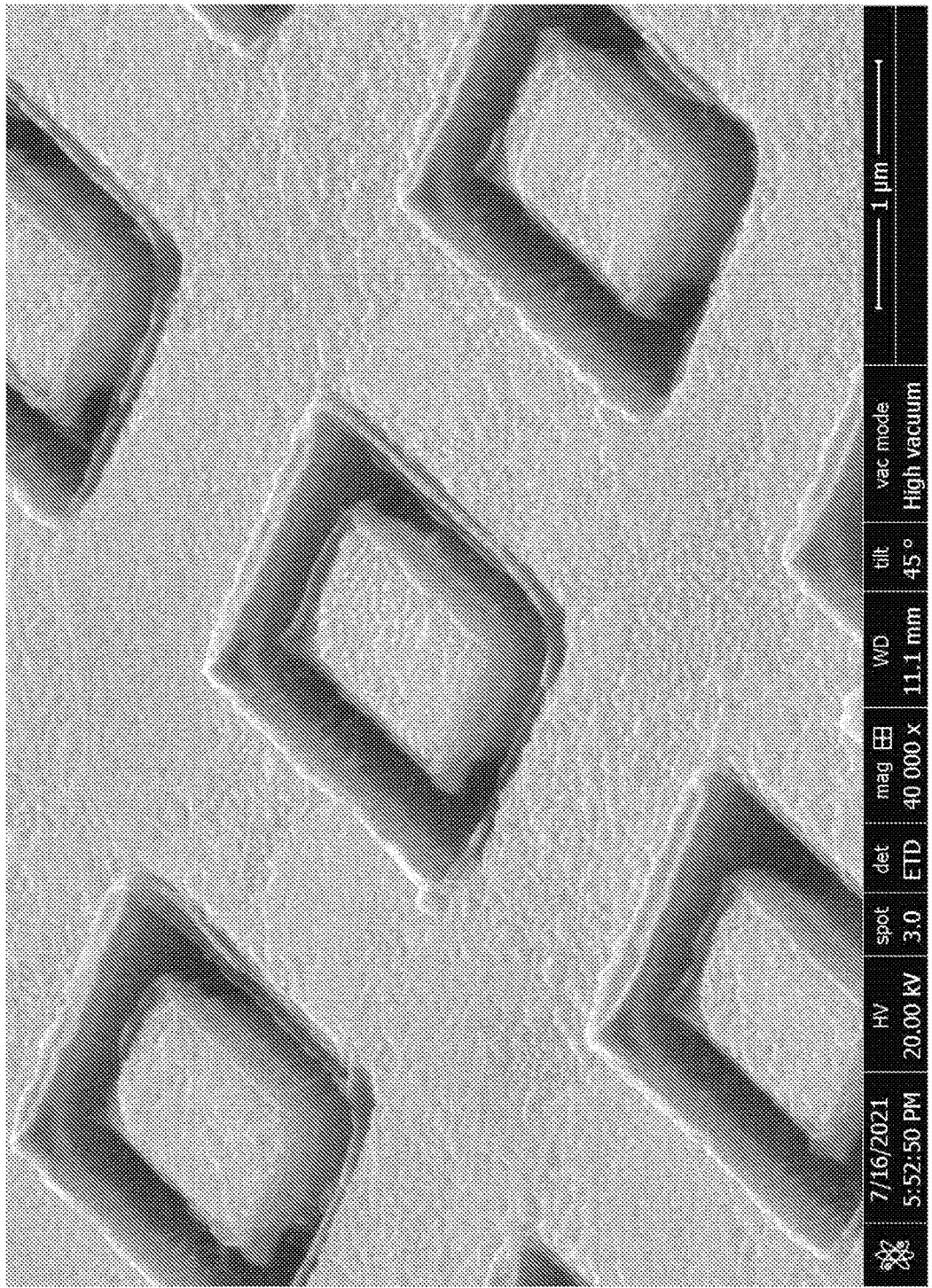
Figure 91A:
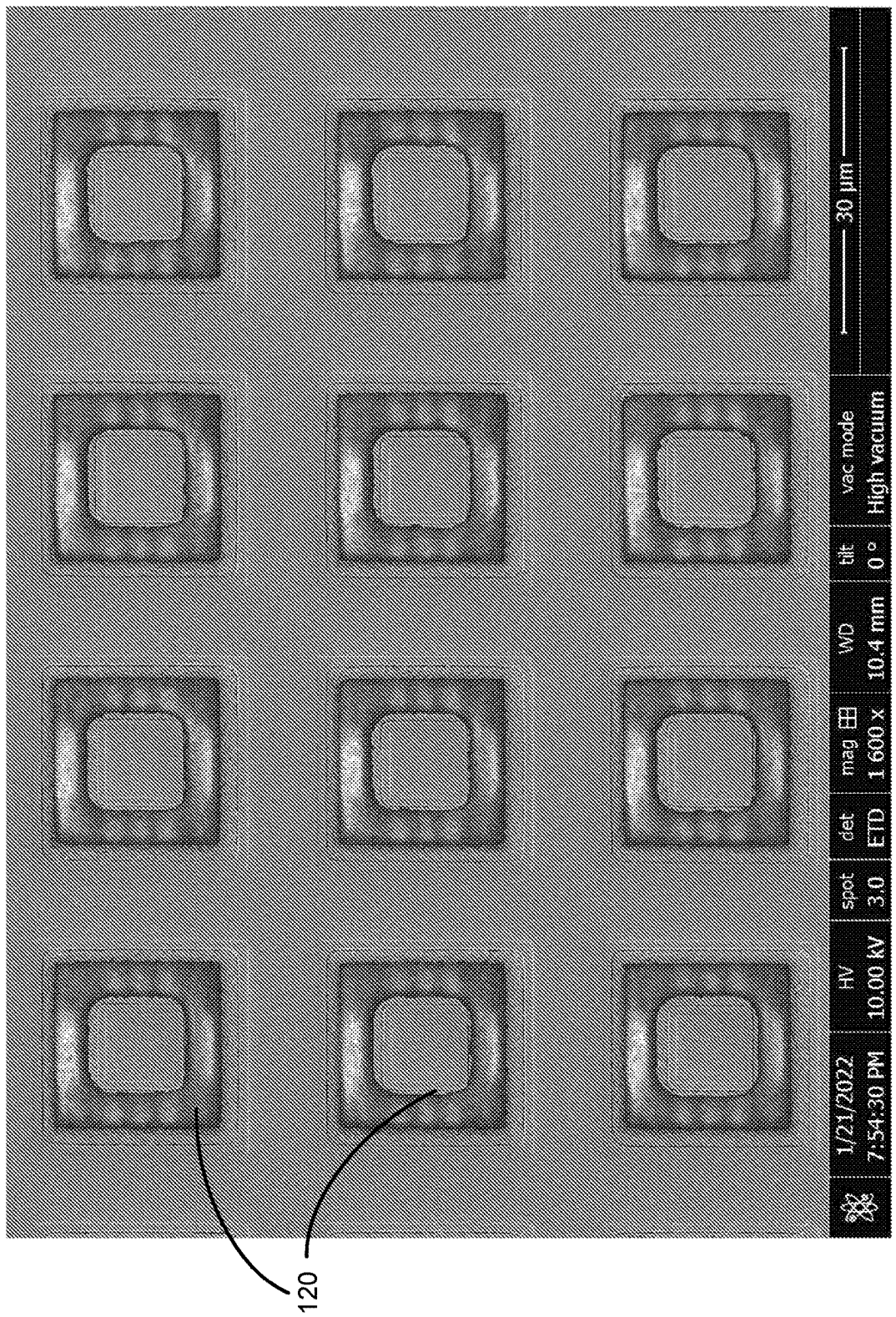
Figure 91B:
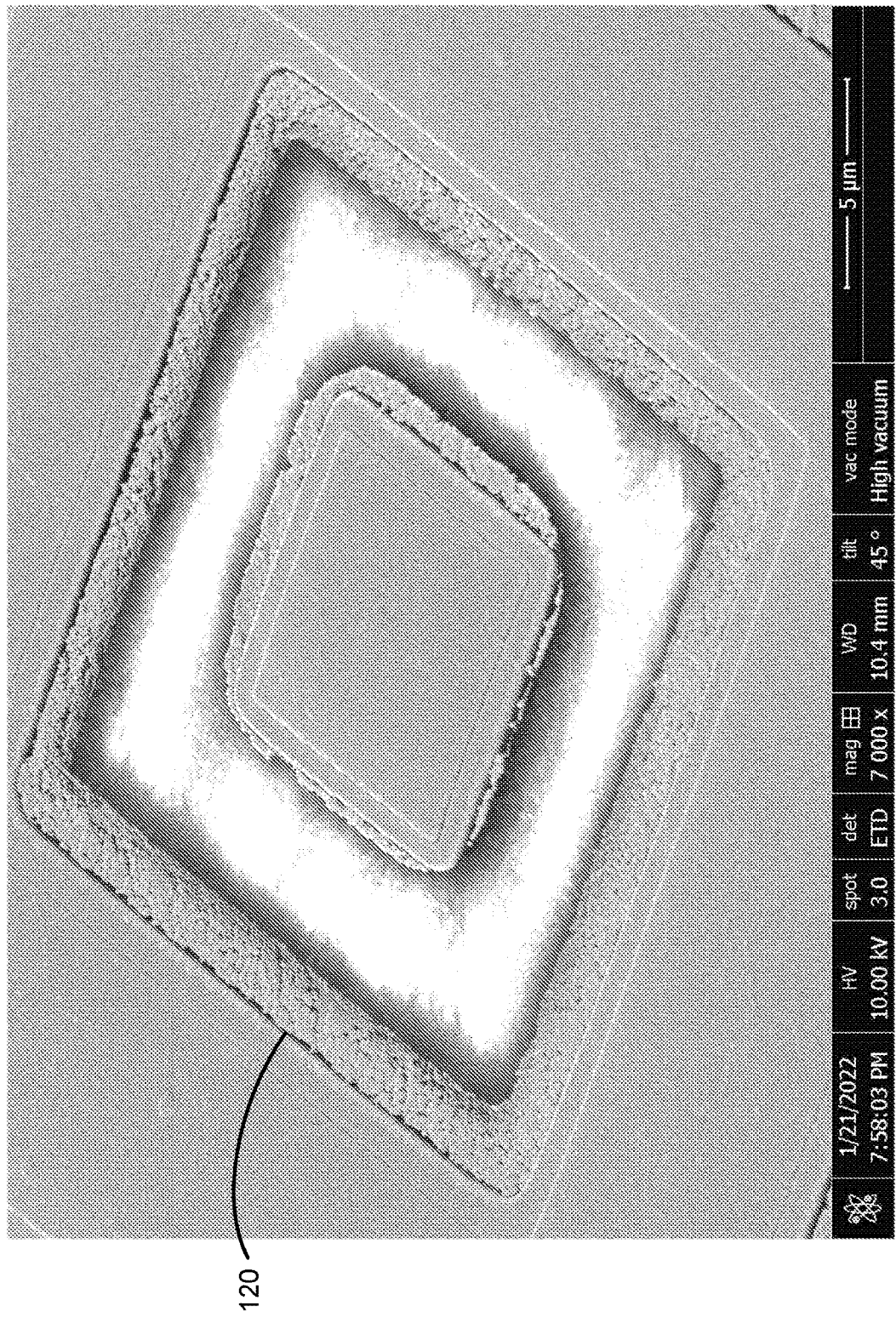
Figure 91C:
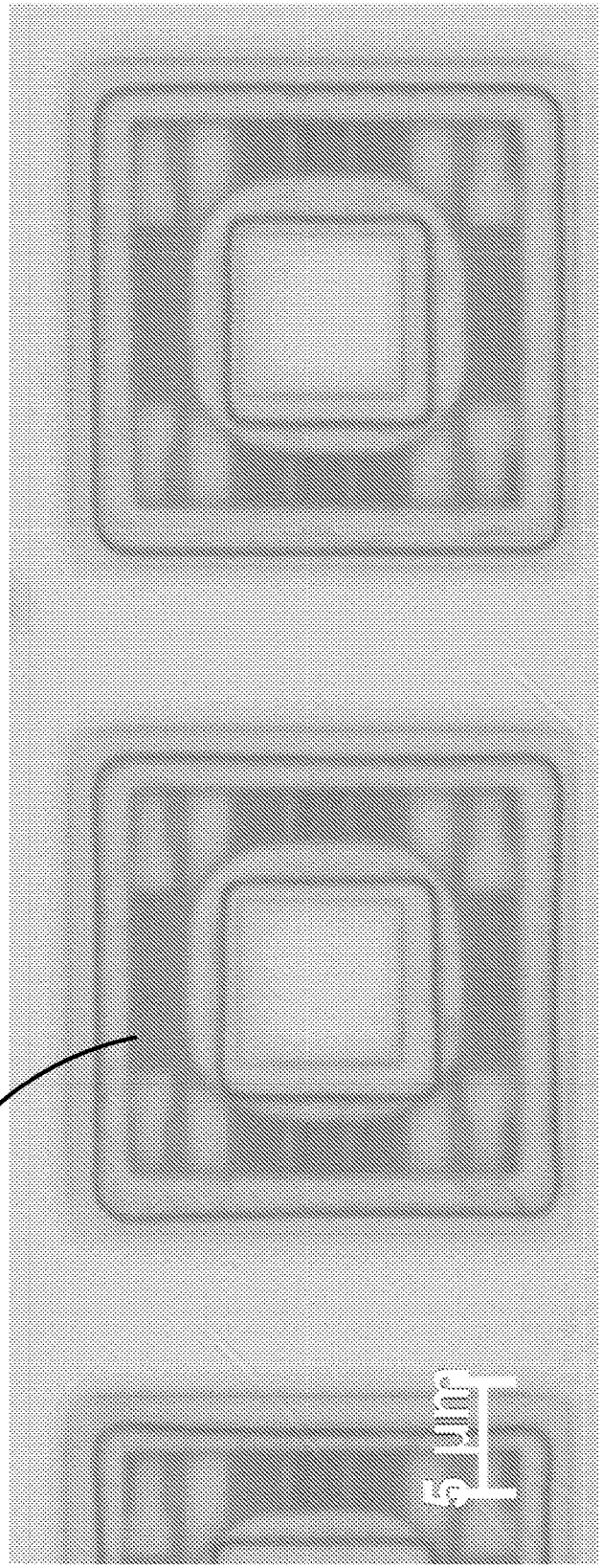

With reference now to FIGS. 89 and 90, illustrated are SEM images of fabricated synthesis pixel arrays in accordance with various exemplary embodiments. FIG. 91A is a SEM image of a fabricated synthesis pixels array, with FIG. 91B a close-up view of a single synthesis pixel thereof, in accordance with various exemplary embodiments. FIG. 91C is an optical image of synthesis pixels in the array of FIG. 91A.

Figure 92:
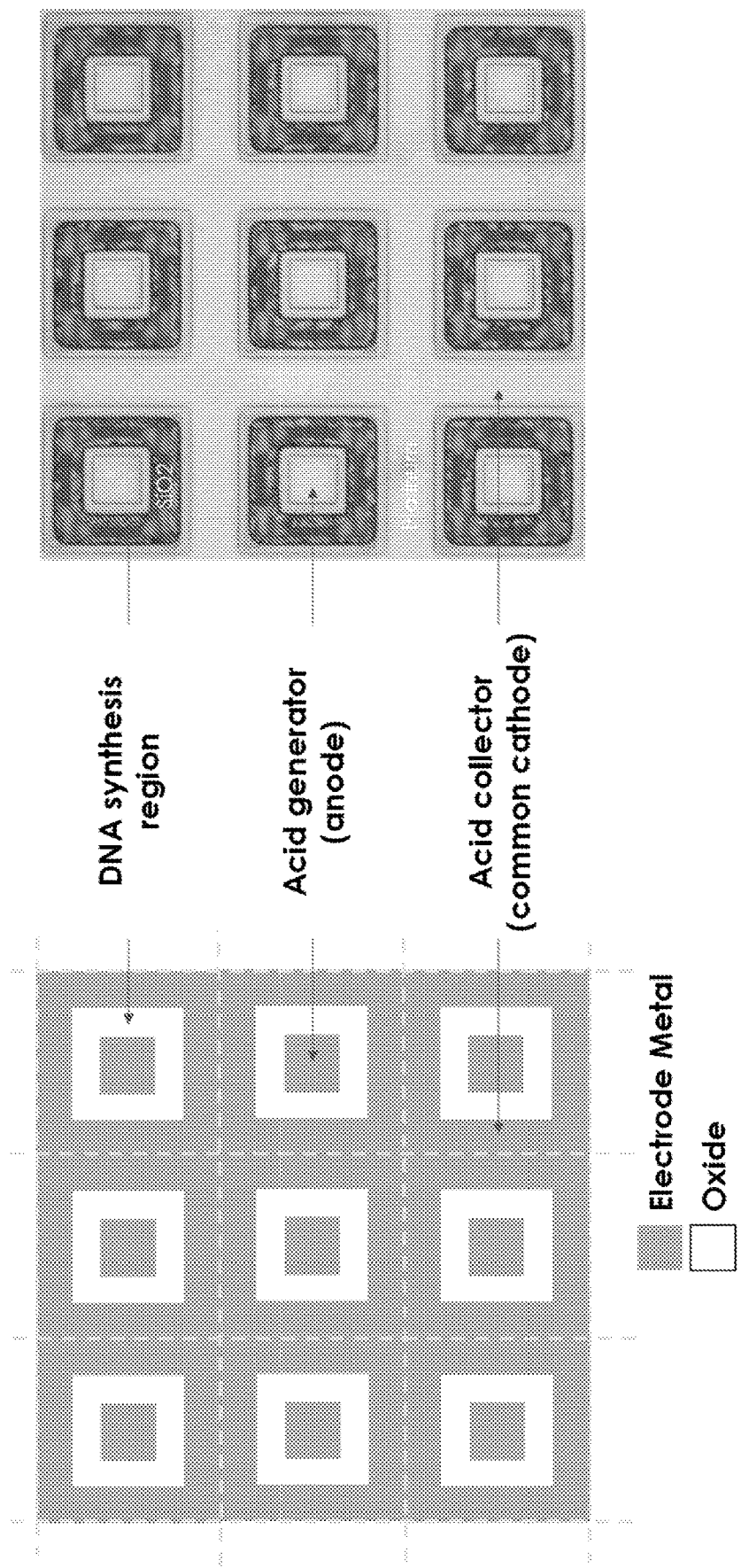

Turning to FIG. 92, illustrated is an exemplary schematic for a synthesis pixel array in accordance with various exemplary embodiments, together with an optical image of the corresponding synthesis pixel array fabricated in a CMOS process.

Figure 93:
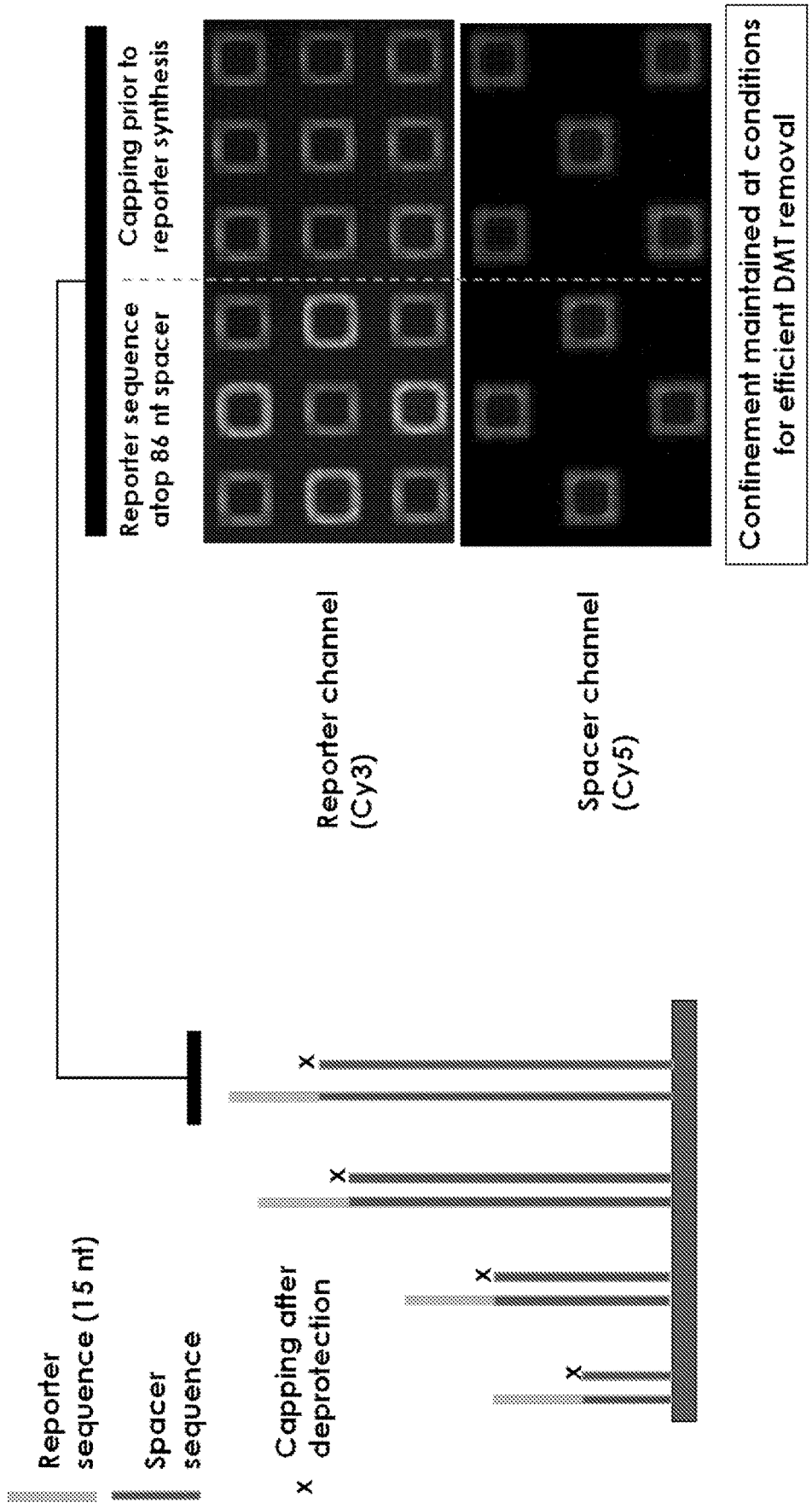

FIG. 93 illustrates use of an exemplary DNA synthesis chip comprising a synthesis pixel array as disclosed in various exemplary embodiments, constructing a 100 nucleotide sequence via an exemplary synthesis process disclosed herein, comprising 86 nt spacer and 15 nt reporter sequences. The synthesized oligos were hybridized to Cy5- and Cy3-labeled oligos complementary to the spacer and reporter sequences, respectively. The spacer sequence was a poly-T homopolymer, which acts as a more rigorous test of acid confinement. Any inadvertent DMT removal at adjacent sites will produce shorter homopolymers near the pixels that hybridize to the labeled poly-A sequence. As the fluorescence micrograph indicates, all detectable signal remains confined within the pixel. The coupling efficiency is above 99%, comparable to commercial DNA synthesizers. These results demonstrate no sign of crosstalk or non-specific binding.

FIGS. 94, 95, and 96 illustrate exemplary synthesis of multiple sequences on a chip. The spatial arrangement of the sequences is depicted in FIG. 94, which illustrates the division of the chip into two sections, one in which the sequences are arranged in a checkerboard, and a second where the pattern contains a blank pixel as a negative control. The results of hybridization are depicted in FIG. 95, which shows fluorescence micrographs from the checkerboard region, indicating the intended sequences were produced at the intended locations. FIG. 96 shows a fluorescence micrograph from the region containing negative control pixels, where only the spacer (and no hybridization target) was synthesized. Notably, there is no evidence of crosstalk or significant non-specific binding detectable, and this example is shown using a recycled DNA synthesis chip, illustrating chip stability across multiple synthesis cycles.

FIGS. 97A, 97B, and 97C illustrate exemplary synthesis approaches and results for synthesizing a 60-mer homopolymer, demonstrating excellent confinement and accuracy as illustrated by the fluorescence micrographs shown (no sign of short homopolymer synthesis in neighboring features, i.e., low crosstalk).

FIG. 98 illustrates exemplary synthesis results, visualized by hybridization with a fluorophore-labeled oligonucleotide complementary to the sequence synthesized, spelling out "Helix."

Definitions and Interpretations

As used herein, the term "DNA synthesis" refers not only to synthesis of DNA strands composed of the four bases A, C, G, T, but also other base analogues, such as U (uracil), I (Inosine), and other well-known universal bases or base analogues or modified or marked bases, including well-known epigenetics marks on bases, such as 5 mC (5-methyl-C), as well as dye-labelled bases, or bases modified for future labelling or conjugation, such as biotinylated bases, or thiolated bases, and in general any other widely known modified forms of bases used in DNA oligos, or modified phosphoramidites used in phosphoramidite synthesis reactions, and in general including synthesis with modifications in the sugar or backbone of DNA as well. Additionally, it will be appreciated that the more general term "polynucleotide synthesis" as used herein includes, but is not limited to, DNA synthesis, and may include synthesis of polynucleotides such as ribonucleic acids (RNA), peptide nucleic acids (PNA), locked nucleic acids (LNA), xeno nucleic acids (XNA), and so forth. Moreover, the term "polynucleotide" or "polynucleotide synthesis" as used here includes DNA as broadly interpreted above, as above, as well as nucleotide oligomers, including any such that may be synthesized by the phosphoramidite method, including RNA, LNA or XNAs, as well as nucleoside oligomers that may be synthesized by a method reliant on acid-based deprotection, such as is used for PNAs. In addition, beyond nucleic acid oligomers, where it makes sense, these references to oligomers and oligomer synthesis are also intended to cover amino acid oligomers, such as peptides, that are synthesized by acid-based deprotection chemistries other than phosphoramidite synthesis, as these would be contemplated as extensions of various embodiments disclosed herein, as understood by those skilled in the arts of chemical synthesis, and particularly those skilled in DNA synthesis and peptide synthesis.

As used herein, the term "amidite", "phosphoramidite" or "phosphoramidite base" generally refers to any or all of the phosphoramidite reagents or molecules that are used in the synthesis of polynucleotides (such as DNA) by the phosphoramidite method, unless the context explicitly indicates otherwise. This term may also be taken to generally mean, in contexts where it makes sense, any alternative reagents that can engage in such a synthesis cycle that includes acid-driven deprotection.

As used herein, the term "acid" may refer to a chemical acid, or may whenever it makes sense, refer directly to H+, or to solutions containing such. In particular, in referring to acid generation, this is meant to refer to the generation of H+, but can more generally refer to generation of a chemical acid that can donate an H+ to the deprotection reactions of interest. In referring to acid removal, this is meant to refer to the elimination of H+, but could more generally refer to elimination of a chemical acid.

As used here in, "phosphoramidite synthesis" or "the phosphoramidite method" or "chemical synthesis" refer to any of the family of standard or well-known chemical cycles employed for synthesis using phosphoramidite bases, such as those used for commercial DNA oligo synthesis, or those deriving from the original methods such as put forth by Marvin Carruthers.

As used herein, the term "electrode" in the context of electrochemical acid generation or elimination refers to any conducting material that can serve as a substrate for the electrochemical acid generation reactions disclosed. Such electrodes are typically composed of metals, but may also be semiconductor materials such as doped semiconductors.

As used herein, the term "anode" refers to an electrode at which acid or H+ is generated, unless otherwise specified. Unless contradicted by this interpretation, the anode typically receives electrons from solution and is at a positive potential relative to the solution.

As used herein, the term "cathode" refers to the electrode at which free acid or H+ is eliminated, unless otherwise specified. Unless contradicted by this interpretation, the cathode typically provides electrons to solution, and is at a negative potential relative to the solution.

As used herein, the terms "voltage" or "potential" are interpreted as relative to the solution potential, or relative to a reference electrode potential in a 2 or 3 electrode potentiostat system that regulates the solution potential.

As used herein, the terms "working electrode", "counter electrode" and "reference electrode" (with acronyms "WE", "CE", and "RE" respectively), typically refer respectively to the anode used for acid generation, the cathode used for acid removal, and a reference electrode of a potentiostat used to control solution potential. In certain contexts that are clear, these terms may refer specifically to the elements of a potentiostat used to control solution potential.

As used herein, the term "chip" refers to a semiconductor integrated circuit chip. In certain contexts where this is clear, it may refer to a CMOS chip.

As used herein, the term "CMOS" is an acronym for "Complementary Metal Oxide Semiconductor," and also refers to chips that are made by a CMOS process.

As used herein, the term "electrochemical" refers to chemical reactions that are driven by the presence of an electrode in contract with a solution, at a suitable applied potential.

As used herein, "pixel" refers to a repeated element of a circuit array on a chip. In certain contexts, this may refer to surface elements comprising anode, cathode and DNA synthesis regions, or may refer to underlying circuitry that controls the electrodes, or may refer to both aspects of the circuitry.

As used herein, "data storage" or "storage" in various contexts may mean writing of data to a storage medium, the writing and storing of such data, or the writing, storing, and reading of such data.

As used herein, the term "digital data" refers to binary data, but in certain contexts where this makes sense, it generally can refer to other common forms of data representation, such as decimal numbers, hexadecimal numbers, ASCII characters, or characters (and special characters) from any suitable alphabet and type set (for example, such as are used to print books or written material).

As used herein, the term "DNA data" refers to information stored in DNA sequences, or the physical embodiment of this information into a pool of DNA material.

As used herein, the terms "encoding" and "decoding" refer to converting digital data into DNA sequence form, and recovering digital data from DNA sequence form. In contexts where this makes sense, the term encoding may be used to refer to both or either of these processes.

As used herein, "DNA synthesis" refers to fabrication of physical DNA through a series of chemical reactions, in accordance with producing a desired specific target sequence or sequences.

As used herein, "DNA sequencing" refers to processes for reading the identities of the series of bases in a DNA strand or strands.

As used herein, the term "blade" refers to a multi-chip DNA synthesis system that is relatively compact and self-contained.

As used herein, the term "PCR," an acronym for Polymerase Chain Reaction, generally refers to any means of amplifying or copying DNA, including by thermo-cycling PCR, or isothermal PCR reactions, or generally any other processes that can be used to amplify or copy DNA.

As used herein, the terms "error correction" or "error correcting code" or "ECC," refer to techniques for transforming a primary data string into another data string or strings such that various types of errors or corruptions of the source string may be detected and corrected to recover the source string. In contexts where this makes sense, these may also refer to the process of using such encodings to correct errors. Many such methods are well-known for error correction for the transmission of binary strings, i.e. strings composed of the two symbols "0" and "1". Many of such well known methods have versions that extend to 4 symbol strings, such as DNA sequences composed of the 4 symbols "A", "C", "G", and "T", or conversely two DNA letters may be used as binary string symbols, such that all binary ECC methods may apply directly. Any such methods are encompassed by use of this term, as they may apply in context.

As used herein, the term "SEM" is an acronym for Scanning Electron Microscope, an imaging system and modality.

As used herein, the terms kB, MB, GB, TB, PB, EB, ZB, or YB refer to amounts of Bytes (8 bits), in the context of describing an amount of binary data. These are acronyms for kilobyte, megabyte, gigabyte, terabyte, petabyte, exabyte, zettabyte, or yottabyte.

Examples of various exemplary embodiments are presented in the following Example Set I. It will be appreciated that all the examples contained in this disclosure are given by way of explanation, and not of limitation. Some non-limiting examples of the disclosure follow: Example 1: A DNA synthesis system, comprising: a substrate having a solution applied thereto; a first electrode on the substrate, operable as an anode to drive electrochemical acid generation in the solution; a second electrode on the substrate operable as a cathode to absorb acid from the solution; a DNA synthesis region near the first electrode and functionalized to support DNA synthesis through the addition of phosphoramidite bases; and control circuitry operable to (i) controllably apply and remove a first potential at the first electrode, and (ii) controllably apply a second potential at the second electrode.

Example 2: The DNA synthesis system of Example 1, wherein the second electrode surrounds the first electrode on the substrate. Example 3: The DNA synthesis system of any of Examples 1 or 2, wherein the first electrode and the second electrode are at least partially interdigitated. Example 4: The DNA synthesis system of any of Examples 1 or 2, further comprising a plurality of first electrodes and a plurality of second electrodes, and wherein the plurality of first electrodes and the plurality of second electrodes are dithered. Example 5: The DNA synthesis system of Example 1, wherein the substrate is configured with a well. Example 6: The DNA synthesis system of Example 5, wherein the first electrode is disposed at the bottom of the well.

Example 7: The DNA synthesis system of Example 6, wherein the second electrode is disposed atop of and surrounds the well. Example 8: The DNA synthesis system of Example 6, wherein the second electrode is disposed in a side wall of the well. Example 9: The DNA synthesis system of Example 8, wherein the second electrode forms a continuous loop around the side walls of the well. Example 10: The DNA synthesis system of Example 6, wherein the second electrode forms the lip of the well.

Example 11: The DNA synthesis system of Example 4, wherein the substrate comprises a well, and wherein the first electrode and second electrodes are disposed on a side of the well. Example 12: The DNA synthesis system of Example 5, wherein the second electrode at least partially overhangs a top opening of the well. Example 13: The DNA synthesis system of Example 1, wherein the first electrode and the second electrode are configured with surface area enhancing features. Example 14: The DNA synthesis system of Example 13, wherein the surface area enhancing features comprise at least one of pillars, fins, ridges, or roughened surface.

Example 15: The DNA synthesis system of Example 1, further comprising a three-dimensional matrix of material proximate to the first electrode. Example 16: The DNA synthesis system of Example 1, wherein the second electrode extends from the substrate to form a portion of a confinement zone for the acid. Example 17: The DNA synthesis system of Example 5, wherein the second electrode is disposed atop the well and covers the majority of an opening thereof. Example 18: The DNA synthesis system of Example 1, further comprising a barrier wall coupled to the substrate and forming an acid confinement zone containing the DNA synthesis region. Example 19: The DNA synthesis system of Example 5, further comprising a barrier disposed atop the well and covering the majority of an opening thereof. Example 20: The DNA synthesis system of Example 1, wherein a portion of the second electrode overhangs the first electrode to form a ceiling over the first electrode.

Example 21: The DNA synthesis system of Example 1, further comprising a third electrode operable as a cathode to absorb acid from the solution, wherein the third electrode is configured as a ceiling over the first electrode and the second electrode. Example 22: The DNA synthesis system of Example 1, further comprising a barrier disposed atop the second electrode and overhanging the first electrode to form a ceiling over the first electrode. Example 23: The DNA synthesis system of Example 1, further comprising a barrier element configured as a ceiling over the first electrode and the second electrode. Example 24: The DNA synthesis system of Example 1, wherein the first electrode and the second electrode comprise at least one of gold, palladium, platinum, iridium, or alloys thereof. Example 25: The DNA synthesis system of Example 1, wherein the solution comprises reversible redox pairs. Example 26: The DNA synthesis system of Example 25, wherein the reversible redox pairs comprise quinone redox pairs. Example 27: The DNA synthesis system of Example 26, wherein the quinone redox pairs comprise hydroquinone (HQ) and its oxidized form benzoquinone (BQ). Example 28: The DNA synthesis system of Example 26, wherein the quinone redox pairs have a lower redox potential than hydroquinone (HQ) and its oxidized form benzoquinone (BQ), and wherein the lower redox potential is below a voltage limit of a CMOS process utilized to form the substrate. Example 29: The DNA synthesis system of Example 26, wherein the quinone redox pairs comprise tetrachloro-quinone (TQ) and its oxidized benzo form (TBQ). Example 29: The DNA synthesis system of Example 26, wherein the quinone redox pairs comprise deuterated forms, such that the result is to produce free deuterium+ (D+).

Additional non-limiting examples are presented in the following Example Set II: Example 1: A DNA synthesis system, comprising: a substrate having a solution applied thereto; an electrode on the substrate, operable as an anode to drive electrochemical acid generation in the solution; and a DNA synthesis region near the electrode and functionalized to anchor and support DNA synthesis through the addition of phosphoramidite bases.

Example 2: The DNA synthesis system of Example 1, wherein the solution comprises a buffer creating a highly confined acid confinement zone near the electrode. Example 3: The DNA synthesis system of Example 1, wherein the solution comprises a plurality of solid state buffer particles. Example 4: The DNA synthesis system of Example 3, wherein the plurality of solid state buffer particles are sized such that the DNA synthesis region is inaccessible to the plurality of solid state buffer particles. Example 5: The DNA synthesis system of Example 3, wherein the substrate is configured with a well having an opening diameter, wherein the electrode is disposed at a bottom of the well, and wherein the plurality of solid state buffer particles are configured with a size greater than the well opening diameter to exclude the plurality of solid state buffer particles from entering the well.

Example 6: The DNA synthesis system of Example 4, wherein the DNA synthesis region is located in a depression in the substrate. Example 7: The DNA synthesis system of Example 4, wherein the substrate comprises a protrusion, wherein the electrode extends from the substrate, and wherein the DNA synthesis region is located in a space formed between the protrusion and the electrode. Example 8: The DNA synthesis system of Example 4, wherein the electrode comprises two portions extending from the substrate, and wherein the DNA synthesis region is located in a space formed between the two portions. Example 9: The DNA synthesis system of Example 4, wherein the electrode is configured with a depression therein, and wherein the DNA synthesis region is located in the depression. Example 10: The DNA synthesis system of Example 4, wherein the electrode extends from the substrate, and wherein the DNA synthesis region is located at an edge where the electrode contacts the substrate. Example 11: The DNA synthesis system of Example 4, wherein the substrate comprises a first protrusion and a second protrusion, and wherein the DNA synthesis region is located in a space defined between the first protrusion and the second protrusion.

Example 12: The DNA synthesis system of Example 3, wherein the substrate comprises a well. Example 13: The DNA synthesis system of Example 12, wherein the well contains a plurality of barrier particles that exclude the solid state buffer particles from at least a lower portion of the well. Example 14: The DNA synthesis system of Example 12, further comprising at least one barrier structure disposed in the well to exclude the solid state buffer particles from at least a lower portion of the well.

Additional non-limiting examples are presented in the following Example Set III: Example 1: An electrochemical DNA synthesis system, comprising: a substrate to which solution can be applied; a surface electrode on the substrate, or buried near the surface of the substrate, capable of attracting H+ in a suitable applied solution with a low concentration of H+, when set to a suitable potential, where said concentration of H+ is at such a level to be capable of chemically removing the protecting group on phosphoramidite bases in said solution; a region over the electrode functionalized to anchor and support DNA synthesis through the addition of phosphoramidites bases; and control circuitry capable of applying to different voltages at the surface electrode, with the effect of turning H+ concentration on and off at the electrode in time.

Example 2: The electrochemical DNA synthesis system of Example 1, wherein a second suitable applied voltage also repels the local H+ from the DNA synthesis regions, to a level below the ambient concentration, and where the difference between the H+ concentration in the repelled state, and the H+ concentration in the attracted or ambient state, is sufficient to selectively deprotect said protected phosphoramidites.

Example 3: An electrochemical DNA synthesis system, comprising: a substrate to which solution can be applied; a surface electrode on the substrate, or buried near the surface of the substrate, capable of attracting acid-bearing particles in the suitable applied solution, when set to a suitable potential, where the resulting concentration of acid-bearing particles is capable of chemically removing the protecting group on phosphoramidite bases in the DNA synthesis zone; a region over the electrode functionalized to anchor and support DNA synthesis through the addition of phosphoramidites bases; and control circuitry capable of applying to different voltages at the surface electrode, with the effect of turning acid-bearing particle attraction on and off at the electrode in time.

Additional non-limiting examples are presented in the following Example Set IV: Example 1: A DNA synthesis system, comprising: a first substrate and a second substrate having a solution disposable therebetween; a first electrode on the first substrate, operable as an anode to drive electrochemical acid generation in the solution; a second electrode on the first substrate operable as a cathode to absorb acid from the solution; a DNA synthesis region on the second substrate and functionalized to anchor and support DNA synthesis through the addition of phosphoramidites; and control circuitry operable to (i) controllably apply and remove a first potential at the first electrode, and (ii) controllably apply and remove a second potential at the second electrode.

Example 2: The DNA synthesis system of Example 1, further comprising control components coupled to the second substrate and operable to advance and retract the second substrate with respect to the first substrate. Example 3: The DNA synthesis system of Example 2, wherein the first substrate comprises a well, wherein the second substrate comprises a peg wherein the DNA synthesis region is located, and wherein, responsive to operation of the control components, the peg may be (i) extended at least partially into the well, and (ii) withdrawn from the well. Example 4: The DNA synthesis system of Example 2, wherein the second substrate comprises at least one protrusion operable to confine acid generated at the first electrode. Example 5: The DNA synthesis system of Example 2, wherein the DNA synthesis region on the second substrate comprises surface area enhancing features comprising at least one of pillars, fins, ridges, or roughened surface. Example 5: The DNA synthesis system of Example 2, further comprising a third electrode on the second surface and operable as a cathode to absorb acid from the solution. Example 6: The DNA synthesis system of Example 5, wherein the third electrode extends from the second substrate to confine acid generated at the first electrode.

Some other non-limiting examples are presented in the following Example Set V: Example 1: A semiconductor integrated circuit device, comprising: an array of synthesis pixels for polynucleotide synthesis, and a common solution applied to all synthesis pixels in the array. Example 2: The device of Example 1, wherein each synthesis pixel in the array of synthesis pixels comprises: an electrode on a substrate, operable as an anode to drive electrochemical acid generation in the solution; and a polynucleotide synthesis region near the electrode and functionalized to anchor and support polynucleotide synthesis through the addition of phosphoramidites. Example 3: The device of Example 2, wherein the polynucleotide synthesis process in each synthesis pixel is independently controllable with respect to each other synthesis pixel. drives an independent synthesis process. Example 4: The device of Example 3, wherein each synthesis pixel in the array of synthesis pixel comprises internal control circuitry associated with that synthesis pixel. Example 5: The device of Example 3, further comprising internal control circuitry associated with a plurality of synthesis pixels in the array of synthesis pixels.

Example 6: The device of Example 3, further comprising a monitoring circuit for readouts from the array of synthesis pixels. Example 7: The device of Example 6, wherein the monitoring circuit is configured to at least one of: monitor anode current; monitor cathode current; perform electrical impedance spectroscopy; or monitor local pH in acid confinement zones of synthesis pixels in the array of synthesis pixels. Example 8: The device of Example 1, wherein the array comprises a single acid absorbing cathode that absorbs acid generated at each synthesis pixel in the array. Example 9: the device of Example 1, wherein the array comprises a plurality of acid absorbing cathodes, and wherein each of the plurality of acid absorbing cathodes absorbs acid generated at at least one of the plurality of synthesis pixels. Example 10: the device of Example 1, wherein each synthesis pixel comprises a cathode to absorb acid generated at the anode of that synthesis pixel.

Example 11: The device of Example 1, wherein the device is a CMOS chip, and wherein the device, including the electrodes of each synthesis pixel in the array, is fabricated within a CMOS chip foundry, using standard CMOS processes. Example 12: the device of Example 11, wherein the number of synthesis pixels in the array is at least 100, at least 1000, at least 10,000, at least 100,000, at least 1,000,000, at least 10,000,000, at least 100,000,000, at least 1,000,000,000, or at least 10,000,000,000. Example 13: The device of Example 11, wherein the pixel pitch of each synthesis pixel in the array is less than 100 microns, less than 50 microns, less than 20 microns, less than 10 microns, less than 5 microns, less than 2 microns, less than 1 micron, less than 500 nm, less than 200 nm, less than 100 nm, less than 50 nm, or less than 20 nm. Example 14: the device of Example 11, wherein the electrodes of each synthesis pixel in the array are fabricated by selectively etching away sacrificial metal layers atop CMOS, exposing the respective contact metal for control of the electrodes, and then depositing the desired electrode metal and geometry of the electrodes deposited atop the respective contact metal.

Example 15: A method for synthesizing polynucleotides on an electrochemical synthesis chip, comprising: synthesizing in parallel, at a plurality of synthesis pixels in an array on a semiconductor integrated circuit coupled to a flow cell, a target polynucleotide sequence associated with each synthesis pixel. Example 16: the method of Example 15, wherein the target polynucleotide sequence associated with a first synthesis pixel is identical to the target polynucleotide sequence associated with a second synthesis pixel. Example 17: the method of Example 15, wherein a first portion of the array synthesizes a first target polynucleotide sequence, and wherein a second portion of the array synthesizes a second target polynucleotide sequence different from the first polynucleotide sequence. Example 18: the method of Example 15, wherein all target polynucleotide sequences across all synthesis pixels are of the same length. Example 19: the method of Example 15, further comprising a monitoring step, such that elements of the method are monitored during the synthesis, and where such monitoring results are recorded off the semiconductor integrated circuit, and where such monitoring results may also be used within a control system to control the timing of an acid deprotection step, or of a coupling step, or to control other process variables during the synthesis method, such as the magnitude of applied voltages, or such as timing patterns such as pulsing on and off of acid generation.

Example 20: An integrated system for synthesizing polynucleotides, comprising: a polynucleotide synthesis chip comprising a synthesis pixel array; a flow cell enclosing the synthesis pixel array; a fluidics delivery module with manifold supplying individual reagents or mixtures of multiple reagents to the flow cell; a control system controlling the operation of the fluidics delivery module and the polynucleotide synthesis chip; a polynucleotide releasing mechanism, capable of releasing polynucleotide fragments from the chip post-synthesis; and a collection module with selectable receptacles for waste or polynucleotide effluent of released polynucleotides from the polynucleotide synthesis chip, under control of the control system.

Example 21: A multi-chip integrated blade system for synthesizing polynucleotides on a plurality of polynucleotide synthesis chips in parallel, comprising: the plurality of polynucleotide synthesis chips, each comprising an array of synthesis pixels; at least one flow cell, wherein each polynucleotide synthesis chip is coupled to at least one flow cell; a fluidics delivery module with manifold, configured to selectively supply individual reagents or mixtures of multiple reagents to the at least one flow cell; a control system controlling the operation of the fluidics delivery module and each of the plurality of polynucleotide synthesis chips; a polynucleotide releasing mechanism, capable of selectively releasing polynucleotide fragments from one or more of the plurality of polynucleotide synthesis chips, post-synthesis; and a collection module with selectable receptacles for waste or polynucleotide effluent of released polynucleotides from one or more of the plurality of polynucleotide synthesis chips, selectively, under control of the control system.

Example 22: The system of Example 21, wherein the array comprises having at least 10, or at least 100, or at least 1000, or at least 10,000 polynucleotide synthesis chips. Example 23: The system of Example 21, where the synthesized polynucleotides collected in separate pools for each chip, or in pools that combined multiple chips as selected, or in a single pool for all chips.

Example 24: A multi-blade integrated system for synthesizing polynucleotides, comprising: a plurality of polynucleotide synthesis chip blades; a fluidics delivery module with manifold supplying individual reagents or mixtures of multiple reagents to each of the blades; a control system controlling the operation of the multi-blade integrated system; and a collection module with selectable receptacles for waste or polynucleotide effluent of released polynucleotides from each blade, selectively, under control of the control system. Example 25: the system of Example 24, having at least 4, at least 8, at least 16, at least 32, or at least 64 polynucleotide synthesis blades. Example 26: the system of Example 24, where the synthesized polynucleotides are collected in (i) separate pools for subsets of chips within blades (sub-blade pooling, preserving subgroups of chips defined per blade, including preserving individual pools from each chip in each blade), (ii) a pool for each blade, (iii) in pools that combined multiple blades as selected, or (iv) in a single pool for all blades. Example 27: the system of Example 24, where the blades are rackmounted in a standard rack.

Example 28: A multi-rack integrated system for synthesizing polynucleotides, comprising: multiple racks of blade servers of claim Example 27; a master controller controlling operations of all racks; an autosampler for final collection of multiple polynucleotide samples, which may be pooled in any way across the released polynucleotides from chips, blades, and racks of the system; a deprotection module to deprotect all pooled samples; and a cleanup module for cleanup of resulting samples.

Example 29: a method of synthesizing a multiplicity of polynucleotide sequences on any of the above example single chip, multi-chip blade, multi-blade rack, or multi-rack systems, comprising: supplying a multiplicity of polynucleotide sequences to the system; assigning such sequences to the synthesis pixels of the chips in the system; specifying the desired pool structure for the final products, with pools that may be at the chip, chip group, blade, blade group, rack or rack group level; carrying out an electrochemical polynucleotide synthesis process disclosed herein on the chips of the system, for the sequences as assigned to each pixel and chip, as appropriate for the system architecture; and collecting the polynucleotide synthesis products from the system in the specified pool structure of pools of the specified polynucleotide sequences.

Example 30: A method for storing digital data in polynucleotides, utilizing a chip-based polynucleotide synthesis system as recited in any of the foregoing examples, the method comprising: converting digital data into polynucleotide sequences; synthesis of the polynucleotide sequences on the polynucleotide synthesis system; collection of the resulting polynucleotide fragments from the chip-based system; and storage of the polynucleotide fragments in a physical polynucleotide storage library.

Example 31: a personal DNA data storage system, comprising a desktop instrument comprising: integrated digital data input transfer options, such as a USB connection or other hardware ports for direct connections, or wireless connectivity such as W-Fi or Bluetooth, or an internet connection, for transfer or streaming of data; am integrated temporary digital data storage buffer, to temporarily store incoming digital data or streaming segments of data, prior to DNA storage; a software encoder that transfers digital data into a set of DNA sequences for synthesis; a chip-based synthesis system, supporting one or multiple chips; A chip port for inserting a chip or chips into the system; A reagent port for inserting synthesis reagent cartridges into the system; A waste receptacle that contains waste reagents from runs; and a DNA encapsulation system for transferring released DNA to a storage capsule, such capsules providing wet or dry storage options. Example 32: the system of Example 31, having capacity for storing up to 1 GB, 1 TB, or 1 PB of data, in less than 24 hours, or 12 hours, or 4 hours, or 2 hours. Example 33: the system of Example 31 with a rapid storage mode as disclosed in the specification, capable of storing up to 1 GB, 10 GB, 100 GB, 1 TB, 10 TB, or 100 TB of data, in less than 1 hour, less than 30 minutes, less than 15 minutes, less than 5 minutes, less than 1 minute, less than 30 seconds, or less than 10 seconds.

Example 34: A method for personal storage of digital data in DNA, comprising: providing the personal DNA data storage system of Example 31; loading the system with reagent cartridges; loading the system with a chip or chips; loading the system with digital data for storage, using any of the data ports for data transfer or data streaming, to load or stream data to the system; performing DNA synthesis via the system; and collecting a storage capsule from the system.

Example 35: A server DNA data storage system, comprising a rackmounted blade system, comprising: A server rack or racks; An integrated hard connection or wireless connection the internet, or to a digital data server, for the transfer or streaming of digital data to the system; An integrated data buffer for temporary storage of input or streamed digital data during synthesis; An integrated reagent storage compartment to hold synthesis reagents; An integrated waste receptacle or line for catching or expelling waste from synthesis; One or more DNA synthesis storage blades for a rackmount system configuration; A means of accessing synthesis blades for adding or removing chips; A capability for taking chips offline for in-place cleaning & refurbishing for re-use; A means for detecting when to take a chip off-line for cleaning & refurbishing, such as by monitoring chip synthesis parameters with on-chip monitors; A receptacle or receptacles for holding capsules to receive the output DNA from the chips or blades, offering wet or dry storage in capsules; A system for packing the capsules with finished DNA from the blades or chips; A bank repository for storing the resulting filled capsules; and an automated transfer system that transfers capsules to the bank repository. Example 36: the system of Example 35, with capacity for storing up to 1 PB, 1 EB, 1 ZB, or 1 YB of data. Example 37: the system of Example 35, capable of storing 1 PB, 1 EB, 1 ZB or 1 YB of data, in less than 1 month, 1 week, 1 day, 12 hours, 6 hours, or 3 hours. Example 37: the system of Example 35 configured with a rapid writing mode capable of storing up to 1 PB, 1 EB, 1 ZB or 1 YB of data, in less than 1 hour, less than 30 minutes, less than 10 minutes, less than 5 minutes, or less than 1 minute.

Example 38: A method for large scale storage of digital data in DNA, comprising: providing the server DNA data storage system of Example 35; loading the system with reagent cartridges; loading the system blades with chips; loading the blades into the rackmounts; streaming digital data volumes to the system for storage; initiating synthesis of DNA on blades; taking chips off-line as needed for refurbishing during synthesis; and populating the bank repositories with the resulting storage capsules.

Example 39: A set of polynucleotide fragments representing digital data, with a format where the payloads are of Length L, having index segments of length k, and digital data message segment of length L-k. Example 40: The set of polynucleotide fragments of Example 39, wherein error correcting codes are utilized in the construction of the index set and the digital data message segment encoding. Example 41: A method for storing digital data in polynucleotides, comprising the production of polynucleotide fragments of Example 39 using a chip-based synthesis system. Example 42: A chip or chips for use in synthesizing the polynucleotide sequences of Example 39, wherein an associated index set is pre-synthesized on the chip or chips. Example 43: A method for storing digital data in polynucleotides, comprising the use of a synthesis chip or chips on which an index set is pre-synthesized.

Example 44: A set of polynucleotide fragments, wherein the fragments comprise DNA digital data stored in an optimal format where the payload of Length L has an index segment of length k=L−1 bases, and a message segment of length l base, or the index segment is of length k=L−w, and the message segments are length w, and w is preferably 3, 4, 5, or up to 10, and where the message segments preferably include error correcting encoding of the message segment. Example 45: A method of rapid storage of digital data in DNA using the storage format of claim Example 44, comprising: using CMOS synthesis chip or chips that have the indexes pre-synthesized; and writing the final w=1 or w=few letters at the of storing the digital data.

Example 46: A DNA data storage chip set, comprising: the set of DNA data storage chips each populated with pre-synthesized index sets, preferably with error correcting encodings have a certain power of error correction, and capable of further message segment synthesis, with the set of chips supporting enough indexes to encode up to 1 kB, 1 MB, 1 GB, 1 TB, 1 PB, or up to 1 EB.

Example 47: A set of polynucleotides comprising digital data stored in a format where the payload of length L has an index segment of length k=approximately L/2 bases, and a message segment of length approximately L/2 bases. Example 48: a method for storing digital data in polynucleotides in the format of Example 47, comprising the synthesis of such polynucleotides on CMOS synthesis chips. Example 49: chip or chips for use in synthesizing the polynucleotide sequences of Example 47, in which the associated index set is pre-synthesized on the chip or chips.

Example 50: A method for storing digital data in DNA, comprising the reuse of CMOS DNA synthesis chips in a multi-chip system, wherein, in an automated and asynchronous fashion, the chips can be taken offline for refurbishing and preparation for re-use, and brought back online for the reuse. Example 51: the use of the method of Example 50 to store an amount of data up to 1 GB, 1 TB, 1 PB, 1 EB or 1 ZB, in short DNA segments, of Length<100 bases, <80 bases, <60 bases, <40 bases, or <30 bases.

Example 51: A method of DNA data storage, comprising the in-place re-use of chips with prefabricated indexes, in which the products are produced by synthesis onto oligos hybridized to the on-chip indexes. Example 52: A method of DNA data storage, comprising the in-place re-use of chips with prefabricated indexes, in which the products are produced by polymerase extension from a primer site. Example 53: A method of DNA data storage, comprising the in-place re-use of chips with prefabricated indexes, in which the products are produced by a process of hybridization, conjugation, cleavage, and ligation. Example 54: a method of DNA data storage with error correction, in which coverage and consensus sequence are used to correct errors, with coverage of at least 2, 3, 5, 6, or 10, and wherein additional disambiguation segments are added to the payload to allow for coverage aggregation. Example 55: a method of DNA data storage with error correction, in which payloads or payload segments are encoded into k-mers having indexes that are mutually spaced apart by more than 2m in the Edit Distance, and such that up to an edit distance of m, corrupted sequences can be corrected back to the original. Example 56: A method of error correction for DNA synthesis, where the index set for use on a synthesis chip is encoded with the Edit Distance method and a capacity of correcting up to m errors. Example 57: A method of data storage using error correcting indexes, synthesized onto a chip, and subsequently synthesizing the message segments, with some additional error correction. Example 58: A method of error correction for DNA data storage, where the index set synthesized onto a synthesis chip and the message segments are separately encoded with the m-Edit Distance methods, using respective $m_1$ and $m_2$ error correction capacities for the indexes and message segments.

Example 59: A method of DNA storage with error correction, comprising the use of both coverage based correction, with coverage of at least C, and the Edit Distance correction method on the index segments, with correction of up to distance m, where C is 2, 3, 4, 5, or up to 10, and m is 1, 2, 4, 4, or up to 10. Example 60: A polynucleotide synthesis chip with a prefabricated index set S, such that message segments can be synthesized on it. Example 61: A system, comprising: an S-chip as in Example 60, and a volume index set V, and means for affiliating volume indexes with the products of the S-chip. Example 62: A method of storing an unlimited amount of message digital data in polynucleotides, comprising synthesizing message segments on S-chips, and applying additional volume indexes from V, sufficient to store the entire input data message. Example 63: A method of storage an unlimited amount of digital message data in polynucleotides, using only short on chip synthesized payloads, of size up to 10, 15, 25, 30, 35, 40, 50 or 60 bases, in which the short payloads are synthesized on S-chips, and further volume indexed per chip using a volume index set V.

Example 64: A polynucleotide synthesis chip set of P chips with a prefabricated index set S, such that message segments can be synthesized on it. Example 65: A blade storage system, comprising a blade with an S-chip-set of pre-indexed chips in the blade, and configured to implement methods of use of this to store unlimited amounts of data in polynucleotides while synthesizing only payloads of length less than 15, 20, 25, 30, 35, 40, 50, or 60 bases, by using volume indexing with volume index set V.

For the sake of brevity, conventional DNA synthesis, semiconductor manufacturing, CMOS chip configuration, micro- or nano-fluidics, data management, computer networking, data compression, error checking, and other aspects of exemplary systems and methods (and components thereof) may not be described in detail herein. Furthermore, the connecting lines shown in the various figures contained herein are intended to represent functional relationships and/or physical or communicative couplings between the various elements. It should be noted that many alternative or additional functional relationships or physical connections may be present in a practical DNA data storage system or related methods.

While the description references specific technologies, system architectures and data management techniques, practitioners will appreciate that this description is of various embodiments, and that other devices and/or methods may be implemented without departing from the scope of principles of the present disclosure. Similarly, while the description references a user interfacing with exemplary systems via a computer user interface, practitioners will appreciate that other interfaces may include mobile devices, kiosks and handheld devices such as mobile phones, smart phones, tablet computing devices, etc.

While the steps outlined herein represent exemplary embodiments of principles of the present disclosure, practitioners will appreciate that there are many suitable computing algorithms and user interfaces that may be applied to create similar results. The steps are presented for the sake of explanation only and are not intended to limit the scope of the present disclosure in any way. Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all of the claims.

Systems, methods, and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. After reading the description, it will be apparent to one skilled in the relevant art(s) how to implement principles of the disclosure in alternative embodiments.

It should be understood that the detailed description and specific examples, indicating exemplary embodiments, are given for purposes of illustration only and not as limitations. Many changes and modifications may be made without departing from the spirit thereof, and principles of the present disclosure include all such modifications. Corresponding structures, materials, acts, and equivalents of all elements are intended to include any structure, material, or acts for performing the functions in combination with other elements. Reference to an element in the singular is not intended to mean "one and only one" unless explicitly so stated, but rather "one or more." Moreover, when a phrase similar to "at least one of A, B, or C" or "at least one of A, B, and C" is used in the claims or the specification, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A polynucleotide synthesis system, comprising:
    a first planar substrate having a solution applied thereto;
    a first electrode coupled to the first substrate and operable as an anode to drive electrochemical acid generation in the solution; and
    a polynucleotide synthesis region on the first planar substrate functionalized to anchor and support polynucleotide synthesis through the addition of phosphoramidites.

2. The polynucleotide synthesis system of claim 1, further comprising control circuitry operable to controllably apply and remove a first potential at the first electrode.

3. The polynucleotide synthesis system of claim 2, further comprising a second electrode coupled to the first substrate and operable as a cathode to absorb acid from the solution.

4. The polynucleotide synthesis system of claim 3, wherein the polynucleotide synthesis region is located between the first electrode and the second electrode.

5. The polynucleotide synthesis system of claim 3, wherein the first electrode and second electrode are planar, and wherein the second electrode surrounds the first electrode when viewed perpendicular to the first substrate.

6. The polynucleotide synthesis system of claim 5, wherein the first electrode and the second electrode are interdigitated.

7. The polynucleotide synthesis system of claim 3, further comprising a plurality of first electrodes configured as an array.

8. The polynucleotide synthesis system of claim 7, wherein the second electrode surrounds each of the plurality of first electrodes in the array such that the second electrode separates each first electrode in the plurality of first electrodes from all other first electrodes in the plurality of first electrodes.

9. The polynucleotide synthesis system of claim 1, wherein the solution comprises a reversible redox pair comprising hydroquinone and tetrachloro-1,4-benzoquinone.

10. The polynucleotide synthesis system of claim 1, wherein the solution comprises a reversible redox pair configured with a redox potential lower than 1.2 volts.

11. The polynucleotide synthesis system of claim 3, wherein at least a portion of the second electrode extends over the first electrode with a gap therebetween occupied by the solution, forming a ceiling over the first electrode.

12. The polynucleotide synthesis system of claim 3, wherein at least a portion of the second electrode extends from the first substrate to a height greater than a height of the first electrode to form a wall to at least partially contain acid generated at the first electrode.

13. The polynucleotide synthesis system of claim 10, wherein the substrate and the first electrode comprise portions of a complementary metal oxide semiconductor (CMOS) chip fabricated on a node of 65 nm or below.

\* \* \* \* \*